US009777335B2

(12) United States Patent
Huletsky et al.

(10) Patent No.: US 9,777,335 B2
(45) **Date of Patent: *Oct. 3, 2017**

(54) **METHOD FOR THE DETECTION AND IDENTIFICATION OF METHICILLIN-RESISTANT *STAPHYLOCOCCUS AUREUS***

(75) Inventors: Ann Huletsky, Sillery (CA); Valery Rossbach, Gatineau (CA)

(73) Assignee: GeneOhm Sciences Canada Inc., Quebec (CA)

( * ) Notice: Subject to any disclaimer, the term of this patent is extended or adjusted under 35 U.S.C. 154(b) by 457 days.

This patent is subject to a terminal disclaimer.

(21) Appl. No.: 11/416,500

(22) Filed: May 2, 2006

(65) Prior Publication Data

US 2006/0252078 A1 Nov. 9, 2006

Related U.S. Application Data

(63) Continuation of application No. 10/479,674, filed as application No. PCT/CA02/00824 on Jun. 4, 2002, now Pat. No. 7,449,289.

(30) Foreign Application Priority Data

Jun. 4, 2001 (CA) ...................................... 2348042

(51) Int. Cl.
*C12Q 1/68* (2006.01)

(52) U.S. Cl.
CPC ....... *C12Q 1/689* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,458,066 | A | 7/1984 | Caruthers et al. |
| 4,683,195 | A | 7/1987 | Mullis et al. |
| 4,683,202 | A | 7/1987 | Mullis |
| 5,272,236 | A | 12/1993 | Lai et al. |
| 5,437,978 | A | 8/1995 | Ubukata et al. |
| 5,475,610 | A | 12/1995 | Atwood et al. |
| 5,496,706 | A | 3/1996 | Kuusela et al. |
| 5,538,871 | A | 7/1996 | Nuovo et al. |
| 5,602,756 | A | 2/1997 | Atwood et al. |
| 5,612,473 | A | 3/1997 | Wu et al. |

(Continued)

FOREIGN PATENT DOCUMENTS

| | | |
|---|---|---|
| AU | 731850 | 4/2001 |
| AU | 775763 | 8/2004 |

(Continued)

OTHER PUBLICATIONS

Walker, G.T. et al. Proceedings of the National Academy of Sciences USA 89:392-396 (Jan 1992).*

(Continued)

*Primary Examiner* — Diana B Johannsen
(74) *Attorney, Agent, or Firm* — Knobbe, Martens, Olson & Bear, LLP

(57) ABSTRACT

The present invention describes novel SCCmec right extremity junction sequences for the detection of methicillin-resistant *Staphyloccocus aureus* (MRSA). It relates to the use of these DNA sequences for diagnostic purposes.

29 Claims, 10 Drawing Sheets

(56) References Cited

U.S. PATENT DOCUMENTS

| | | | |
|---|---|---|---|
| 5,702,895 | A | 12/1997 | Matsunaga et al. |
| 5,776,712 | A | 7/1998 | Kuusela et al. |
| 5,780,610 | A | 7/1998 | Collins et al. |
| 5,783,638 | A | 7/1998 | Lai et al. |
| 5,866,366 | A | 2/1999 | Kallender |
| 5,994,066 | A | 11/1999 | Bergeron et al. |
| 6,001,564 | A | 12/1999 | Bergeron et al. |
| 6,083,587 | A | 7/2000 | Smith et al. |
| 6,090,592 | A | 7/2000 | Adams et al. |
| 6,117,635 | A | 9/2000 | Nazarenko et al. |
| 6,117,986 | A | 9/2000 | Nardone et al. |
| 6,156,507 | A | 12/2000 | Hiramatsu et al. |
| 6,271,351 | B1 | 8/2001 | Gawryl et al. |
| 6,380,370 | B1 | 4/2002 | Doucette-Stamm et al. |
| 7,108,974 | B2 | 9/2006 | Ecker et al. |
| 7,205,111 | B2 | 4/2007 | Christensen et al. |
| 7,226,739 | B2 | 6/2007 | Ecker et al. |
| 7,255,992 | B2 | 8/2007 | Ecker et al. |
| 7,399,590 | B2 | 7/2008 | Piepenburg et al. |
| 7,435,561 | B2 | 10/2008 | Piepenburg et al. |
| 7,449,289 | B2 | 11/2008 | Huletsky et al. |
| 7,466,908 | B1 | 12/2008 | Lem et al. |
| 7,666,588 | B2 | 2/2010 | Ecker et al. |
| 7,666,592 | B2 | 2/2010 | Ecker et al. |
| 7,718,354 | B2 | 5/2010 | Ecker et al. |
| 7,741,036 | B2 | 6/2010 | Ecker et al. |
| 7,781,162 | B2 | 8/2010 | Ecker et al. |
| 7,838,221 | B2 | 11/2010 | Huletsky et al. |
| 7,955,796 | B2 | 6/2011 | Schrenzel et al. |
| 7,956,175 | B2 | 6/2011 | Sampath et al. |
| 8,013,142 | B2 | 9/2011 | Sampath et al. |
| 8,017,322 | B2 | 9/2011 | Ecker et al. |
| 8,017,337 | B2 | 9/2011 | Paitan |
| 8,017,358 | B2 | 9/2011 | Ecker et al. |
| 8,017,743 | B2 | 9/2011 | Ecker et al. |
| 8,034,588 | B2 | 10/2011 | Bergeron et al. |
| 8,062,850 | B2 | 11/2011 | Piepenburg et al. |
| 8,067,207 | B2 | 11/2011 | Bergeron et al. |
| 8,071,309 | B2 | 12/2011 | Ecker et al. |
| 8,084,207 | B2 | 12/2011 | Sampath et al. |
| 8,097,416 | B2 | 1/2012 | Hall et al. |
| 8,114,601 | B2 | 2/2012 | Bergeron et al. |
| 8,163,895 | B2 | 4/2012 | Sampath et al. |
| 8,182,992 | B2 | 5/2012 | Sampath |
| 8,182,996 | B2 | 5/2012 | Bergeron et al. |
| 8,187,812 | B2 | 5/2012 | Zhang et al. |
| 8,187,814 | B2 | 5/2012 | Ecker et al. |
| 8,214,154 | B2 | 7/2012 | Ecker et al. |
| 8,242,254 | B2 | 8/2012 | Sampath et al. |
| 8,265,878 | B2 | 9/2012 | Ecker et al. |
| 8,268,565 | B2 | 9/2012 | Ecker et al. |
| 8,288,523 | B2 | 10/2012 | Sampath et al. |
| 8,323,898 | B2 | 12/2012 | Niimi et al. |
| 8,362,228 | B2 | 1/2013 | Paitan |
| 8,367,337 | B2 | 2/2013 | Jay et al. |
| 8,394,945 | B2 | 3/2013 | Sampath et al. |
| 8,426,137 | B2 | 4/2013 | Bergeron et al. |
| 8,518,646 | B2 | 8/2013 | Jean et al. |
| 2002/0055101 | A1 | 5/2002 | Bergeron et al. |
| 2002/0103338 | A1 | 8/2002 | Choi |
| 2002/0106646 | A1 | 8/2002 | Remacle et al. |
| 2003/0027135 | A1 | 2/2003 | Ecker et al. |
| 2003/0049636 | A1 | 3/2003 | Bergeron et al. |
| 2003/0054436 | A1 | 3/2003 | Kunsch et al. |
| 2003/0124556 | A1 | 7/2003 | Ecker et al. |
| 2003/0175695 | A1 | 9/2003 | Ecker et al. |
| 2003/0175696 | A1 | 9/2003 | Ecker et al. |
| 2003/0175697 | A1 | 9/2003 | Ecker et al. |
| 2003/0180733 | A1 | 9/2003 | Bergeron et al. |
| 2003/0190605 | A1 | 10/2003 | Ecker et al. |
| 2003/0198943 | A1 | 10/2003 | Remacle et al. |
| 2004/0082002 | A1 | 4/2004 | Choi |
| 2004/0110138 | A1 | 6/2004 | Lem et al. |
| 2004/0110169 | A1 | 6/2004 | Ecker et al. |
| 2004/0121309 | A1 | 6/2004 | Ecker et al. |
| 2004/0121310 | A1 | 6/2004 | Ecker et al. |
| 2004/0121311 | A1 | 6/2004 | Ecker et al. |
| 2004/0121313 | A1 | 6/2004 | Ecker et al. |
| 2004/0121314 | A1 | 6/2004 | Ecker et al. |
| 2004/0121335 | A1 | 6/2004 | Ecker et al. |
| 2004/0161770 | A1 | 8/2004 | Ecker et al. |
| 2004/0180328 | A1 | 9/2004 | Ecker et al. |
| 2004/0185437 | A1 | 9/2004 | Hermet et al. |
| 2004/0185438 | A1 | 9/2004 | Ecker |
| 2004/0185478 | A1 | 9/2004 | Bergeron et al. |
| 2004/0202997 | A1 | 10/2004 | Ecker et al. |
| 2004/0219517 | A1 | 11/2004 | Ecker et al. |
| 2004/0241824 | A1 | 12/2004 | Schrenzel et al. |
| 2004/0253583 | A1 | 12/2004 | Ecker et al. |
| 2004/0253619 | A1 | 12/2004 | Ecker et al. |
| 2005/0019893 | A1 * | 1/2005 | Huletsky et al. .......... 435/252.3 |
| 2005/0037408 | A1 | 2/2005 | Christensen et al. |
| 2005/0059064 | A1 | 3/2005 | Obst et al. |
| 2005/0112631 | A1 | 5/2005 | Piepenburg et al. |
| 2005/0115903 | A1 | 6/2005 | Hallier-Soulier et al. |
| 2006/0057613 | A1 | 3/2006 | Ramakrishnan et al. |
| 2006/0105354 | A1 | 5/2006 | Remacle et al. |
| 2006/0121520 | A1 | 6/2006 | Ecker et al. |
| 2006/0205040 | A1 | 9/2006 | Sampath |
| 2006/0240412 | A1 | 10/2006 | Hall et al. |
| 2006/0252069 | A1 | 11/2006 | Zhang et al. |
| 2006/0252078 | A1 | 11/2006 | Huletsky et al. |
| 2006/0263810 | A1 | 11/2006 | Bergeron et al. |
| 2006/0275749 | A1 | 12/2006 | Sampath et al. |
| 2006/0275788 | A1 | 12/2006 | Ecker et al. |
| 2006/0281112 | A1 | 12/2006 | Remacle et al. |
| 2007/0009947 | A1 | 1/2007 | Bergeron et al. |
| 2007/0037187 | A1 | 2/2007 | Alexandre et al. |
| 2007/0048735 | A1 | 3/2007 | Ecker et al. |
| 2007/0054296 | A1 | 3/2007 | Piepenburg et al. |
| 2007/0082340 | A1 | 4/2007 | Huletsky et al. |
| 2007/0099204 | A1 | 5/2007 | Alexandre et al. |
| 2007/0105129 | A1 | 5/2007 | Bergeron et al. |
| 2007/0218489 | A1 | 9/2007 | Sampath et al. |
| 2007/0224614 | A1 | 9/2007 | Sampath et al. |
| 2007/0238116 | A1 | 10/2007 | Sampath et al. |
| 2007/0243544 | A1 | 10/2007 | Sampath et al. |
| 2007/0248969 | A1 | 10/2007 | Sampath et al. |
| 2007/0298423 | A1 | 12/2007 | Remacle et al. |
| 2008/0038737 | A1 | 2/2008 | Smith et al. |
| 2008/0057544 | A1 | 3/2008 | Lem et al. |
| 2008/0085515 | A1 | 4/2008 | Remacle et al. |
| 2008/0138808 | A1 | 6/2008 | Hall et al. |
| 2008/0145847 | A1 | 6/2008 | Hall et al. |
| 2008/0146455 | A1 | 6/2008 | Hall et al. |
| 2008/0160512 | A1 | 7/2008 | Ecker et al. |
| 2008/0220428 | A1 | 9/2008 | Aichinger et al. |
| 2008/0227087 | A1 | 9/2008 | Huletsky et al. |
| 2008/0233570 | A1 | 9/2008 | Hall et al. |
| 2008/0311558 | A1 | 12/2008 | Ecker et al. |
| 2009/0004643 | A1 | 1/2009 | Ecker et al. |
| 2009/0035780 | A1 | 2/2009 | McCarthy et al. |
| 2009/0047665 | A1 | 2/2009 | Hall et al. |
| 2009/0047669 | A1 | 2/2009 | Zhang et al. |
| 2009/0047671 | A1 | 2/2009 | Bergeron et al. |
| 2009/0053702 | A1 | 2/2009 | Bergeron et al. |
| 2009/0053703 | A1 | 2/2009 | Bergeron et al. |
| 2009/0061446 | A1 | 3/2009 | Niimi et al. |
| 2009/0068641 | A1 | 3/2009 | Bergeron et al. |
| 2009/0111134 | A1 | 4/2009 | Zhang et al. |
| 2009/0148829 | A1 | 6/2009 | Ecker et al. |
| 2009/0148836 | A1 | 6/2009 | Ecker et al. |
| 2009/0148837 | A1 | 6/2009 | Ecker et al. |
| 2009/0181395 | A1 | 7/2009 | Becker et al. |
| 2009/0182511 | A1 | 7/2009 | Ecker et al. |
| 2009/0203013 | A1 | 8/2009 | Jay et al. |
| 2009/0220937 | A1 | 9/2009 | Sampath |
| 2009/0239224 | A1 | 9/2009 | Ecker et al. |
| 2009/0280471 | A1 | 11/2009 | Ecker et al. |
| 2010/0035232 | A1 | 2/2010 | Ecker et al. |
| 2010/0035239 | A1 | 2/2010 | Sampath et al. |
| 2010/0099860 | A1 | 4/2010 | Remacle et al. |
| 2010/0129811 | A1 | 5/2010 | Sampath et al. |
| 2010/0136515 | A1 | 6/2010 | Sampath et al. |

(56) References Cited

U.S. PATENT DOCUMENTS

| | | | |
|---|---|---|---|
| 2010/0145626 | A1 | 6/2010 | Ecker et al. |
| 2010/0152432 | A1 | 6/2010 | Wu et al. |
| 2010/0204266 | A1 | 8/2010 | Ecker et al. |
| 2010/0267012 | A1 | 10/2010 | Bergeron et al. |
| 2010/0304366 | A1 | 12/2010 | Wu et al. |
| 2011/0091886 | A1 | 4/2011 | Hirama et al. |
| 2011/0151452 | A1 | 6/2011 | Jean et al. |
| 2012/0015349 | A1 | 1/2012 | Sampath et al. |
| 2012/0015367 | A1 | 1/2012 | Piepenburg et al. |
| 2012/0035071 | A1 | 2/2012 | Bergeron et al. |
| 2012/0058487 | A1 | 3/2012 | Bergeron et al. |
| 2012/0077684 | A1 | 3/2012 | O'Hara |
| 2012/0107795 | A1 | 5/2012 | Ecker et al. |
| 2012/0122086 | A1 | 5/2012 | Ecker et al. |
| 2012/0122096 | A1 | 5/2012 | Sampath et al. |
| 2012/0122097 | A1 | 5/2012 | Sampath et al. |
| 2012/0122098 | A1 | 5/2012 | Sampath et al. |
| 2012/0122099 | A1 | 5/2012 | Sampath et al. |
| 2012/0122100 | A1 | 5/2012 | Sampath et al. |
| 2012/0122101 | A1 | 5/2012 | Sampath et al. |
| 2012/0122102 | A1 | 5/2012 | Sampath et al. |
| 2012/0122103 | A1 | 5/2012 | Sampath et al. |
| 2012/0142085 | A1 | 6/2012 | Ecker et al. |
| 2012/0164625 | A1 | 6/2012 | Ecker et al. |
| 2012/0171679 | A1 | 7/2012 | Ecker et al. |
| 2012/0171692 | A1 | 7/2012 | Rangarajan et al. |
| 2012/0208179 | A1 | 8/2012 | Sampath et al. |
| 2013/0065774 | A1 | 3/2013 | Zhang et al. |
| 2013/0266942 | A1 | 10/2013 | Menard et al. |
| 2013/0338036 | A1 | 12/2013 | Jean et al. |
| 2013/0338037 | A1 | 12/2013 | Jean et al. |
| 2015/0232919 | A1 | 8/2015 | Menard et al. |

FOREIGN PATENT DOCUMENTS

| | | | |
|---|---|---|---|
| AU | 2008255266 | | 1/2009 |
| AU | 2010202418 | | 7/2010 |
| AU | 2012247038 | | 11/2012 |
| CA | 2283458 | | 3/2001 |
| CA | 2348042 | A1 | 12/2002 |
| CN | 1505685 | | 6/2004 |
| DE | 10051174 | | 5/2002 |
| EP | 0 497 272 | | 8/1992 |
| EP | 0 526 876 | A1 | 2/1993 |
| EP | 0 527 628 | | 2/1993 |
| EP | 0 543 942 | | 6/1993 |
| EP | 0887424 | | 12/1998 |
| EP | 1 136 566 | A | 9/2001 |
| EP | 1 522 595 | | 4/2005 |
| EP | 1 529 847 | A | 5/2005 |
| EP | 1 541 696 | A | 6/2005 |
| EP | 1 659 183 | A | 5/2006 |
| EP | 1 788 095 | A1 | 5/2007 |
| EP | 1 903 116 | A1 | 3/2008 |
| EP | 1 997 886 | A1 | 12/2008 |
| EP | 0 943 009 | B1 | 6/2009 |
| EP | 1 397 510 | B1 | 11/2009 |
| EP | 2 128 268 | A1 | 12/2009 |
| EP | 2 150 625 | A2 | 2/2010 |
| EP | 2 236 621 | A1 | 10/2010 |
| EP | 2 253 712 | A1 | 11/2010 |
| EP | 1 934 613 | B1 | 1/2011 |
| EP | 2 302 074 | | 3/2011 |
| EP | 2 311 992 | | 4/2011 |
| EP | 2 322 649 | | 5/2011 |
| EP | 2 322 655 | A1 | 5/2011 |
| EP | 2 322 661 | A1 | 5/2011 |
| EP | 2 322 663 | A1 | 5/2011 |
| EP | 2 322 664 | A1 | 5/2011 |
| EP | 2 322 666 | A2 | 5/2011 |
| EP | 2 322 667 | A2 | 5/2011 |
| EP | 2 322 668 | A2 | 5/2011 |
| EP | 2 322 930 | A2 | 5/2011 |
| EP | 2 325 643 | A2 | 5/2011 |
| EP | 2 325 644 | A2 | 5/2011 |
| EP | 2 325 645 | A2 | 5/2011 |
| EP | 2 325 646 | A2 | 5/2011 |
| EP | 2 325 647 | A2 | 5/2011 |
| EP | 2 333 118 | | 6/2011 |
| EP | 2 336 364 | A1 | 6/2011 |
| EP | 2 336 365 | A1 | 6/2011 |
| EP | 2 336 366 | A2 | 6/2011 |
| EP | 2 339 033 | A1 | 6/2011 |
| EP | 2 339 034 | A1 | 6/2011 |
| EP | 2 345 746 | A1 | 7/2011 |
| EP | 2 385 140 | A1 | 11/2011 |
| EP | 2 064 332 | B1 | 7/2012 |
| EP | 2 016 186 | B1 | 1/2013 |
| EP | 1 929 049 | B1 | 4/2013 |
| JP | 11056371 | | 3/1999 |
| JP | 2006271370 | | 10/2006 |
| JP | 2010057495 | | 3/2010 |
| KR | 20030003576 | | 1/2003 |
| MX | PA03007927 | | 10/2004 |
| MY | 141881 | A | 7/2010 |
| WO | WO 92/02638 | | 8/1991 |
| WO | WO 92/05281 | | 4/1992 |
| WO | WO 95/13395 | | 5/1995 |
| WO | WO 96/08582 | | 3/1996 |
| WO | WO 97/31125 | | 8/1997 |
| WO | WO 98/20157 | | 5/1998 |
| WO | WO 9947706 | A1 * | 9/1999 |
| WO | WO 01/16292 | | 3/2001 |
| WO | WO 01/23604 | A2 | 4/2001 |
| WO | WO 01/77372 | | 10/2001 |
| WO | WO 02/070664 | | 9/2002 |
| WO | WO 02/082086 | | 10/2002 |
| WO | WO 02/099034 | | 12/2002 |
| WO | WO 2004/052175 | | 6/2004 |
| WO | WO 2004/053076 | | 6/2004 |
| WO | WO 2004/053141 | | 6/2004 |
| WO | WO 2004/053164 | | 6/2004 |
| WO | WO 2004/055205 | | 7/2004 |
| WO | WO 2004/060278 | | 7/2004 |
| WO | WO 2005/014857 | | 2/2005 |
| WO | WO 2005/024046 | | 3/2005 |
| WO | WO 2005/094421 | | 10/2005 |
| WO | WO 2005/098047 | | 10/2005 |
| WO | WO 2005/100538 | | 10/2005 |
| WO | WO 2006/028601 | | 3/2006 |
| WO | WO 2006/053769 | | 5/2006 |
| WO | WO 2006/053770 | | 5/2006 |
| WO | WO 2006/071241 | | 7/2006 |
| WO | WO 2006/094238 | | 9/2006 |
| WO | WO 2006/111028 | | 10/2006 |
| WO | WO 2006/116127 | | 11/2006 |
| WO | WO 2006/135400 | | 12/2006 |
| WO | WO 2007/023461 | | 3/2007 |
| WO | WO 2007/044873 | | 4/2007 |
| WO | WO 2007/086904 | | 8/2007 |
| WO | WO 2007/096702 | | 8/2007 |
| WO | WO 2007/100397 | | 9/2007 |
| WO | WO 2007/130951 | A2 | 11/2007 |
| WO | WO 2007/131995 | | 11/2007 |
| WO | WO 2007/131999 | | 11/2007 |
| WO | WO 2007/132001 | | 11/2007 |
| WO | WO 2007/132002 | | 11/2007 |
| WO | WO 2007/133732 | | 11/2007 |
| WO | WO 2008/061376 | | 5/2008 |
| WO | WO 2008/080620 | | 7/2008 |
| WO | WO 2008/140612 | | 11/2008 |
| WO | WO 2008/143627 | | 11/2008 |
| WO | WO 2009/049007 | | 4/2009 |
| WO | WO 2009/090310 | | 7/2009 |
| WO | WO 2009/123667 | | 10/2009 |
| WO | WO 2011/038197 | | 3/2011 |

OTHER PUBLICATIONS

Al-Soud, et al. "Capacity of nine thermostable DNA Polymerases to mediate DNA amplification in the presence of PCR-Inhibiting samples." *Appl. Environ. Microbiol.* 64(10): 3748-3753 (1998).

(56) References Cited

OTHER PUBLICATIONS

Al-Soud, et. al. "Effects of amplification facilitators on diagnostic PCR in the presence of blood, feces, and meat." *J. Clin. Microbiol.* 38(12): 4463-4470 (2002).
Arnheim, et al. "Polymerase Chain Reaction." C&EN. 36-47 (1990).
Archer and Niemeyer. "Origin and Evolution of DNA Associated with Resistance to Methicillin in *Staphylococci*." Trends in Microbiology. 2(10):343-347 (1994).
Archer, et al. "Dissemination among *Staphylococci* of DNA Sequences Associated with Methicillin Resistance." Antimicrobial Agents and Chemotherapy. 38(3):447-54 (1994).
Baba et al., "Genome and Virulence Determinants of High Virulence Community-acquired MRSA." Lancet, England, May 25, 2002; vol. 359, No. 9320; pp. 1819-1827.
Barberis-Maino. IS431, a *staphylococcal* insertion sequence-like element related to IS26 from *Proteus vulgaris*. Gene. 59:107-13 (1983).
Barringer, et al. "Blunt-end and single strand ligations by *Escherichia coli* ligase: influence on an in vitro amplification scheme." *Gene*. 89:117-122 (1990).
Berger-Bachi, et al. Insertional Inactivation of *Staphylococcal* Methicillin Resistance by Tn551. Journal of Bacteriology. 154(1):479-87 (1983).
Chakrabarti et al. "Novel Sulfoxides Facilitate GC-Rich Template Amplification." *Biotechniques*. 32: 866-874 (2002).
Database EMBL 'Online! May 14, 2001; retrieved from EBI, Database Accession No. AB037671, XP002238391.
Database EMBL 'Online! Jan. 7, 2000; retrieved from EBI Database Accession No. AB014433; XP002238392.
De Lencastre et al. Methicillin-Resistant *Staphylococcus aureus* disease in a Portuguese Hospital: Characterization of clonal Types by a Combination of DNA Typing Methods. Eur. *J. Clin. Microbiol. Infect. Dis.* 13: 64-73 (1994).
Deplano et al. "In Vivo deletion of the methicillin resistance mec region from the chromosome of I *Staphylococcus aureus* strains." *J. Antimicrob. Chemotherapty*, 46-617-619 (2000).
Derbise et al. "Mapping the Regions Carrying the Three Contiguous Antibiotic Resistance Genes aadE, sat4, and aphA-3 in the Genomes of *Staphylococci*." Antimicrobial Agents and Chemotherapy. 41(5): 1024-32 (1997).
Dubin et al., "Physical Mapping of the mec Region of an American Methicillin-Resistant *Staphylococcus aureus* Strain." Antimicrobial Agents and Chemotherapy. 35(8):1661-65 (1991).
Egholm et al. "PNA hybridizes to complementary oligoncleotides obeying the Watson-Crick hydrogen-bonding rules." *Nature*. 365: 566-568 (1993).
Elghanian et al. "Selective Colorimetric Detection of Polynucleotides Based on the Distance-Dependent Optical Properties of Gold Nanoparticles." (1997) Science 277:1078-1081.
Flores et. al. "A rapid, inexpensive method for eluting DNA from Agarose or Acrylamide gel slices without toxic or chaotropic materials." *Biotechniques*. 13: 205-206 (1992).
GenBank accession No. AB014440, version AB014440.1, Jul. 6, 1999, Ito et al.
GenBank accession No. AB063172, version AB063172.2, Jun. 12, 2001, Ito et al.
GenBank accession No. AB121219, version AB121219.1, Sep. 26, 2003, Ito et al.
GenBank accession No. AF270046, version AF270046.1, May 22, 2000, Taylor et al.
GenBank accession No. BK001539, version BK001539.1, Aug. 15, 2003, Mongkolrattanothai et al.
GenBank accession No. BX571856, version BX57156.1, Jun. 23, 2004, Holden et al.
GenBank accession No. U10927, version U10927.2, Nov. 1, 2001, Lin et al.
GenBank accession No. AF422691, version AR422691.1, Apr. 29, 2002, Oliveira et al.
GenBank accession No. AF411934, version AF411934.1, Mar. 5, 2002, Oliveira et al.
Gerberding, et al. Comparison of conventional susceptibility Tests with Direct Detection of Penicillin-Binding Protein 2a in borderline Oxacillin-Resistant Strains of *Staphylococcus aureus*. Antimicrobial Agents and Chemotherapy. 35(12):2574-79 (1991).
Guatelli, et al. "Isotherma, in vitro amplification of nucleic acids by a multenzyme reaction modeled after retroviral replication." *Proc. Natl. Acad. Sci. USA*, 87:1874-1878 (1990).
Hiramatsu et al. "Analysis of Borderline-Resistant Strains of Methicillin-Resistant *Staphylococcus aureus* Using Polymerase Chain Reaction." *Microbiol. Immunol.* 36: 445-453 (1992).
Hiramatsu et al., "Genetic Basis for Molecular Epidemiology of MRSA" J. Infect. Chemother. 1996, 2:117-129. XP001122060.
Hiramatsu, et al. "The emergence and evolution of methicillin-resistant *Staphylococcus aureus*." *Trends in Microbiology*. 9(10): 486-493 (2001).
Hiramatsu, et al. "Molecular Cloning and Nucleotide Sequence Determination of the Regulator Region of mecA gene in methicillin-resistant *staphylococcus aureus*." FEBS. 298(2.3):133-36 (1992).
Huletsky, et al. "New Real-Time PCR Asay for Rapid Detection of Methicillin-Resistant *Staphylococcus aureus* Directly from Specimens Containing a Mixture of *Staphylococci*." Journal of Clinical Microbiology. 42(5): 1875-84 (2004).
Inglis, et al. "Induced deletions within a cluster of resistance genes in the mec region of the chromosome of *Staphylococcus aureus*." *Gen. Microbiol.* 136:2231-2239 (1990).
Inglis, et al. "Methicillin-Sensitive and Resistant Homologues of *Staphylococcus aureus* Occur together among Clinical Isolates." J. *Infect. Dis.* N167:323-328 (1993).
Ito et al. "Acquisition of Methicillin Resistance and Progression of Multiantibiotic Resistance in Methicillin-Resistant *Staphylococcus aureus*." Yonsei Medical Journal. 39(6):526-33 (1998).
Ito et al. Novel Type V *Staphylococcal* Cassette Chromosome mec Driven by a Novel Cassette Chromosome Recombinase, ccrC. Antimicrob. Agents Chemother. 48:2637-2651 (2004).
Ito et al., "Cloning and Nucleotide Sequence Determination of the entire mvc DNA of pre-methicillin-resistant *Staphylococcus aureus* N315," Antimicrob. Agents Chemother. US, Jun. 1999; vol. 43, No. 6, pp. 1449-1468. XP002238386;ISSN: 0066-4804.
Ito et al., "Structural Comparison of Three Types of *Staphylococcal* Cassette Chromosome Med Integrated in the Chromosome in Methicillini-resistant *Staphylococcus aureaus*." Antimicrob. Agents Chemother. U.S. May, 2001, 45:1323-1336.
Katayama, et al. "A New Class of Genetic Element, *Staphylococcus* Cassette Chromosome mec, Encodes Methicillin resistance in *Staphylococcus aureus*." *Antimicrob. Agents Chemother*. 44(6):1549-1555 (2000).
Kellogg, et al. "TaqStart Antibody™: "Hot Start" PCR facilitated by a neutralizing monoclonal antibody directed against Taq DNA Polymerase." *Biotechniques*. 16:1134-1137 (1994).
Kimmel, et al. "Preparations of cDNA and the Generation of cDNA Libraries: Overview." Methods in Enzymology. 152:307-316 (1987).
Kitagawa, et al. "Rapid Diagnosis of Methicillin-Resistant *Staphylococcus aureus* Bacteremia by Nested Polymerase Chain Reaction." Annals of Surgery. 224(5):665-71 (1996).
Kluytmans. Food-Initiated Outbreak of Methicillin-Resistant *Staphylococcus aureus* Analyzed by Pheno and Genotyping. Journal of clinical Microbiology. 33(5):1121-28 (1995).
Koshkin, et al. "LNA (locked nucleic acids): Synthesis of the Adenine, Cytosine, Guanine, 5-Methylcytosine, Thymine and Uracil Bicyclonucleoside Monomers, Oligomerisation, and unprecedented nucleic acid recognition." *Tetrahedron*. 54:3607-3630 (1998).
Kuroda, et al. "Whole genome sequencing of methicillin-resistant *Staphylococcus aureus*." *The Lancet*. 357: 9264; pp. 1225-1240, (2001).
Kwoh, et al. "Transcription-based amplification system and detection of amplified human immunodeficiency virus type 1 with a bead-based sandwich hybridization format." Proc. Natl. Acad. Sci. USA 86:1173-1177 (1989).

(56) References Cited

OTHER PUBLICATIONS

Landegren, et al. "A Ligase-Mediated Gene Detection Technique." (1988) Science 241:1077-1080.
Lawrence et al. "Consecutive isolation of homologous strains of methicillin-resistant and methicillin-susceptible *Staphylococcus aureus* from a hospitalized child." *J. Hosp. Infect.* 33:49-53 (1996).
Lawrence et al. "Use of the Coagulase Gene Typing Method for Detection of Carriers of Methicillin-Resistant *Staphylococcus aureus*." *Journal of Antimicrobial Chemotherapy*. 37:687-696 (1996).
Leach et al. "Theoretical Investigations of Novel Nucleic Acid Bases." (1992) J. Am. Chem. Soc. 114:3675-3683.
Lin et al. "Sequence Analysis and Molecular Characterization of Genes Required for the Biosynthesis of Type 1 Capsular Polysaccharide in *Staphylococcus aureus*." Journal of Bacteriology. 176(22):7005-16 (1994).
Lomell, et al. "Quantitative Assays Based on the Use of Replicatable Hybridization Probes." Clinical Chemistry. 35(9):1826-1831 (1989).
Luchansky and Pattee. "Isolation of Transposon Tn551 Insertions Near Chromosomal Markers of Interest in *Staphylococcus aureus*." Journal of Bacteriology. 159(3):894-99 (1984).
Luijendijk, et al. "Comparison of Five Tests for Identification of *Staphylococcus aureus* Clinical Samples." Journal of Clinical Microbiology. 34(9)2267-69 (1996).
Luong, et al. "Type I Capsule Genes of *Staphylococcus aureus* Are Carried in a *Staphyloccal* Cassette Chromosome genetic Element." Antimicrobial Agents and Chemotherapy. 46(4):1147-52 (2002).
Ma et al, "Novel Type of *Staphylococcal* Cassette Chromosome Mec Identified in Community-acquired Methicillin-resistant *Staphylococcus Aureus* Strains." Antimicrob. Agents Chemother. vol. 46, No. 4, Apr. 2002, pp. 1147-1152.
Mantsch et al. "Structural and Enzymatic Properties of Adenine 1-Oxide Nucleotides." (1975) Biochem. 14(26):5593-5601.
Martineau, et. al. "Correlation between the Resistance Genotype Determined by Multiplex PCR Assays and the Antibiotic Susceptibility Patterns of *Staphylococcus aureaus* and *Staphylococcus epidermis*." *Antimicrob. Chemotherapy*. 44(2): 231-238 (2000).
Mulligan, et al. "Methicillin-Resistant *Staphylococcus aureus*: a Consensus Review of the Microbiology, Pathogenesis, and Epidemiology with Implications for Prevention and Management." Am J Med. 94(3):313-28 (1993).
Murakami, et al. "Identification of Methicillin-Resistant Strains of *Staphylococci* by Polymerase Chain Reaction." *J. Clin Microbial.* 29(10):2240-2244 (1991).
Muraki. Detection of Methicillin-Resistant *Staphylococcus aureus* using PCR and non-radioactive DNA probes (II). Rinsho Byori. 41(10): 1159-66 (1993).
Newton et al. "Instrumentation, Reagents and Consumables." PCR, 2nd Ed., Springer-Verlag (New York: 1997), Chapter 2, p. 8-28.
Nichols, et al. "A universal nucleoside for use at ambiguous sites in DNA primers." *Nature*. 369:492-493 (1994).
Oliveira et al., "Genetic Organization of the Downstream Region of the mecA Element in Methicillin-resistant *Staphylococcus aureus* Isolates Carrying Different Polymorphisms of this Region," Antimicrobial Agents and Chemotherapy. US, Jul. 2000, vol. 44, No. 7, pp. 1906-1910; XP002238385; ISSN:0066-4804.
Oliveira, et al, "Multiplex PCR Strategy for Rapid Identification of Structural Types and Variants of the mec Element in Methicillin-Resistant *Staphylococcus aureus*." Antimicrob. Agents Chemother. 46:2155-2161 (2002).
Oliveira et al., "The Evolution of Pandemic Clones of Methicillin-resistant *Staphylococcus aureus*: Identification of Two Ancestral Genetic Backgrounds and the Associated mec Elements." Microb. Drug Resist. vol. 7, No. 4, Jan. 2001, pp. 349-361.
Oliveira et al. "Secrets of success of a human pathogen: molecular evolution of pandemic clones of maticillin-resistant *Staphylococcus aureus*." Lancet Infect Dis. 2:180-9 (2002).
Partial International Search Report for International Application No. PCT/CA 02/00824 dated May 12, 2003.
Pattee, et al., "Genetic and Physical Mapping of the Chromosome of *Staphylococcus aureus*." Molecular Biology of the *Staphylococci*. VCH Publishers. 41-58 (1990).
Piccirilli et al. "Enzymatic incorporation of a new base pair into DNA and RNA extends the genetic alphabet." (1990) Nature. 343:33-37.
Saito, et. al. "Immunological Detection of Penicillin Protein 2' of Methicillin-Resistant *Staphylococci* by Using Monoclonal Antibodies Prepared from Synthetic Peptides." *J. Clin. Microbiol.* 33(9): 2498-2500 (1995).
Simor, et al. "Characterization and Proposed Nomenclature of Epidemic Strains of Methicillin-Resistant *Staphylococcus aureus* in Canada." *CCDR* 25-12: 105-112 (Jun. 15, 1999).
Sooknanan, R. NASBA. A detection and amplification system uniquely suited for RNA. (1995) Biotechnology 13:563-564.
Stewart, et al. "IS257 and Small Plasmid Insertions in the mec Region of the Chromosome of *Staphylococcus aureus*." Plasmid. 31:12-20 (1994).
Suzuki, et al., "Distribution of mec Regulator Genes in Methicillin-Resistant *Staphylococcus* Clinical Strains." Antimicrobial Agents and Chemotherapy. 37(6):1219-26 (1993).
Suzuki, et al., "Survey of Methicillin-Resistant Clincal Strains of Coagulase-Negative *Staphylococci* for mecA Gene Distribution." *Antimicrob. Agents Chemother.* 36(2): 429-434 (1992).
Switzer et al., "Enzymatic Recognition of the Base Pair between Isocytidine and Isoguanosine." (1993) Biochemistry 32:10489-10496.
Thewll, et al. "Mode of action and application of Scorpion primers to mutation detection." (2000), Nucl. Acids Res. 28(19):3752-3761.
Tokue, et al. "Comparison of a Polymerase Chain Reaction Assay and a Convetional Microbiologic Methods for Detection of Methicillin-Resistant *Staphylococcus aureus*." Antimicrobial Agents and Chemotherapy. 36(1):6-9 (1992).
Tor et al. "Site-Specific Enzymatic Incorporation of an Unnatural Base, $N^6$-(6-Aminohexyl)isoguanosine, into RNA." (1993) J. Am. Chem. Soc. 115:4461-4467.
Tyagi et al. "Molecular Beacons: Probes that Fluoresce upon Hybridization." (1996) Nat. Biotech. 14:303-308.
Ubukata, et. al. "Homology of mecA Gene in Methicillin-Resistant *Staphylococcus aureusto* that of *Staphylococcus aureus*." *Antimicrob, Agents Chemother*. 34(1):170-172 (1990).
Ubukata, et. al. "Rapid Detection of mecA Gene in Methicillin-Resistant *Staphylococci* by Enzymatic Detection of Polymerase Chain Reaction Products." *J. Clin. Microbiol.* 30(7):1728-1733 (1992).
Ubukata, et al. "Restriction Maps of the Regions Coding for Methicillin and Tobramycin Resistances on Chromosomal DNA in Methicillin-Resistant *Staphylococci*." Antimicrobial Agents and Chemotherapy. 33(9):1624-26 (1989).
Unal, et al. "Detection of Methicillin-Resistant *Staphylococci* by Using the Polymerase Chain Reaction." Journal of Clinical Microbiology. 30(7):1685-91 (1992).
Unal, et al. "Comparison of Tests for Detection of Methicillin-Resistant *Staphylococci aureus* in a Clinical Microbiology Laboratory." Antimicrobial Agents and Chemotherapy. 38(2):345-47 (1994).
Van Belkum, et al. "Comparison of Phage Typing and DNA Fingerprinting by Polymerase Chain Reaction of Discrimination of Methicillin-Resistant *Staphylococcus aureus* Strains." Journal of Clinical Microbiology. 31(4):798-803 (1993).
Van Brunt, J. "Amplifying Genes: PCR and its Alternatives." Biotechnology, 8:291-294 (1990).
Vannuffel, et al. "Specific Detection of Methicillin-Resistant *Staphylococcus* Species by Multiplex PCR." Journal of Clinical Microbiology. 33(11):2864-67 (1995).
Wada, et al. "Southern Hybridization Analysis of the mecA Deletion from Methicillin-Resistant *Staphylococcus aureus*." Biochem. *Biophys. Res. Comm.*, 176: 1319-1326 (1991).
Wallet, et al. "Choice of a Routine Method for Detecting Methicillin-Resistance in *Staphylococci*." Journal of Antimicrobial Chemotherapy. 37:901-909 (1996).
Westin, et al. "Anchored multiplex amplification on a microelectronic chip array." *Nat. Biotechnol.* 18:199-204 (2000).

(56) References Cited

OTHER PUBLICATIONS

Wilson, Ian. "Inhibition and Facilitation of Nucleic Acid Amplification." *Appl. Environ. Microbiol.* 63:3741-3751 (1997).
Wu, et al. "Genetic Organization of the mecA Region in Methicillin-Susceptible and Methicillin-Resistant Strains of *Staphylococcus sciuri*." Journal of Bacteriology. 180(2):236-42 (1998).
Wu, et a. "The Ligation Amplification Reaction (LAR)-Amplification of Specific DNA Sequences Using Sequential Rounds of Template-Dependent Ligation." (1989) Genomics 4:560-569.
Hagen, et al. "Development of a real-time PCR assay for rapid identification of methicillin-resistant *Staphylococcus aureus* from clinical samples." International Journal of Medical Microbiology, Urban and Fischer, DE. 295(2):77-86 (2005).
Holden, et al. "Complete genomes of two clinical *Staphylococcus aureus* strains: Evidence for the rapid evolution of virulence and drug resistance." PNAS. 101(26):9786-9791 (2004).
Zhang, et al. "Genome-based analysis of virulence genes in a non-biofilm-forming *Staphylococcus* epidermidis strain (ATCC 12228)." Molecular Microbiology. 49(6): 1577-1593 (2003).
Supplementary European Search Report for European Application No. 06825875 dated Apr. 7, 2009.
International Search Report dated Sep. 24, 2003 for International Patent Application No. PCT/CA02/000824, filed Jun. 4, 2002.
Barany et al., "Genetic disease detection and DNA amplification using cloned thermostable ligase," Proc Natl Acad Sci. USA (Jan. 1991) 88: 189-193.
Barski et al., "Rapid assay for detection of methicillin-resistant *Staphylococcus aureus* using multiplex PCR," Mol Cell Probes (1996) 10(6):471-475.
Beaucage et al. "Deoxynucleoside Phosphoramidites—A New Class of Key Intermediates for Deoxypolynucleotide Syntesis," Tetra Lttrs. (1981) 22(20): 1859-1862.
Benson et al., "Direct detection of mecA and nuc genes for rapid species and resistance determination of *Staphylococci* from blood cultures," Abstracts of the Interscience Conference on Antimicrobial Agents and Chemotherapy, (1999) vol. 39, Abstract #877; pp. 208. cd-rom; 39th Interscience Conference on Antimicrobial Agents and Chemotherapy. San Francisco, California, USA. Sep. 26-29, 1999. American Society for Microbiology.
Boye et al., "A new multiplex PCR for easy screening of methicillin-resistant *Staphylococcus aureus* SCCmec types I-V.", Clin Microbiol Infect. (Jul. 2007) 13(7): 725-727.
Brakstad et al., "Multiplex polymerase chain reaction for detection of genes for *Staphylococcus aureus* thermonuclease and methicillin resistance and correlation with oxacillin resistance," APMIS (1993) 101(:681-688.
Brakstad et al., "Simultaneous detection of the *Staphylococcal* MecA and Nuc genes by a multiplex PCR," Zentralblatt für Bakteriologie (Inter'l J Med Microbiol.), (1994) Supplement 26, 246-248.
Brown et al., "Chemical Synthesis and Cloning of a Tyrosine tRNA Gene," Meth Enzymol. (1979) 68: 109-151.
Brown et al., "Real-time PCR detection of S-aureus and MRSA from wound, fluid and respiratory samples," Abstracts of the General Meeting of the American Society for Microbiology, (2006) vol. 106, Abs. C-074, pp. 110-111; 106th General Meeting of the American Society for Microbiology. Orlando, FL, USA. May 21-25, 2006.
Carroll, K.C. "Rapid diagnostics for methicillin-resistant *Staphylococcus aureus*", Mol Diagn Therapy, (Jan. 2008) 12(1): 15-24.
Cho et al., "Detection of methicillin resistance in *Staphylococcus aureus* isolates using two-step triplex PCR and conventional methods", J Microbiol Biotechnol. (Apr. 2007) 17(4): 673-676.
Denis et al., "Rapid screening of methicillin resistant *Staphylococcus aureus* carriers by direct PCR on enrichment broth culture of superficial swab samples," Abstracts of the Interscience Conference on Antimicrobial Agents and Chemotherapy, (2002) vol. 42, Abs. K-101, pp. 304; 42nd Interscience Conference on Antimicrobial Agents and Chemotherapy. San Diego, CA, USA. Sep. 27-30, 2002. American Society for Microbiology.
De San et al., Controlled Evaluation of the IDI-MRSA Assay for Detection of Colonization by Methicillin-Resistant *Staphylococcus aureus* in Diverse Mucocutaneous Specimens, J Clin Microbiol. (2007) 45(4): 1098-1101.
Desbouchages et al., "Direct screening of MRSA from swab specimens using duplex real-time PCR assay: implication for antibiotic prophylaxis," International Journal of Antimicrobial Agents, (2004) vol. 24 (212/47O, pp. S104-S105; 6th European Congress of Chemotherapy and Infection/24th Interdisciplinary Meeting on Anti-Infectious Chemotherapy. Paris, France. Dec. 1-3, 2004.
Fan et al., "Rapid detection of methicillin-resistant *Staphylococci* by DNA probe," Linchuang Jianyan Zazhi 24(5) 351-352 (2006).
Fang et al. "Rapid Screening and Identification of Methicillin-Resistant *Staphylococcus aureus* from Clinical Samples by Selective-Broth and Real-Time PCR Assay." (Jul. 2003) 41(7): 2894-2899 and 1 page Erratum.
Francois et al., "Evaluation of Three Molecular Assays for Rapid Identification of Methicillin-Resistant *Staphylococcus aureus*", J Clin Microbiol. (2007) 45(6): 2011-2013.
García-Álvarez et al. "Methicillin-resistant *Staphylococcus aureus* with a novel mecA homologue in human and bovine populations in the UK and Denmark: a descriptive study," Lancet Infect Dis. (Aug. 2011) 11(8): 595-603.
Goldmeyer et al., "Identification of *Staphylococcus aureus* and Determination of Methicillin Resistance Directly from Positive Blood Cultures by Isothermal Amplification and a Disposable Detection Device," J. Clin. Microbiol. (2008) vol. 46 No. 4, 1534-1536.
Grisold et al., "Detection of Methicillin-Resistant *Staphylococcus aureus* and Simultaneous Confirmation by Automated Nucleic Acid Extraction and Real-Time PCR," J Clin. Microbiol. (2002) 40(7):2392-2397.
Gröbner et al., "Development of a real-time *Staphylococcus aureus* and MRSA (SAM-) PCR for routine blood culture," European Journal of Clinical Microbiology & Infectious Diseases (2007) (26)10:751-754.
Guintu et al., "Detection of MRSA Directly from Positive Blood Culture Bottles using MRSA Evigene (Advandx)," Abstracts of the Interscience Conference on Antimicrobial Agents and Chemotherapy, 45th Interscience Conference on Antimicrobial Agents and Chemotherapy. Washington, DC, USA.; Abs. D-1716; (2005) vol. 45, pp. 151.
Hanaki et al., Loop-mediated isothermal amplification assays for identification of antiseptic- and methicillin-resistant *Staphylococcus aureus*, J Microbiol Meth. (2011) 84(2): 251-254; Epub Dec. 16, 2010.
He et al., "Identification of *Staphylococcus aureus* and detection of its multiple-resistant genes by multiplex PCR," Linchuang Jianyan Zazhi (2004) 22(4): 249-251.
Hope et al., "A PCR method for the identification of methicillin-resistant *Staphylococcus aureus* (MRSA) from screening swabs," Pathology (2004) 36(3):265-268.
Hougardy et al., "Direct and fast detection of methicillin resistant *Staphylococcus aureus* carriage by automated nucleic acid extraction and real time PCR" [English Abstract Only], Pathologie-Biologie, (Oct.-Nov. 2006) vol. 54, No. 8-9, pp. 477-481. Electronic Publication Date: Oct. 5, 2006.
Jayaratne et al., "DNA-based detection of methicillin-resistant *Staphylococcus aureus* (MRSA) from nosocomial screening: Comparison with culture and cost-benefit analysis," Abstracts of the Interscience Conference on Antimicrobial Agents and Chemotherapy, 38th Interscience Conference on Antimicrobial Agents and Chemotherapy. San Diego, California, USA. Sep. 24-27, 1998. American Society for Microbiology (1998) vol. 38, Abs. D-56; pp. 144-145.
Jiang et al., "Review on Progress of *Staphylococcus aureus* by PCR", Shipin Kexue (Beijing, China) (2006), 27(5): 265-269.
Jonas et al., "Evaluation of the mecA femB duplex polymerase chain reaction for detection of methicillin-resistant *Staphylococcus aureus*," Eur J Clin Microbiol Infect Dis. (1999) 18(9):643-647.
Jonas et al., "Rapid PCR-based identification of methicillin-resistant *Staphylococcus aureus* from screening swabs," J Clin. Microbiol. (2002) 40(5):1821-1823.

(56) References Cited

OTHER PUBLICATIONS

Jovanic et al., "Rapid detection of methicillin-resistant *Staphylococcus aureus* by real-time PCR from clinical specimens", International Journal of Antimicrobial Agents, Abs P907; (Mar. 2007) 29(Suppl. 2): S235-S236.
Klotz et al., "Detection of *Staphylococcus aureus* Enterotoxins A to D by Real-Time Fluorescence PCR Assay," J Clin Microbiol. (2003) 41(10): 4683-4687.
Kobayashi et al., "Detection of mecA, femA, and femB genes in clinical strains of *Staphylococci* using polymerase chain reaction," Epidemiol Infect. (1994) 113(2):259-266.
Kowalski et al., "Evaluation of the SmartCycler II System for Real-Time Detection of Viruses and *Chlamydia*from Ocular Specimens", Arch Ophthalmol. (Aug. 2006) 124: 1135-1139.
Lee et al., "Detection of MecA gene in clinical isolates of *Staphylococcus aureus* by multiplex-PCR, and antimicrobial susceptibility of MRSA," Journal of Microbiology and Biotechnology 13(3) 354-359 (2003).
Lem et al., "Direct detection of mecA, nuc and 16S rRNA genes in BacT/Alert blood culture bottles," Diagn Microbiol Infect Dis. 41(3):165-168 (2001).
Levi et al., "Evaluation of an Isothermal Signal Amplification Method for Rapid Detection of Methicillin-Resistant *Staphylococcus aureus* from Patient-Screening Swabs", J Clin Microbiol. (Jul. 2003) 41(7): 3187-3191.
Li et al., "Typing SCCmec Gene of Methicillin-Resistant *Staphylococcus aureus* by Novel Multiplex PCR Method," Journal of Modern Laboratory Medicine (2008) 23(1): 32-35. [English Abstract].
Liao et al., "Blinded comparison of repetitive-sequence PCR and multilocus sequence typing for genotyping methicillin-resistant *Staphylococcus aureus* isolates from a children's hospital in St. Louis, Missouri", J Clin Microbiol. (Jun. 2006) 44(6): 2254-2257.
Lizardi et al., "Exponential Amplification of Recombinant-RNA Hybridization Probes," BioTech. (Oct. 1988) 6: 1197-1202.
Louahabi et al., "Screening of methicillin-resistant *Staphylococcus aureus* directly from clinical specimens by real-time PCR," International Journal of Antimicrobial Agents, (Dec. 2004) vol. 24S, Abstract 365/79P, pp. S130. Meeting Info.: 6th European Congress of Chemotherapy and Infection/24th Interdisciplinary Meeting on Anti-Infectious Chemotherapy. Paris, France. Dec. 1-3, 2004.
Louie et al., "Rapid Detection of Methicillin-Resistant *Staphylococci* from Blood Culture Bottles by Using a Multiplex PCR Assay," J Clin Microbiol. 40(8):2786-2790 (2002).
Lu et al., "One tube multiplex PCR for simple screening of SCCmec I-V types of methicillin-resistant *Staphylococcus aureus*", J Chemother. (Dec. 2008) 20(6): 690-696.
Marin et al., "Molecular Diagnosis of Infective Endocarditis by Real-Time Broad-Range Polymerase Chain Reaction (PCR) and Sequencing Directly From Heart Valve Tissue," Medicine (2007) 86(4) 195-202.
Martineau et al., "Species-Specific and Ubiquitous-DNA-Based Assays for Rapid Identification of *Staphylococcus aureus*," J Clin Microb. (Mar. 1998) 36(3): 618-623.
Mason et al., "Multiplex PCR Protocol for the Daignosis of *Staphylococcal* Infection," J Clin Microbiol. 39(9): 3332-3338 (2001).
McBride et al., "Quantitative PCR Technology" in *Gene Quantification*, The Immune Response Corporation, Francois Ferre (Ed.), Birkhaeuser Boston (1998) pp. 97-110.
Menon et al., "Comparison of rapid method of DNA extraction using microwave irradiation with conventional phenol chloroform technique for use in multiplex PCR for mec A and fem B genes to identify genotypes of MRSA from cultures," Medical Journal Armed Forces India, (2001) 57(3): 194-196.
Merlino et al., "Detection and expression of methicillin/oxacillin resistance in multidrug-resistant and non-multidrug-resistant *Staphylococcus aureus* in Central Sydney, Australia," J Antimicrob Chemother. (2002) 49: 793-801.
Narang et al. "Improved Phosphotriester Method for the Synthesis of Gene Fragments," Meth Enzymol. (1979) 68: 90-98.
NCBI BLAST 2 Sequences downloaded Aug. 13, 2013 from http://blast.ncbi.nlm.nih.gov/Blast.cgi, 4 pages.
Niemeyer et al., "Rapid DNA extraction for direct PCR identification of methicillin resistant *Staphylococci* in clinical samples," Abstracts of the General Meeting of the American Society for Microbiology, (1998) vol. 98, Abs. C-419, pp. 201; 98th General Meeting of the American Society for Microbiology. Atlanta, Georgia, USA. May 17-21, 1998. American Society for Microbiology.
Ohno, Akira, Japan Medical Journal (2001) 4051: 19-24. [English translation unavailable].
Perez-Roth et al., "Multiplex PCR for Simultaneous Identification of *Staphylococcus aureus* and Detection of Methicillin and Mupirocin Resistance," J Clin Microbiol. 39(11):4037-4041 (2001).
Podzorski et al., Evaluation of the MVPlex Assay for Direct and Rapid Detection of Methicillin-Resistant *Staphylcoccus aureus* from Nares and Other Swab Speciments, (Abstract C-237), American Society for Microbiology 107$^{th}$ Meeting, Toronto, Canada May 21-25, 2007, p. 186.
Ramos-Trujillo et al., Multiplex PCR for simultaneous detection of enterococcal genes vanA and vanB and *Staphylococcal* genes mecA, ileS-2 and femB, Int Microbiol. (2003) 6(2):113-115.
Reischl et al., "Rapid identification of methicillin-resistant *Staphylococcus aureus* and simultaneous species confirmation using real-time fluorescence PCR," J Clin. Microbiol. (2000) 38:2429-2433.
Ruiz-Pérez de Pipaón et al., "Detection of methicillin resistance and identification of *Staphylococcus* spp. from positive blood culture bottles using the mecA and nucA genes with the LightCycler System", Enfermedades infecciosas y microbiologia clinica (2005) vol. 23, No. 4, pp. 208-212.
Rushdy et al., "Detection of methicillin/oxacillin resistant *Staphylococcus aureus* isolated from some clinical hospitals in Cairo using Meca/Nuc genes and antibiotic susceptibility profile," Internaitonal Journal of Agriculture and Biology (2007) 9(6):800-806.
Sabat et al., "Comparison of PCR-based methods for typing *Stapholococcus aureus* isolates," J Clin Micrbiol. 44(10) 3804-3807 (2006).
Sabet et al., "Simultaneous species identification and detection of methicillin resistance in *Staphylococci* using triplex real-time PCR assay", Diagn Microbiol Infect Dis. Sep. 2006;56(1):13-8. Epub May 2, 2006.
Saiful et al., "Detection of methicillin-resistant *Staphylococcus aureus* using mecA/nuc genes and antibiotic susceptibility profile of Malaysian clnical isolates," World J Microbiol Biotechnol. (2006) 22: 1289-1294 [online: Apr. 20, 2006].
Saiki et al., "Enzymatic amplification of beta-globin genomic sequences and restriction site analysis for diagnosis of sickle cell anemia," Science (Dec. 1985) 230(4732): 1350-1354.
Sekiguchi et al., "Rapid and simple method for detecting qacA, mecA and femB in antiseptics—and methicillin-resistant *Staphylococcus aureus* by loop-mediated isothermal amplification," Abstracts of the General Meeting of the American Society for Microbiology, (2006) vol. 106, pp. 108; 106th General Meeting of the American Society for Microbiology. Orlando, FL, USA. May 21-25, 2006. Amer Soc Microbiol.
Singleton P., DNA Methods in Clinical Microbiology, (2000) Dordrecht, Boston: Kluwer Academic. TOC only.
Sinsimer et al., "Use of a Multiplex Molecular Beacon Platform for Rapid Detection of Methicillin and Vancomycin Resistance in *Staphylococcus aureus*", J Clin Microbiol. (2005) 45(9): 4585-4591.
Spiess et al. "Trehalose is a Potent Pcr Enhancer: Lowering of Dna Melting Temperature and Thermal Stabilization of Taq Polymerase by the Disaccharide Trehalose," Clin Chem., Jul. 2004, 50(7):1256-1259.
Stratidis et al., Use of real-time polymerase chain reaction for identification of methicillin-resistant *Staphylococcus aureus* directly from positive blood culture bottles, Diagn Microbiol Infect Dis. (2007) 58(2): 199-202.
Tan et al., "Rapid identification of methicillin-resistant *Staphylococcus aureus* from positive blood cultures by real-time fluorescence PCR," Journal of Clinical Microbiology (2001) 39(12):4529-4531.

(56) References Cited

OTHER PUBLICATIONS

Thomas et al., "Development of a real-time *Staphylococcus aureus* and MRSA (SAM-) PCR for routine blood culture," J Microbiol Methods (2007) 38(2):296-302 [Online: Oct. 12, 2006].
Tijssen, Laboratory Techniques in Biochemistry and Molecular Biology—Hybridization with Nucleic Acid Probes, (1993) Part I, Chapter 2, pp. 19-78 (Elsevier, New York).
Towner et al., "Development and evaluation of a PCR-based immunoassay for the rapid detection of methicillin-resistant *Staphylococcus aureus*," J Med Microbiol (1998) 47(7):607-613.
Van Hal et al., "Methicillin-Resistant *Staphylococcus aureus* (MRSA) Detection: Comparison of Two Molecular Methods (IDI-MRSA PCR Assay and GenoType MRSA Direct PCR Assay) with Three Selective MRSA Agars (MRSA ID, MRSASelect, and CHROMagar MRSA) for Use with Infection-Control Swabs", J Clin Mlcrobial. (Aug. 2007) 45(8): 2486-2490.
Vanguilder et al., "Twenty-five years of quantitative PCR for gene expression analysis", Biotechniques 25th Anniversary (2008) 44(5): 619-626.
Walker et al., "Strand displacement amplification—an isothermal, in vitro DNA amplification technique," Nucl Acids Res. (1992) 20(7): 1691-1696.
Wang at al., "Rapid detection of methicillin-resistant *Staphylococcus aureus* with duplex real-time PCR assay," Zhongguo Kangshengsu Zazhi (2007) 32(4) 225-228.
Wei et al., "Detection of *Staphylococcus* isolates and their multidrug resistance genes by multiple PCR," Zhongguo Renshou Gonghuanbing Zazhi (Sep. 2004) 20(9), 814.
Wichelhaus et al., "Rapid molecular typing of methicillin-resistant *Staphylococcus aureus* by PCR-RFLP", Infect Cont Hosp Epidem. (May 2001) 22(5): 294-298.
Wittwer et al., "Fluorescence Monitoring of Rapid Cycle PCR for Quantification" in *Gene Quantification*, The Immune Response Corporation, Francois Ferre (Ed.), Birkhaeuser Boston (1998) pp. 97-110.
Woron et al., "Multiplex rt-PCR detection of MRSA from bacterial isolates," Abstracts of the General Meeting of the American Society for Microbiology, (2004) vol. 104, Abs C-116, pp. 143; 104th General Meeting of the American Society for Microbiology. New Orleans, LA, USA.
Wren et al., "Rapid molecular detection of methillin-resistant *Staphylococcus aureus*," Journal of Clinical Microbiology (2006) 44(4):1604-1605.
Wu et al., "Rapid detection of *Staphylococcus aureus* and methicillin resistance from blood cultures using a real-time PCR SmartCycler assay," Abstracts of the General Meeting of the American Society for Microbiology, 105th General Meeting of the American-Society-for-Microbiology. Atlanta, GA, USA; Abs. C-085; (2005) vol. 105, pp. 119.
Zhang et al., "Novel multiplex PCR assay for simultaneous identification of community-associated methicillin-resistant *Staphylococcus aureus* strains USA300 and USA400 and detection of mecA and Panton-Valentine leukocidin genes, with discrimination of *Staphylococcus aureus* from coagulase-negative *Staphylococci*", J Clin Microbiol. (Mar. 2008) 46(3): 1118-1122; Epub Dec. 26, 2007.
CLUSTALW2 Multiple nucleotide sequence alignment (generated using ClustalW2). The sequence of each of MREJ types I to XX (excluding type x) is aligned around the integratioin site. The sequence of the rjmec primer from D7 is also included; [D9] cited on May 8, 2013; p. 1.
Blast Sequence-Alignment between the orfX sequence from *Staphyloccocus aureus* and the equivalent *Staphylococcus epidermidis* sequence taken from a number of strains; [D19] cited on May 8, 2013; pp. 1-6.
Partial International Search Report dated Dec. 19, 2008 for International Application No. PCT/US07/088004, filed Dec. 18, 2007.
International Search Report and Written Opinion dated Aug. 13, 2013 for International Patent Application No. PCT/IB2013/000900, filed Mar. 14, 2013.
European Search Report dated Dec. 3, 2009 for European Application No. 07874372.1, filed Dec. 18, 2007.
European Extended Search Report dated Aug. 25, 2014 in European Patent Application No. 14168417.5, filed May 15, 2014.
European Extended Search Report dated Aug. 25, 2014 in European Patent Application No. 14168420.9, filed May 15, 2014.
Japanese Office Action dated Dec. 24, 2013 in Japanese Patent Application No. 2009-543155, filed Dec. 18, 2007.
EPO Opposition Notice dated May 17, 2013 by Beckman Coulter, Inc. against European Patent No. 2236621, granted Aug. 8, 2012.
Patentee Appeal dated Jun. 3, 2013 and Grounds for Appeal dated Aug. 12, 2013 against EPO Decision of Apr. 5, 2013 to Revoke Patent No. 1397510 [T 1294/13-3.3.08].
Opponent Beckman Coulter's Response dated Dec. 16, 2013 to Patentee's EPO Appeal and Grounds for Appeal in T 1294/13-3.3.08 against EPO Decision in Re EP Patent No. 1397510.
EPO Opposition Notice dated May 8, 2013 by Beckman Coulter, Inc. against European Patent No. 2236621, granted Aug. 8, 2012.
Patentee Reply filed Dec. 23, 2013 in EP Opposition proceedings against Patent No. 2236621.
Patentee Appeal dated Sep. 12, 2013 and Grounds for Appeal dated Dec. 11, 2013 against EPO Decision of Aug. 2, 2013 to Revoke Patent No. 1934613 [T 2002/13-3.3.08].
Opponent Koenig et al. Response dated Apr. 30, 2014 to Patentee's EPO Appeal and Grounds for Appeal in T 2002/13-3.3.08 against EPO Decision in Re EP Patent No. 1934613.
Electronic File History [Part 3] Inter Partes Reexam Control No. 95/001,599, filed Apr. 8, 2011 including PTO Appeal Actions of Jul. 18, 2012 and Aug. 28, 2014, Appellant's Appeal, Responses & Briefs Feb. 29, 2012; Aug. 16, 2012; Oct. 17, 2012 & Nov. 21, 2012 and 3rd Party Submissions of Mar. 29, 2012, May 4, 2012, and Sep. 3, 2013.
U.S. PTAB Record of Oral Hearing dated Jul. 16, 2014 in Inter Partes Reexam Control No. 95/001,599 [Appeal No. 2014-002900]; 65 pages.
PTO 3rd Action closing prosecution dated Sep. 3, 2014, Patentee Responses and 3rd Party Comments in Inter Partes Reexamination Control No. 95/002,216, filed Sep. 13, 2012 for U.S. Appl. No. 11/248,438, filed Oct. 11, 2005 (U.S. Pat. No. 7,838,221).
U.S. PTAB Decision on Appeal dated Aug. 28, 2014 in Inter Partes Reexam Control No. 95/001,599 [Appeal No. 2014-002900]; 43 pages.
Requests for Rehearing and PTAB Decision for Requests dated Sep. 26, 2014, Sep. 29, 2014 and May 26, 2015 in Inter Partes Reexam Control No. 95/001,599 [Appeal No. 2014-002900]; 45 pages.
Third Party [Applicant Requestor] Appeal Brief dated Nov. 26, 2014 in Inter Partes Reexamination Control No. 95/002,216, filed Sep. 13, 2012 for U.S. Appl. No. 11/248,438, filed Oct. 11, 2005 (U.S. Pat. No. 7,838,221).
Respondent's Brief on Appeal dated Dec. 29, 2014 in Inter Partes Reexamination Control No. 95/002,216, filed Sep. 13, 2012 for U.S. Appl. No. 11/248,438, filed Oct. 11, 2005 (U.S. Pat. No. 7,838,221); 409 pages.
Australian Office Action dated May 1, 2015 for Australian Application No. 2013200217, filed Jan. 16, 2013.
Australian Office Action dated May 1, 2015 for Australian Application No. 2013200218, filed Jan. 16, 2013.
Australian Office Action dated May 1, 2015 for Australian Application No. 2013200220, filed Jan. 16, 2013.
Canadian Office Action dated Feb. 13, 2014 for Canadian Application No. 2,673,357, filed Dec. 18, 2007.
Canadian Office Action dated Jul. 23, 2014 for Canadian Application No. 2,625,072, filed Oct. 10, 2006.
European Office Action dated Dec. 9, 2014 in European Patent Application No. 14168417.5, filed May 15, 2014.
European Office Action dated Dec. 17, 2014 in European Patent Application No. 14168420.9, filed May 15, 2014.
EPO Interlocutory Decision of Apr. 10, 2015 in EP Opposition proceedings against Patent No. EP 2236621.
Bustin S.A., "Absolute quantification of mRNA using real-time reverse transcription polymerase chain reaction assays", J Mol Endocrinol. (2000) 25: 169-193.

(56) References Cited

OTHER PUBLICATIONS

NCBI BLAST Sequence ID No. 18 downloaded Feb. 13, 2015 from http://blast.ncbi.nlm.nih.gov/Blast.cgi, 14 pages.
NCBI BLAST AX720590: Sequence 167 from Patent WO02099034; [D16—Exhibit in European Opposition Proceeding: EP 2 322 655] downloaded on Aug. 21, 2015; 57 pages.
Shore et al., "Detection of *Staphylococcal* Cassette Chromosome mec Type XI Carrying Highly Divergent mecA, mecl, mecR1, blZ, and ccr Genes in Human Clinical Isolates of Clonal Complex 130 Methicillin-Resistant *Staphylococcus aureus*", Antimicrob Agents Chemother. (Aug. 2011) 55(8): 3765-3773.
Tyagi et al., "Molecular Beacons: Hybridization Probes for Detection of Nucleic Acids in Homogeneous Solutions," in *Nonradioactive Analysis of Biomolecules* (Part D); Springer Lab Manuals pp. 606-616 ; [Exh. D29]; 2000; 8 pages.
D8—Exhibit in European Opposition Proceeding: EP 2 322 661, EP 2 322 664 and EP 2 322 655; MREJ type i, ii and iii sequences with orfX and SCCmec portions highlighted—WO2002099034 Sequence 1; 14 pages.
D9—Exhibit in European Opposition Proceeding: EP 2 322 661, EP 2 322 664 and EP 2 322 655; Alignment of type ii (SEQ ID No. 2) and type viii (SEQ ID No. 167) MREJ sequences confirming lack of MREJ specificity of primers in patent; 2 pages.
D10—Exhibit in European Opposition Proceeding: EP 2 322 661, EP 2 322 664 and EP 2 322 655; Alignment of type ii (SEQ ID No. 2) and type ix (SEQ ID No. 168) MREJ sequences confirming lack of MREJ specificity of primers in Patent; AX720425; 2 pages.
D11—Exhibit in European Opposition Proceeding: EP 2 322 661, EP 2 322 664 & EP 2 322 655 Alignment of type iii (SEQ ID No. 104) and type vii (SEQ ID No. 165) MREJ sequences confirming lack of MREJ specificity of primers in patent; 1 page.
D12—Exhibit in European Opposition Proceeding: EP 2 322 664 and EP 2 322 655; Alignment of type vi (SEQ ID No. 171) and S. xylosus MREJ sequences confirming lack of MRSA specificity of primers in the patent; 2 pages.
D12a—Exhibit in European Opposition Proceeding: EP 2 322 661; Example of overlap between type ix (SEQ ID No. 168) and other category of MRSA sequences confirming lack of MREJ specificity of primers claimed in the Patent; AB774374; 3 pages.
D12b—Exhibit in European Opposition Proceeding: EP 2 322 661; Example of overlap between type ix (SEQ ID No. 168) and other category of MRSA sequences confirming lack of MREJ specificity of primers claimed in the Patent; HF569115; 2 pages.
D16—Exhibit in European Opposition Proceeding: EP 2 322 664; Results of BLAST search using MREJ type vi sequence as query (SEQ ID NO. 171)—AB665981; 19 pages.
D22—Exhibit in European Opposition Proceeding: EP 2 322 664 and EP 2 322 655; Alignment of MREJ type iii sequence from D1 and MREJ type vi sequence of SEQ ID No. 171—AX720594; 1 page.
D22—Exhibit in European Opposition Proceeding: EP 2 322 661; Alignment of MREJ type ii sequence from D1 and MREJ type ix sequence of SEQ ID No. 168; Mec lower junction around DNA of MRSA; E13725; p. 1.
Examiner's Answer dated Apr. 21, 2015, Rebuttal Brief dated May 21, 2015 & Patent Board Decision on Appeal dated Feb. 25, 2016 in Inter Partes Reexamination Control No. 95/002,216, filed Sep. 13, 2012 for U.S. Appl. No. 11/248,438, filed Oct. 11, 2015 (U.S. Pat. No. 7,838,221).
Notice of Observations by 3rd Party dated Nov. 18, 2015 in European Patent Application No. 14168417.5, filed May 15, 2014.
European Extended Search Report dated Oct. 9, 2015 in European Patent Application No. 13772940.6, filed Oct. 24, 2014.
EPO Notice of Opposition and supporting documents filed by Beckman Coulter on Dec. 17, 2015 against European Patent No. 2322663, dated Mar. 18, 2015.
EPO Notice of Opposition and supporting documents filed by R-Biopharm AG on Dec. 18, 2015 against European Patent No. 2322663, dated Mar. 18, 2015.
EPO Notice of Opposition and supporting documents filed by Beckman Coulter on Aug. 25, 2015 against European Patent No. 2322664, dated Oct. 30, 2014.
EPO Notice of Opposition and supporting documents filed by R-Biopharm AG on Aug. 26, 2015 against European Patent No. 2322664, dated Oct. 30, 2014.
EPO Notice of Opposition and supporting documents filed by Beckman Coulter on Aug. 26, 2015 against European Patent No. 2322655, dated Nov. 26, 2014.
EPO Notice of Opposition and supporting documents filed by R-Biopharm AG on Aug. 26, 2015 against European Patent No. 2322655, dated Nov. 26, 2014.
EPO Notice of Opposition and supporting documents filed by Beckman Coulter on Aug. 26, 2015 against European Patent No. 2322661, dated Nov. 26, 2014.
EPO Notice of Opposition and supporting documents filed by R-Biopharm AG on Aug. 26, 2015 against European Patent No. 2322661, dated Nov. 26, 2014.
Appeal by Patentee/Appellant against EPO Interlocutory Decision filed May 28, 2015 including Grounds for Appeal filed Aug. 5, 2015 in EP Opposition proceedings against Patent No. 2236621.
Opponent Beckman Coulter's Reply to Patentee's Grounds for Appeal filed Dec. 29, 2015 & Opponent's Reply to same filed Jan. 4, 2016 in EP Opposition proceedings against Patent No. 2236621.
Cuny et al., "Rare Occurrence of Methicillin-Resistant *Staphylococcus aureus* CC130 with a Novel mecA Homologue in Humans in Germany", PloS One (2011) 6(9):e24360; 5 pages.
Lowe et al., "A Computer Program for Selection of Oligonucleotide Primers for Polymerase Chain Reactions", Nucl Acids Res. (1990) 18(7): 1757-1761.
Turlej et al., "*Staphylococcal* Cassette Chromosome mec (SCCmec) Classification and Typing Methods: an Overview", Polish J Microbiol. (2011) 60(2):95-103.
Canadian Office Action dated Nov. 7, 2016 in Application No. 2,899,816, filed Jun. 4, 2002.
European Extended Search Report dated Aug. 10, 2016 in European Patent Application No. 15195621.6, filed Nov. 20, 2015.
Patent Proprietor's Reply to both Oppositions and supporting documents filed Apr. 11, 2016 in EP 23226661 dated Nov. 26, 2014 (446 pages).
D49—Exhibit in European Opposition Proceeding: FDA Approval of K033415 (IDI-MRSA Assay) to market; Letter, Mar. 18, 2004 with Summary & Indications for Use; 7 pages.
D51—Exhibit in European Opposition Proceeding: Gentechnische Methoden: Eine Sammlung von Arbeitsanleitungen fur das Molekularbiologische Labor. Publ. Gangolf Schrimpf (2002) Spektrum Akademischer Verlag GmbH; 3rd Edition; pp. 147-168. (reviewed Figures and English language portion).
D55b—Exhibit in European Opposition Proceeding: NCBI—Nucleotide AY267380.1; AY267381.1; AY267376.1; AY267377.1. *Staphylococcus aureus* strain CCRI-1311 SCCmec . . . ; (2004); 6 pages.
D63—Exhibit in European Opposition Proceeding: NCBI—Nucleotide H569115-569102/4. *Staphylococcus aureus* subsp. Aureus SCCmec . . . ; (Dec. 2012); 3 pages.
Patent Proprietor's Reply to both Oppositions and supporting documents filed Aug. 3, 2016 in EP 2322663, dated Mar. 18, 2015 (231 pages).
Patent Proprietor's Reply to both Oppositions and supporting documents filed Apr. 11, 2016 in EP 2322664, dated Oct. 30, 2014 (201 pages).
Patent Proprietor's Reply to both Oppositions and supporting documents filed Apr. 10, 2016 in EP 2322655, dated Nov. 26, 2014 (251 pages).
EPO Opposition Notice dated Dec. 2, 2016 with supporting documentation by Beckman Coulter Inc. against European Patent No. 2781603, dated Mar. 2, 2016; 234 pages.
EPO Opposition Notice dated Dec. 2, 2016 with supporting documentation by Beckman Coulter Inc. against European Patent No. 2781604, dated Mar. 2, 2016; 186 pages.
Opponents' Replies dated Apr. 30, 2014 to Patentee's EPO Appeal and Grounds for Appeal in T 2002/13-3.3.08 against EPO Decision in Re EP Patent No. 1934613; 100 pages.

(56) References Cited

OTHER PUBLICATIONS

Arakere, et al. "A novel type-III *Staphylococcal* cassette chromosome mec (SCCmec) variant among Indian isolates of methicillin-resistant *Staphylococcus aureus*." FEMS Microbiol. Lett. 292(1): 141-148 (Mar. 2009).

Ausubel et al., Current Protocols in Molecular Biology, 3rd Ed. Wiley Interscience Publishers (1995) [Table of Contents Only].

Bartels et al., "An unexpected location of the Arginine Catabolic Mobile Element (ACME) in a USA300-related MRSA." PLoS One 6(1): e16193 (Jan. 2011).

Bastos et al., "Molecular characterization and transfer among *Staphylococcus* strains of a plasmid conferring high-level resistance to mupirocin ", Eur. J. Clin. Microbiol. Infect. Dis. (1999) 18(6):393-8.

Becker et al., "Thermonuclease gene as a target for specific identification of *Staphylococcus intermedius* isolates: use of a PCR-DNA enzyme immunoassay", Diagn. Microbiol. Infect. Dis. (Apr. 2005) 51(4):237-44.

Becker et al., "Does Nasal Cocolonization by Methicillin-Resistant Coagulase-Negative *Staphylococci* and Methicillin-Susceptible *Staphylococcus aureus* Strains Occur Frequently Enough to Represent a Risk of False Positive Methicillin-Resistant *S. aureus* Determinations by Molecular Methods?", J Clin Microbiol. (Jan. 2006) 44(1): 229-231.

Bishop et al., "Concurrent Analysis of Nose and Groin Swab Specimens by the IDI-MRSA PCR Assay is Comparable to Analysis by Individual-Specimen PCR and Routine Culture Assays for Detection of Colonization by Methicillin-Resistant *Staphylococcus aureus*", J Clin Microbiol. (Aug. 2006) 44(8): 2904-2908.

Brakstad et al., "Detection of *Staphylococcus aureus* by polymerase chain reaction amplification of the nuc gene", *J. Clin. Microbiol.* (1992) 30(7):1654-60.

Brakstad et al., "Comparison of tests designed to identify *Staphylococcus aureus* thermostable nuclease", *APMIS* (1995) 103(3):219-24.

Chesneau et al., "Thermonuclease gene as a target nucleotide sequence for specific recognition of *Staphylococcus aureus*", Mol. Cell. Probes. (1993) 7(4):301-10.

Chongtrakool et al., "*Staphylococcal* cassette chromosome mec (SCCmec) typing of methicillin-resistant *Staphylococcus aureus* strains isolated in 11 Asian countries: a proposal for a new nomenclature for SCCmec elements", Antimicrob. Agents Chemother. (2006) 50(3):1001-12.

Costa et al., "Rapid detection of mecA and nuc genes in *staphylococci* by real-time multiplex polymerase chain reaction", Diagn. Microbiol. Infect. Dis. (Jan. 2005) 51(1):13-17.

Cuny et al., "PCR for the identification of methicillin-resistant *Staphylococcus aureus* (MRSA) strains using a single primer pair specific for SCCmec elements and the neighbouring chromosome-borne orfX."—Research Note, Clin Microbiol Infect., 11(10): 834-837 (Oct. 2005).

Database Geneseq [Online]. "Polymorphic right extremity junction (MREJ) DNA #1." EBI accession No. GSN:ACD02065; Database accession No. ACD02065 (2003).

Desjardins et al., "Evaluation of the IDI-MRSA Assay for Detection of Methicillin-Resistant *Staphylococcus aureus* from Nasal and Rectal Specimens Pooled in a Selective Broth", J Clin Microbiol. (Apr. 2006) 44(4): 1219-1223.

Domann et al. "Schneller and zuverlaessiger Nachweis multiresistenter multiplex-PCR." Deutsche Medizinische Wochenschrift. 125(20): 613-618 (2000).

Donnio et al., "Partial Excision of the Chromosomal Cassette Containing the Methicillin Resistance Determinant Results in Methicillin-Susceptible *Staphylococcus aureus*", J Clin Microbiol. (Aug. 2005) 43(8): 4191-4193.

Elsayed et al., "Development and Validation of a Molecular Beacon Probe-Based Real-Time Polymerase Chain Reaction Assay for Rapid Detection of Methicillin Resistance in *Staphylococcus aureus*", Arch Pathol Lab Med. (Jul. 2003) 127(7): 845-849.

Grisold et al., "Use of hybridization probes in a real-time PCR assay on the LightCycler® for the detection of methicillin-resistant *Staphylococcus aureus*", Methods Mol. Biol. (2006) 345:79-89.

Hanssen et al., "Local Variants of *Staphylococcal* Cassette Chromosome mec in Sporadic Methicillin-Resistant *Staphylococcus aureus* and Methicillin-Resistant Coagulase-Negative *Staphylococci*: Evidence of Horizontal Gene Transfer?" Antimicrob Agents Chemothera., 48(1): 285-296 (Jan. 2004).

Hanssen et al., Mini Review "SCCmec in *Staphylococci*: genes on the move." FEMS Immunol Med Microbiol., 46: 8-20 (Sep. 2005).

Innis et al Eds. PCR Protocols, A Guide to Methods and Applications, Academic Press (1990) Table of Contents.

GenBank accession No. AB037671, "*Staphylococcus aureus* DNA, type-III *Staphylococcal* cassette chromosome mec and SCCmercury: strain 85/2082", May 12, 2000, pp. 30.

BLAST Sequence-Alignment 1 between AB037671 (strain 85/2082) and SEQ ID No. 42, printed on Apr. 1, 2011, pp. 2.

Sequence Alignment 3 printed on Mar. 31, 2011 aligning the Nucleotide Sequence of *Staphylococcal aureus* strains 85/2082, HDG2, and N315 (D86934) downstream of mecA, pp. 23.

Kang et al., "The enhancement of PCR amplification of a random sequence DNA library by DMSO and betaine: application to in vitro combinatorial selection of aptamers", J Biochem Biophys Methods. (Aug. 2005) 64(2):147-51.

Kearns et al., "Rapid detection of methicillin-resistant *Staphylococci* by multiplex PCR." Journal of Hospital Infection. 43(1):33-37 (1999).

Kloos et al., "Updated on clinical significance of coagulase-negative *Staphylococci*", Clin. Microbiol. Rev. (1994) 7(1):117-40.

Kovacevic et al., "Secretion of *Staphylococcal* nuclease by Bacillus subtilis", J. Bacteriol. (1985), 162(2):521-8.

Levenson, Deborah, "The Path to Better MRSA Control", Clin Lab News. (Aug. 2007) 33(8): 6 pages.

Levi et al., "Detection of methicillin-resistant *Staphylococcus aureus* (MRSA) in blood with the Evigene MRSA detection kit", J. Clin. Microbiol. (2003) 41(8):3890-2.

Maes et al., "Evaluation of a triplex PCR assay to discriminate *Staphylococcus aureus* from coagulase-negative *Staphylococci* and determine methicillin resistance from blood cultures", J. Clin. Microbiol. (2002) 40(4):1514-7.

McDonald et al., "Development of a triplex real-time PCR assay for detection of Panton-Valentine leukocidin toxin genes in clinical isolates of methicillin-resistant *Staphylococcus aureus*", J. Clin. Microbiol. (Dec. 2005) 43(12):6147-9.

Mongkolrattanothai et al. "Novel Non-mecA-Containing *Staphylococcal* Chromosomal Cassette Composite Island Containing pbp4 and tagF Genes in a Commensal *Staphylococcal* Species: a Possible Reservoir for Antibiotic Resistance Islands in *Staphylococcus aureus*." Antimicrob. Agents Chemother. (May 2004) 48(5): 1823-1836.

Murray et al., Manual of Clinical Microbiology, 8th Ed., ASM Press (2003) [Content pages only].

NCBI BLAST 2 Sequence-AF411934.1—*Staphylococcus aureus* strain HDG2 genomic sequence downstream of mecA, printed on Mar. 16, 2012, pp. 2.

Okuma et al., "Dissemination of new methicillin-resistant *Staphylococcus aureus* clones in the community." J Clin Microbio., 40(11): 4289-4294 (Nov. 2002).

Alignment of SEQ ID Nos. 42-46 and 51 with HDG2 sequence; GenBank Accession Version No. AF411934; Exhibit D9a in European Opposition of Patent No. 1397510, issued Mar. 17, 2004; pp. 10.

Oliveira et al., "Redefining a structural variant of *Staphylococcal* cassette chromosome mec, SCCmec type VI", Antimicrob. Agents Chemother. (Oct. 2006) 50(10):3457-9.

Podzorski et al., Evaluation of the MVPlex Assay for Direct and Rapid Detection of Methicillin-Resistant *Staphylococcus aureus* from Nares and Other Swab Specimens, (Abstract C-237), American Society for Microbiology 107th Meeting, Toronto, Canada May 21-25, 2007, p. 186.

Podzorski et al., MVPlex Assay for Direct Detection of Methicillin-Resistant *Staphylococcus aureus* in Naris and Other Swab Specimens, J Clin Microbiol. (Sep. 2008) 46(9): 3107-3109.

(56) References Cited

OTHER PUBLICATIONS

Poulsen et al., "Detection of methicillin resistance in coagulase-negative *Staphylococci* and in *staphylococci* directly from simulated blood cultures using the EVIGENE MRSA Detection Kit", J. Antimicrob. Chemother. (2003) 51(2):419-21.
Ralser et al., "An efficient and economic enhancer mix for PCR", Biochem. Biophys. Res. Comm. (Sep. 2006) 347(3):747-51.
Rupp et al., "Be Aware of the Possibility of False-Positive Results in Single-Locus PCR Assays for Methicillin-Resistant *Staphylococcus aureus*", (Jun. 2006) 44(6): 2317-8.
Schuenck et al., "Improved and rapid detection of methicillin-resistant *Staphylococcus aureus* nasal carriage using selective broth and multiplex PCR", Res. Microbiol. (Sep. 2006) 157(10):971-5.
Shittu et al., "Molecular identification and characterization of mannitol-negative methicillin-resistant *Staphylococcus aureus*", Diagn. Microbiol. Infect Dis. (2007) 57(1):93-5.
Shore et al. "Characterization of a Novel Arginine Catabolic Mobile Element (ACME) and *Staphylococcal* Chromosomal Cassette mec Composite Island with Significant Homology to *Staphylococcus epidermidis* ACME Type II in Methicillin-Resistant *Staphylococcus aureus* Genotype ST22-MRSA-IV." Antimicrob Agents Chemother. (May 2011) 55(5): 1896-1905.
Simor, et al. "Characterization and proposed nomenclature of epidemic strains of methicillin-resistant *Staphylococcus aureus* in Canada." Can J Infect Dis. Sep.-Oct. 1999; 10(5): 333-336.
Tang et al., StaphPlex System for Rapid and Simultaneous Identification of Antibiotic Resistance Determinants and Panton-Valentine Leukocidin Detection of *Staphylococci* from Positive Blood Cultures, J Clin Microbiol. (Jul. 2007) 45(6): 1867-1873.
Warren et al., "Detection of Methicillin-Resistant *Staphylococcus aureus* Directly from Nasal Swab Specimens by a Real-Time PCR Assay", J Clin Microbiol. (Dec. 2004) 42(12): 5578-5581.
White, "Molecular Cloning to Genetic Engineering ", in Methods in Molecular Biology Humana Press (1997) vol. 67, Contents pages only.
Wilson et al., "Detection of enterotoxigenic *Staphylococcus aureus* in dried skimmed milk: use of the polymerase chain reaction for amplification and detection of *Staphylococcal* enterotoxin genes entB and entC1 and the thermonuclease gene nuc", Appl. Environ. Microbiol. (1991) 57:1793-8.
Wisplinghoff et al., "Related clones containing SCCmec type IV predominate among clinically significant *Staphylococcus epidermidis* Isolates." Antimicrob Agents Chemothera. 47(11): 3574-3579 (2003).
Zhang et al., "New quadriplex PCR assay for detection of methicillin and mupirocin resistance and simultaneous discrimination of *Staphylococcus aureus* from coagulase-negative *Staphylococci*", J. Clin. Microbiol. (2004) 42(11):4947-55.
Zhang et al., "Novel multiplex PCR assay for characterization and concomitant subtyping of *Staphylococcal* cassette chromosome mec types I to V in methicillin-resistant *Staphylococcus aureus.*", J. Clin. Microbiol. (Oct. 2005) 43(10): 5026-33.
Electronic File History [Part 2] Inter Partes Reexam Control No. 95/001599, filed Apr. 8, 2011 including Examiner's Answer Aug. 2, 2013, Rebuttal Brief of Sep. 3, 2013, and Third Party Request for Oral Hearing Oct. 1, 2013.
PTO Action closing prosecution dated Sep. 20, 2013 of Inter Partes Reexamination Control No. 95/002,216, filed Sep. 13, 2012 for U.S. Appl. No. 11/248,438, filed Oct. 11, 2005 (now U.S. Pat. No. 7,838,221) Part 2.
Comparison of the nucleotide sequence of MRSA strains V14 (deposited under Accession No. AB425427) with the nucleotide sequence of SEQ ID No. 165 from the Patent. Primer binding sites for some of the primers claimed in claim 4 of the EP2236621 [D12] cited on May 8, 2013; pp. 1-7.
Nucleotide Sequence of MRSA strain M08/1026 ACME/SC-CmecCI of ST22-MRSA-Ivh deposited in Genbank Accession No. FR753166 with orfX and SCCmec portions of Seq ID No. 165 highlighted thereon. Also shown are primers binding sites for the primers of SEQ ID Nos. 64 and 112 from claim 5 of the EP2236621 [D14] cited on May 8, 2013; pp. 1-16.
CLUSTALW2 Multiple nucleotide sequence alignment (generated using ClustalW2). The sequence of each of MREJ types I to xx (excluding type x) is aligned around the integration site. The sequence of the rjmec primer from D7 is also included; [D9] cited on May 8, 2013; p. 1.
Nucleotide Sequence alignment of SEQ ID No. 165 of EP2236621 [D17] with *Staphylococcus epidermidis* strain ATCC 12228 (Accession No. AE015929.1) cited on May 8, 2013; p. 1.
BLAST Sequence-Alignment between the orfX sequence from *Staphylococcus aureus* and the equivalent *Staphylococcus epidermidis* sequence taken from a number of strains; [D19] cited on May 8, 2013; pp. 1-6.
SEQ ID No. 6—Figure 19 of D1 and D2. Primer biding sites for SEQ ID Nos. 64 and 98 from EP2236621 as underlined; [D22] cited on May 8, 2013; p. 1.
European Decision T 1496/11 of the Technical Boards of Appeal in re EP Patent No. 930979 [D28] of Sep. 12, 2012; pp. 1-28.
Annotated version of figure 4A of EP 2236621 cited on May 8, 2013; p. 1.
Sequence Alignment of SEQ ID No. 64 and SEQ ID No. 98 on SEQ ID No. 165 and SEQ ID No. 166 of EP2236621 [D31] cited on May 8, 2013; pp. 1-3.
International Preliminary Report on Patentability and Written Opinion dated Jul. 2, 2009 for International Application No. PCT/US07/088004, filed Dec. 18, 2007.
European Office Action dated Sep. 28, 2011 for European Application No. 07874372.1, filed Dec. 18, 2007.
European Office Action dated Apr. 16, 2012 for European Application No. 07874372.1, filed Dec. 18, 2007.
Australian Office Action dated Sep. 5, 2012 for Australian Application No. 2007353522, filed Dec. 19, 2006.
Japanese Office Action dated Nov. 27, 2012 in Japanese Patent Application No. 2009-543155, filed Dec. 18, 2007.
European Extended Search Report dated Aug. 10, 2010 in European Patent Application No. 09174581.0, filed Jun. 4, 2002. [D33].
Response to Extended Search Report filed Mar. 3, 2011 in European Patent Application No. 09174581.0, filed Jun. 4, 2002. [D34].
Supplementary Response to Extended Search Report filed Nov. 16, 2011 in European Patent Application No. 09174581.0, filed Jun. 4, 2002. [D35].
Minutes of the Oral Proceedings on Jan. 30, 2013 in European Opposition to Patent No. No 1397510 [D37] dated Apr. 5, 2013.
EPO Decision of the Opposition Division of Apr. 5, 2013 in European Opposition to Patent No. No 1397510 [ D36].
Notice of Opposition filed May 8, 2013 against European Patent No. 2236621, dated Aug. 8, 2012.
Notice of Opposition & Discussion filed Oct. 19, 2011 against European Patent No. 1934613 (Koenig et al.).
Notice of Opposition and Statement filed Oct. 18, 2011 against European Patent No. 1934613 (BC).
EPO Communication dated Nov. 25, 2011 in European Opposition to Patent No. 1934613.
EPO Board Decision and Minutes of Oral Proceedings dated Aug. 2, 2013 in European Opposition to Patent No. 1934613.
Baba et al. "*Staphylococcus aureus* subsp. Aureus MW2 DNA, complete genome", retrieved from EBI Database accession No. AP004822 (May 27, 2002), replaced by Accession No. BA000033.
Buck, et al. "Design strategies and performance of custom DNA sequencing primers." Biotechniques, 27(3): 528-536, (Sep. 1999).
Cheng et al., "Effective amplification of long targets from cloned inserts and human genomic DNA," Proc Natl Acad Sci. USA, (Jun. 1994) 91: 5695-5699.
Crisóstomo et al., "The evolution of methicillin resistance in *Staphylococcus aureus*: Similarity of genetic backgrounds in historically early methicillin-susceptible and -resistant isolates and contemporary epidemic clones", Proc Natl Acad Sci USA, 98(17): 9865-9870 (Aug. 2001).
Database Geneseq [Online]. Sequence provided in Fig. 4 of JP11056371. Retrieved from EBI accession No. GSN:AAX32450 (Jun. 22 1999).

(56) References Cited

OTHER PUBLICATIONS

Database Geneseq [Online]. "Identification method" JP1999056371, Retrieved from EBI accession No. EM-PRO:E60314 (Feb. 22, 2001).
Database Geneseq [Online]. "Sequence of Primer KC1". Retrieved from EBI accession No. GSN:AAX32446 (Jun. 22, 1999).
Diefenbach, Dveksler. "PCR Primer: A Laboratory Manual", 1995, Cold Spring Harbor Laboratory Press.
Edwards et al., "Multiplex PCR: advantages, development, and applications", Genome Res. 3: S65-75 (1994).
Ito et al. "*Staphylococcus aureus* DNA, 3' flanking region of mecDNA, strain 64/4176." GenBank accession No. AB014434, Jan. 7, 2000—Abstract only.
Kobayashi et al., "Genomic diversity of mec regulator genes in methicillin-resistant *Staphylococcus aureus* and *Staphylococcus epidermidis*", Epidemiol Infect. 117(2): 289-295 (1996).
Lee et al., "Nucleic Acid Amplification Technologies: Application to Disease Diagnosis", 1997, Eaton PublishingLEWIN, "Genes IV", 1990, John Wiley & Sons, Chapter 3, Genes are Mutable Units, pp. 41-56.
Lewin, "Genes IV", 1990, John Wiley & Sons, Chapter 3, Genes are Mutable Units, pp. 41-56.
Ma et al. "*Staphylococcus aureus* DNA, type-IV.2 (Ivb) *staphylococcal* cassette chromosome mec: strain JCSC1978 (8/6-3P)", EBI GenBank accession No. AB063173, Nov. 21, 2001.
Oliveira et al. "*Staphylococcus aureus* strain HDE288 type-VI SCCmec element, complete sequence" GenBank Accession Version No. AF411935, Mar. 5, 2002, pp. 8.
Oliveira et al. "*Staphylococcus aureus* strain PL72 genomic sequence upstream of mecA" GenBank Accession Version No. AF411936, Mar. 5, 2002, pp. 3.
Persing et al., Diagnostic Molecular Microbiology: Principles and Applications, American Society for Microbiology, Washington, D.C. (1993), Contents pages only.
Sambrook et al., "Molecular Cloning: A Laboratory Manual", 1989 Cold Spring Harbor Laboratory Press (Cover & Contents pages only).
Seki et al., Amplification of long targets of approximately 50 kb from cloned cosmid inserts of *Arabidopsis thaliana*, DNA Research (Jul. 1996) 3: 107-108.
Turbeville et al., "Amplification of the complete mitochondrial genome of two protostome worms: a useful technique for comparative studies of metazoan mitochondrial DNA", Mol Marine Bio Biotech., 6(2): 141-143 (1997).
Van Leeuwen et al., "Genetic diversification of methicillin-resistant *Staphylococcus aureus* as a function of prolonged geographic dissemination and as measured by binary typing and other genotyping methods," Res Microbiol, 149: 497-507 (1998).
Watson et al., "Molecular Biology of the Gene", 1987, The Benjamin/Cummings Publishing Company.
Third Party Observations dated Jan. 17, 2008 in European Patent Application No. 02740158.7, filed Jun. 5, 2002.
EPO Communication dated Sep. 10, 2010 in European Patent Application No. 02740158.7, filed Jun. 4, 2002.
Cuny et al., "PCR for the identification of methicillin-resistant *Staphylococcus aureus* (MRSA) strains using a single primer pair specific for SCCmec elements and the neighbouring chromosome-borne orfX"—Research Note, Clin Microbio Infect., 11(10): 834-837 (Oct. 2005).
Domann et al. "Schneller and zuverlaessiger Nachweis multiresistenter multiplex-PCR." Deutsche Medizinische Wochenschrift. 125(20): 613-618 (2000). w/EN Abstract.
Hanssen et al., Mini Review "SCCmecin *Staphylococci*: genes on the move." FEMS Immunol Med Microbiol., 46: 8-20 (Sep. 2005).
NCBI BLAST Sequence Alignment 1 between AB037671 (strain 85/2082) and SEQ ID No. 42, printed on Apr. 1, 2011.
PCR Methods and Applications, Cold Spring Harbor Laboratory Press (from 1991 to 1995), Contents pages only.
PCR Strategies, Academic Press, Inc. (1995), Contents pages only.
Ralser et al., "An efficient and economic enhancer mix for PCR", Biochem. Biophys. Res. Communi. (Sep. 2006) 347(3):747-51.
Sequence Alignment 3 printed on Mar. 31, 2011 aligning the Nucleotide Sequence of *Staphylococcal aureas* strains 85/2082, HDG2, and N315(d86934) downs stream of mecA, pp. 10.
Wisplinghoff et al., "Related clonges containing SCCmec type IV predominate among clinically significant *Staphylococcus epidermidis* Isolates." Antimicrob Agents Chemothera. 47(11): 3574-3579 (2003).
Electronic File History of Inter Partes Reexamination Control No. 95/001599, filed Apr. 8, 2011 containing Office Actions dated Apr. 19, 2011, Jun. 1, 2011 and Dec. 29, 2011, Requestor submissions Apr. 8, 2011, and Aug. 31, 2011 and Applicant Response filed Aug. 5, 2011.
International Search Report and Written Opinion dated Nov. 23, 2007 for International Patent Application No. PCT/US06/39996, filed Oct. 10, 2006.
International Preliminary Report on Patentability (Rule 44bis) dated Apr. 16, 2008 for International Patent Application No. PCT/US06/39996, filed Oct. 10, 2006.
Partial European Search Report dated Mar. 31, 2011 for European Patent Application No. 10016072.0, filed Oct. 10, 2006.
Extended European Search Report dated Aug. 10, 2011 for European Patent Application No. 10016072.0, filed Oct. 10, 2006.
Partial European Search Report dated Mar. 31, 2011 for European Patent Application No. 10016073.8, filed Oct. 10, 2006.
Extended European Search Report dated Aug. 10, 2011 for European Patent Application No. 10016073.8, filed Oct. 10, 2006.
Partial European Search Report dated Mar. 10, 2011 for European Patent Application No. 10016074.6, filed Oct. 10, 2006.
Extended European Search Report dated Jul. 20, 2011 for European Patent Application No. 10016074.6, filed Oct. 10, 2006.
Partial European Search Report dated Mar. 31, 2011 for European Patent Application No. 10016031.6, filed Oct. 10, 2006.
Extended European Search Report dated Aug. 10, 2011 for European Patent Application No. 10016031.6, filed Oct. 10, 2006.
Partial European Search Report dated Mar. 30, 2011 for European Patent Application No. 10016019.1, filed Oct. 10, 2006.
Extended European Search Report dated Aug. 10, 2011 for European Patent Application No. 10016019.1, filed Oct. 10, 2006.
Partial European Search Report dated Mar. 30, 2011 for European Patent Application No. 10016020.9, filed Oct. 10, 2006.
Extended European Search Report dated Aug. 10, 2011 for European Patent Application No. 10016020.9, filed Oct. 10, 2006.
Partial International Search Report dated Dec. 19, 2008 for International Application No. PCT/US072/088004, filed Dec. 18, 2007.
International Preliminary Report on Patentability and Written Opinion dated Jul. 2, 2009 for International Application No. PCT/US072/088004, filed Dec. 18, 2007.
Notice of Opposition & Discussion filed Oct. 19, 2011against European Patent No. 1934613, dated Jan. 19, 2011 (Koenig et al.).
Notice of Opposition and Statement filed Oct. 18, 2011 against European Patent No. 1934613, dated Jan. 19, 2011.
EPO Communication dated Nov. 25, 2011 in European Patent No. 1934613, issued Jan. 19, 2011.
Dieffenbach et al. "General Concepts for PCR Primer Design." Genome Res. 3: S30-S37 (1993).
GenBank accession No. X53818.1, "*Staphylococcus aureus* IS431mec gene associated with methicillin resistance", Oct. 23, 2008.
Huletsky, A.—Declaration in Reexamination of U.S. Pat. No. 7,449,289 dated Jul. 30, 2011; pp. 3.
Oliveira, D.—Email re Sequence Question with Hema Pande, Beckman Coulter, Inc. (Jul. 2010).
Oliveira, D—Declaration in Opposition to EP Patent 1397510 dated Nov. 29, 2012; pp. 2.
Random House Unabridged Dictionary, (1993) Definition of "extremity", p. 686.
Sanches et al., "Tracing the Origin of an Outbreak of Methicillin-Resistant *Staphylococcus aureus* Infections in a Portuguese Hospital by Molecular Fingerprinting Methods." Microbial Drug Resist. 2(3): 319-329 (1996).

(56) References Cited

OTHER PUBLICATIONS

Singh et al. "PCR Primer Design." Mol Biol Today 2(2): 27-32 (2001).
D3—Exhibit in European Opposition Proceeding: Applicant Response dated Dec. 2, 2009 in EP Application No. 06825875.5, filed Oct. 10, 2006; 5 pages.
D6—Exhibit in European Opposition Proceeding:: BLAST alignment of SEQ ID 46 from EP 1 397 510 and SEQ ID 19 from EP 1 934 613; 1 page.
D7—Exhibit in European Opposition Proceeding:: EP 1 93 4613 Claimed sequences with EP 1 397 510 primer binding sites shown; 3 pages.
D13—Exhibit in European Opposition Proceeding: CLUSTALW2 Multiple sequence alignment of rjmec primer from Cuny et al. and various MREJ type sequences; 1 page.
D14—Exhibit in European Opposition Proceeding: Primer binding sites of Cuny et al. in EP 1 934 613; 2 pages.
D17—Exhibit in European Opposition Proceeding: Primer binding site for SEQ ID No. 35 in SEQ ID No. 20 of EP 1 934 613; 1 page.
D18—Exhibit in European Opposition Proceeding: Overlap between ORFX2r primer binding sites of Cuny et al. and primer binding site of SEQ ID No. 45 from EP 1 934 613 in type xi MREJ sequences claimed in the EP patent; 6 pages.
D19—Exhibit in European Opposition Proceeding: Primer binding sites for primers of Cuny et al. in MREJ Types I-XX (sequences taken from EP 1934 613 and EP 1 397 510; 10 pages.
D32—Exhibit in European Opposition Proceeding: Lawrence et al. "Poisonous EPC Divisionals—Implications for Risk Management and Opportunistic Advantage." epi Information Feb. 2011; 54-61.
D36—Exhibit in European Opposition Proceeding: Alignment of SEQ ID No. 18 from U.S. Appl. No. 11/248,438 and WO 2007/044873 with orfX sequence from Ito et al., AB014440; 3 pages.
D37—Exhibit in European Opposition Proceeding: Alignment of SEQ ID No. 19 from U.S. Appl. No. 11/248,438 and WO 2007/044873 with orfX sequence from Ito et al., AB014440; 1 page.
D38—Exhibit in European Opposition Proceeding: Alignment of MREJ type xi (SEQ ID No. 17) and mrej Type iii (SEQ ID No. 184 from WO 2002/099034 showing asserted binding sites of primers pair (SEQ ID NOs. 64/98) from WO 2002/099034; 3 pages.
D39—Exhibit in European Opposition Proceeding: Alignment of MREJ type xi (SEQ ID No. 17) and MREJ type iii (SEQ ID No. 184 From WO 2002/099034 showing asserted binding sites of primers (SEQ ID NOs. 1-5) from EP 1 529 847; 1 page.
Electronic File History of Inter Partes Reexamination Control No. 95/002,216, filed Sep. 13, 2012 for U.S. Appl. No. 11/248,438, filed Oct. 11, 2005 (now U.S. Pat. No. 7,838,221) as of Feb. 26, 2013.
Office Action dated Sep. 11, 2012 for European Patent Application No. 10016072.0, filed Oct. 10, 2006.
Office Action dated Sep. 11, 2012 for European Patent Application No. 10016073.8, filed Oct. 10, 2006.
Office Action dated Sep. 11, 2012 for European Patent Application No. 10016074.6, filed Oct. 10, 2006.
Office Action dated Sep. 11, 2012 for European Patent Application No. 10016031.6, filed Oct. 10, 2006.
Office Action dated Sep. 11, 2012 for European Patent Application No. 10016019.1, filed Oct. 10, 2006.
Office Action dated Sep. 12, 2012 for European Patent Application No. 10016020.9, filed Oct. 10, 2006.
Japanese Office Action dated Nov. 27, 2012 in Japanese Patent Application No. 2009543155, filed Dec. 18, 2007.
Patentee Response dated Nov. 19, 2012 to EP Summons to Oral Proceeding in European Opposition to Patent No. 1397510.
Opposer Hain Lifescience GmbH Response dated Nov. 26, 2012 to EP Summons to Oral Proceeding in European Opposition to Patent No. 1397510. (English Translation Only).
Opposer Beckman Coulter, Inc. further Response dated Nov. 30, 2012 to EP Summons to Oral Proceeding in European Opposition to Patent No. 1397510.
Patentee Reply filed May 30, 2012 in European Opposition to Patent No. 1934613.
EPO Summons to Oral Proceedings dated Nov. 23, 2012 in European Opposition to Patent No. 1934613.
Australian Office Action dated Jun. 6, 2011 for Australian Application No. 2006302044, filed Oct. 10, 2006.
EPO Communication dated May 10, 2012 re Oral Proceeding Schedule in European Opposition No. 02740158.7, filed Jun. 4, 2002.
Japanese Office Action dated Aug. 8, 2012 for JP Patent Application No. 2008-535692, filed Oct. 10, 2006.
Ciardo et al., "GeneXpert Captures Unstable Methicillin-Resistant *Staphylococcus aureus* Prone to Rapidly Losing the mecAGene," J. Clin. Microbio. (Aug. 2010) 48(8):3030-3031.
Database EMBL [Online]. "*Staphylococcus aureus* DNA, 3' flanking region of MecDNA, strain 64/4176", Retrieved from EBI accession No. AB014434 (Jan. 7, 2000).
Database EMBL [Online]. "*Staphylococcus aureus* M type 1 capsular polysaccharide biosynthesis gene cluster, complete sequence and unknown genes", Retrieved from EBI accession No. SA10927 (Nov. 8, 1994).
Database EMBL [Online]. "*Staphylococcus aureus* DNA, type-IV.1 (Iva) *Staphylococcal* cassette chromosome mec: strain CA05 (JCSC1968)", retrieved from EBI accession No. AB063172 (Nov. 21, 2001).
Database Geneseq [Online]. "*Staphylococcus aureus* downstream junction sequence Psj10-3J3rc.", Retrieved from EBI accession No. GSN:AAT84818 (Mar. 23, 1998).
GenBank accession No. D86934.1, "*Staphylococcus aureus* genes, mec region, partial and complete cds.", Jul. 3, 1999.
Huletsky, et al. "Identification of Methicillin-Resistant *Staphylococcus aureus* Carriage in Less than 1 Hour during a Hospital Surveillance Program." Clin. Infect. Dis. (Apr. 2005) 40: 976-981.
Kobayashi et al., "Analysis on distribution of insertion sequence IS431 in clinical isolates of *Staphylococci*", Diag. Micro. Infect. Dis. (2001) 39: 61-64.
European Extended Search Report dated Apr. 18, 2011 in European Patent Application No. 10181533.0, filed Jun. 4, 2002.
European Extended Search Report dated Apr. 18, 2011 in European Patent Application No. 10181534.8, filed Jun. 4, 2002.
European Extended Search Report dated Apr. 18, 2011 in European Patent Application No. 1-0181535 8 filed Jun. 4, 2002.
European Extended Search Report dated Apr. 15, 2011 in European Patent Application No. 10181536.3, filed Jun. 4, 2002.
European Office Action dated Apr. 26, 2011 in European Patent Application No. 09174581.0, filed Jun. 4, 2002.
Patentee Response to European Opposition dated Mar. 17, 2011 in European Patent Application No. 02740158.7, filed Jun. 4, 2002.

* cited by examiner

MREP type i
MREP type ii
MREP type iii
SCCmec integration site
orfX
S. aureus chromosome
52
53
54
55
56
57
58
59
60
61
62
63
or Prime
S. aureus Chromosome
orfX
MREP type i
MREP type ii
MREP type iii

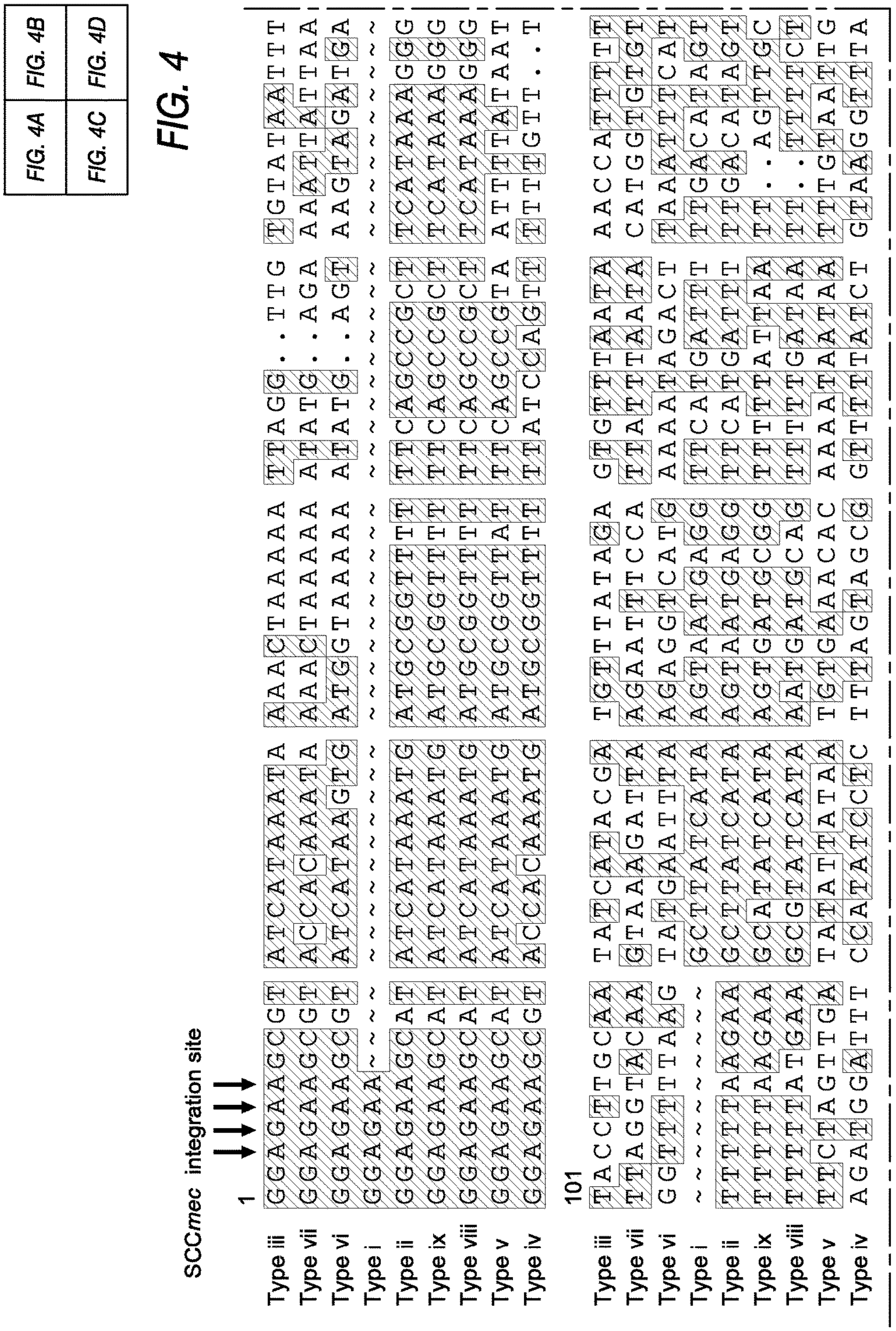

| | FIG. 4A | FIG. 4B |
|---|---|---|
| | FIG. 4C | FIG. 4D |

SCCmec integration site

```
              1
Type iii    GGAGAAGCGT  ATCATAAATA  AAACTAAAAA  TTAGG...TTG  TGTATAATTT
Type vii    GGAGAAGCGT  ACCACAAATA  AAACTAAAAA  ATATG...AGA  AAATTATTAA
Type vi     GGAGAAGCGT  ATCATAAGTG  ATGGTAAAAA  ATATG...AGT  AAGTAGATGA
Type i      GGAGAA~         ?           ?           ?           ?
Type ii     GGAGAAGCAT  ATCATAAATG  ATGCCGGTTT  CAGCCCGCTA  TCATAAAGGG
Type ix     GGAGAAGCAT  ATCATAAATG  ATGCCGGTTT  CAGCCCGCTT  TCATAAAGGG
Type viii   GGAGAAGCAT  ATCATAAATG  ATGCCGGTTT  CAGCCCGCTT  TCATAAAGGG
Type v      GGAGAAGCGT  ATCATAAATG  ATGCCGGTTT  CAGCCCGTA   ATTTTATAAT
Type iv     GGAGAAGCGT  ACCACAAATG  ATGCCGGTTT  TATCCAGTT   TTTTGTT..T

            101
Type iii    TACCTTGCAA  TATCATACGA  TGTTTATAGA  GTTAATA     AACCATTTTT
Type vii    TTAGGTACAA  GTAAAGATTA  AGAAATTTCCA CATGGTGTGT
Type vi     GGTTTTTAAG  TATGAATTTA  AGAGGTCATG  TAAATAGACT  TAAATTTCAT
Type i      TTTTTAAGAA  GCTTATCATA  AGTAATGAGG  TTCATGATTT  TTGACATAGT
Type ii     TTTTTAAGAA  GCATATCATA  AGTAATGAGG  TTCATGATTT  TTGACATAGT
Type ix     TTTTTATGAA  GCATATCATA  AGTAATGAGG  TTCATGATTT  AGTTTGC
Type viii   TTCTAGTTGA  GCGTATCATA  AATGATGATG  TATTTATAAT  ..AGTTGC
Type v      AGATGGATTT  CCATATCCTC  TTTAGTGCAG  TATATATAAT  TTGTAATTG
Type iv     AGATGGATTT  CCATATCCTC  TTTAGTGCG   AATGATCT    GTAAGGTTA
```

METHOD FOR THE DETECTION AND IDENTIFICATION OF METHICILLIN-RESISTANT *STAPHYLOCOCCUS AUREUS*

CROSS-REFERENCE TO RELATED APPLICATIONS

This application is a continuation of U.S. patent application Ser. No. 10/479,674, to Huletsky, et al., "SEQUENCES FOR DETECTION AND IDENTIFICATION OF METHICILLIN-RESISTANT *STAPHYLOCOCCUS AUREUS*," filed Sep. 7, 2004 which is a National Phase Application of International Patent Application PCT/CA02/00824, filed Jun. 4, 2002, now closed, which claims priority to Canadian Patent Application No. 2,348,042, filed Jun. 4, 2001, now abandoned.

REFERENCE TO SEQUENCE LISTING, TABLE, OR COMPUTER PROGRAM LISTING

The present application is being filed along with duplicate copies of a CD-ROM marked "Copy 1" and "Copy 2" containing a Sequence Listing in electronic format. The duplicate copies of CD-ROM entitled The "Copy 1" and "Copy 2" each contains a file entitled GENOM051C1.txt created on May 2, 2006 which is 200,704 Bytes in size. The information on these duplicate CD-ROMs is incorporated herein by reference in its entirety.

BACKGROUND OF THE INVENTION

Clinical Significance of *Staphylococcus Aureus*

The coagulase-positive species *Staphylococcus aureus* is well documented as a human opportunistic pathogen. Nosocomial infections caused by *S. aureus* are a major cause of morbidity and mortality. Some of the most common infections caused by *S. aureus* involve the skin, and they include furuncles or boils, cellulitis, impetigo, and postoperative wound infections at various sites. Some of the more serious infections produced by *S. aureus* are bacteremia, pneumonia, osteomyelitis, acute endocarditis, myocarditis, pericarditis, cerebritis, meningitis, scalded skin syndrome, and various abcesses. Food poisoning mediated by staphylococcal enterotoxins is another important syndrome associated with *S. aureus*. Toxic shock syndrome, a community-acquired disease, has also been attributed to infection or colonization with toxigenic *S. aureus* (Murray et al. Eds, 1999, Manual of Clinical Microbiology, 7$^{th}$ Ed., ASM Press, Washington, D.C.).

Methicillin-resistant *S. aureus* (MRSA) emerged in the 1980s as a major clinical and epidemiologic problem in hospitals. MRSA are resistant to all β-lactams including penicillins, cephalosporins, carbapenems, and monobactams, which are the most commonly used antibiotics to cure *S. aureus* infections. MRSA infections can only be treated with more toxic and more costly antibiotics, which are normally used as the last line of defence. Since MRSA can spread easily from patient to patient via personnel, hospitals over the world are confronted with the problem to control MRSA. Consequently, there is a need to develop rapid and simple screening or diagnostic tests for detection and/or identification of MRSA to reduce its dissemination and improve the diagnosis and treatment of infected patients.

Methicillin resistance in *S. aureus* is unique in that it is due to acquisition of DNA from other coagulase-negative staphylococci (CNS), coding for a surnumerary β-lactam-resistant penicillin-binding protein (PBP), which takes over the biosynthetic functions of the normal PBPs when the cell is exposed to β-lactam antibiotics. *S. aureus* normally contains four PBPs, of which PBPs 1, 2 and 3 are essential. The low-affinity PBP in MRSA, termed PBP 2a (or PBP2'), is encoded by the choromosomal mecA gene and functions as a β-lactam-resistant transpeptidase. The mecA gene is absent from methicillin-sensitive *S. aureus* but is widely distributed among other species of staphylococci and is highly conserved (Ubukata et al., 1990, Antimicrob. Agents Chemother. 34:170-172).

By nucleotide sequence determination of the DNA region surrounding the mecA gene from *S. aureus* strain N315 (isolated in Japan in 1982), Hiramatsu et al. have found that the mecA gene is carried by a novel genetic element, designated staphylococcal cassette chromosome mec (SCCmec), inserted into the chromosome. SCCmec is a mobile genetic element characterized by the presence of terminal inverted and direct repeats, a set of site-specific recombinase genes (ccrA and ccrB), and the mecA gene complex (Ito et al., 1999, Antimicrob. Agents Chemother. 43:1449-1458; Katayama et al., 2000, Antimicrob. Agents Chemother. 44:1549-1555). The element is precisely excised from the chromosome of *S. aureus* strain N315 and integrates into a specific *S. aureus* chromosomal site in the same orientation through the function of a unique set of recombinase genes comprising ccrA and ccrB. Two novel genetic elements that shared similar structural features of SCCmec were found by cloning and sequencing the DNA region surrounding the mecA gene from MRSA strains NCTC 10442 (the first MRSA strain isolated in England in 1961) and 85/2082 (a strain from New Zealand isolated in 1985). The three SCCmec have been designated type I (NCTC 10442), type II (N315) and type III (85/2082) based on the year of isolation of the strains (Ito et al., 2001, Antimicrob. Agents Chemother. 45:1323-1336) (FIG. 1). Hiramatsu et al. have found that the SCCmec DNAs are integrated at a specific site in the methicillin-sensitive *S. aureus* (MSSA) chromosome. They characterized the nucleotide sequences of the regions around the left and right boundaries of SCCmec DNA (i.e. attL and attR, respectively) as well as those of the regions around the SCCmec DNA integration site (i.e. attBscc which is the bacterial chromosome attachment site for SCCmec DNA). The attBscc site was located at the 3' end of a novel open reading frame (ORF), orfX. The orfX potentially encodes a 159-amino acid polypeptide sharing identity with some previously identified polypeptides, but of unknown function (Ito et al., 1999, Antimicrob. Agents Chemother. 43:1449-1458). Recently, a new type of SCCmec (type IV) has been described by both Hiramatsu et al. (Ma et al, 2002, Antimicrob. Agents Chemother. 46:1147-1152) and Oliveira et al. (Oliveira et al, 2001, Microb. Drug Resist. 7:349-360). The sequences of the right extremity of the new type IV SCCmec from *S. aureus* strains CA05 and 8/6-3P published by Hiramatsu et al. (Ma et al., 2002, Antimicrob. Agents Chemother. 46:1147-1152) were nearly identical over 2000 nucleotides to that of type II SCCmec of *S. aureus* strain N315 (Ito et al., 2001, Antimicrob. Agents Chemother. 45:1323-1336). No sequence at the right extremity of the SCCmec type IV is available from the *S. aureus* strains HDE288 and PL72 described by Oliveira et al. (Oliveira et al., 2001, Microb. Drug Resist. 7:349-360).

Previous methods used to detect and identify MRSA (Saito et al., 1995, J. Clin. Microbiol. 33:2498-2500; Ubukata et al., 1992, J. Clin. Microbiol. 30:1728-1733; Murakami et al., 1991, J. Clin. Microbiol. 29:2240-2244; Hiramatsu et al., 1992, Microbiol. Immunol. 36:445-453), which are based on the detection of the mecA gene and *S. aureus*-specific chromosomal sequences, encountered difficulty in discriminating MRSA from methicillin-resistant coagulase-negative staphylococci (CNS) because the mecA gene is widely distributed in both *S. aureus* and CNS species (Suzuki et al., 1992, Antimicrob. Agents. Chemother. 36:429-434). Hiramatsu et al. (U.S. Pat. No. 6,156,507) have described a PCR assay specific for MRSA by using primers that can specifically hybridize to the right extremities of the 3 types of SCCmec DNAs in combination with a primer specific to the *S. aureus* chromosome, which corresponds to the nucleotide sequence on the right side of the SCCmec integration site. Since nucleotide sequences surrounding the SCCmec integration site in other staphylococcal species (such as *S. epidermidis* and *S. haemolyticus*) are different from those found in *S. aureus*, this PCR assay was specific for the detection of MRSA. This PCR assay also supplied information for MREP typing (standing for <<mec right extremity polymorphism>>) of SCCmec DNA (Ito et al., 2001, Antimicrob. Agents Chemother. 45:1323-1336; Hiramatsu et al., 1996, J. Infect. Chemother. 2:117-129). This typing method takes advantage of the polymorphism at the right extremity of SCCmec DNAs adjacent to the integration site among the three types of SCCmec. Type III has a unique nucleotide sequence while type II has an insertion of 102 nucleotides to the right terminus of SCCmec type I. The MREP typing method described by Hiramatsu et al. (Ito et al., 2001, Antimicrob. Agents Chemother. 45:1323-1336; Hiramatsu et al., 1996, J. Infect. Chemother. 2:117-129) defines the SCCmec type I as MREP type i, SCCmec type II as MREP type ii and SCCmec type III as MREP type iii. It should be noted that the MREP typing method cannot differentiate the new SCCmec type IV described by Hiramatsu et al. (Ma et al., 2002, Antimicrob. Agents Chemother. 46:1147-1152) from SCCmec type II because these two SCCmec types exhibit the same nucleotide sequence to the right extremity.

The set of primers described by Hiramatsu et al. as being the optimal primer combination (SEQ ID NOs.: 22, 24, 28 in U.S. Pat. No. 6,156,507 corresponding to SEQ ID NOs.: 56, 58 and 60, respectively, in the present invention) have been used in the present invention to test by PCR a variety of MRSA and MSSA strains (FIG. 1 and Table 1). Twenty of the 39 MRSA strains tested were not amplified by the Hiramatsu et al. multiplex PCR assay (Tables 2 and 3). Hiramitsu's method indeed was successful in detecting less than 50% of the tested 39 MRSA strains.

This finding demonstrates that some MRSA strains have sequences at the right extremity of SCCmec-chromosome right extremity junction different from those identified by Hiramatsu et al. Consequently, the system developed by Hiramatsu et al. does not allow the detection of all MRSA. The present invention relates to the generation of SCCmec-chromosome right extremity junction sequence data required to detect more MRSA strains in order to improve the Hiramatsu et al. assay. There is a need for developing more ubiquitous primers and probes for the detection of most MRSA strains around the world.

SUMMARY OF THE INVENTION

It is an object of the present invention to provide a specific, ubiquitous and sensitive method using probes and/or amplification primers for determining the presence and/or amount of nucleic acids from all MRSA strains.

Ubiquity of at least 50% amongst the strains representing MRSA strains types IV to X is an objective of this invention.

Therefore, in accordance with the present invention is provided a method to detect the presence of a methicillin-resistant *Staphylococcus aureus* (MRSA) strain in a sample, the MRSA strain being resistant because of the presence of an SCCmec insert containing a mecA gene, said SCCmec being inserted in bacterial nucleic acids thereby generating a polymorphic right extremity junction (MREJ), the method comprising the step of annealing the nucleic acids of the sample with a plurality of probes and/or primers, characterized by:

the primers and/or probes are specific for MRSA strains and capable of annealing with polymorphic MREJ nucleic acids, the polymorphic MREJ comprising MREJ types i to x; and the primers and/or probes altogether can anneal with at least four MREJ types selected from MREJ types i to x.

In a specific embodiment, the primers and/or probes are all chosen to anneal under common annealing conditions, and even more specifically, they are placed altogether in the same physical enclosure.

A specific method has been developed using primers and/or probes having at least 10 nucleotides in length and capable of annealing with MREJ types i to iii, defined in any one of SEQ ID NOs: 1, 20, 21, 22, 23, 24, 25, 41, 199; 2, 17, 18, 19, 26, 40, 173, 174, 175, 176, 177, 178, 179, 180, 181, 182, 183, 185, 186, 197; 4, 5, 6, 7, 8, 9, 10, 11, 12, 13, 14, 15, 16, 104, 184, 198 and with one or more of MREJ types iv to ix, having SEQ ID NOs: 42, 43, 44, 45, 46, 51; 47, 48, 49, 50; 171; 165, 166; 167; 168. To be perfectly ubiquitous with the all the sequenced MREJs, the primers and/or probes altogether can anneal with said SEQ ID NOs of MREJ types i to ix.

The following specific primers and/or probes having the following sequences have been designed:

66, 100, 101, 105, 52, 53, 54, 55, 56, 57, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type i 66, 97, 99, 100, 101, 106, 117, 118, 124, 125, 52, 53, 54, 55, 56, 57, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89 for the detection of MREJ type ii 67, 98, 102, 107, 108, 64, 71, 72, 73, 74, 75, 76, 70, 103, 130, 132, 158, 159, 58, 59, 62, 126, 127, 128, 129, 131, 200, 201, 60, 61, 63, 32, 83, 84, 160, 161, 162, 163, 164, 85, 86, 87, 88, 89, for the detection of MREJ type iii 79, 77, 145, 146, 147, 64, 71, 72, 73, 74, 75, 76, 70, 103, 130, 132, 158, 159, 59, 62, 126, 127, 128, 129, 131, 200, 201, 60, 61, 63, 68, 32, 83, 84, 160, 161, 162, 163, 164, 85, 86, 87, 88, 89, for the detection of MREJ type iv 65, 80, 154, 155, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type v 202, 203, 204, 4, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type vi 112, 113, 114, 119, 120, 121, 122, 123, 150, 151, 153, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type vii 115, 116, 187, 188, 207, 208, 64, 71, 72, 73, 74, 75, 76, 70, 103, 130, 132, 158, 159

59, 62, 126, 127, 128, 129, 131, 200, 201, 60, 61, 63, 32, 83, 84, 160, 161, 162, 163, 164, 85, 86, 87, 88, 89, for the detection of MREJ type viii 109, 148, 149, 205, 206, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type ix.

Amongst these, the following primer pairs having the following sequences are used:

64/66, 64/100, 64/101; 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57, for the detection of type i MREJ 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57 for the detection of type ii MREJ 64/67, 64/98, 64/102; 59/58, 60/58, 61/58, 62/58, 63/58 for the detection of type iii MREJ 64/79 for the detection of type iv MREJ 64/80 for the detection of type v MREJ 64/204 for the detection of type vi MREJ 64/112, 64/113 for the detection of type vii MREJ 64/115, 64/116 for the detection of type viii MREJ 64/109 for the detection of type ix MREJ As well, amongst these, the following probes having the following sequences are used:

SEQ ID NOs: 32, 83, 84, 160, 161, 162, 163, 164 for the detection of MREJ types i to ix.

In the most preferred embodied method, the following primers and/or probes having the following nucleotide sequences are used together. The preferred combinations make use of:

SEQ ID NOs: 64, 66, 84, 163, 164 for the detection of MREJ type i

SEQ ID NOs: 64, 66, 84, 163, 164 for the detection of MREJ type ii

SEQ ID NOs: 64, 67, 84, 163, 164 for the detection of MREJ type iii

SEQ ID NOs: 64, 79, 84, 163, 164 for the detection of MREJ type iv

SEQ ID NOs: 64, 80, 84, 163, 164 for the detection of MREJ type v

SEQ ID NOs: 64, 112, 84, 163, 164 for the detection of MREJ type vii.

All these probes and primers can even be used together in the same physical enclosure.

It is another object of this invention to provide a method for typing a MREJ of a MRSA strain, which comprises the steps of: reproducing the above method with primers and/or probes specific for a determined MREJ type, and detecting an annealed probe or primer as an indication of the presence of a determined MREJ type.

It is further another object of this invention to provide a nucleic acid selected from SEQ ID NOs:

SEQ ID NOs: 42, 43, 44, 45, 46, 51 for sequence of MREJ type iv;

SEQ ID NOs: 47, 48, 49, 50 for sequence of MREJ type v;

SEQ ID NOs: 171 for sequence of MREJ type vi;

SEQ ID NOs: 165, 166 for sequence of MREJ type vii;

SEQ ID NOs: 167 for sequence of MREJ type viii;

SEQ ID NOs: 168 for sequence of MREJ type ix.

Oligonucleotides of at least 10 nucleotides in length which hybridize with any of these nucleic acids and which hybridize with one or more MREJ of types selected from iv to ix are also objects of this invention. Amongst these, primer pairs (or probes) having the following SEQ ID NOs:

64/66, 64/100, 64/101; 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57 for the detection of type i MREJ 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57 for the detection of type ii MREJ 64/67, 64/98, 64/102; 59/58, 60/58, 61/58, 62/58, 63/58 for the detection of type iii MREJ 64/79 for the detection of type iv MREJ 64/80 for the detection of type v MREJ 64/204 for the detection of type vi MREJ 64/112, 64/113 for the detection of type vii MREJ 64/115, 64/116 for the detection of type viii MREJ 64/109 for the detection of type ix MREJ, are also within the scope of this invention.

Further, internal probes having nucleotide sequences defined in any one of SEQ ID NOs: 32, 83, 84, 160, 161, 162, 163, 164, are also within the scope of this invention. Compositions of matter comprising the primers and/or probes annealing or hybridizing with one or more MREJ of types selected from iv to ix as well as with the above nucleic acids, comprising or not primers and/or probes, which hybridize with one or more MREJ of types selected from i to iii, are further objects of this invention. The preferred compositions would comprise the primers having the nucleotide sequences defined in SEQ ID NOs:

64/66, 64/100, 64/101; 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57, for the detection of type i MREJ 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57 for the detection of type ii MREJ 64/67, 64/98, 64/102; 59/58, 60/58, 61/58, 62/58, 63/58 for the detection of type iii MREJ 64/79 for the detection of type iv MREJ 64/80 for the detection of type v MREJ 64/204 for the detection of type vi MREJ 64/112, 64/113 for the detection of type vii MREJ 64/115, 64/116 for the detection of type viii MREJ 64/109 for the detection of type ix MREJ, or probes, which SEQ ID NOs are: 32, 83, 84, 160, 161, 162, 163, 164, or both.

DETAILED DESCRIPTION OF THE INVENTION

Figure 1:
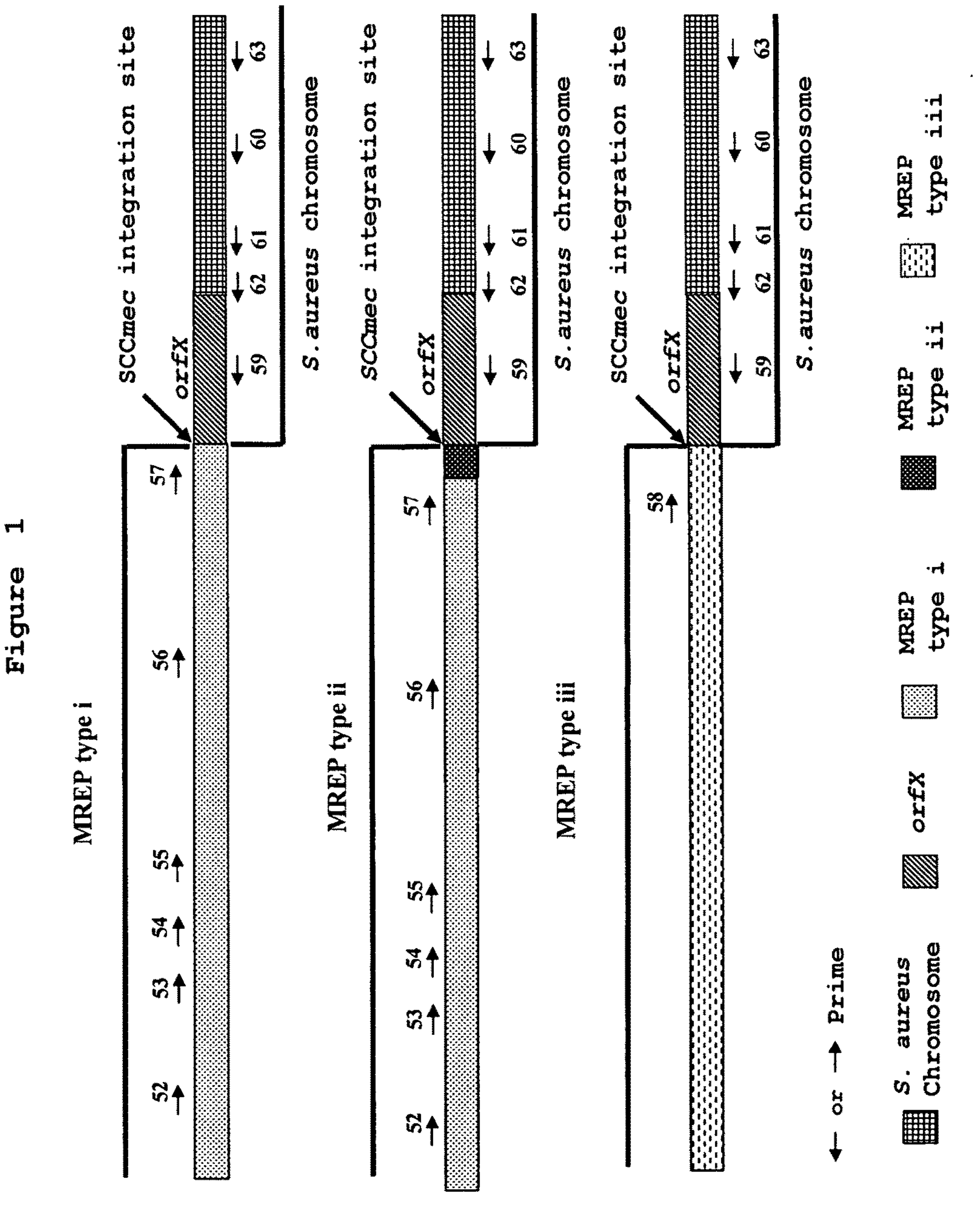
FIG. 1 is a diagram illustrating the position of the primers developed by Hiramatsu et al. (U.S. Pat. No. 6,156,507) in the SCCmec-chromosome right extremity junction for detection and identification of MRSA.

Here is particularly provided a method wherein each of MRSA nucleic acids or a variant or part thereof comprises a selected target region hybridizable with said primers or probes developed to be ubiquitous;

wherein each of said nucleic acids or a variant or part thereof comprises a selected target region hybridizable with said primers or probes;

said method comprising the steps of contacting said sample with said probes or primers and detecting the presence and/or amount of hybridized probes or amplified products as an indication of the presence and/or amount of MRSA.

In the method, sequences from DNA fragments of SCC-mec-chromosome right extremity junction, thereafter named MREJ standing for <<mec right extremity junction>> including sequences from SCCmec right extremity and chromosomal DNA to the right of the SCCmec integration site are used as parental sequences from which are derived the primers and/or the probes. MREJ sequences include our proprietary sequences as well as sequences obtained from public databases and from U.S. Pat. No. 6,156,507 and were selected for their capacity to sensitively, specifically, ubiquitously and rapidly detect the targeted MRSA nucleic acids.

Our proprietary DNA fragments and oligonucleotides (primers and probes) are also another object of this invention.

Compositions of matter such as diagnostic kits comprising amplification primers or probes for the detection of MRSA are also objects of the present invention.

In the above methods and kits, probes and primers are not limited to nucleic acids and may include, but are not restricted to, analogs of nucleotides. The diagnostic reagents constituted by the probes and the primers may be present in any suitable form (bound to a solid support, liquid, lyophilized, etc.).

In the above methods and kits, amplification reactions may include but are not restricted to: a) polymerase chain reaction (PCR), b) ligase chain reaction (LCR), c) nucleic acid sequence-based amplification (NASBA), d) self-sustained sequence replication (3SR), e) strand displacement amplification (SDA), f) branched DNA signal amplification (bDNA), g) transcription-mediated amplification (TMA), h) cycling probe technology (CPT), i) nested PCR, j) multiplex PCR, k) solid phase amplification (SPA), l) nuclease dependent signal amplification (NDSA), m) rolling circle amplification technology (RCA), n) Anchored strand displacement amplification, o) Solid-phase (immobilized) rolling circle amplification.

In the above methods and kits, detection of the nucleic acids of target genes may include real-time or post-amplification technologies. These detection technologies can include, but are not limited to fluorescence resonance energy transfer (FRET)-based methods such as adjacent hybridization of probes (including probe-probe and probe-primer methods), TaqMan probe, molecular beacon probe, Scorpion probe, nanoparticle probe and Amplifluor probe. Other detection methods include target gene nucleic acids detection via immunological methods, solid phase hybridization methods on filters, chips or any other solid support. In these systems, the hybridization can be monitored by fluorescence, chemiluminescence, potentiometry, mass spectrometry, plasmon resonance, polarimetry, colorimetry, flow cytometry or scanometry. Nucleotide sequencing, including sequencing by dideoxy termination or sequencing by hybridization (e.g. sequencing using a DNA chip) represents another method to detect and characterize the nucleic acids of target genes.

In a preferred embodiment, a PCR protocol is used for nucleic acid amplification.

A method for detection of a plurality of potential MRSA strains having different MREJ types may be conducted in separate reactions and physical enclosures, one type at the time. Alternatively, it could be conducted simultaneously for different types in separate physical enclosures, or in the same physical enclosures. In the latter scenario a multiplex PCR reaction could be conducted which would require that the oligonucleotides are all capable of annealing with a target region under common conditions. Since many probes or primers are specific for a determined MREJ type, typing a MRSA strain is a possible embodiment. When a mixture of oligonucleotides annealing together with more than one type is used in a single physical enclosure or container, different labels would be used to distinguish one type from another.

We aim at developing a DNA-based test or kit to detect and identify MRSA. Although the sequences from orfX genes and some SCCmec DNA fragments are available from public databases and have been used to develop DNA-based tests for detection of MRSA, new sequence data allowing to improve MRSA detection and identification which are object of the present invention have either never been characterized previously or were known but not shown to be located at the right extremity of SCCmec adjacent to the integration site (Table 4). These novel sequences could not have been predicted nor detected by the MRSA-specific PCR assay developed by Hiramatsu et al. (U.S. Pat. No. 6,156,507). These sequences will allow to improve current DNA-based tests for the diagnosis of MRSA because they allow the design of ubiquitous primers and probes for the detection and identification of more MRSA strains including all the major epidemic clones from around the world.

The diagnostic kits, primers and probes mentioned above can be used to detect and/or identify MRSA, whether said diagnostic kits, primers and probes are used for in vitro or in situ applications. The said samples may include but are not limited to: any clinical sample, any environmental sample, any microbial culture, any microbial colony, any tissue, and any cell line.

It is also an object of the present invention that said diagnostic kits, primers and probes can be used alone or in combination with any other assay suitable to detect and/or identify microorganisms, including but not limited to: any assay based on nucleic acids detection, any immunoassay, any enzymatic assay, any biochemical assay, any lysotypic assay, any serological assay, any differential culture medium, any enrichment culture medium, any selective culture medium, any specific assay medium, any identification culture medium, any enumeration culture medium, any cellular stain, any culture on specific cell lines, and any infectivity assay on animals.

In the methods and kits described herein below, the oligonucleotide probes and amplification primers have been derived from larger sequences (i.e. DNA fragments of at least 100 base pairs). All DNA sequences have been obtained either from our proprietary sequences or from public databases (Tables 5, 6, 7, 8 and 9).

It is clear to the individual skilled in the art that oligonucleotide sequences other than those described in the present invention and which are appropriate for detection and/or identification of MRSA may also be derived from the proprietary fragment sequences or selected public database sequences. For example, the oligonucleotide primers or probes may be shorter but of a length of at least 10 nucleotides or longer than the ones chosen; they may also be selected anywhere else in the proprietary DNA fragments or in the sequences selected from public databases; they may also be variants of the same oligonucleotide. If the target DNA or a variant thereof hybridizes to a given oligonucleotide, or if the target DNA or a variant thereof can be amplified by a given oligonucleotide PCR primer pair, the converse is also true; a given target DNA may hybridize to a variant oligonucleotide probe or be amplified by a variant oligonucleotide PCR primer. Alternatively, the oligonucleotides may be designed from said DNA fragment sequences for use in amplification methods other than PCR. Consequently, the core of this invention is the detection and/or identification of MRSA by targeting genomic DNA sequences which are used as a source of specific and ubiquitous oligonucleotide probes and/or amplification primers. Although the selection and evaluation of oligonucleotides suitable for diagnostic purposes require much effort, it is quite possible for the individual skilled in the art to derive, from the selected DNA fragments, oligonucleotides other than the ones listed in Tables 5, 6, 7, 8 and 9 which are suitable for diagnostic purposes. When a proprietary fragment or a public database sequence is selected for its specificity and ubiquity, it increases the probability that subsets thereof will also be specific and ubiquitous.

The proprietary DNA fragments have been obtained as a repertory of sequences created by amplifying MRSA nucleic acids with new primers. These primers and the repertory of nucleic acids as well as the repertory of nucleotide sequences are further objects of this invention (Tables 4, 5, 6, 7, 8 and 9).

Claims therefore are in accordance with the present invention.

Sequences for Detection and Identification of MRSA

In the description of this invention, the terms <<nucleic acids>> and <<sequences>> might be used interchangeably. However, <<nucleic acids>> are chemical entities while <<sequences>> are the pieces of information encoded by these <<nucleic acids>>. Both nucleic acids and sequences are equivalently valuable sources of information for the matter pertaining to this invention.

Oligonucleotide Primers and Probes Design and Synthesis

As part of the design rules, all oligonucleotides (probes for hybridization and primers for DNA amplification by PCR) were evaluated for their suitability for hybridization or PCR amplification by computer analysis using standard programs (i.e. the GCG Wisconsin package programs, the primer analysis software Oligo™ 6 and MFOLD 3.0). The potential suitability of the PCR primer pairs was also evaluated prior to their synthesis by verifying the absence of unwanted features such as long stretches of one nucleotide and a high proportion of G or C residues at the 3' end (Persing et al., 1993, Diagnostic Molecular Microbiology: Principles and Applications, American Society for Microbiology, Washington, D.C.). Oligonucleotide amplification primers were synthesized using an automated DNA synthesizer (Applied Biosystems). Molecular beacon designs were evaluated using criteria established by Kramer et al. (http://www.molecular-beacons.org).

The oligonucleotide sequence of primers or probes may be derived from either strand of the duplex DNA. The primers or probes may consist of the bases A, G, C, or T or analogs and they may be degenerated at one or more chosen nucleotide position(s) (Nichols et al., 1994, Nature 369:492-493). Primers and probes may also consist of nucleotide analogs such as Locked Nucleic Acids (LNA) (Koskin et al., 1998, Tetrahedron 54:3607-3630), and Peptide Nucleic Acids (PNA) (Egholm et al., 1993, Nature 365:566-568). The primers or probes may be of any suitable length and may be selected anywhere within the DNA sequences from proprietary fragments, or from selected database sequences which are suitable for the detection of MRSA.

Variants for a given target microbial gene are naturally occurring and are attributable to sequence variation within that gene during evolution (Watson et al., 1987, Molecular Biology of the Gene, $4^{th}$ ed., The Benjamin/Cummings Publishing Company, Menlo Park, Calif.; Lewin, 1989, Genes IV, John Wiley & Sons, New York, N.Y.). For example, different strains of the same microbial species may have a single or more nucleotide variation(s) at the oligonucleotide hybridization site. The person skilled in the art is well aware of the existence of variant nucleic acids and/or sequences for a specific gene and that the frequency of sequence variations depends on the selective pressure during evolution on a given gene product. The detection of a variant sequence for a region between two PCR primers may be demonstrated by sequencing the amplification product. In order to show the presence of sequence variations at the primer hybridization site, one has to amplify a larger DNA target with PCR primers outside that hybridization site. Sequencing of this larger fragment will allow the detection of sequence variation at this primer hybridization site. A similar strategy may be applied to show variations at the hybridization site of a probe. Insofar as the divergence of the target nucleic acids and/or sequences or a part thereof does not affect significantly the sensitivity and/or specificity and/or ubiquity of the amplification primers or probes, variant microbial DNA is under the scope of this invention. Variants of the selected primers or probes may also be used to amplify or hybridize to a variant target DNA.

DNA Amplification

For DNA amplification by the widely used PCR method, primer pairs were derived from our proprietary DNA fragments or from public database sequences.

During DNA amplification by PCR, two oligonucleotide primers binding respectively to each strand of the heat-denatured target DNA from the microbial genome are used to amplify exponentially in vitro the target DNA by successive thermal cycles allowing denaturation of the DNA, annealing of the primers and synthesis of new targets at each cycle (Persing et al, 1993, Diagnostic Molecular Microbiology: Principles and Applications, American Society for Microbiology, Washington, D.C.).

Briefly, the PCR protocols on a standard thermocycler (PTC-200 from MJ Research Inc., Watertown, Mass.) were as follows: Treated standardized bacterial suspensions or genomic DNA prepared from bacterial cultures or clinical specimens were amplified in a 20 μl PCR reaction mixture. Each PCR reaction contained 50 mM KCl, 10 mM Tris-HCl (pH 9.0), 2.5 mM $MgCl_2$, 0.4 μM of each primer, 200 μM of each of the four dNTPs (Pharmacia Biotech), 3.3 μg/μl bovine serum albumin (BSA) (Sigma-Aldrich Canada Ltd, Oakville, Ontario, Canada) and 0.5 unit of Taq DNA polymerase (Promega Corp., Madison, Wis.) combined with the TaqStart™ antibody (BD Biosciences, Palo Alto, Calif.). The TaqStart™ antibody, which is a neutralizing monoclonal antibody to Taq DNA polymerase, was added to all PCR reactions to enhance the specificity and the sensitivity of the amplifications (Kellogg et al., 1994, Biotechniques 16:1134-1137). The treatment of bacterial cultures or of clinical specimens consists in a rapid protocol to lyse the microbial cells and eliminate or neutralize PCR inhibitors (described in application U.S. 60/306,163). For amplification from purified genomic DNA, the samples were added directly to the PCR amplification mixture. An internal control, derived from sequences not found in the target MREJ sequences or in the human genome, was used to verify the efficiency of the PCR reaction and the absence of significant PCR inhibition.

The number of cycles performed for the PCR assays varies according to the sensitivity level required. For example, the sensitivity level required for microbial detection directly from a clinical specimen is higher than for detection from a microbial culture. Consequently, more sensitive PCR assays having more thermal cycles are probably required for direct detection from clinical specimens.

The person skilled in the art of nucleic acid amplification knows the existence of other rapid amplification procedures such as ligase chain reaction (LCR), reverse transcriptase PCR (RT-PCR), transcription-mediated amplification (TMA), self-sustained sequence replication (3SR), nucleic acid sequence-based amplification (NASBA), strand displacement amplification (SDA), branched DNA (bDNA), cycling probe technology (CPT), solid phase amplification (SPA), rolling circle amplification technology (RCA), solid phase RCA, anchored SDA and nuclease dependent signal amplification (NDSA) (Lee et al., 1997, Nucleic Acid Amplification Technologies: Application to Disease Diagnosis, Eaton Publishing, Boston, Mass.; Persing et al., 1993, Diagnostic Molecular Microbiology: Principles and Applications, American Society for Microbiology, Washington, D.C.; Westin et al., 2000, Nat. Biotechnol. 18:199-204). The scope of this invention is not limited to the use of amplification by PCR, but rather includes the use of any nucleic acid amplification method or any other procedure which may be used to increase the sensitivity and/or the rapidity of nucleic acid-based diagnostic tests. The scope of the present invention also covers the use of any nucleic acids amplification and detection technology including real-time or post-amplification detection technologies, any amplification technology combined with detection, any hybridization nucleic acid chips or array technologies, any amplification chips or combination of amplification and hybridization chip technologies. Detection and identification by any nucleotide sequencing method is also under the scope of the present invention.

Any oligonucleotide derived from the *S. aureus* MREJ DNA sequences and used with any nucleic acid amplification and/or hybridization technologies are also under the scope of this invention.

Evaluation of the MRSA Detection Method Developed by Hiramatsu et al.

According to Hiramatsu et al. (Ito et al., 1999, Antimicrob. Agents Chemother. 43:1449-1458; Katayama et al., 2000, Antimicrob. Agents Chemother. 44:1549-1555; Ito et al., 2001, Antimicrob. Agents Chemother. 45:1323-1336, Ma et al., 2002, Antimicrob. Agents Chemother. 46:1147-1152), four types of SCCmec DNA are found among MRSA strains. They have found that SCCmec DNAs are integrated at a specific site of the MSSA chromosome (named orfX). They developed a MRSA-specific multiplex PCR assay including primers that can hybridize to the right extremity of SCCmec types I, II and III (SEQ ID NOs.: 18, 19, 20, 21, 22, 23, 24 in U.S. Pat. No. 6,156,507 corresponding to SEQ ID NOs.: 52, 53, 54, 55, 56, 57, 58, respectively, in the present invention) as well as primers specific to the *S. aureus* chromosome to the right of the SCCmec integration site (SEQ ID NO.: 25, 28, 27, 26, 29 in U.S. Pat. No. 6,156,507 corresponding to SEQ ID NOs.: 59, 60, 61, 62, 63, respectively, in the present invention) (Table 1 and FIG. 1). The set of primers described by Hiramatsu et al. as being the optimal primer combination (SEQ ID NOs.: 22, 24 and 28 in U.S. Pat. No. 6,156,507 corresponding to SEQ ID NOs.: 56, 58 and 60 in the present invention) was used in the present invention to test by PCR a variety of MRSA, MSSA, methicillin-resistant CNS (MRCNS) and methicillin-sensitive CNS (MSCNS) strains (Table 2). A PCR assay performed using a standard thermocycler (PTC-200 from MJ Research Inc.) was used to test the ubiquity, the specificity and the sensitivity of these primers using the following protocol: one μl of a treated standardized bacterial suspension or of a genomic DNA preparation purified from bacteria were amplified in a 20 μl PCR reaction mixture. Each PCR reaction contained 50 mM KCl, 10 mM Tris-HCl (pH 9.0), 0.1% Triton X-100, 2.5 mM $MgCl_2$, 0.4 μM of each of the SCCmec- and *S. aureus* chromosome-specific primers (SEQ ID NOs.: 22, 24 and 28 in U.S. Pat. No. 6,156,507 corresponding to SEQ ID NOs.: 56, 58 and 60 in the present invention), 200 μM of each of the four dNTPs (Pharmacia Biotech), 3.3 μg/μl BSA (Sigma), and 0.5 U Taq polymerase (Promega) coupled with TaqStart™ Antibody (BD Biosciences).

PCR reactions were then subjected to thermal cycling 3 min at 94° C. followed by 40 cycles of 60 seconds at 95° C. for the denaturation step, 60 seconds at 55° C. for the annealing step, and 60 seconds at 72° C. for the extension step, then followed by a terminal extension of 7 minutes at 72° C. using a standard thermocycler (PTC-200 from MJ Research Inc.). Detection of the PCR products was made by electrophoresis in agarose gels (2%) containing 0.25 μg/ml of ethidium bromide. Twenty of the 39 MRSA strains tested were not amplified with the PCR assay developed by Hiramatsu et al. (Example 1, Tables 2 and 3).

Figure 2:
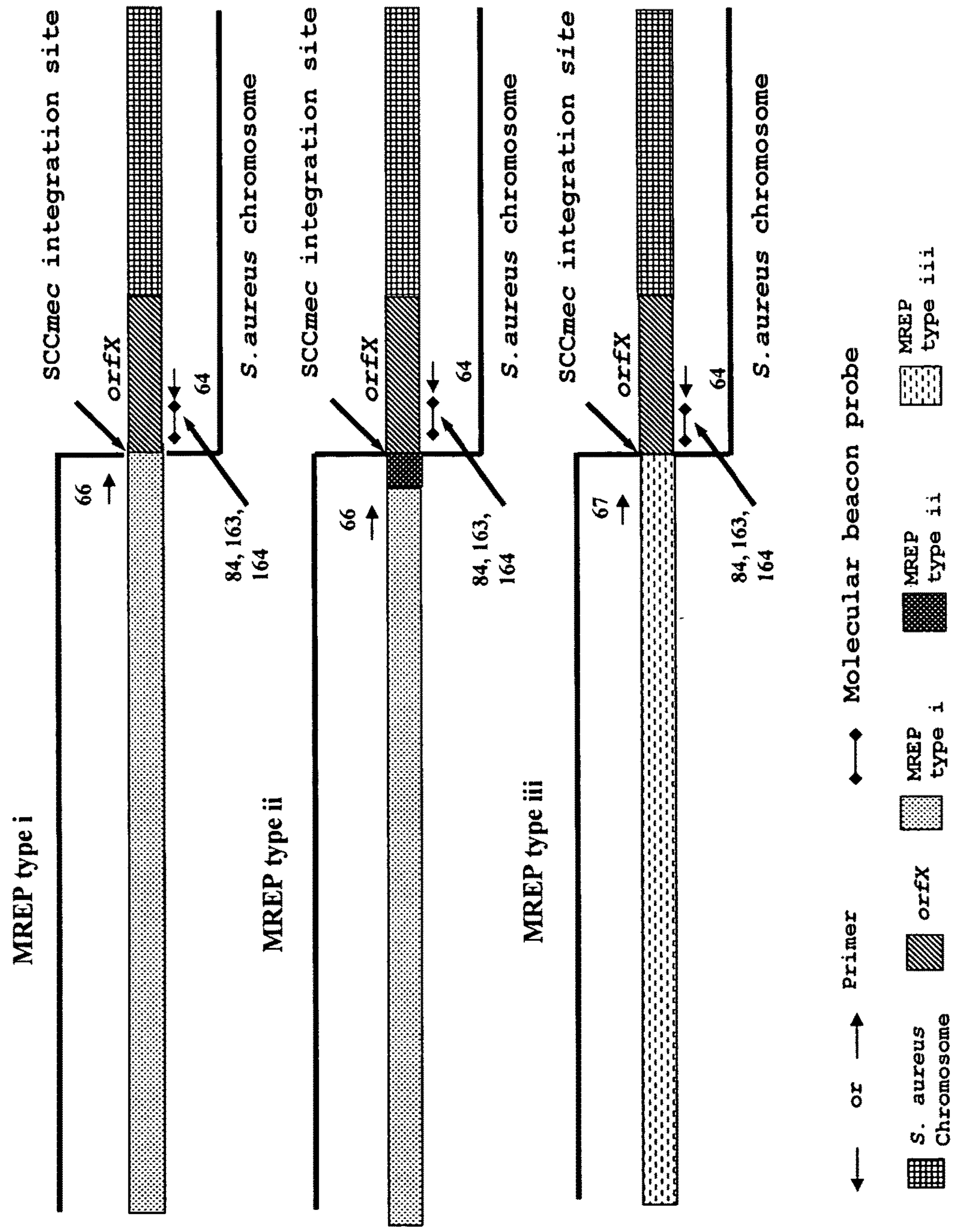
FIG. 2 is a diagram illustrating the position of the primers selected in the present invention in the SCCmec-orfX right extremity junction for detection and identification of MRSA.
Figure 2:
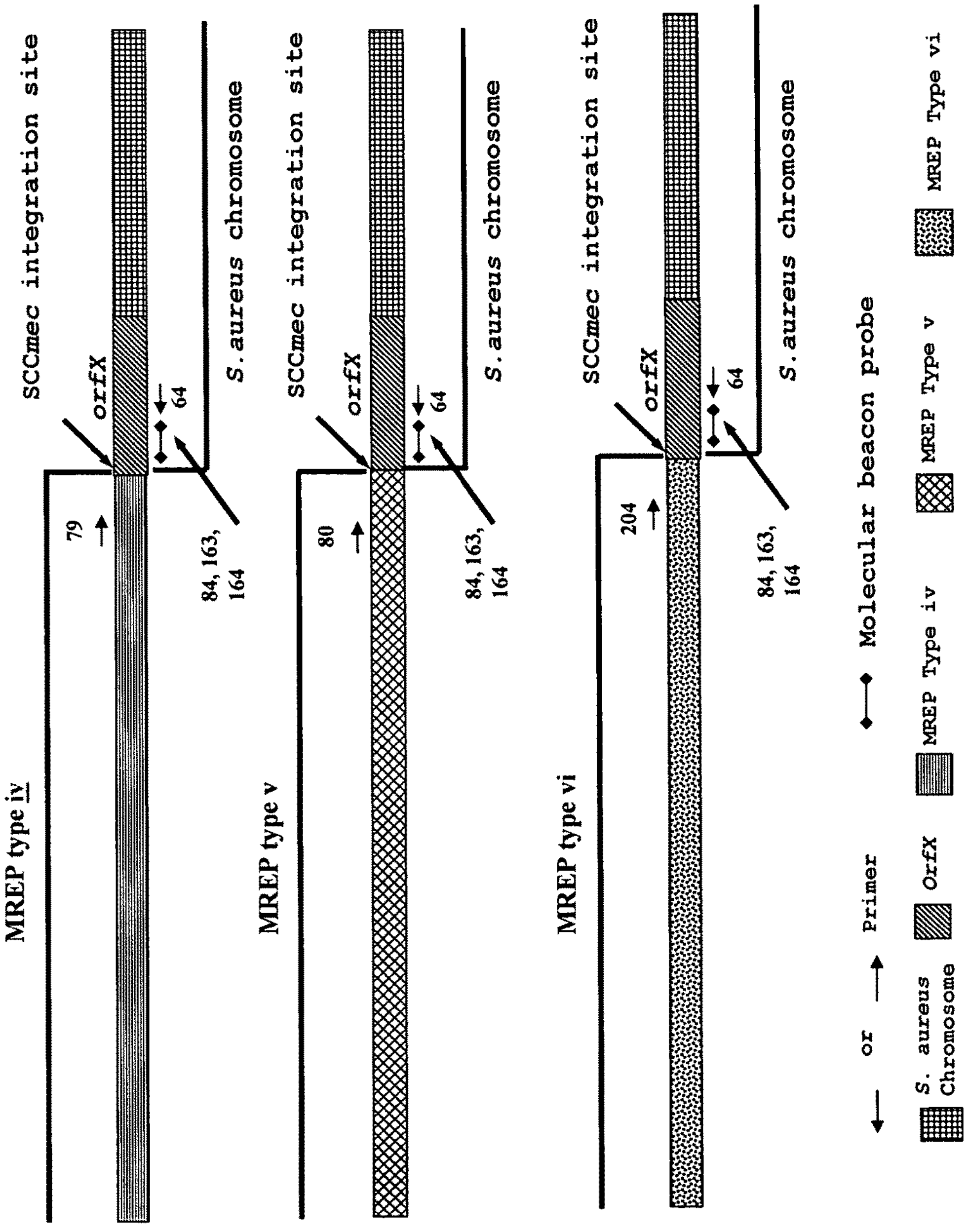
Figure 2:
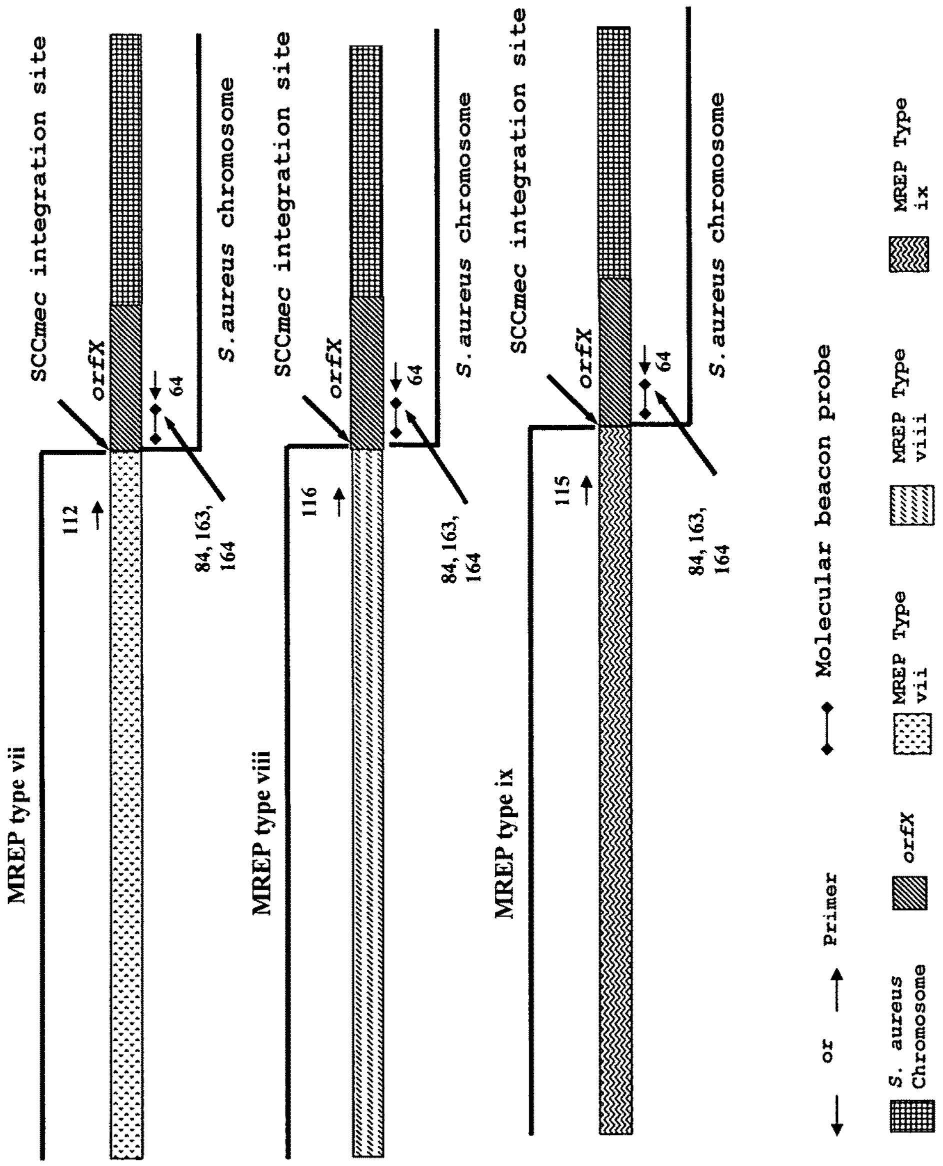

With a view of establishing a rapid diagnostic test for MRSAs, the present inventors developed new sets of primers specific to the right extremity of SCCmec types I and II (SEQ ID NOs.: 66, 100 and 101) (Annex 1), SCCmec type II (SEQ ID NOs.: 97 and 99), SCCmec type III (SEQ ID NOs.: 67, 98 and 102) and in the *S. aureus* chromosome to the right of the SCCmec integration site (SEQ ID NOs.: 64, 70, 71, 72, 73, 74, 75 and 76) (Table 5). These primers, amplifying short amplicons (171 to 278 bp), are compatible for use in rapid PCR assays (Table 7). The design of these primers was based on analysis of multiple sequence alignments of orfX and SCCmec sequences described by Hiramatsu et al. (U.S. Pat. No. 6,156,507) or available from GenBank (Table 10, Annex I). These different sets of primers were used to test by PCR a variety of MRSA, MSSA, MRCNS and MSCNS strains. Several amplification primers were developed to detect all three SCCmec types (SEQ ID NOs.: 97 and 99 for SCCmec type II, SEQ ID NOs.: 66, 100 and 101 for SCCmec types I and II and SEQ ID NOs.: 67, 98 and 102 for SCCmec type III). Primers were chosen according to their specificity for MRSA strains, their analytical sensitivity in PCR and the length of the PCR product. A set of two primers was chosen for the SCCmec right extremity region (SEQ ID NO.: 66 specific to SCCmec types I and II; SEQ ID NO.: 67 specific to SCCmec type III). Of the 8 different primers designed to anneal on the *S. aureus* chromosome to the right of the SCCmec integration site (targeting orfX gene) (SEQ ID NOs.: 64, 70, 71, 72, 73, 74, 75 and 76), only one (SEQ ID.: 64) was found to be specific for MRSA based on testing with a variety of MRSA, MSSA, MRCNS and MSCNS strains (Table 12). Consequently, a PCR assay using the optimal set of primers (SEQ ID NOs.: 64, 66 and 67) which could amplify specifically MRSA strains containing SCCmec types I, II and III was developed (FIG. 2, Annex I). While the PCR assay developed with this novel set of primers was highly sensitive (i.e allowed the detection of 2 to 5 copies of genome for all three SCCmec types) (Table 11), it had the same shortcomings (i.e. lack of ubiquity) of the test developed by Hiramatsu et al. The 20 MRSA strains which were not amplified by the Hiramatsu et al. primers were also not detected by the set of primers comprising SEQ ID NOs.: 64, 66 and 67 (Tables 3 and 12). Clearly, diagnostic tools for achieving at least 50% ubiquity amongst the tested strains are needed.

With a view to establish a more ubiquitous (i.e. ability to detect all or most MRSA strains) detection and identification method for MRSA, we determined the sequence of the MREJ present in these 20 MRSA strains which were not amplified. This research has led to the discovery and identification of seven novel distinct MREJ target sequences which can be used for diagnostic purposes. These seven new MREJ sequences could not have been predicted nor detected with the system described in U.S. Pat. No. 6,156,507 by Hiramatsu et al. Namely, the present invention represents an improved method for the detection and identification of MRSA because it provides a more ubiquitous diagnostic method which allows for the detection of all major epidemic MRSA clones from around the world.

Sequencing of MREJ Nucleotide Sequences from MRSA Strains not Amplifiable with Primers Specific to SCCmec types I, II and III Since DNA from twenty MRSA strains were not amplified with the set of primers developed by Hiramatsu et al. (SEQ ID NOs.: 22, 24 and 28 in U.S. Pat. No. 6,156,507 corresponding to SEQ ID NOs.: 56, 58 and 60 in the present invention) (Tables 2 and 3) nor with the set of primers developed in the present invention based on the same three SCCmec types (I, II and III) sequences (SEQ ID NOs.: 64, 66 and 67) (Table 12), the nucleotide sequence of the MREJ was determined for sixteen of these twenty MRSA strains.

Figure 3:
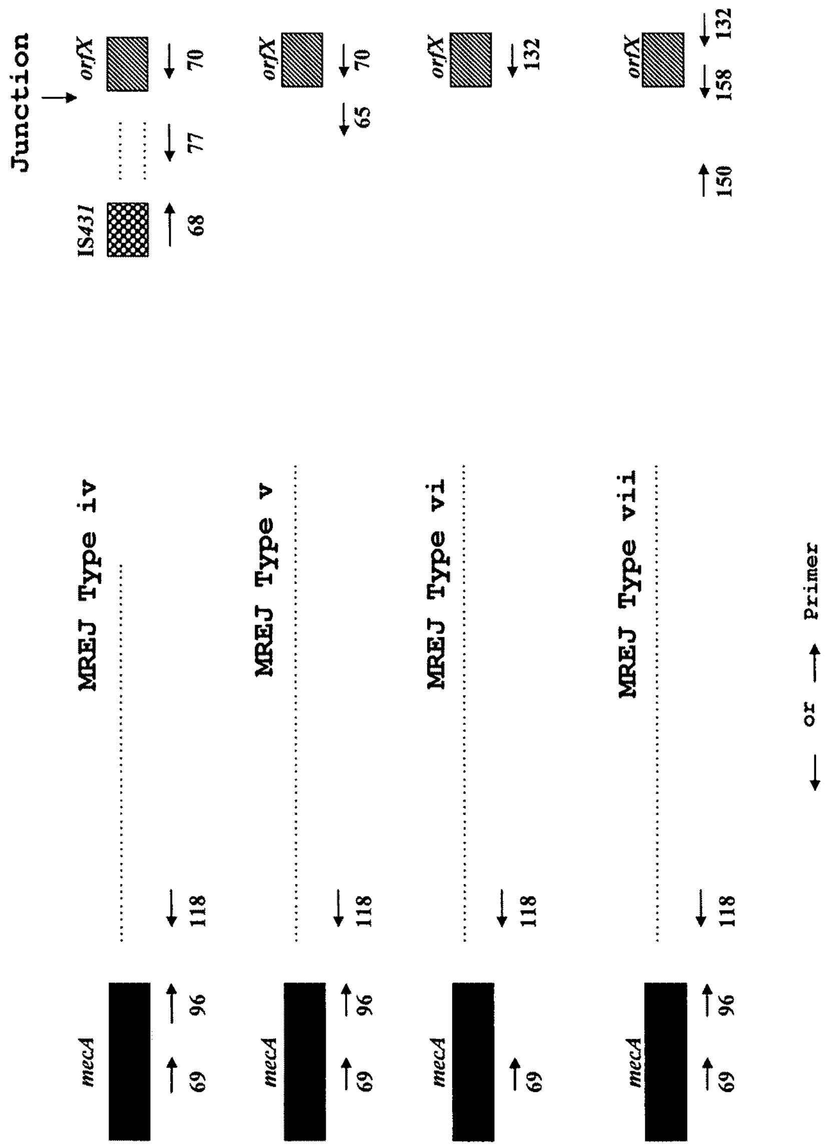
FIG. 3 is a diagram illustrating the position of the primers selected in the present invention to sequence new MREP types.
Figure 3:
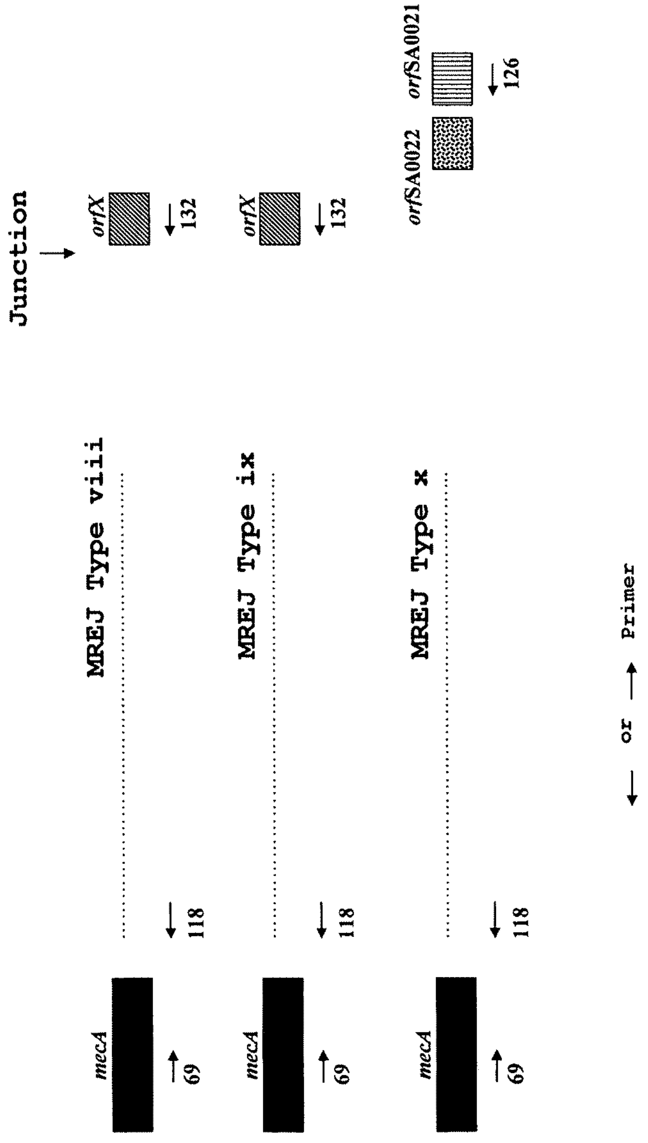

Transposase of IS431 is often associated with the insertion of resistance genes within the mec locus. The gene encoding this transposase has been described frequently in one or more copies within the right segment of SCCmec (Oliveira et al., 2000, Antimicrob. Agents Chemother. 44:1906-1910; Ito et al., 2001, Antimicrob. Agents Chemother. 45:1323-36). Therefore, in a first attempt to sequence the novel MREJ for 16 of the 20 MRSA strains described in Table 3, a primer was designed in the sequence of the gene coding for the transposase of IS431 (SEQ ID NO.: 68) and combined with an orfX-specific primer to the right of the SCCmec integration site (SEQ ID NO.: 70) (Tables 5 and 8). The strategy used to select these primers is illustrated in FIG. 3.

The MREJ fragments to be sequenced were amplified using the following amplification protocol: one µL of treated cell suspension (or of a purified genomic DNA preparation) was transferred directly into 4 tubes containing 39 µL of a PCR reaction mixture. Each PCR reaction contained 50 mM KCl, 10 mM Tris-HCl (pH 9.0), 0.1% Triton X-100, 2.5 mM $MgCl_2$, 1 µM of each of the 2 primers (SEQ ID NOs.: 68 and 70), 200 µM of each of the four dNTPs, 3.3 µg/µl of BSA (Sigma-Aldrich Canada Ltd) and 0.5 unit of Taq DNA polymerase (Promega) coupled with the TaqStart™ Antibody (BD Bisociences). PCR reactions were submitted to cycling using a standard thermocycler (PTC-200 from MJ Research Inc.) as follows: 3 min at 94° C. followed by 40 cycles of 5 sec at 95° C. for the denaturation step, 30 sec at 55° C. for the annealing step and 2 min at 72° C. for the extension step.

Subsequently, the four PCR-amplified mixtures were pooled and 10 µL of the mixture were resolved by electrophoresis in a 1.2% agarose gel containing 0.25 µg/mL of ethidium bromide. The amplicons were then visualized with an Alpha-Imager (Alpha Innotech Corporation, San Leandro, Calif.) by exposing to UV light at 254 nm. Amplicon size was estimated by comparison with a 1 kb molecular weight ladder (Life Technologies, Burlington, Ontario, Canada). The remaining PCR-amplified mixture (150 µL, total) was also resolved by electrophoresis in a 1.2% agarose gel. The amplicons were then visualized by staining with methylene blue (Flores et al., 1992, Biotechniques, 13:203-205). Amplicon size was once again estimated by comparison with a 1 kb molecular weight ladder. Of the sixteen strains selected from the twenty described in Table 3, six were amplified using SEQ ID NOs.: 68 and 70 as primers (CCRI-178, CCRI-8895, CCRI-8903, CCRI-1324, CCRI-1331 and CCRI-9504). For these six MRSA strains, an amplification product of 1.2 kb was obtained. The band corresponding to this specific amplification product was excised from the agarose gel and purified using the QIAquick™ gel extraction kit (QIAGEN Inc., Chatsworth, Calif.). The gel-purified DNA fragment was then used directly in the sequencing protocol. Both strands of the MREJ amplification products were sequenced by the dideoxynucleotide chain termination sequencing method by using an Applied Biosystems automated DNA sequencer (model 377) with their Big Dye™ Terminator Cycle Sequencing Ready Reaction Kit (Applied Biosystems, Foster City, Calif.). The sequencing reactions were performed by using the same primers (SEQ ID NOs.: 68 and 70) and 10 ng/100 bp per reaction of the gel-purified amplicons. Sequencing of MREJ from the six MRSA strains (CCRI-178, CCRI-8895, CCRI-8903, CCRI-1324, CCRI-1331 and CCRI-9504) described in Table 3 yielded SEQ ID NOs.: 42, 43, 44, 45, 46 and 51, respectively (Table 4).

In order to ensure that the determined sequence did not contain errors attributable to the sequencing of PCR artefacts, we have sequenced two preparations of the gel-purified MREJ amplification products originating from two independent PCR amplifications. For most target fragments, the sequences determined for both amplicon preparations were identical. Furthermore, the sequences of both strands were 100% complementary thereby confirming the high accuracy of the determined sequence. The MREJ sequences determined using the above strategy are described in the Sequence Listing and in Table 4.

In order to sequence MREJ in strains for which no amplicon had been obtained using the strategy including primers specific to the transposase gene of IS431 and orfX, another strategy using primers targeting mecA and orfX sequences was used to amplify longer genomic fragments. A new PCR primer targeting mecA (SEQ ID NO.: 69) (Table 8) to be used in combination with the same primer in the orfX sequence (SEQ ID NO.: 70). The strategy used to select these primers is illustrated in FIG. 3.

The following amplification protocol was used: Purified genomic DNA (300 ng) was transferred to a final volume of 50 μl of a PCR reaction mixture. Each PCR reaction contained 1× Herculase buffer (Stratagene, La Jolla, Calif.), 0.8 μM of each of the 2 primers (SEQ ID NOs.: 69 and 70), 0.56 mM of each of the four dNTPs and 5 units of Herculase (Stratagene). PCR reactions were subjected to cycling using a standard thermal cycler (PTC-200 from MJ Research Inc.) as follows: 2 min at 92° C. followed by 35 or 40 cycles of 10 sec at 92° C. for the denaturation step, 30 sec at 55° C. for the annealing step and 30 min at 68° C. for the extension step.

Subsequently, 10 μL of the PCR-amplified mixture were resolved by electrophoresis in a 0.7% agarose gel containing 0.25 μg/mL of ethidium bromide. The amplicons were then visualized as described above. Amplicon size was estimated by comparison with a 1 kb molecular weight ladder (Life Technologies). A reamplification reaction was then performed in 2 to 5 tubes using the same protocol with 3 μl of the first PCR reaction used as test sample for the second amplification. The PCR-reamplified mixtures were pooled and also resolved by electrophoresis in a 0.7% agarose gel. The amplicons were then visualized by staining with methylene blue as described above. An amplification product of approximately 12 kb was obtained using this amplification strategy for all strains tested. The band corresponding to the specific amplification product was excised from the agarose gel and purified as described above. The gel-purified DNA fragment was then used directly in the sequencing protocol as described above. The sequencing reactions were performed by using the same amplification primers (SEQ ID NOs.: 69 and 70) and 425-495 ng of the gel-purified amplicons per reaction. Subsequently, internal sequencing primers (SEQ ID NOs.: 65, 77 and 96) (Table 8) were used to obtain sequence data on both strands for a larger portion of the amplicon. Five of the 20 MRSA strains (CCRI-1331, CCRI-1263, CCRI-1377, CCRI-1311 and CCRI-2025) described in Table 3 were sequenced using this strategy, yielding SEQ ID NOs.: 46, 47, 48, 49 and 50, respectively (Table 4). Sequence within mecA gene was also obtained from the generated amplicons yielding SEQ ID NOs: 27, 28, 29, 30 and 31 from strains CCRI-2025, CCRI-1263, CCRI-1311, CCRI-1331 and CCRI-1377, respectively (Table 4). Longer sequences within the mecA gene and from downstream regions were also obtained for strains CCRI-2025, CCRI-1331, and CCRI-1377 as described below.

In order to obtain longer sequences of the orfX gene, two other strategies using primers targeting mecA and orfX sequences (at the start codon) was used to amplify longer chromosome fragments. A new PCR primer was designed in orfX (SEQ ID NO.: 132) to be used in combination with the same primer in the mecA gene (SEQ ID NO.: 69). The strategy used to select these primers is illustrated in FIG. 3. Eight *S. aureus* strains were amplified using primers SEQ ID NOs.: 69 and 132 (CCRI-9860, CCRI-9208, CCRI-9504, CCRI-1331, CCRI-9583, CCRI-9681, CCRI-2025 and CCRI-1377). The strategy used to select these primers is illustrated in FIG. 3.

The following amplification protocol was used: Purified genomic DNA (350 to 500 ng) was transferred to a 50 μl PCR reaction mixture. Each PCR reaction contained 1× Herculase buffer (Stratagene), 0.8 μM of each of the set of 2 primers (SEQ ID NOs.: 69 and 132), 0.56 mM of each of the four dNTPs and 7.5 units of Herculase (Stratagene) with 1 mM $MgCl_2$. PCR reactions were subjected to thermocycling as described above.

Subsequently, 5 μL of the PCR-amplified mixture were resolved by electrophoresis in a 0.8% agarose gel containing 0.25 μg/mL of ethidium bromide. The amplicons were then visualized as described above. For one *S. aureus* strain (CCRI-9583), a reamplification was then performed by using primers SEQ ID NOs.: 96 and 158 (FIG. 3) in 4 tubes, using the same PCR protocol, with 2 μl of the first PCR reaction as test sample for the second amplification. The PCR-reamplified mixtures were pooled and also resolved by electrophoresis in a 0.8% agarose gel. The amplicons were then visualized by staining with methylene blue as described above. A band of approximately 12 to 20 kb was obtained using this amplification strategy depending on the strains tested. The band corresponding to the specific amplification product was excised from the agarose gel and purified using the QIAquick™ gel extraction kit or QIAEX II gel extraction kit (QIAGEN Inc.). Two strains, CCRI-9583 and CCRI-9589, were also amplified with primers SEQ ID NOs.: 132 and 150, generating an amplification product of 1.5 kb. Long amplicons (12-20 kb) were sequenced using 0.6 to 1 μg per reaction, while short amplicons (1.5 kb) were sequenced using 150 ng per reaction. Sequencing reactions were performed using different sets of primers for each *S. aureus* strain: 1) SEQ ID NOs.: 68, 70, 132, 145, 146, 147, 156, 157 and 158 for strain CCRI-9504; 2) SEQ ID NOs.: 70, 132, 154 and 155 for strain CCRI-2025; 3) SEQ ID NOs.: 70, 132, 148, 149, 158 and 159 for strain CCRI-9681; 4) SEQ ID NOs.: 70, 132, 187, and 188 for strain CCRI-9860; 5) SEQ ID NOs: 70, 132, 150 and 159 for strain CCRI-9589, 6) SEQ ID NOs.: 114, 123, 132, 150 and 158 for strain CCRI-9583; 7) SEQ ID NOs: 70, 132, 154 and 155 for strain CCRI-1377, 8) SEQ ID NOs.: 70, 132, 158 and 159 for strain CCRI-9208; 9) SEQ ID NOs: 68, 70, 132, 145, 146, 147 and 158 for strain CCRI-1331; and 10) SEQ ID NOs.: 126 and 127 for strain CCRI-9770.

In one strain (CCRI-9770), the orfX and orfSA0022 genes were shown to be totally or partially deleted based on amplification using primers specific to these genes (SEQ ID NOs: 132 and 159 and SEQ ID NOs.: 128 and 129, respectively) (Table 8). Subsequently, a new PCR primer was designed in orfSA0021 (SEQ ID NO.: 126) to be used in combination with the same primer in the mecA gene (SEQ ID NO.: 69). An amplification product of 4.5 kb was obtained with this primer set. Amplification, purification of amplicons and sequencing of amplicons were performed as described above.

To obtain the sequence of the SSCmec region containing mecA for ten of the 20 MRSA strains described in Table 3 (CCRI-9504, CCRI-2025, CCRI-9208, CCRI-1331, CCRI-9681, CCRI-9860, CCRI-9770, CCRI-9589, CCRI-9583 and CCRI-1377), the primer described above designed in mecA (SEQ ID NO.: 69) was used in combination with a primer designed in the downstream region of mecA (SEQ ID NO.: 118) (Table 8). An amplification product of 2 kb was obtained for all the strains tested. For one strain, CCRI-9583, a re-amplification with primers SEQ ID NOs.: 96 and 118 was performed with the amplicon generated with primers SEQ ID NOs.: 69 and 132 described above. The amplification, re-amplification, purification of amplicons and sequencing reactions were performed as described above. Sequencing reactions were performed with amplicons generated with SEQ ID NOs.: 69 and 132 described above or SEQ ID NOs.: 69 and 118. Different sets of sequencing primers were used for each *S. aureus* strain: 1) SEQ ID NOs.: 69, 96, 117, 118, 120, 151, 152 for strains CCRI-9504, CCRI-2025, CCRI-1331, CCRI-9770 and CCRI-1377; 2) SEQ ID NOs.: 69, 96, 118 and 120 for strains CCRI-9208, CCRI-9681 and CCRI-9589; 3) SEQ ID NOs.: 69, 96, 117, 118, 120 and 152 for strain CCRI-9860; and 4) SEQ ID NOs.: 96, 117, 118, 119, 120, 151 and 152 for strain CCRI-9583.

The sequences obtained for 16 of the 20 strains non-amplifiable by the Hiramatsu assay (Table 4) were then compared to the sequences available from public databases. In all cases, portions of the sequence had an identity close to 100% to publicly available sequences for orfX (SEQ ID NOs.: 42-51, 165-168 and 171) or mecA and downstream region (SEQ ID NOs.: 27-31, 189-193, 195, 197-199 and 225). However, while the orfX portion of the fragments (SEQ ID NOs.: 42-51, 165-168 and 171) shared nearly 100% identity with the orfX gene of MSSA strain NCTC 8325 described by Hiramatsu et al. (SEQ ID NO.: 3), the DNA sequence within the right extremity of SCCmec itself was shown to be very different from those of types I, II, III and IV described by Hiramatsu et al. (Table 13, FIG. 4). Six different novel sequence types were obtained.

It should be noted that Hiramatsu et al. demonstrated that SCCmec type I could be associated with MREP type i, SCCmec types II and IV are associated with MREP type ii, and SCCmec type III is associated with MREP type iii. Our MREJ sequencing data from various MRSA strains led to the discovery of 6 novel MREP types designated types iv, v, vi, vii, viii, and ix. The MREJ comprising distinct MREP types were named according to the MREP numbering scheme. Hence, MREP type i is comprised within MREJ type i, MREP type ii is comprised within MREJ type ii and so on up to MREP type ix.

The sequences within the right extremity of SCCmec obtained from strains CCRI-178, CCRI-8895, CCRI-8903, CCRI-1324, CCRI-1331 and CCRI-9504 (SEQ ID NOs.: 42, 43, 44, 45, 46 and 51) were nearly identical to each other and exhibited nearly 100% identity with IS431 (GenBank accession numbers AF422691, ABO37671, AF411934). However, our sequence data revealed for the first time the location of this IS431 sequence at the right extremity of SCCmec adjacent to the integration site. Therefore, as the sequences at the right extremity of SCCmec from these 6 MRSA strains were different from those of SCCmec type I from strain NCTC 10442, SCCmec type II from strain N315, SCCmec type III from strain 85/2082 and SCCmec type IV from strains CA05 and 8/6-3P described by Hiramatsu et al. (Ito et al., 2001, Antimicrob. Agents Chemother. 45:1323-1336; Ma et al., 2002, Antimicrob. Agents Chemother. 46:1147-1152), these new sequences were designated as MREP type iv (SEQ ID NOs.: 42-46 and 51). A BLAST search with the SCCmec portion of MREP type iv sequences produced significant alignments with sequences coding for portions of a variety of known transposases. For example, when compared to Genbank accession no. AB037671, MREP type iv from SEQ ID NO. 51 shared 98% identity with the putative transposase of IS431 and its downstream region; two gaps of 7 nucleotides each were also present in the alignment.

Sequences obtained from strains CCRI-1263, CCRI-1377, CCRI-1311 and CCRI-2025 (SEQ ID NOs.: 47-50) were nearly identical to each other and different from all three SCCmec types and MREP type iv and, consequently, were designated as MREP type v. When compared with Genbank sequences using BLAST, MREP type v sequences did not share any significant homology with any published sequence, except for the first 28 nucleotides. That short stretch corresponded to the last 11 coding nucleotides of orfX, followed by the 17 nucleotides downstream, including the right inverted repeat (IR-R) of SCCmec.

Sequence obtained from strain CCRI-9208 was also different from all three SCCmec types and MREP types iv and v and, consequently, was designated as MREP type vi (SEQ ID NO.: 171). Upon a BLAST search, MREP type vi was shown to be unique, exhibiting no significant homology to any published sequence.

Sequences obtained from strains CCRI-9583 and CCRI-9589 were also different from all three SCCmec types and MREP types iv to vi and were therefore designated as MREP type vii (SEQ ID NOs.: 165 and 166). Upon a BLAST search, MREP type vii was also shown to be unique, exhibiting no significant homology to any published sequence.

Sequence obtained from strain CCRI-9860 was also different from all three SCCmec types and MREP types iv to vii and was therefore designated as MREP type viii (SEQ ID NO.: 167). Sequence obtained from strain CCRI-9681 was also different from all three SCCmec types and MREP types iv to viii and was therefore designated as MREP type ix (SEQ ID NO.: 168). BLAST searches with the SCCmec portion of MREP types viii and ix sequences yielded significant alignments, but only for the first ~150 nucleotides of each MREP type. For example, the beginning of the MREP type viii sequence had 88% identity with a portion of Genbank accession no. AB063173, but no significant homology with any published sequence was found for the rest of the sequence. In the same manner, the first ~150 nucleotides of MREP type ix had 97% identity with the same portion of AB063173, with the rest of the sequence being unique. The short homologous portion of MREP types viii and ix corresponds in AB063173 to the last 14 coding nucleotides of orfX, the IR-R of SCCmec, and a portion of orfCM009. Although sharing resemblances, MREP types viii and ix are very different from one another; as shown in Table 13, there is only 55.2% identity between both types for the first 500 nucleotides of the SCCmec portion.

Finally, we did not obtain any sequence within SSCmec from strain CCRI-9770. However, as described in the section "Sequencing of MREJ nucleotide sequences from MRSA strains not amplifiable with primers specific to SCCmec types I, II and III", this strain has apparently a partial or total deletion of the orfX and orfSA0022 genes in the chromosomal DNA to the right of the SCCmec integration site and this would represent a new right extremity junction. We therefore designated this novel sequence as MREP type x (SEQ ID NO.: 172). Future sequencing should reveal whether this so called MREJ type x contains a novel MREP type x or if the lack of amplification is indeed caused by variation in the chromosomal part of the MREJ.

The sequences of the first 500-nucleotide portion of the right extremity of all SCCmec obtained in the present invention were compared to those of SCCmec types I, II and III using GCG programs Pileup and Gap. Table 13 depicts the identities at the nucleotide level between SCCmec right extremities of the six novel sequences with those of SCCmec types I, II and III using the GCG program Gap. While SCCmec types I and II showed nearly 79.2% identity (differing only by a 102 bp insertion present in SCCmec type II) (FIGS. 1, 2 and 4), all other MREP types showed identities varying from 40.9 to 57.1%. This explains why the right extremities of the novel MREP types iv to ix disclosed in the present invention could not have been predicted nor detected with the system described by Hiramatsu et al.

Four strains (CCRI-1312, CCRI-1325, CCRI-9773 and CCRI-9774) described in Table 3 were not sequenced but rather characterized using PCR primers. Strains CCRI-1312 and CCRI-1325 were shown to contain MREP type v using specific amplification primers described in Examples 4, 5 and 6 while strains CCRI-9773 and CCRI-9774 were shown to contain MREP type vii using specific amplification primers described in Example 7.

To obtain the complete sequence of the SCCmec present in the MRSA strains described in the present invention, primers targeting the S. aureus chromosome to the left (upstream of the mecA gene) of the SCCmec integration site were developed. Based on available public database sequences, 5 different primers were designed (SEQ ID NOs.: 85-89) (Table 9). These primers can be used in combination with S. aureus chromosome-specific primers in order to sequence the entire SCCmec or, alternatively, used in combination with a mecA-specific primer (SEQ ID NO.: 81) in order to sequence the left extremity junction of SCCmec. We have also developed several primers specific to known SCCmec sequences spread along the locus in order to obtain the complete sequence of SCCmec (Table 9). These primers will allow to assign a SCCmec type to the MRSA strains described in the present invention.

Selection of Amplification Primers from SCCmec/orfX Sequences

The MREJ sequences determined by the inventors or selected from public databases were used to select PCR primers for detection and identification of MRSA. The strategy used to select these PCR primers was based on the analysis of multiple sequence alignments of various MREJ sequences.

Upon analysis of the six new MREP types iv to ix sequence data described above, primers specific to each new MREP type sequence (SEQ ID NOs.: 79, 80, 109, 112, 113, 115, 116 and 204) were designed (FIG. 2, Table 5, Examples 3, 4, 5, 6, 7 and 8). Primers specific to MREP types iv, v and vii (SEQ ID NOs.: 79, 80 and 112) were used in multiplex with the three primers to detect SCCmec types I, II and III (SEQ ID NOs: 64, 66 and 67) and the primer specific to the S. aureus orfX (SEQ ID NO. 64) (Examples 3, 4, 5, 6 and 7). Primers specific to MREP types vi, viii and ix (SEQ ID NOs.: 204, 115, 116 and 109) were also designed and tested against their specific target (Example 8).

Detection of Amplification Products

Classically, the detection of PCR amplification products is performed by standard ethidium bromide-stained agarose gel electrophoresis as described above. It is however clear that other methods for the detection of specific amplification products, which may be faster and more practical for routine diagnosis, may be used. Examples of such methods are described in co-pending patent application WO01/23604 A2.

Amplicon detection may also be performed by solid support or liquid hybridization using species-specific internal DNA probes hybridizing to an amplification product. Such probes may be generated from any sequence from our repertory and designed to specifically hybridize to DNA amplification products which are objects of the present invention. Alternatively, amplicons can be characterized by sequencing. See co-pending patent application WO01/23604 A2 for examples of detection and sequencing methods.

In order to improve nucleic acid amplification efficiency, the composition of the reaction mixture may be modified (Chakrabarti and Schutt, 2002, Biotechniques, 32:866-874; Al-Soud and Radstrom, 2002, J. Clin. Microbiol., 38:4463-4470; Al-Soud and Radstrom, 1998, Appl. Environ. Microbiol., 64:3748-3753; Wilson, 1997, Appl. Environ. Microbiol., 63:3741-3751). Such modifications of the amplification reaction mixture include the use of various polymerases or the addition of nucleic acid amplification facilitators such as betaine, BSA, sulfoxides, protein gp32, detergents, cations, tetramethylamonium chloride and others.

In a preferred embodiment, real-time detection of PCR amplification was monitored using molecular beacon probes in a SMART CYCLER® apparatus (Cepheid, Sunnyvale, Calif.). A multiplex PCR assay containing primers specific to MREP types i to v and orfX of S. aureus (SEQ ID NOs.: 64, 66, 67, 79 and 80), a molecular beacon probe specific to the orfX sequence (SEQ ID NO. 84, see Annex II and FIG. 2) and an internal control to monitor PCR inhibition was developed. The internal control contains sequences complementary to MREP type iv- and orfX-specific primers (SEQ ID NOs. 79 and and 64). The assay also contains a molecular beacon probe labeled with tetrachloro-6-carboxyfluorescein (TET) specific to sequence within DNA fragment generated during amplification of the internal control. Each PCR reaction contained 50 mM KCl, 10 mM Tris-HCl (pH 9.0), 0.1% Triton X-100, 3.45 mM $MgCl_2$, 0.8 µM of each of the MREP-specific primers (SEQ ID NOs.: 66 and 67) and orfX-specific primer (SEQ ID NO.: 64), 0.4 µM of each of the MREP-specific primers (SEQ ID NOs.: 79 and 80), 80 copies of the internal control, 0.2 µM of the TET-labeled molecular beacon probe specific to the internal control, 0.2 µM of the molecular beacon probe (SEQ ID NO.: 84) labeled with 6-carboxyfluorescein (FAM), 330 µM of each of the four dNTPs (Pharmacia Biotech), 3.45 µg/µl of BSA (Sigma), and 0.875 U Taq polymerase (Promega) coupled with TaqStart™ Antibody (BD Biosciences). The PCR amplification on the SMART CYCLER® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. Sensitivity tests performed by using purified genomic DNA from one MRSA strain of each MREP type (i to v) showed a detection limit of 2 to 10 genome copies (Example 5). None of the 26 MRCNS or 10 MSCNS tested were positive with this multiplex assay. The eight MRSA strains (CCRI-9208, CCRI-9770, CCRI-9681, CCRI-9860, CCRI-9583, CCRI-9773, CCRI-9774, CCRI-9589) which harbor the new MREP types vi, viii, ix and x sequences described in the present invention remained undetectable (Example 5).

In a preferred embodiment, detection of MRSA using the real-time multiplex PCR assay on the SMART CYCLER® apparatus (Cepheid, Sunnyvale, Calif.) directly from clinical specimens was evaluated. A total of 142 nasal swabs were collected during a MRSA hospital surveillance program at the Montreal General Hospital (Montreal, Quebec, Canada). The swab samples were tested at the Centre de Recherche en Infectiologie de l'Université Laval within 24 hours of collection. Upon receipt, the swabs were plated onto mannitol agar and then the nasal material from the same swab was prepared with a simple and rapid specimen preparation protocol described in patent application number U.S.

60/306,163. Classical identification of MRSA was performed by standard culture methods.

The PCR assay detected 33 of the 34 samples positive for MRSA based on the culture method. As compared to culture, the PCR assay detected 8 additional MRSA positive specimens for a sensitivity of 97.1% and a specificity of 92.6% (Example 6). This multiplex PCR assay represents a rapid and powerful method for the specific detection of MRSA carriers directly from nasal specimens and can be used with any types of clinical specimens such as wounds, blood or blood culture, CSF, etc.

In a preferred embodiment, a multiplex PCR assay containing primers specific to MREP types i, ii, iii, iv, v and vi and orfX of *S. aureus* (SEQ ID NOs.: 66, 67, 79, 80 and 112), and three molecular beacons probes specific to orfX sequence which allowed detection of the two sequence polymorphisms identified in this region of the orfX sequence was developed. Four of the strains which were not detected with the multiplex assay for the detection of MREP types i to v were now detected with this multiplex assay while the four MRSA strains (CCRI-9208, CCRI-9770, CCRI-9681, CCRI-9860) which harbor the MREP types vi, viii, ix and x described in the present invention remained undetectable (Example 7). Primers specific to MREP types vi, viii and ix (SEQ ID NOs.: 204, 115, 116 and 109) were also designed and were shown to detect their specific target strains (Example 8). While the primers and probes derived from the teaching of Hiramatsu et al., permitted the detection of only 48.7% (19 strains out of 39) of the MRSA strains of Table 2, the primers and probes derived from the present invention enable the detection of 97.4% of the strains (38 strains out of 39) (see examples 7 and 8). Therefore it can be said that our assay has a ubiquity superior to 50% for the MRSA strains listed in Table 2.

Specificity, Ubiquity and Sensitivity Tests for Oligonucleotide Primers and Probes The specificity of oligonucleotide primers and probes was tested by amplification of DNA or by hybridization with staphylococcal species. All of the staphylococcal species tested were likely to be pathogens associated with infections or potential contaminants which can be isolated from clinical specimens. Each target DNA could be released from microbial cells using standard chemical and/or physical treatments to lyse the cells (Sambrook et al., 1989, Molecular Cloning: A Laboratory Manual, $2^{nd}$ ed., Cold Spring Harbor Laboratory Press, Cold Spring Harbor, N.Y.) or alternatively, genomic DNA purified with the GNOME™ DNA kit (Qbiogene, Carlsbad, Calif.) was used. Subsequently, the DNA was subjected to amplification with the set of primers. Specific primers or probes hybridized only to the target DNA.

Oligonucleotides primers found to amplify specifically DNA from the target MRSA were subsequently tested for their ubiquity by amplification (i.e. ubiquitous primers amplified efficiently most or all isolates of MRSA). Finally, the analytical sensitivity of the PCR assays was determined by using 10-fold or 2-fold dilutions of purified genomic DNA from the targeted microorganisms. For most assays, sensitivity levels in the range of 2-10 genome copies were obtained. The specificity, ubiquity and analytical sensitivity of the PCR assays were tested either directly with bacterial cultures or with purified bacterial genomic DNA.

Molecular beacon probes were tested using the SMART CYCLER® platform as described above. A molecular beacon probe was considered specific only when it hybridized solely to DNA amplified from the MREJ of *S. aureus*. Molecular beacon probes found to be specific were subsequently tested for their ubiquity (i.e. ubiquitous probes detected efficiently most or all isolates of the MRSA) by hybridization to bacterial DNAs from various MRSA strains.

Bacterial Strains

The reference strains used to build proprietary SCCmec-chromosome right extremity junction sequence data subrepertories, as well as to test the amplification and hybridization assays, were obtained from (i) the American Type Culture Collection (ATCC), (ii) the Laboratoire de santé publique du Québec (LSPQ) (Ste-Anne de Bellevue, Québec, Canada), (iii) the Centers for Disease Control and Prevention (CDC) (Atlanta, Ga.), (iv) the Institut Pasteur (Paris, France), and V) the Harmony Collection (London, United Kingdom) (Table 14). Clinical isolates of MRSA, MSSA, MRCNS and MSCNS from various geographical areas were also used in this invention (Table 15). The identity of our MRSA strains was confirmed by phenotypic testing and reconfirmed by PCR analysis using *S. aureus*-specific primers and mecA-specific primers (SEQ ID NOs.: 69 and 81) (Martineau et al., 2000, Antimicrob. Agents Chemother. 44:231-238).

For sake of clarity, below is a list of the Examples, Tables, Figures and Annexes of this invention.

DESCRIPTION OF THE EXAMPLES

Example 1:

Primers developed by Hiramatsu et al. can only detect MRSA strains belonging to MREP types i, ii, and iii while missing prevalent novel MREP types.

Example 2:

Detection and identification of MRSA using primers specific to MREP types i, ii and iii sequences developed in the present invention.

Example 3:

Development of a multiplex PCR assay on a standard thermocycler for detection and identification of MRSA based on MREP types i, ii, iii, iv and v sequences.

Example 4:

Development of a real-time multiplex PCR assay on the SMART CYCLER® for detection and identification of MRSA based on MREP types i, ii, iii, iv and v sequences.

Example 5:

Development of a real-time multiplex PCR assay on the SMART CYCLER® for detection and identification of MRSA based on MREP types i, ii, iii, iv and v sequences and including an internal control.

Example 6:

Detection of MRSA using the real-time multiplex assay on the SMART CYCLER® based on MREP types i, ii, iii, iv and v sequences for the detection of MRSA directly from clinical specimens.

Example 7:

Development of a real-time multiplex PCR assay on the SMART CYCLER® for detection and identification of MRSA based on MREP types i, ii, iii, iv, v, vi and vii sequences.

Example 8:

Development of real-time PCR assays on the SMART CYCLER® for detection and identification of MRSA based on MREP types vi, viii and ix.

DESCRIPTION OF THE TABLES

Table 1 provides information about all PCR primers developed by Hiramatsu et al. in U.S. Pat. No. 6,156,507.

Table 2 is a compilation of results (ubiquity and specificity) for the detection of SCCmec-orfX right extremity junction using primers described by Hiramatsu et al. in U.S. Pat. No. 6,156,507 on a standard thermocycler.

Table 3 is a list of MRSA strains not amplifiable using primers targeting types I, II and III of SCCmec-orfX right extremity junction sequences.

Table 4 is a list of novel sequences revealed in the present invention.

Table 5 provides information about all primers developed in the present invention.

Table 6 is a list of molecular beacon probes developed in the present invention.

Table 7 shows amplicon sizes of the different primer pairs described by Hiramatsu et al. in U.S. Pat. No. 6,156,507 or developed in the present invention.

Table 8 provides information about primers developed in the present invention to sequence the SCCmec-chromosome right extremity junction.

Table 9 provides information about primers developed in the present invention to obtain sequence of the complete SCCmec.

Table 10 is a list of the sequences available from public databases (GenBank, genome projects or U.S. Pat. No. 6,156,507) used in the present invention to design primers and probes.

Table 11 gives analytical sensitivity of the PCR assay developed in the present invention using primers targeting types I, II and III of SCCmec-orfX right extremity junction sequences and performed using a standard thermocycler.

Table 12 is a compilation of results (ubiquity and specificity) for the detection of MRSA using primers developed in the present invention which target types I, II and III of SCCmec-orfX right extremity junction sequences and performed using a standard thermocycler.

Table 13 shows a comparison of sequence identities between the first 500 nucleotides of SCCmec right extremities between 9 types of MREP.

Table 14 provides information about the reference strains of MRSA, MSSA, MRCNS and MSCNS used to validate the PCR assays developed in the present invention.

Table 15 provides information about the origin of clinical strains of MRSA, MSSA, MRCNS and MSCNS used to validate the PCR assays described in the present invention.

Table 16 depicts the analytical sensitivity of the PCR assay developed in the present invention using primers targeting 5 types of MREP sequences and performed on a standard thermocycler.

Table 17 is a compilation of results (ubiquity and specificity) for the PCR assay developed in the present invention using primers targeting 5 types of MREP sequences and performed on a standard thermocycler.

Table 18 depicts the analytical sensitivity of the PCR assay developed in the present invention using the SMART CYCLER® platform for the detection of 5 types of MREP.

Table 19 is a compilation of results (ubiquity and specificity) for the PCR assay developed in the present invention using primers and a molecular beacon probe targeting 5 types of MREP sequences and performed on the SMART CYCLER® platform.

Table 20 depicts the analytical sensitivity of the PCR assay developed in the present invention using the SMART CYCLER® platform for the detection of 6 MREP types.

Table 21 is a compilation of results (ubiquity and specificity) for the PCR assay developed in the present invention using primers and a molecular beacon probe targeting 6 types of MREP sequences and performed on the SMART CYCLER® platform.

FIGURE LEGENDS

FIG. 1. Schematic organization of types I, II and III SCCmec-orfX right extremity junctions and localization of the primers (SEQ ID NOs: 52-63) described by Hiramatsu et al. for the detection and identification of MRSA. Amplicon sizes are depicted in Table 7.

FIG. 2. Schematic organization of MREP types i, ii, iii, iv, v, vi, vii, viii and ix and localization of the primers and molecular beacon targeting all MREP types (SEQ ID NOs. 20, 64, 66, 67, 79, 80, 84, 112, 115, 116, 84, 163 and 164) which were developed in the present invention. Amplicon sizes are depicted in Table 7.

FIG. 3. Schematic organization of the SCCmec-chromosome right extremity junctions and localization of the primers (SEQ ID NOs. 65, 68, 69, 70, 77, 96, 118, 126, 132, 150 and 158) developed in the present invention for the sequencing of MREP types iv, v, vi, vii, viii, ix and x.

Figure 4B:
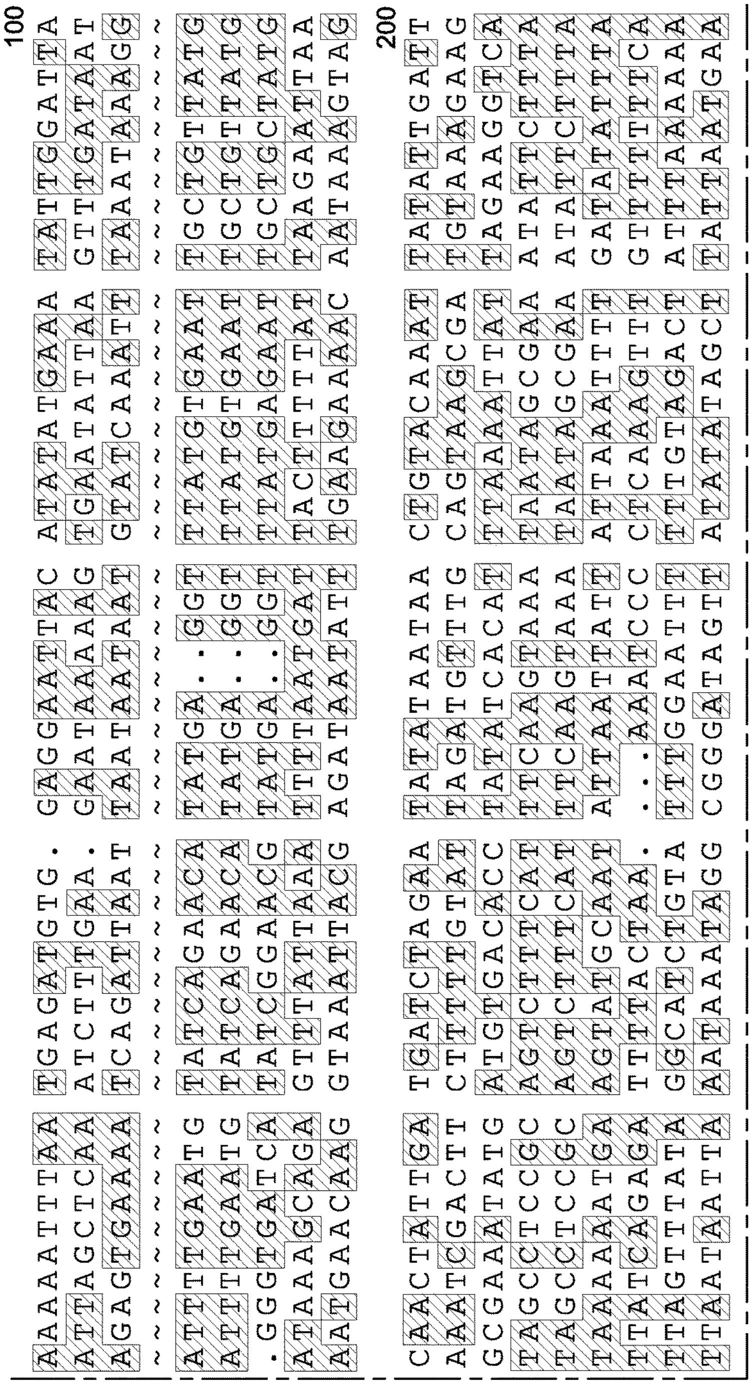
FIG. 4. Multiple sequence alignment of representatives of nine MREJ types (represented by the reverse complement of nucleotides 2193-2588 of SEQ ID NO: 1, for type i, the reverse complement of nucleotides 1972-2469 of SEQ ID NO: 2 for type ii, the reverse complement of nucleotides 305-797 of SEQ ID NO: 104 for type iii, nucleotides 435-932 of SEQ ID NO: 51 for type iv, nucleotides 427-924 of SEQ ID NO: 50 for type v, nucleotides 451-948 of SEQ ID NO: 171 for type vi, nucleotides 451-947 of SEQ ID NO:165 for type vii, nucleotides 445-935 of SEQ ID NO:167 for type viii, and nucleotides 442-937 of SEQ ID NO: 168 for type ix).
Figure 4C:
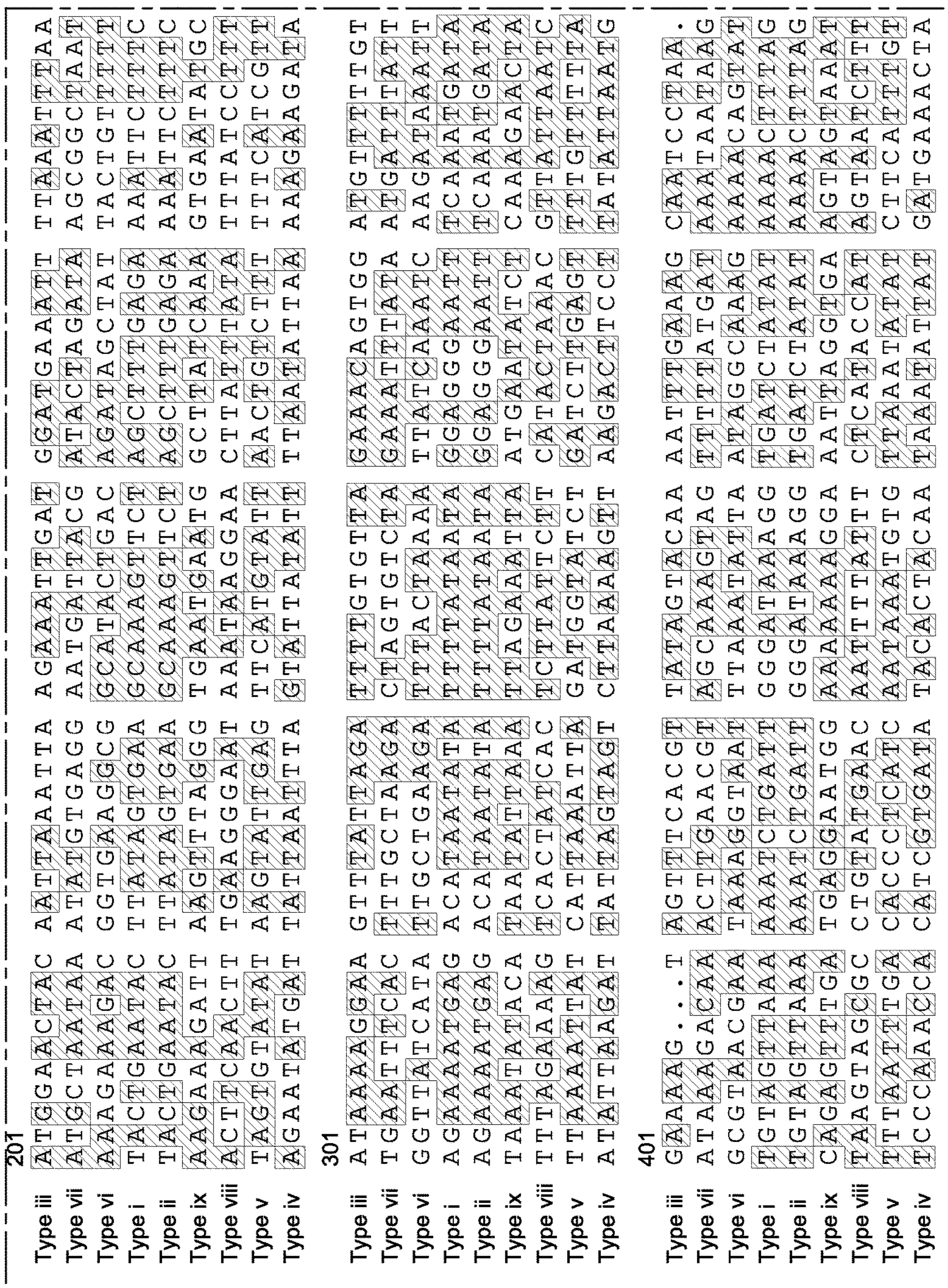
Figure 4D:
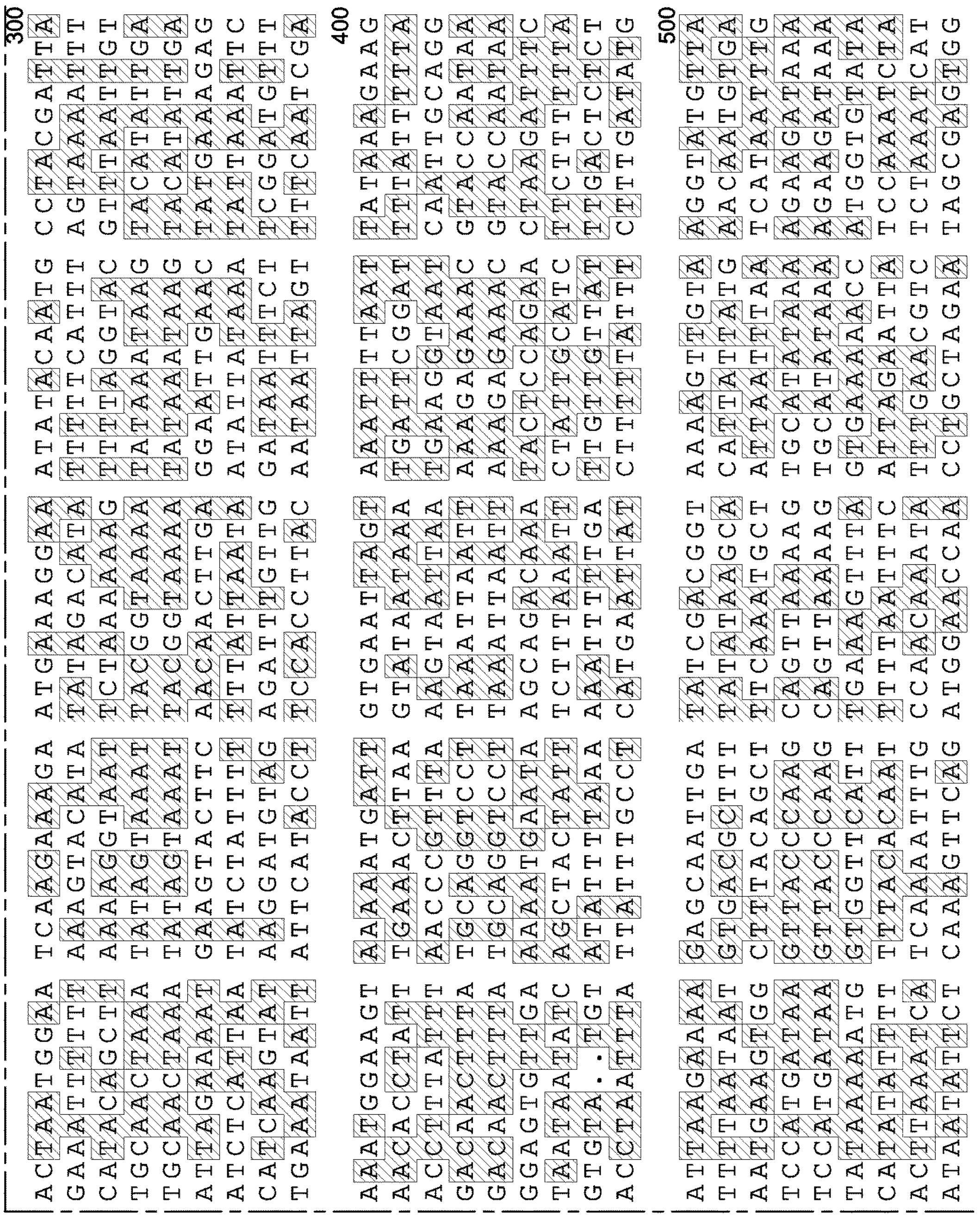

FIG. 4. Multiple sequence alignment of representatives of nine MREP types (represented by portions of SEQ ID NOs.: 1, 2, 104, 51, 50, 171, 165, 167 and 168 for types i, ii, iii, iv, v, vi, vii, viii and ix, respectively).

DESCRIPTION OF THE ANNEXES

The Annexes show the strategies used for the selection of primers and internal probes:

Annex I illustrates the strategy for the selection of primers from SCCmec and or orfX sequences specific for SCCmec types I and II.

Annex II illustrates the strategy for the selection of specific molecular beacon probes for the real-time detection of SCCmec-orfX right extremity junctions.

As shown in these Annexes, the selected amplification primers may contain inosines and/or base ambiguities. Inosine is a nucleotide analog able to specifically bind to any of the four nucleotides A, C, G or T. Alternatively, degenerated oligonucleotides which consist of an oligonucleotide mix having two or more of the four nucleotides A, C, G or T at the site of mismatches were used. The inclusion of inosine and/or of degeneracies in the amplification primers allows mismatch tolerance thereby permitting the amplification of a wider array of target nucleotide sequences (Dieffenbach and Dveksler, 1995, PCR Primer: A Laboratory Manual, Cold Spring Harbor Laboratory Press, Plainview, N.Y.).

EXAMPLES

Example 1

Primers Developed by Hiramatsu et al. Can Only Detect MRSA Strains Belonging to MREP Types i, ii, and iii while Missing Prevalent Novel MREP Types.

As shown in FIG. 1, Hiramatsu et al. have developed various primers that can specifically hybridize to the right extremities of types I, II and III SCCmec DNAs. They combined these primers with primers specific to the *S. aureus* chromosome region located to the right of the SCCmec integration site for the detection of MRSA. The primer set (SEQ ID NOs.: 22, 24 and 28 in U.S. Pat. No. 6,156,507 corresponding to SEQ ID NOs.: 56, 58 and 60 in the present invention) was shown by Hiramatsu et al. to be the most specific and ubiquitous for detection of MRSA.

This set of primers gives amplification products of 1.5 kb for SCCmec type I, 1.6 kb for SCCmec type II and 1.0 kb for SCCmec type III (Table 7). The ubiquity and specificity of this multiplex PCR assay was tested on 39 MRSA strains, 41 MSSA strains, 9 MRCNS strains and 11 MSCNS strains (Table 2). One µL of a treated standardized bacterial suspension or of a bacterial genomic DNA preparation purified from bacteria were amplified in a 20 µl PCR reaction mixture. Each PCR reaction contained 50 mM KCl, 10 mM Tris-HCl (pH 9.0), 0.1% Triton X-100, 2.5 mM $MgCl_2$, 0.4 µM of each of the SCCmec- and orfX-specific primers (SEQ ID NOs.: 56, 58 and 60), 200 µM of each of the four dNTPs (Pharmacia Biotech), 3.3 µg/µl of BSA (Sigma), and 0.5 U Taq polymerase (Promega) coupled with TaqStart™ Antibody (BD Biosciences).

PCR reactions were then subjected to thermal cycling: 3 min at 94° C. followed by 40 cycles of 60 seconds at 95° C. for the denaturation step, 60 seconds at 55° C. for the annealing step, and 60 seconds at 72° C. for the extension step, then followed by a terminal extension of 7 minutes at 72° C. using a standard thermocycler (PTC-200 from MJ Research Inc.). Detection of the PCR products was made by electrophoresis in agarose gels (2%) containing 0.25 µg/ml of ethidium bromide.

None of the MRCNS or MSCNS strains tested were detected with the set of primers detecting SCCmec types I, II and III. Twenty of the 39 MRSA strains tested were not detected with this multiplex PCR assay (Tables 2 and 3). One of these undetected MRSA strains corresponds to the highly epidemic MRSA Portuguese clone (strain CCRI-9504; De Lencastre et al., 1994. Eur. J. Clin. Microbiol. Infect. Dis. 13:64-73) and another corresponds to the highly epidemic MRSA Canadian clone CMRSA1 (strain CCRI-9589; Simor et al. CCDR 1999, 25-12, June 15). These data demonstrate that the primer set developed by Hiramatsu et al. (SEQ ID NOs.: 22, 24 and 28 in U.S. Pat. No. 6,156,507 corresponding to SEQ ID NOs.: 56, 58 and 60 in the present invention) is not ubiquitous for the detection of MRSA and suggest that some MRSA strains have sequences at the SCCmec right extremity junction which are different from those identified by Hiramatsu et al. other types of SCCmec sequences or other sequences at the right extremity of SCCmec (MREP type) are found in MRSA. A limitation of this assay is the non-specific detection of 13 MSSA strains (Table 2).

Example 2

Detection and Identification of MRSA using Primers Specific to MREP Types i, ii and iii Sequences Developed in the Present Invention.

Based on analysis of multiple sequence alignments of orfX and SCCmec sequences described by Hiramatsu et al. or available from GenBank, a set of primers (SEQ ID NOs: 64, 66, 67) capable of amplifying short segments of types I, II and III of SCCmec-orfX right extremity junctions from MRSA strains and discriminating from MRCNS (Annex I and FIG. 2) were designed. The chosen set of primers gives amplification products of 176 bp for SCCmec type I, 278 pb for SCCmec type II and 223 bp for SCCmec type III and allows rapid PCR amplification. These primers were used in multiplex PCR to test their ubiquity and specificity using 208 MRSA strains, 252 MSSA strains, 41 MRCNS strains and 21 MRCNS strains (Table 12). The PCR amplification and detection was performed as described in Example 1. PCR reactions were then subjected to thermal cycling (3 minutes at 94° C. followed by 30 or 40 cycles of 1 second at 95° C. for the denaturation step and 30 seconds at 60° C. for the annealing-extension step, and then followed by a terminal extension of 2 minutes at 72° C.) using a standard thermocycler (PTC-200 from MJ Research Inc.). Detection of the PCR products was made as described in Example 1.

None of the MRCNS or MSCNS strains tested were detected with this set of primers (Table 12). However, the twenty MRSA strains which were not detected with the primer set developed by Hiramatsu et al. (SEQ ID NOs: 56, 58 and 60) were also not detected with the primers developed in the present invention (Tables 3 and 12). These data also demonstrate that some MRSA strains have sequences at the SCCmec-chromosome right extremity junction which are different from those identified by Hiramatsu et al. Again, as observed with the Hiramatsu primers, 13 MSSA strains were also detected non-specifically (Table 12). The clinical significance of this finding remains to be established since these apparent MSSA strains could be the result of a recent deletion in the mec locus (Deplano et al., 2000, J. Antimicrob. Chemotherapy, 46:617-619; Inglis et al., 1990, J. Gen. Microbiol., 136:2231-2239; Inglis et al., 1993, J. Infect. Dis., 167:323-328; Lawrence et al. 1996, J. Hosp. Infect., 33:49-53; Wada et al., 1991, Biochem. Biophys. Res. Comm., 176:1319-1326).

Example 3

Development of a Multiplex PCR Assay on a Standard Thermocycler for Detection and Identification of MRSA Based on MREP Types i, ii, iii, iv and v Sequences.

Upon analysis of two of the new MREP types iv and v sequence data described in the present invention, two new primers (SEQ ID NOs.: 79 and 80) were designed and used in multiplex with the three primers SEQ ID NOs.: 64, 66 and 67 described in Example 2. PCR amplification and detection of the PCR products was performed as described in Example 2. Sensitivity tests performed by using ten-fold or two-fold dilutions of purified genomic DNA from various MRSA strains of each MREP type showed a detection limit of 5 to 10 genome copies (Table 16). Specificity tests were performed using 0.1 ng of purified genomic DNA or 1 µl of a standardized bacterial suspension. All MRCNS or MSCNS strains tested were negative with this multiplex assay (Table 17). Twelve of the 20 MRSA strains which were not detected with the multiplex PCR described in Examples 1 and 2 were now detected with this multiplex assay. Again, as observed with the Hiramatsu primers, 13 MSSA strains were also detected non-specifically (Table 12). The eight MRSA strains (CCRI-9208, CCRI-9583, CCRI-9773, CCRI-9774, CCRI-9589, CCRI-9860, CCRI-9681, CCRI-9770) and which harbor the new MREP types vi, vii, viii, ix and x sequences described in the present invention remained undetectable.

Example 4

Development of a Real-Time Multiplex PCR Assay on the SMART CYCLER® for Detection and Identification of MRSA Based on MREP Types i, ii, iii, iv and v Sequences.

The multiplex PCR assay described in Example 3 containing primers (SEQ ID NOs.: 64, 66, 67, 79 and 80) was adapted to the SMART CYCLER® platform (Cepheid). A molecular beacon probe specific to the orfX sequence was developed (SEQ ID NO. 84, see Annex II). Each PCR reaction contained 50 mM KCl, 10 mM Tris-HCl (pH 9.0), 0.1% Triton X-100, 3.5 mM $MgCl_2$, 0.4 µM of each of the SCCmec- and orfX-specific primers (SEQ ID NOs.: 64, 66, 67, 79 and 80), 0.2 μM of the FAM-labeled molecular beacon probe (SEQ ID NO.: 84), 200 μM of each of the four dNTPs, 3.3 μg/μl of BSA, and 0.5 U Taq polymerase coupled with TaqStart™ Antibody. The PCR amplification on the SMART CYCLER® was performed as follows: 3 min. at 94° C. for initial denaturation, then forty-five cycles of three steps consisting of 5 seconds at 95° C. for the denaturation step, 15 seconds at 59° C. for the annealing step and 10 seconds at 72° C. for the extension step. Fluorescence detection was performed at the end of each annealing step. Sensitivity tests performed by using purified genomic DNA from several MRSA strains of each MREP type showed a detection limit of 2 to 10 genome copies (Table 18). None of the MRCNS or MSCNS were positive with this multiplex assay (Table 19). Again, as observed with the Hiramatsu primers, 13 MSSA strains were also detected non-specifically. Twelve of the twenty MRSA strains which were not detected with the multiplex PCR described in Examples 1 and 2 were detected by this multiplex assay. As described in Example 3, the eight MRSA strains which harbor the new MREP types vi, vii, viii, ix and x sequences described in the present invention remained undetectable.

Example 5

Development of a Real-Time Multiplex PCR Assay on the SMART CYLCER® for Detection and Identification of MRSA Based on MREP Types i, ii, iii, iv and v Sequences Including an Internal Control.

The multiplex PCR assay described in Example 4 containing primers specific to MREP types i to v and orfX of *S. aureus* (SEQ ID NOs.: 64, 66, 67, 79 and 80) and a molecular beacon probe specific to the orfX sequence (SEQ ID NO. 84, see Annex II) was optimized to include an internal control to monitor PCR inhibition. This internal control contains sequences complementary to MREP type iv- and orfX-specific primers (SEQ ID NOs. 79 and and 64). The assay also contains a TET-labeled molecular beacon probe specific to sequence within the amplicon generated by amplification of the internal control. Each PCR reaction contained 50 mM KCl, 10 mM Tris-HCl (pH 9.0), 0.1% Triton X-100, 3.45 mM $MgCl_2$, 0.8 μM of each of the MREP-specific primers (SEQ ID NOs.: 66 and 67) and or orfX-specific primer (SEQ ID NO.: 64), 0.4 μM of each of the MREP-specific primers (SEQ ID NOs.: 79 and 80), 80 copies of the internal control, 0.2 μM of the TET-labeled molecular beacon probe specific to the internal control, 0.2 μM of the FAM-labeled molecular beacon probe (SEQ ID NO.: 84), 330 μM of each of the four dNTPs (Pharmacia Biotech), 3.45 μg/μl of BSA (Sigma), and 0.875 U Taq polymerase (Promega) coupled with TaqStart™ Antibody (BD Biosciences). The PCR amplification on the SMART CYCLER® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. Sensitivity tests performed by using purified genomic DNA from one MRSA strain of each MREP type (i to v) showed a detection limit of 2 to 10 genome copies. None of the 26 MRCNS or 10 MSCNS were positive with this multiplex assay. Again, as observed with the Hiramatsu primers, 13 MSSA strains were also detected non-specifically. As described in Examples 3 and 4, the eight MRSA strains which harbor the new MREP types vi to x sequences described in the present invention remained undetectable.

Example 6

Detection of MRSA using the Real-Time Multiplex Assay on the SMART CYLCER® Based on MREP Types i, ii, iii iv and v Sequences Directly from Clinical Specimens.

The assay described in Example 5 was adapted for detection directly from clinical specimens. A total of 142 nasal swabs collected during a MRSA hospital surveillance program at the Montreal General Hospital (Montreal, Quebec, Canada) were tested. The swab samples were tested at the Centre de Recherche en Infectiologie de l'Université Laval within 24 hours of collection. Upon receipt, the swabs were plated onto mannitol agar and then the nasal material from the same swab was prepared with a simple and rapid specimen preparation protocol described in patent application number U.S. 60/306,163. Classical identification of MRSA was performed by standard culture methods.

The PCR assay described in Example 5 detected 33 of the 34 samples positive for MRSA based on the culture method. As compared to culture, the PCR assay detected 8 additional MRSA positive specimens for a sensitivity of 97.1% and a specificity of 92.6%. This multiplex PCR assay represents a rapid and powerful method for the specific detection of MRSA carriers directly from nasal specimens and can be used with any type of clinical specimens such as wounds, blood or blood culture, CSF, etc.

Example 7

Development of a Real-Time Multiplex PCR Assay on the SMART CYCLER® for Detection and Identification of MRSA Based on MREP Types i, ii iii, iv, v and vii Sequences.

Upon analysis of the new MREP type vii sequence data described in the present invention (SEQ ID NOs.: 165 and 166), two new primers (SEQ ID NOs.: 112 and 113) were designed and tested in multiplex with the three primers SEQ ID NOs.: 64, 66 and 67 described in Example 2. Primer SEQ ID NO.: 112 was selected for use in the multiplex based on its sensitivity. Three molecular beacon probes specific to the orfX sequence which allowed detection of two sequence polymorphisms identified in this region of the orfX sequence, based on analysis of SEQ ID NOs.: 173-186, were also used in the multiplex (SEQ ID NOs.: 84, 163 and 164). Each PCR reaction contained 50 mM KCl, 10 mM Tris-HCl (pH 9.0), 0.1% Triton X-100, 3.45 mM $MgCl_2$, 0.8 μM of each of the SCCmec-specific primers (SEQ ID NOs.: 66 and 67) and orfX-specific primer (SEQ ID NO.: 64), 0.4 μM of each of the SCCmec-specific primers (SEQ ID NOs.: 79 and 80), 0.2 μM of the FAM-labeled molecular beacon probe (SEQ ID NO.: 84), 330 μM of each of the four dNTPs (Pharmacia Biotech), 3.45 μg/μl of BSA (Sigma), and 0.875 U of Taq polymerase (Promega) coupled with TaqStart™ Antibody (BD Biosciences). The PCR amplification on the SMART CYCLER® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. The detection of fluorescence was done at the end of each annealing step. Sensitivity tests performed by using purified genomic DNA from several MRSA strains of each MREP type showed a detection limit of 2 genome copies (Table 20). None of the 26 MRCNS or 8 MSCNS were positive with this multiplex assay. Again, as observed with the Hiramatsu primers, 13 MSSA strains were also detected non-specifically (Table 21). Four of the strains which were not detected with the multiplex assay for the detection of MREP types i to v were now detected with this multiplex assay while the four MRSA strains (CCRI-9208, CCRI-9770, CCRI-9681, CCRI-9860) which harbor the MREP types vi, viii, ix and x described in the present invention remained undetectable.

Example 8

Development of Real-Time PCR Assays on the SMART CYCLER® for Detection and Identification of MRSA Based on MREP Types vi, viii, ix.

Upon analysis of the new MREP types vi, viii and ix sequence data described in the present invention, one new primers specific to MREP type vi (SEQ ID NO.: 201), one primer specific to MREP type viii (SEQ ID NO.: 115), a primer specific to MREP type ix (SEQ ID NO.: 109) and a primer specific to both MREP types viii and ix (SEQ ID NO.: 116) were designed. Each PCR primer was used in combination with the orfX-specific primer (SEQ ID NO.: 64) and tested against its specific target strain. Each PCR reaction contained 50 mM KCl, 10 mM Tris-HCl (pH 9.0), 0.1% Triton X-100, 3.45 mM $MgCl_2$, 0.4 µM of each of the SCCmec- and orfX-specific primers, 200 µM of each of the four dNTPs, 3.4 µg/µl of BSA, and 0.875 U Taq polymerase coupled with TaqStart™ Antibody. The PCR amplification was performed as described en Example 7. Sensitivity tests performed by using genomic DNA purified from their respective MRSA target strains showed that the best primer pair combination was SEQ ID NOs.: 64 and 115 for the detection of MREP types viii and ix simultaneously. These new SCCmec-specific primers may be used in multiplex with primers specific to MREP types i, ii, ii, iv, v and vii (SEQ ID NOs.: 64, 66, 67, 79 and 80) described in previous examples to provide a more ubiquitous MRSA assay.

In conclusion, we have improved the ubiquity of detection of MRSA strains. New MREJ types iv to x have been identified. Amongst strains representative of these new types, Hiramatsu's primers and/or probes succeeded in detecting less than 50% thereof. We have therefore amply passed the bar of at least 50% ubiquity, since our primers and probes were designed to detect 100% of the strains tested as representatives of MREJ types iv to ix. Therefore, although ubiquity depends on the pool of strains and representatives that are under analysis, we know now that close to 100% ubiquity is an attainable goal, when using the sequences of the right junctions (MREJ) to derive probes and primers dealing with polymorphism in this region. Depending on how many unknown types of MREJ exist, we have a margin of maneuver going from 50% (higher than Hiramatsu's primers for the tested strains) to 100% if we sequence all the existing MREJs to derive properly the present diagnostic tools and methods, following the above teachings.

This invention has been described herein above, and it is readily apparent that modifications can be made thereto without departing from the spirit of this invention. These modifications are under the scope of this invention, as defined in the appended claims.

TABLE 1

PCR amplification primers reported by Hiramatsu et al. in U.S. Pat. No. 6,156,507 found in the sequence listing

| SEQ ID NO.: (present invention) | Target | Position[a,b] | SEQ ID NO.: (U.S. Pat. No. 6,156,507) |
|---|---|---|---|
| 52 | MREP types i and ii | 480 | 18 |
| 53 | MREP types i and ii | 758 | 19 |

TABLE 1-continued

PCR amplification primers reported by Hiramatsu et al. in U.S. Pat. No. 6,156,507 found in the sequence listing

| SEQ ID NO.: (present invention) | Target | Position[a,b] | SEQ ID NO.: (U.S. Pat. No. 6,156,507) |
|---|---|---|---|
| 54 | MREP types i and ii | 927 | 20 |
| 55 | MREP types i and ii | 1154 | 21 |
| 56 | MREP types i and ii | 1755 | 22 |
| 57 | MREP types i and ii | 2302 | 23 |
| 58 | MREP type iii | 295[c] | 24 |
| 59 | orfX | 1664 | 25 |
| 60 | orfSA0022[d] | 3267 | 28 |
| 61 | orfSA0022[d] | 3585 | 27 |
| 62 | orfX | 1389 | 26 |
| 63 | orfSA0022[d] | 2957 | 29 |

[a]Position refers to nucleotide position of the 5' end of primer.

[b]Numbering for SEQ ID NOs.: 52-57 refers to SEQ ID NO.: 2; numbering for SEQ ID NO.: 58 refers to SEQ ID NO.: 4; numbering for SEQ ID NOs.: 59-63 refers to SEQ ID NO.: 3.

[c]Primer is reverse-complement of target sequence.

[d]orfSA0022 refers to the open reading frame designation from GenBank accession number AP003129 (SEQ ID NO.: 231).

TABLE 2

Specificity and ubiquity tests performed on a standard thermocycler using the optimal set of primers described by Hiramatsu et al. (SEQ ID NOs.: 22, 24 and 28 in U.S. Pat. No. 6,156,507 corresponding to SEQ ID NOs.: 56, 58 and 60, respectively, in the present invention) for the detection of MRSA

| | PCR results for SCCmec - orfX right extremity junction | |
|---|---|---|
| Strains | Positive (%) | Negative (%) |
| MRSA - 39 strains | 19 (48.7) | 20 (51.2) |
| MSSA - 41 strains | 13 (31.7) | 28 (68.3) |
| MRCNS - 9 strains* | 0 (0%) | 9 (100%) |
| MSCNS - 11 strains* | 0 (0%) | 11 (100%) |

*Details regarding CNS strains:
MRCNS:   S. caprae (1)
         S. cohni cohnii (1)
         S. epidermidis (1)
         S. haemolyticus (2)
         S. hominis (1)
         S. sciuri 1)
         S. simulans (1)
         S. warneri (1)
MSCNS:   S. cohni cohnii (1)
         S. epidermidis (1)
         S. equorum (1)
         S. gallinarum (1)
         S. haemolyticus (1)
         S. lentus (1)
         S. lugdunensis (1)
         S. saccharolyticus (1)
         S. saprophyticus (2)
         S. xylosus (1)

TABLE 3

Origin of MRSA strains not amplifiable using primers developed by Hiramatsu et al. (SEQ ID NOs.: 22, 24 and 28 in U.S. Pat. No. 6,156,507 corresponding to SEQ ID NOs.: 56, 58 and 60, respectively, in the present invention) as well as primers developed in the present invention targeting MREP types i, ii and iii (SEQ ID NOs.: 64, 66 and 67)

| *Staphylococcus aureus* strain designation: Original | CCRI[a] | Origin |
|---|---|---|
| ATCC BAA-40[b] | CCRI-9504 | Portugal |
| ATCC 33592 | CCRI-178 | USA |
| R991282 | CCRI-2025 | Québec, Canada |
| 4508 | CCRI-9208 | Québec, Canada |
| 19121 | CCRI-8895 | Denmark |
| Z109 | CCRI-8903 | Denmark |
| 45302 | CCRI-1263 | Ontario, Canada |
| R655 | CCRI-1324 | Québec, Canada |
| MA 50428 | CCRI-1311 | Québec, Canada |
| MA 50609 | CCRI-1312 | Québec, Canada |
| MA 51363 | CCRI-1331 | Québec, Canada |
| MA 51561 | CCRI-1325 | Québec, Canada |
| 14A0116 | CCRI-9681 | Poland |
| 23 (CCUG 41787) | CCRI-9860 | Sweden |
| SE26-1 | CCRI-9770 | Ontario, Canada |
| SE1-1 | CCRI-9583 | Ontario, Canada |
| ID-61880[c] | CCRI-9589 | Ontario, Canada |
| SE47-1 | CCRI-9773 | Ontario, Canada |
| SE49-1 | CCRI-9774 | Ontario, Canada |
| 39795-2 | CCRI-1377 | Québec, Canada |

[a]CCRI stands for "Collection of the Centre de Recherche en Infectiologie".
[b]Portuguese clone.
[c]Canadian clone EMRSA1.

TABLE 4

*Staphylococcus aureus* MREJ nucleotide sequences revealed in the present invention

| SEQ ID NO. | *Staphylococcus aureus* strain designation: Original | CCRI[a] | Genetic Target |
|---|---|---|---|
| 27 | R991282 | CCRI-2025 | mecA |
| 28 | 45302 | CCRI-1263 | mecA |
| 29 | MA 50428 | CCRI-1311 | mecA |
| 30 | MA 51363 | CCRI-1331 | mecA |
| 31 | 39795-2 | CCRI-1377 | mecA and 1.5 kb of downstream region |
| 42 | ATCC 33592 | CCRI-178 | MREP type iv |
| 43 | 19121 | CCRI-8895 | MREP type iv |
| 44 | Z109 | CCRI-8903 | MREP type iv |
| 45 | R655 | CCRI-1324 | MREP type iv |
| 46 | MA 51363 | CCRI-1331 | MREP type iv |
| 47 | 45302 | CCRI-1263 | MREP type v |
| 48 | 39795-2 | CCRI-1377 | MREP type v |
| 49 | MA 50428 | CCRI-1311 | MREP type v |
| 50 | R991282 | CCRI-2025 | MREP type V |

TABLE 4-continued

*Staphylococcus aureus* MREJ nucleotide sequences revealed in the present invention

| | | | |
|---|---|---|---|
| 51 | ATCC BAA-40 | CCRI-9504 | MREP type iv |
| 165 | SE1-1 | CCRI-9583 | MREP type vii |
| 166 | ID-61880 | CCRI-9589 | MREP type vii |
| 167 | 23 (CCUG 41787) | CCRI-9860 | MREP type viii |
| 168 | 14A016 | CCRI-9681 | MREP type ix |
| 171 | 4508 | CCRI-9208 | MREP type vi |
| 172 | SE26-1 | CCRI-9770 | orfSA0021[b] and 75 bp of orfSA0022[b] |
| 173 | 26 (98/10618) | CCRI-9864 | MREP type ii |
| 174 | 27 (98/26821) | CCRI-9865 | MREP type ii |
| 175 | 28 (24344) | CCRI-9866 | MREP type ii |
| 176 | 12 (62305) | CCRI-9867 | MREP type ii |
| 177 | 22 (90/14719) | CCRI-9868 | MREP type ii |
| 178 | 23 (98/14719) | CCRI-9869 | MREP type ii |
| 179 | 32 (97599) | CCRI-9871 | MREP type ii |
| 180 | 33 (97S100) | CCRI-9872 | MREP type ii |
| 181 | 38 (825/96) | CCRI-9873 | MREP type ii |
| 182 | 39 (842/96) | CCRI-9874 | MREP type ii |
| 183 | 43 (N8-892/99) | CCRI-9875 | MREP type ii |
| 184 | 46 (9805-0137) | CCRI-9876 | MREP type iii |
| 185 | 1 | CCRI-9882 | MREP type ii |
| 186 | 29 | CCRI-9885 | MREP type ii |
| 189 | SE1-1 | CCRI-9583 | mecA and 2.2 kb of downstream region, including IS431mec |
| 190 | ATCC BAA-40 | CCRI-9504 | mecA and 1.5 kb of downstream region |
| 191 | 4508 | CCRI-9208 | mecA and 0.9 kb of downstream region |
| 192 | ID-61880 | CCRI-9589 | mecA and 0.9 kb of downstream region |
| 193 | 14A016 | CCRI-9681 | mecA and 0.9 kb of downstream region |
| 195 | SE26-1 | CCRI-9770 | mecA and 1.5 kb of downstream region, including IS431mec |
| 197 | ATCC 43300 | CCRI-175 | MREP type ii |
| 198 | R522 | CCRI-1262 | MREP type iii |

TABLE 4-continued

| *Staphylococcus aureus* MREJ nucleotide sequences revealed in the present invention | | | |
|---|---|---|---|
| 199 | 13370 | CCRI-8894 | MREP type i |
| 219 | ATCC BAA-40 | CCRI-9504 | tetK |
| SEQ ID NO. | *Staphylococcus aureus* strain designation: Original | CCRI[b] | Genetic Target[a] |
| 220 | MA 51363 | CCRI-1331 | mecA and 1.5 kb of downstream region |
| 221 | 39795-2 | CCRI-1377 | IS431mec and 0.6 kb of upstream region |
| 222 | R991282 | CCRI-2025 | mecA and 1.5 kb of downstream region |
| 223 | R991282 | CCRI-2025 | IS431mec and 0.6 kb of upstream region |
| 224 | 23 (CCUG 41787) | CCRI-9860 | mecA and 1.5 kb of downstream region |
| 225 | 23 (CCUG 41787) | CCRI-9860 | IS431mec and 0.6 kb of upstream region |
| 233 | 14A016 | CCRI-9681 | MREP type ix |

[a]CCRI stands for "Collection of the Centre de Recherche en Infectiologie".
[b]orfSA0021 and orfSA0022 refer to the open reading frame designation from GenBank accession number AP003129 (SEQ ID NO.: 231).

TABLE 5

PCR primers developed in the present invention

| SEQ ID NO. | Target | Originating DNA Position[a] | Originating DNA SEQ ID NO. |
|---|---|---|---|
| 64 | orfX | 1720 | 3 |
| 70 | orfX | 1796 | 3 |
| 71 | orfX | 1712 | 3 |
| 72 | orfX | 1749 | 3 |
| 73 | orfX | 1758 | 3 |
| 74 | orfX | 1794 | 3 |
| 75 | orfX | 1797 | 3 |
| 76 | orfX | 1798 | 3 |
| 66 | MREP types i and ii | 2327 | 2 |
| 100 | MREP types i and ii | 2323 | 2 |
| 101 | MREP types i and ii | 2314 | 2 |
| 97 | MREP type ii | 2434 | 2 |
| 99 | MREP type ii | 2434 | 2 |
| 67 | MREP type iii | 207[b] | 4 |
| 98 | MREP type iii | 147[b] | 4 |
| 102 | MREP type iii | 251[b] | 4 |
| 79 | MREP type iv | 74[b] | 43 |
| 80 | MREP type v | 50[b] | 47 |
| 109 | MREP type ix | 652[b] | 168 |
| 204 | MREP type vi | 642[b] | 171 |
| 112 | MREP type vii | 503[b] | 165 |
| 113 | MREP type vii | 551[b] | 165 |
| 115 | MREP type viii | 514[b] | 167 |
| 116 | MREP type viii | 601[b] | 167 |

[a]Position refers to nucleotide position of 5' end of primer.
[b]Primer is reverse-complement of target sequence.

TABLE 6

Molecular beacon probes developed in the present invention

| SEQ ID NO. | Target | Position |
|---|---|---|
| 32 | orfX | 86[a] |
| 83 | orfX | 86[a] |
| 84 | orfX | 34[a,b] |
| 160 | orfX | 55[a,b] |
| 161 | orfX | 34[a,b] |
| 162 | orfX | 114[a] |
| 163 | orfX | 34[a,b] |
| 164 | orfX | 34[a,b] |

[a]Position refers to nucleotide position of the 5' end of the molecular beacon's loop on SEQ ID NO.: 3.
[b]Sequence of molecular beacon's loop is reverse-complement of SEQ ID NO.: 3.

TABLE 7

Length of amplicons obtained with the diferent primer pairs which are objects of the present invention

| SEQ ID NO. | Target[d] | Amplicon length[a] |
|---|---|---|
| 59/52[b] | orfX/MREP type i and ii | 2079 (type i); 2181 (type ii) |
| 59/53[b] | orfx/MREP type i and ii | 1801 (type i); 1903 (type ii) |
| 59/54[b] | orfX/MREP type i and ii | 1632 (type i); 1734 (type ii) |
| 59/55[b] | orfX/MREP type i and ii | 1405 (type i); 1507 (type ii) |
| 59/56[b] | orfX/MREP type i and ii | 804 (type i); 906 (type ii) |
| 59/57[b] | orfX/MREP type i and ii | 257 (type i); 359 (type ii) |
| 60/52[b] | orfSA0022/MREP type i and ii | 2794 (type i); 2896 (type ii) |
| 60/53[b] | orfSA0022/MREP type i and ii | 2516 (type i); 2618 (type ii) |
| 60/54[b] | orfSA0022/MREP type i and ii | 2347 (type i); 2449 (type ii) |
| 60/55[b] | orfSA0022/MREP type i and ii | 2120 (type i); 2222 (type ii) |
| 60/56[b] | orfSA0022/MREP type i and ii | 1519 (type i); 1621 (type ii) |
| 60/57[b] | orfSA0022/MREP type i and ii | 972 (type i); 1074 (type ii) |
| 61/52[b] | orfSA0022/MREP type i and ii | 2476 (type i); 2578 (type ii) |
| 61/53[b] | orfSA0022/MREP type i and ii | 2198 (type i); 2300 (type ii) |
| 61/54[b] | orfSA0022/MREP type i and ii | 2029 (type i); 2131 (type ii) |
| 61/55[b] | orfSA0022/MREP type i and ii | 1802 (type i); 1904 (type ii) |
| 61/56[b] | orfSA0022/MREP type i and ii | 1201 (type i); 1303 (type ii) |
| 61/57[b] | orfSA0022/MREP type i and ii | 654 (type i); 756(type ii) |
| 62/52[b] | orfX/MREP type i and ii | 2354 (type i); 2456 (type ii) |
| 62/53[b] | orfX/MREP type i and ii | 2076 (type i); 2178 (type ii) |
| 62/54[b] | orfX/MREP type i and ii | 1907 (type i); 2009 (type ii) |
| 62/55[b] | orfX/MREP type i and ii | 1680 (type i); 1782 (type ii) |
| 62/56[b] | orfX/MREP type i and ii | 1079 (type i); 1181 (type ii) |
| 62/57[b] | orfX/MREP type i and ii | 532 (type i); 634 (type ii) |
| 63/52[b] | orfSA0022/MREP type i and ii | 3104 (type i); 3206 (type ii) |
| 63/53[b] | orfSA0022/MREP type i and ii | 2826 (type i); 2928 (type ii) |
| 63/54[b] | orfSA0022/MREP type i and ii | 2657 (type i); 2759 (type ii) |
| 63/55[b] | orfSA0022/MREP type i and ii | 2430 (type i); 2532 (type ii) |
| 63/56[b] | orfSA0022/MREP type i and ii | 1829 (type i); 1931 (type ii) |
| 63/57[b] | orfSA0022/MREP type i and ii | 1282 (type i); 1384 (type ii) |
| 59/58[b] | orfX/MREP type iii | 361 |
| 60/58[b] | orfSA0022/MREP type iii | 1076 |
| 61/58[b] | orfSA0022/MREP type iii | 758 |
| 62/58[b] | orfX/MREP type iii | 656 |
| 63/58[b] | orfSA0022/MREP type iii | 1386 |
| 70/66 | orfX/MREP type i and ii | 100 (type i); 202 (type ii) |
| 70/67 | orfX/MREP type iii | 147 (type iii) |
| 64/66[c] | orfX/MREP type i and ii | 176 (type i); 278 (type ii) |
| 64/67[c] | orfX/MREP type iii | 223 |
| 64/79[c] | orfX/MREP type iv | 215 |
| 64/80[c] | orfX/MREP type v | 196 |
| 64/97[c] | orfX/MREP type ii | 171 |
| 64/98[c] | orfX/MREP type iii | 163 |
| 64/99[c] | orfX/MREP type ii | 171 |
| 64/100[c] | orfX/MREP types i and ii | 180 (type i); 282 (type ii) |
| 64/101[c] | orfX/MREP types i and ii | 189 (type i); 291 (type ii) |
| 64/102[c] | orfX/MREP type iii | 263 |
| 64/109[c] | orfX/MREP type ix | 369 |
| 64/204[c] | orfX/MREP type vi | 348 |
| 64/112[c] | orfX/MREP type vii | 214 |
| 64/113[c] | orfX/MREP type vii | 263 |

TABLE 7-continued

Length of amplicons obtained with the diferent primer pairs which are objects of the present invention

| SEQ ID NO. | Target[d] | Amplicon length[a] |
|---|---|---|
| 64/115[c] | orfX/MREP type viii | 227 |
| 64/116[c] | orfX/MREP type viii | 318 |

[a]Amplicon length is given in base pairs for MREP types amplified by the set of primers.
[b]Set of primers described by Hiramatsu et al. in U.S. Pat. 6,156,507.
[c]Set of primers developed in the present invention.
[d]orfSA0022 refers to the open reading frame designation from GenBank accession number AP003129 (SEQ ID NO.: 231).

TABLE 8

Other primers developed in the present invention

| | | Originating DNA | |
|---|---|---|---|
| SEQ ID NO. | Target | Position[a] | SEQ ID NO. |
| 77 | MREP type iv | 993 | 43 |
| 65 | MREP type v | 636 | 47 |
| 70 | orfX | 1796 | 3 |
| 68 | IS431 | 626 | 92 |
| 69 | mecA | 1059 | 78 |
| 96 | mecA | 1949 | 78 |
| 81 | mecA | 1206 | 78 |
| 114 | MREP type vii | 629[b] | 165 |
| 117 | MREP type ii | 856 | 194 |
| 118 | MREP type ii | 974[b] | 194 |
| 119 | MREP type vii | 404 | 189 |
| 120 | MREP type vii | 477[b] | 189 |
| 123 | MREP type vii | 551 | 165 |
| 124 | MREP type ii | 584 | 170 |
| 125 | MREP type ii | 689[b] | 170 |
| 126 | orfSA0021 | 336 | 231 |
| 127 | orfSA0021 | 563 | 231 |
| 128 | orfSA0022[d] | 2993 | 231 |
| 129 | orfSA0022[d] | 3467[b] | 231 |
| 132 | orfX | 3700 | 231 |
| 145 | MREP type iv | 988 | 51 |
| 146 | MREP type iv | 1386 | 51 |
| 147 | MREP type iv | 891[b] | 51 |
| 148 | MREP type ix | 664 | 168 |
| 149 | MREP type ix | 849[b] | 168 |
| 150 | MREP type vii | 1117[b] | 165 |
| 151 | MREP type vii | 1473 | 189 |
| 152 | IS431mec | 1592[b] | 189 |
| 154 | MREP type v | 996[b] | 50 |
| 155 | MREP type v | 935 | 50 |
| 156 | tetK from plasmid pT181 | 1169[b] | 228 |
| 157 | tetK from plasmid pT181 | 136 | 228 |
| 158 | orfX | 2714[b] | 2 |
| 159 | orfX | 2539 | 2 |
| 187 | MREP type viii | 967[b] | 167 |
| 188 | MREP type viii | 851 | 167 |

[a]Position refers to nucleotide position of the 5' end of primer.
[b]Primer is reverse-complement of target sequence.

TABLE 9

Amplification and/or sequencing primers developed in the present invention

| | | Originating DNA | |
|---|---|---|---|
| SEQ ID NO. | Target | Position[a] | SEQ ID NO. |
| 85 | *S. aureus* chromosome | 197[b] | 35 |
| 86 | *S. aureus* chromosome | 198[b] | 37 |
| 87 | *S. aureus* chromosome | 197[b] | 38 |
| 88 | *S. aureus* chromosome | 1265[b] | 39 |
| 89 | *S. aureus* chromosome | 1892 | 3 |
| 103 | orfX | 1386 | 3 |
| 105 | MREP type i | 2335 | 2 |
| 106 | MREP type ii | 2437 | 2 |
| 107 | MREP type iii | 153[b] | 4 |
| 108 | MREP type iii | 153[b] | 4 |
| 121 | MREP type vii | 1150 | 165 |
| 122 | MREP type vii | 1241[b] | 165 |
| 130 | orfX | 4029[b] | 231 |
| 131 | region between orfSA0022 and orfSA0023[d] | 3588 | 231 |
| 133 | merB from plasmid pI258 | 262 | 226 |
| 134 | merB from plasmid pI258 | 539[b] | 226 |
| 135 | merR from plasmid pI258 | 564 | 226 |
| 136 | merR from plasmid pI258 | 444 | 227 |
| 137 | merR from plasmid pI258 | 529 | 227 |
| 138 | merR from plasmid pI258 | 530[b] | 227 |
| 139 | rep from plasmid pUB110 | 796 | 230 |
| 140 | rep from plasmid pUB110 | 761[b] | 230 |
| 141 | rep from plasmid pUB110 | 600 | 230 |
| 142 | aadD from plasmid pUB110 | 1320[b] | 229 |
| 143 | aadD from plasmid pUB110 | 759 | 229 |
| 144 | aadD from plasmid pUB110 | 646 | 229 |
| 153 | MREP type vii | 1030 | 165 |
| 200 | orfSA0022[d] | 871[c] | 231 |
| 201 | orfSA0022[d] | 1006 | 231 |
| 202 | MREP type vi | 648 | 171 |
| 203 | MREP type vi | 883[b] | 171 |
| 205 | MREP type ix | 1180 | 168 |
| 206 | MREP type ix | 1311[b] | 233 |
| 207 | MREP type viii | 1337 | 167 |
| 208 | MREP type viii | 1441[b] | 167 |
| 209 | ccrA | 184 | 232 |
| 210 | ccrA | 385 | 232 |
| 211 | ccrA | 643[b] | 232 |
| 212 | ccrA | 1282[b] | 232 |
| 213 | ccrB | 1388 | 232 |
| 214 | ccrB | 1601 | 232 |
| 215 | ccrB | 2139[b] | 232 |
| 216 | ccrB | 2199[b] | 232 |
| 217 | ccrB | 2847[b] | 232 |
| 218 | ccrB | 2946[b] | 232 |

[a]Position refers to nucleotide position of the 5' end of primer.
[b]Primer is reverse-complement of target sequence.
[c]Primer contains two mismatches.
[d]orfSA0022 and orfSA0023 refer to the open reading frame designation from GenBank accession number AP003129 (SEQ ID NO.: 231).

TABLE 10

Origin of the nucleic acids and/or sequences available from public databases found in the sequence listing

| SEQ ID NO. | Staphylococcal strain | Source | Accession number | Genetic Target[a,b] |
|---|---|---|---|---|
| 1 | NCTC 10442 | Database | AB033763 | SCCmec type I MREJ |
| 2 | N315 | Database | D86934 | SCCmec type II MREJ |
| 3 | NCTC 8325 | Database | AB014440 | MSSA chromosome |
| 4 | 86/560 | Database | AB013471 | SCCmec type III MREJ |
| 5 | 86/961 | Database | AB013472 | SCCmec type III MREJ |
| 6 | 85/3907 | Database | AB013473 | SCCmec type III MREJ |
| 7 | 86/2652 | Database | AB013474 | SCCmec type III MREJ |

TABLE 10-continued

Origin of the nucleic acids and/or sequences available from public databases found in the sequence listing

| SEQ ID NO. | Staphylococcal strain | Source | Accession number | Genetic Target[a,b] |
|---|---|---|---|---|
| 8 | 86/1340 | Database | AB013475 | SCCmec type III MREJ |
| 9 | 86/1762 | Database | AB013476 | SCCmec type III MREJ |
| 10 | 86/2082 | Database | AB013477 | SCCmec type III MREJ |
| 11 | 85/2111 | Database | AB013478 | SCCmec type III MREJ |
| 12 | 85/5495 | Database | AB013479 | SCCmec type III MREJ |
| 13 | 85/1836 | Database | AB013480 | SCCmec type III MREJ |
| 14 | 85/2147 | Database | AB013481 | SCCmec type III MREJ |
| 15 | 85/3619 | Database | AB013482 | SCCmec type III MREJ |
| 16 | 85/3566 | Database | AB013483 | SCCmec type III MREJ |
| 17 | 85/2232 | Database | AB014402 | SCCmec type II MREJ |
| 18 | 85/2235 | Database | AB014403 | SCCmec type II MREJ |
| 19 | MR108 | Database | AB014404 | SCCmec type II MREJ |
| 20 | 85/9302 | Database | AB014430 | SCCmec type I MREJ |
| 21 | 85/9580 | Database | AB014431 | SCCmec type I MREJ |
| 22 | 85/1940 | Database | AB014432 | SCCmec type I MREJ |
| 23 | 85/6219 | Database | AB014433 | SCCmec type I MREJ |
| 24 | 64/4176 | Database | AB014434 | SCCmec type I MREJ |
| 25 | 64/3846 | Database | AB014435 | SCCmec type I MREJ |
| 26 | HUC19 | Database | AF181950 | SCCmec type II MREJ |
| 33 | G3 | U.S. Pat. No. 6,156,507 | SEQ ID NO.: 15 | *S. epidermidis* SCCmec type II MREJ |
| 34 | SH 518 | U.S. Pat. No. 6,156,507 | SEQ ID NO.: 16 | *S. haemolyticus* SCCmec type II MREJ |
| 35 | ATCC 25923 | U.S. Pat. No. 6,156,507 | SEQ ID NO.: 9 | *S. aureus* chromosome |
| 36 | STP23 | U.S. Pat. No. 6,156,507 | SEQ ID NO.: 10 | *S. aureus* chromosome |
| 37 | STP43 | U.S. Pat. No. 6,156,507 | SEQ ID NO.: 12 | *S. aureus* chromosome |
| 38 | STP53 | U.S. Pat. No. 6,156,507 | SEQ ID NO.: 13 | *S. aureus* chromosome |
| 39 | 476 | Genome project[c] | | *S. aureus* chromosome |
| 40 | 252 | Genome project[c] | | SCCmec type II MREJ |
| 41 | COL | Genome project[d] | | SCCmec type I MREJ |
| 78 | NCTC 8325 | Database | X52593 | mecA |
| 82 | NCTC 10442 | Database | AB033763 | mecA |
| 90 | N315 | Database | D86934 | mecA |
| 91 | 85/2082 | Database | AB037671 | mecA |
| 92 | NCTC 10442 | Database | AB033763 | IS431 |
| 93 | N315 | Database | D86934 | IS431 |
| 94 | HUC19 | Database | AF181950 | IS431 |
| 95 | NCTC 8325 | Database | X53818 | IS431 |
| 104 | 85/2082 | Database | AB037671 | SCCmec type III MREJ |
| 226 | unknown | Database | L29436 | merB on plasmid pI258 |
| 227 | unknown | Database | L29436 | merR on plasmid pI258 |
| 228 | unknown | Database | S67449 | tetK on plasmid pT181 |
| 229 | HUC19 | Database | AF181950 | aadD on plasmid pUB110 |
| 230 | HUC19 | Database | AF181950 | rep on plasmid pUB110 |
| 231 | N315 | Database | AP003129 | orfSA0021, orfSA0022, orfSA0023 |
| 232 | 85/2082 | Database | AB037671 | ccrA/ccrB |

[a]MREJ refers to mec right extremity junction and includes sequences from SCCmec-right extremity and chromosomal DNA to the right of SCCmec integration site.
[b]Unless otherwise specified, all sequences were obtained from *S. aureus* strains.
[c]Sanger Institute genome project (http://www.sanger.ac.uk).
[d]TIGR genome project (http://www.tigr.org).

TABLE 11

Analytical sensitivity of the MRSA-specific PCR assay targeting MREP types i, ii and iii on a standard thermocycler using the set of primers developed in the present invention (SEQ ID NOs.: 64, 66 and 67)

| Strain designation: Original | Strain designation: CCRI[a] (MREP type) | Detection limit (number of genome copies) |
|---|---|---|
| 13370 | CCRI-8894 (I) | 5 |
| ATCC 43300 | CCRI-175 (II) | 2 |
| 35290 | CCRI-1262 (III) | 2 |

[a]CCRI stands for "Collection of the Centre de Recherche en Infectiologie".

TABLE 12

Specificity and ubiquity tests performed on a standard thermocycler using the set of primers targeting MREP types i, ii and iii developed in the present invention (SEQ ID NOs.: 64, 66 and 67) for the detection of MRSA

| Strains | PCR results for MREJ: Positive (%) | PCR results for MREJ: Negative (%) |
|---|---|---|
| MRSA - 208 strains | 188 (90.4) | 20 (9.6) |
| MSSA - 252 strains | 13 (5.2) | 239 (94.8) |
| MRCNS - 41 strains* | 0 | 42 (100) |
| MSCNS - 21 strains* | 0 | 21 (100) |

*Details regarding CNS strains:
MRCNS *S. caprae* (2)
*S. cohni cohnii* (3)

TABLE 12-continued

| | |
|---|---|
| | *S. cohni urealyticum* (4) |
| | *S. epidermidis* (8) |
| | *S. haemolyticus* (9) |
| | *S. hominis* (4) |
| | *S. sciuri* (4) |
| | *S. sciuri sciuri* (1) |
| | *S. simulans* (3) |
| | *S. warneri* (3) |
| MSCNS | *S. cohni cohnii* (1) |
| | *S. epidermidis* (3) |
| | *S. equorum* (2) |
| | *S. felis* (1) |
| | *S. gallinarum* (1) |
| | *S. haemolyticus* (1) |
| | *S. hominis* (1) |
| | *S. lentus* (1) |
| | *S. lugdunensis* (1) |
| | *S. saccharolyticus* (1) |
| | *S. saprophyticus* (5) |
| | *S. simulans* (1) |
| | *S. warneri* (1) |
| | *S. xylosus* (1) |

TABLE 13

Percentage of sequence identity for the first 500 nucleotides of SCCmec right extremities between all 9 types of MREP[a,b]

| MREP type | i | ii | iii | iv | v | vi | vii | viii | ix |
|---|---|---|---|---|---|---|---|---|---|
| i | — | 79.2 | 42.8 | 42.8 | 41.2 | 44.4 | 44.6 | 42.3 | 42.1 |
| ii | | | 43.9 | 47.5 | 44.7 | 41.7 | 45.0 | 52.0 | 57.1 |
| iii | | | | 46.8 | 44.5 | 42.9 | 45.0 | 42.8 | 45.2 |
| iv | | | | | 45.8 | 41.4 | 44.3 | 48.0 | 41.3 |
| v | | | | | | 45.4 | 43.7 | 47.5 | 44.3 |
| vi | | | | | | | 45.1 | 41.1 | 47.2 |
| vii | | | | | | | | 42.8 | 40.9 |
| viii | | | | | | | | | 55.2 |
| ix | | | | | | | | | — |

[a]"First 500 nucleotides" refers to the 500 nucleotides within the SCCmec right extremity, starting from the integration site of SCCmec in the *Staphylococcus aureus* chromosome as shown on FIG. 4.

[b]Sequences were extracted from SEQ ID NOs.: 1, 2, 104, 51, 50, 171, 165, 167, and 168 for types i to ix, respectively.

TABLE 14

Reference strains used to test sensitivity and/or specificity and/or ubiquity of the MRSA-specific PCR assays targeting MREJ sequences

| Staphylococcal species | Strains | Source[a] |
|---|---|---|
| MRSA (n = 45) | 33591 | ATCC |
| | 33592 | ATCC |
| | 33593 | ATCC |
| | BAA-38 | ATCC |
| | BAA-39 | ATCC |
| | BAA-40 | ATCC |
| | BAA-41 | ATCC |
| | BAA-42 | ATCC |
| | BAA-43 | ATCC |
| | BAA-44 | ATCC |
| | F182 | CDC |
| | 23 (CCUG 41787) | HARMONY Collection |
| | ID-61880 (EMRSA1) | LSPQ |
| | MA 8628 | LSPQ |
| | MA 50558 | LSPQ |
| | MA 50428 | LSPQ |
| | MA 50609 | LSPQ |
| | MA 50884 | LSPQ |
| | MA 50892 | LSPQ |
| | MA 50934 | LSPQ |
| | MA 51015 | LSPQ |
| | MA 51056 | LSPQ |

TABLE 14-continued

Reference strains used to test sensitivity and/or specificity and/or ubiquity of the MRSA-specific PCR assays targeting MREJ sequences

| | | |
|---|---|---|
| | MA 51085 | LSPQ |
| | MA 51172 | LSPQ |
| | MA 51222 | LSPQ |
| | MA 51363 | LSPQ |
| | MA 51561 | LSPQ |
| | MA 52034 | LSPQ |
| | MA 52306 | LSPQ |
| | MA 51520 | LSPQ |
| | MA 51363 | LSPQ |
| | 98/10618 | HARMONY Collection |
| | 98/26821 | HARMONY Collection |
| | 24344 | HARMONY Collection |
| | 62305 | HARMONY Collection |
| | 90/10685 | HARMONY Collection |
| | 98/14719 | HARMONY Collection |
| | 97S99 | HARMONY Collection |
| | 97S100 | HARMONY Collection |
| | 825/96 | HARMONY Collection |
| | 842/96 | HARMONY Collection |
| | N8-890/99 | HARMONY Collection |
| | 9805-01937 | HARMONY Collection |
| | 1 | Kreiswirth-1 |
| | 29 | Kreiswirth-1 |
| MRCNS (n = 4) | 29060 | ATCC |
| | 35983 | ATCC |
| | 35984 | ATCC |
| | 2514 | LSPQ |

| Staphylococcal species | Strains | Source |
|---|---|---|
| MSSA (n = 28) | MA 52263 | LSPQ |
| | 6538 | ATCC |
| | 13301 | ATCC |
| | 25923 | ATCC |
| | 27660 | ATCC |
| | 29213 | ATCC |
| | 29247 | ATCC |
| | 29737 | ATCC |
| | RN 11 | CDC |
| | RN 3944 | CDC |
| | RN 2442 | CDC |
| | 7605060113 | CDC |
| | BM 4611 | Institut Pasteur |
| | BM 3093 | Institut Pasteur |
| | 3511 | LSPQ |
| | MA 5091 | LSPQ |
| | MA 8849 | LSPQ |
| | MA 8871 | LSPQ |
| | MA 50607 | LSPQ |
| | MA 50612 | LSPQ |
| | MA 50848 | LSPQ |
| | MA 51237 | LSPQ |
| | MA 51351 | LSPQ |
| | MA 52303 | LSPQ |
| | MA 51828 | LSPQ |
| | MA 51891 | LSPQ |
| | MA 51504 | LSPQ |
| | MA 52535 | LSPQ |
| | MA 52783 | LSPQ |
| MSCNS (n = 17) | 12228 | ATCC |
| | 14953 | ATCC |
| | 14990 | ATCC |
| | 15305 | ATCC |
| | 27836 | ATCC |
| | 27848 | ATCC |
| | 29070 | ATCC |
| | 29970 | ATCC |
| | 29974 | ATCC |
| | 35539 | ATCC |
| | 35552 | ATCC |
| | 35844 | ATCC |
| | 35982 | ATCC |
| | 43809 | ATCC |
| | 43867 | ATCC |

TABLE 14-continued

| Reference strains used to test sensitivity and/or specificity and/or ubiquity of the MRSA-specific PCR assays targeting MREJ sequences | |
|---|---|
| 43958 | ATCC |
| 49168 | ATCC |

[a]ATCC stands for "American Type Culture Collection". LSPQ stands for "Laboratoire de Santé Publique du Québec". CDC stands for "Center for Disease Control and Prevention".

TABLE 15

Clinical isolates used to test the sensitivity and/or specificity and/or ubiquity of the MRSA-specific PCR assays targeting MREJ sequences

| Staphylococcal species | Number of strains | Source |
|---|---|---|
| MRSA (n = 177) | 150 | Canada |
| | 10 | China |
| | 10 | Denmark |
| | 9 | Argentina |
| | 1 | Egypt |
| | 1 | Sweden |
| | 1 | Poland |
| | 3 | Japan |
| | 1 | France |
| MSSA (n = 224) | 208 | Canada |
| | 10 | China |
| | 4 | Japan |
| | 1 | USA |
| | 1 | Argentina |
| MRCNS (n = 38) | 32 | Canada |
| | 3 | China |
| | 1 | France |
| | 1 | Argentina |
| | 1 | USA |
| MSCNS (n = 17) | 14 | UK |
| | 3 | Canada |

TABLE 16

Analytical sensitivity of tests performed on a standard thermocycler using the set of primers targeting MREP types i, ii, iii, iv and v (SEQ ID NOs.: 64, 66, 67, 79 and 80) developed in the present invention for the detection and identification of MRSA

| *Staphylococcus aureus* strain designation: | | Detection limit |
|---|---|---|
| Original | CCRI[a] (MREP type) | (number of genome copies) |
| 13370 | CCRI-8894 (i) | 10 |
| ATCC 43300 | CCRI-175 (ii) | 5 |
| 9191 | CCRI-2086 (ii) | 10 |
| 35290 | CCRI-1262 (iii) | 5 |
| 352 | CCRI-1266 (iii) | 10 |
| 19121 | CCRI-8895 (iv) | 5 |
| ATCC 33592 | CCRI-178 (iv) | 5 |
| MA 50428 | CCRI-1311 (v) | 5 |
| R991282 | CCRI-2025 (v) | 5 |

[a]CCRI stands for "Collection of the Centre de Recherche en Infectiologie".

TABLE 17

Specificity and ubiquity tests performed on a standard thermocycler using the set of primers targeting MREP types i, ii, iii, iv and v (SEQ ID NO.: 64, 66, 67, 79 and 80) developed in the present invention for the detection and identification of MRSA

| | PCR results for SCCmec - orfX right extremity junction | |
|---|---|---|
| Strains | Positive (%) | Negative (%) |
| MRSA - 35 strains[a] | 27 (77.1) | 8 (22.9) |
| MSSA - 44 strains | 13 (29.5) | 31 (70.5) |
| MRCNS - 9 strains* | 0 | 9 (100) |
| MSCNS - 10 strains* | 0 | 10 (100) |

[a]MRSA strains include the 20 strains listed in Table 3.
*Details regarding CNS strains:

| | |
|---|---|
| MRCNS | *S. caprae* (1) |
| | *S. cohni cohnii* (1) |
| | *S. epidermidis* (1) |
| | *S. haemolyticus* (2) |
| | *S. hominis* (1) |
| | *S. sciuri* (1) |
| | *S. simulans* (1) |
| | *S. warneri* (1) |
| MSCNS | *S. cohni* (1) |
| | *S. epidermidis* (1) |
| | *S. equorum* (1) |
| | *S. haemolyticus* (1) |
| | *S. lentus* (1) |
| | *S. lugdunensis* (1) |
| | *S. saccharolyticus* (1) |
| | *S. saprophyticus* (2) |
| | *S. xylosus* (1) |

TABLE 18

Analytical sensitivity of tests performed on the SMART CYCLER ® thermocycler using the set of primers targeting MREP types i, ii, iii, iv and v (SEQ ID NOs.: 64, 66, 67, 79 and 80) and molecular beacon probe (SEQ ID NO.: 84) developed in the present invention for the detection and identification of MRSA

| *Staphylococcus aureus* strain designation: | | Detection limit |
|---|---|---|
| Original | CCRI[a](MREP type) | (number of genome copies) |
| 13370 | CCRI-8894 (i) | 2 |
| ATCC 43300 | CCRI-175 (ii) | 2 |
| 9191 | CCRI-2086 (ii) | 10 |
| 35290 | CCRI-1262 (iii) | 2 |
| 352 | CCRI-1266 (iii) | 10 |
| ATCC 33592 | CCRI-178 (iv) | 2 |
| MA 51363 | CCRI-1331(iv) | 5 |
| 19121 | CCRI-8895 (iv) | 10 |
| Z109 | CCRI-8903 (iv) | 5 |
| 45302 | CCRI-1263 (v) | 10 |
| MA 50428 | CCRI-1311 (v) | 5 |
| MA 50609 | CCRI-1312 (v) | 5 |
| MA 51651 | CCRI-1325 (v) | 10 |
| 39795-2 | CCRI-1377 (v) | 10 |
| R991282 | CCRI-2025 (v) | 2 |

[a]CCRI stands for "Collection of the Centre de Recherche en Infectiologie".

TABLE 19

Specificity and ubiquity tests performed on the SMART CYCLER ® thermocycler using the set of primers targeting MREP types i, ii, iii, iv and v (SEQ ID NO.: 64, 66, 67, 79 and 80) and molecular beacon probe (SEQ ID NO.: 84) developed in the present invention for the detection of MRSA

| | PCR results for MREJ | |
|---|---|---|
| Strains | Positive (%) | Negative (%) |
| MRSA - 29 strains[a] | 21 (72.4) | 8 (27.6) |
| MSSA - 35 strains | 13 (37.1) | 22 (62.9) |
| MRCNS - 14 strains | 0 | 14 (100) |
| MSCNS - 10 strains | 0 | 10 (100) |

[a]MRSA strains include the 20 strains listed in Table 3.

Details regarding CNS strains:

MRCNS *S. epidermidis* (1)
*S. haemolyticus* (5)
*S. simulans* (5)
*S. warneri* (3)

MSCNS *S. cohni cohnii* (1)
*S. epidermidis* (1)
*S. gallinarum* (1)
*S. haemolyticus* (1)
*S. lentus* (1)
*S. lugdunensis* (1)
*S. saccharolyticus* (1)
*S. saprophyticus* (2)
*S. xylosus* (1)

TABLE 20

Analytical sensitivity of tests performed on the SMART CYCLER ® thermocycler using the set of primers targeting MREP types i, ii, iii, iv, v and vii (SEQ ID NOs.: 64, 66, 67, 79 and 80) and molecular beacon probe (SEQ ID NO.: 84) developed in the present invention for the detection and identification of MRSA

| *Staphylococcus aureus* strain designation: | | Detection limit |
|---|---|---|
| Original | CCRI[a](MREP type) | (number of genome copies) |
| 13370 | CCRI-8894 (i) | 2 |
| ATCC 43300 | CCRI-175 (ii) | 2 |
| 35290 | CCRI-1262 (iii) | 2 |
| ATCC 33592 | CCRI-178 (iv) | 2 |

TABLE 20-continued

Analytical sensitivity of tests performed on the SMART CYCLER ® thermocycler using the set of primers targeting MREP types i, ii, iii, iv, v and vii (SEQ ID NOs.: 64, 66, 67, 79 and 80) and molecular beacon probe (SEQ ID NO.: 84) developed in the present invention for the detection and identification of MRSA

| *Staphylococcus aureus* strain designation: | | Detection limit |
|---|---|---|
| Original | CCRI[a](MREP type) | (number of genome copies) |
| R991282 | CCRI-2025 (v) | 2 |
| SE-41-1 | CCRI-9771 (vii) | 2 |

[a]CCRI stands for “Collection of the Centre de Recherche en Infectiologie”.

TABLE 21

Specificity and ubiquity tests performed on the SMART CYCLER ® thermocycler using the set of primers targeting MREP types i, ii, iii, iv, vi and vii (SEQ ID NOs.: 64, 66, 67, 79 and 80) and molecular beacon probe (SEQ ID NO.: 84) developed in the present invention for the detection and identification of MRSA

| | PCR results for MREJ | |
|---|---|---|
| Strains | Positive (%) | Negative (%) |
| MRSA - 23 strains[a] | 19 (82.6) | 4 (17.4) |
| MSSA - 25 strains | 13 (52) | 12 (48) |
| MRCNS - 26 strains | 0 | 26 (100) |
| MSCNS - 8 strains | 0 | 8 (100) |

[a]MRSA strains include the 20 strains listed in Table 3.

Details regarding CNS strains:

MRCNS *S. capitis* (2)
*S. caprae* (1)
*S. cohnii* (1)
*S. epidermidis* (9)
*S. haemolyticus* (5)
*S. hominis* (2)
*S. saprophyticus* (1)
*S. sciuri* (2)
*S. simulans* (1)
*S. warneri* (2)

MSCNS *S. cohni cohnii* (1)
*S. epidermidis* (1)
*S. haemolyticus* (1)
*S. lugdunensis* (1)
*S. saccharolyticus* (1)
*S. saprophyticus* (2)
*S. xylosus* (1)

Annex I:
Strategy for the selection of specific amplification primers for types i and ii MREP

| Derived from SEQ ID NO: | SEQ ID NO: | Types i and ii MREP | orfX |
|---|---|---|---|
| | | 2324 2358 | 2607 |
| 2 | 234 | TAT **GTCAAAAATC ATGAACCTCA TTACTTATGA TA**...CCT | **TGTGCAGGCC GTTTGATCCG** CC |
| 1 | 235 | TAT **GTCAAAAATC ATGAACCTCA TTACTTATGA TA**...CCT | **TGTGCAGGCC GTTTGATCCG** CC |
| 17[a] | 236 | TAT **GTCAAAAATC ATGAACCTCA TTACTTATGA TA**...CCT | **TGTGCAGGCC GTTTGATCCG** CC |
| 18[a] | 237 | TAT **GTCAAAAATC ATGAACCTCA TTACTTATGA TA**...CCT | **TGTGCAGGCC GTTTGATCCG** CC |
| 19[a] | 238 | TAT **GTCAAAAATC ATGAACCTCA TTACTTATGA TA**...CCT | **TGTGCAGGCC GTTTGATCCG** CC |
| 20[a] | 239 | TAT **GTCAAAAATC ATGAACCTCA TTACTTATGA TA**...CCT | **TGTGCAGGCC GTTTGATCCG** CC |
| 21[a] | 240 | TAT **GTCAAAAATC ATGAACCTCA TTACTTATGA TA**...CCT | **TGTGCAGGCC GTTTGATCCG** CC |
| 22[a] | 241 | TAT **GTCAAAAATC ATGAACCTCA TTACTTATGA TA**...CCT | **TGTGCAGGCC GTTTGATCCG** CC |
| 23[a] | 242 | TAT **GTCAAAAATC ATGAACCTCA TTACTTATGA TA**...CCT | **TGTGCAGGCC GTTTGATCCG** CC |
| 24[a] | 243 | TAT **GTCAAAAATC ATGAACCTCA TTACTTATGA TA**...CCT | **TGTGCAGGCC GTTTGATCCG** CC |
| 25[a] | 244 | TAT **GTCAAAAATC ATGAACCTCA TTACTTATGA TA**...CCT | **TGTGCAGQCC GTTTGATCCG** CC |
| 26 | 245 | TAT **GTCAAAAATC ATGAACCTCA TTACTTATGA TA**...CCT | **TGTGCAGGCC GTTTGATCCG** CC |
| 33[c] | 246 | CtT | **gGTGtAaaCC aTTgGAgCCa** CC |
| 34[c] | 247 | CCT | **caTGCAatCC aTTTGATC** |
| Selected sequence for type i MREP and ii primer | | | |
| (SEQ ID No: 66) | 248 | **GTCAAAAATC ATGAACCTCA TTACTTATG** | |
| Selected sequence for orfX primer[b] | | | |
| (SEQ ID NO: 64) | 249 | | **TGTGCAGGCC GTTTGATCC** |

The sequence positions refer to SEQ ID NO: 2.
Nucleotides in capitals are identical to the selected sequences or match those sequences.
Mismatches are indicated by lower-case letters. Dots indicate gaps in the displayed sequences.
[a]These sequences are the reverse-complements of SEQ ID NOs.: 17-25.
[b]This sequence is the reverse-complement of the selected primer.
[c]SEQ ID NOs.: 33 and 34 were obtained from CNS species.

ANNEX II

Strategy for the selection of a specific molecular beacon probe for the real-time detection of MREJ

| SEQ ID NO: | SEQ ID NO: | orfX 327 371 |
|---|---|---|
| 165 | 250 | ACAAG GACGT CTTACAACGC AGTAACTAtG CACTA |
| 180 | 251 | ACAAG GACGT CTTACAACGC AGTAACTAtG CACTA |
| 181 | 252 | ACAAG GACGT CTTACAACGC AGTAACTAtG CACTA |
| 182 | 253 | ACAAG GACGT CTTACAACGC AGTAACTAtG CACTA |
| 183 | 254 | ACAAG GACGT CTTACAACGC AGTAACTAtG CACTA |
| 184 | 255 | ACAAG GACGT CTTACAACGC AGTAACTAtG CACTA |
| 186 | 256 | ACAAG GACGT CTTACAACGC AGTAACTAtG CACTA |
| 174 | 257 | ACAAG GACGT CTTACAACGt AGTAACTACG CACTA |

ANNEX II-continued

Strategy for the selection of a specific molecular beacon probe for the real-time detection of MREJ

| SEQ ID NO: | SEQ ID NO: | orfX 327 371 |
|---|---|---|
| 175 | 258 | ACAAG GACGT CTTACAACGt AGTAACTACG CACTA |
| 178 | 259 | ACAAG GACGT CTTACAACGt AGTAACTACG CACTA |
| 176 | 260 | ACAAG GACGT CTTACAACGt AGTAACTACG CACTA |
| 173 | 261 | ACAAG GACGT CTTACAACGt AGTAACTACG CACTA |
| 177 | 262 | ACAAG GACGT CTTACAACGt AGTAACTACG CACTA |
| 169 | 263 | ACAAG GACGT CTTACAACGC AGTAACTACG CACTA |
| 199 | 264 | ACAAG GACGT CTTACAACGC AGTAACTACG CACTA |
| 33[a,b] | 265 | ACcAa GACGT CTTACAACGC AGcAACTAtG CACTA |
| 34[a,b] | 266 | AtgAG GACGT CTTACAACGC AGcAACTACG CACTt |
| Selected sequence for orfX molecular beacon probes | | |
| (SEQ ID NO: 163)[c] | 267 | GACGT CTTACAACGC AGTAACTAtG |
| (SEQ ID NO: 164)[c] | 268 | GACGT CTTACAACGt AGTAACTACG |
| (SEQ ID NO: 84)[c] | 269 | GACGT CTTACAACGC AGcAACTACG |

Nucleotide discrepancies between the orfX sequences and SEQ ID NO.: 84 are shown in lower-case. Other entries in the sequence listing also present similar variations. The stem of the molecular beacon probes are not shown for sake of clarity. The sequence positions refer to SEQ ID NO.: 165.

[a]These sequences are the reverse-complements of SEQ ID NOs.: 33 and 34.

[b]SEQ ID NOs.: 33 and 34 were obtained from CNS species.

[c]The sequences presented are the reverse-complement of the selected molecular beacon probes.

What is claimed is:

1. A method to detect the presence of an MREJ type vii methicillin-resistant *Staphylococcus aureus* (MRSA) strain comprising:

a.) performing an amplification reaction comprising contacting a sample to be analyzed for the presence of said MREJ type vii MRSA strain with a first amplification primer and a second amplification primer to generate a first amplicon if said MREJ type vii MRSA strain is present in said sample, said MREJ type vii MRSA strain including a staphylococcal cassette chromosome mec (SCCmec) element containing a mecA gene inserted into chromosomal DNA, said chromosomal DNA being orfX, thereby generating a polymorphic right extremity junction (MREJ) type vii sequence that comprises sequences from both the SCCmec element right extremity and orfX adjoining said right extremity;

wherein said first primer is at least 10 nucleotides in length and specifically hybridizes at least under conditions of 50 mM KCl, 10 mM Tris-HCl (pH 9.0), 0.1% Triton X-100, 2.5 mM $MgCl_2$ at 55° C. with an SCCmec element right extremity of an MREJ nucleic acid type vii sequence selected from the group consisting of: SEQ ID NO: 165, SEQ ID NO: 166, and the complements thereof, wherein said second primer is at least 10 nucleotides in length and specifically hybridizes at least under conditions of 50 mM KCl, 10 mM Tris-HCl (pH 9.0), 0.1% Triton X-100, 2.5 mM $MgCl_2$ at 55° C. with orfX, wherein said first amplicon generated if said MREJ type vii MRSA strain is present in said sample comprises polymorphic right extremity junction (MREJ) type vii sequence and orfX sequence, including the junction of the two, and is indicative of the presence of MREJ type vii MRSA strain in said sample; and b.) detecting said first amplicon if present.

2. The method of claim 1, wherein said first amplification primer that specifically hybridizes with said SCCmec element right extremity of an MREJ type vii sequence comprises at least 10 consecutive residues of SEQ ID NO:112, or the complement thereof.

3. The method of claim 1, wherein said first amplification primer that specifically hybridizes with said SCCmec element right extremity of an MREJ type vii sequence comprises at least 10 consecutive residues of SEQ ID NO: 113, or the complement thereof.

4. The method of claim 2, wherein said second amplification primer comprises at least ten consecutive residues of SEQ ID NO: 64 or the complement thereof.

5. The method of claim 3, wherein said second amplification primer comprises at least ten consecutive residues of SEQ ID NO: 64 or the complement thereof.

6. The method of claim 1, wherein said amplification reaction comprises PCR.

7. The method of claim 1, wherein said method comprises the use of at least one first or second amplification primer and/or a probe comprising a nucleic acid sequence or complement thereof selected from the group consisting of SEQ ID NOs: 112, 113, 114, 119, 120, 121, 122, 123, 150, 151, 153, 64, 71, 72, 73, 74, 75, 76, 70, 103, 130, 132, 158, 159, 59, 62, 32, 83, 84, 160, 161, 162, 163, and 164 for the detection of MREJ type vii.

8. The method of claim 1, wherein said second and first amplification primers are a primer pair consisting of SEQ ID NOs: 64 and 112 or SEQ ID NOs: 64 and 113, or the complements thereof.

9. The method of claim 8, further comprising the use of at least one probe having a sequence selected from the group consisting of SEQ ID NOs: 32, 83, 84, 160, 161, 162, 163, 164, and the complements thereof.

10. The method of claim 1, wherein said method comprises the use of at least one first or second amplification primer and/or a probe comprising a nucleic acid sequence or complement thereof selected from the group consisting of: SEQ ID NOs: 64, 112, 113, 84, 163, and 164, for the detection of MREJ type vii.

11. The method of claim 1, further comprising detecting the presence of at least one further methicillin-resistant *Staphylococcus aureus* (MRSA) strain in said sample, said at least one further MRSA strain including an SCCmec element containing a mecA gene inserted into chromosomal DNA, thereby generating a polymorphic right extremity junction (MREJ) type i, ii, iii, iv, v, vi, viii or ix nucleic acid sequence that comprises sequences from both the SCCmec element right extremity and chromosomal DNA adjoining said right extremity, wherein said method further comprises contacting said sample with at least one additional primer to generate a second amplicon if said at least one further MREJ type i, ii, iii, iv, v, vi, viii or ix MRSA strain is present in said sample, wherein said at least one additional primer is at least 10 nucleotides in length and specifically hybridizes at least under conditions of 50 mM KCl, 10 mM Tris-HCl (pH 9.0), 0.1% Triton X-100, 2.5 mM $MgCl_2$ at 55° C. with said polymorphic sequences from the SCCmec element right extremity of said at least one of MREJ type i, ii, iii, iv, v, vi, viii and ix nucleic acid sequences, or complements thereof, selected from the group consisting of:

a) SEQ ID NOs: 1, 20-25, and 41 for MREJ type i;
b) SEQ ID NOs: 2, 17-19, 26, 40, 173-183, 185, 186 and 197 for MREJ type ii;
c) SEQ ID NOs: 4-16, 104, 184 and 198 for MREJ type iii;
d) SEQ ID NOs: 42-46 and 51 for MREJ type iv;
e) SEQ ID NOs: 47-50 for MREJ type v;
f) SEQ ID NO: 171 for MREJ type vi;
g) SEQ ID NO: 167 for MREJ type viii; and
h) SEQ ID NO: 168 for MREJ type ix, wherein said second amplicon generated if said at least one further MREJ type i, ii, iii, iv, v, vi, viii or ix MRSA strain is present in said sample comprises polymorphic right extremity junction (MREJ) type i, ii, iii, iv, v, vi, viii or ix sequence and orfX sequence, including the junction of the two, and is indicative of the presence of said at least one further MREJ type i, ii, iii, iv, v, vi, viii or ix MRSA strain in said sample; and detecting said second amplicon if present.

12. The method of claim 11, wherein said at least one additional primer comprises at least one primer selected from the following SEQ ID NOs or complements thereof: 66, 100, 101, 105, 52, 53, 54, 55, 56, 57, 97, 99, 106, 117, 118, 124, 125, 58, 67, 98, 102, 107, 108, 79, 77, 145, 146, 147, 65, 80, 154, 155, 202, 203, 204, 115, 116, 187, 188, 207, 208, 109, 148, 149, 205, and 206.

13. The method of claim 12, further comprising use of at least one second amplification primer and/or a probe selected from the following SEQ ID NOs or complements thereof: 64, 71, 72, 73, 74, 75, 76, 70, 103, 130, 132, 158, 159, 59, 62, 32, 83, 84, 160, 161, 162, 163, and 164.

14. The method of claim 11, further comprising the use of at least one primer pair selected from the following SEQ ID NOs, or the complements thereof:

a) 64/66, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56 and 63/57, for the detection of type i MREJ;
b) 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56 and 63/57, for the detection of type ii MREJ;
c) 64/67, 64/98, 64/102, 59/58, 60/58, 61/58, 62/58 and 63/58, for the detection of type iii MREJ;
d) 64/79, for the detection of type iv MREJ;
e) 64/80, for the detection of type v MREJ;
f) 64/204, for the detection of type vi MREJ;
g) 64/115 and 64/116, for the detection of type viii MREJ; and
h) 64/109, for the detection of type ix MREJ.

15. The method of claim 14, comprising the use of at least one probe having a sequence, or the complement thereof, selected from the group consisting of: SEQ ID NOs: 32, 83, 84, 160, 161, 162, 163 and 164.

16. The method of claim 11, comprising the use of primers and probes having the following nucleotide sequences, or the complements thereof:

a) SEQ ID NOs: 64, 66, and at least one of 84, 163, 164 for the detection of MREJ type i or ii;
b) SEQ ID NOs: 64, 67, and at least one of 84, 163, 164 for the detection of MREJ type iii;
c) SEQ ID NOs: 64, 79, and at least one of 84, 163, 164 for the detection of MREJ type iv; and
d) SEQ ID NOs: 64, 80, and at least one of 84, 163, 164 for the detection of MREJ type v.

17. The method of claim 11, wherein multiple primers and/or probes are used together in the same physical enclosure.

18. The method of claim 11, further comprising distinctively detecting each amplicon if present as an indication of the presence of said MREJ type vii and said at least one further MREJ type selected from MREJ types i, ii, iii, iv, v, vi, viii and ix, wherein the presence or absence of an amplicon produced by a primer is indicative of the presence or absence, respectively, of the corresponding MREJ type MRSA.

19. The method of claim 11, wherein a plurality of primers and/or probes all chosen to hybridize under the same hybridization conditions are used.

20. The method of claim 1, comprising detecting the presence or absence of at least three further MRSA strains in said sample, said at least three further MRSA strain including an SCCmec element containing a mecA gene inserted into chromosomal DNA, thereby generating a polymorphic right extremity junction (MREJ) type i, ii, iii, iv, v, vi, viii or ix nucleic acid sequence that comprises sequences from both the SCCmec element right extremity and chromosomal DNA adjoining said right extremity, wherein said method further comprises contacting said sample with at least three additional primers to generate a second, third or fourth amplicon if said at least three further MREJ type i, ii, iii, iv, v, vi, viii or ix MRSA strains are present in said sample, wherein said at least three additional primers are at least 10 nucleotides in length and each specifically hybridizes under conditions of 50 mM KCl, 10 mM Tris-HCl (pH 9.0), 0.1% Triton X-100, 2.5 mM $MgCl_2$ at 55° C. with said polymorphic sequences from the SCCmec element right extremity of one of said at least three further MRSA strains of MREJ type i-vi, and viii-ix nucleic acid sequences, or complements thereof, selected from the group consisting of:

a) SEQ ID NOs: 1, 20-25, and 41 for MREJ type i;

b) SEQ ID NOs: 2, 17-19, 26, 40, 173-183, 185, 186 and 197 for MREJ type ii;

c) SEQ ID NOs: 4-16, 104, 184 and 198 for MREJ type iii;

d) SEQ ID NOs: 42-46 and 51 for MREJ type iv;

e) SEQ ID NOs: 47-50 for MREJ type v;

f) SEQ ID NO: 171 for MREJ type vi;

g) SEQ ID NO: 167 for MREJ type viii; and h) SEQ ID NO: 168 for MREJ type ix wherein said second, third and fourth amplicon generated if said at least three further MREJ type i, ii, iii, iv, v, vi, viii or ix MRSA strains are present in said sample comprises polymorphic right extremity junction (MREJ) type i, ii, iii, iv, v, vi, viii or ix sequence and orfX sequence, including the junction of the two, and said second, third and fourth amplicons are indicative of the presence of said at least three further MREJ type i, ii, iii, iv, v, vi, viii or ix MRSA strains in said sample; and detecting the presence or absence of each amplicon distinctively, wherein the presence or absence of an amplicon produced by a primer is indicative of the presence or absence, respectively, of the corresponding MREJ type MRSA, thereby determining the presence or absence in a sample of at least four MREJ types of MRSA, one of which is MREJ type vii.

21. The method of claim 20, for determining the presence or absence of MREJ type vii, type i, type ii, and type iii.

22. The method of claim 20, for determining the presence or absence of MREJ type vii, type i, type ii, type iii and type iv.

23. The method of claim 20, for determining the presence or absence of MREJ type vii, type i, type ii, type iii, type iv, type v, type vi, type viii and type ix.

24. The method of claim 20, for determining the presence or absence of MREJ type vii, type i, type ii, type iii, type iv and type vi.

25. The method of claim 1, wherein said method comprises the use of at least one second amplification primer and/or a probe specific for the *S. aureus* chromosome comprising a sequence, or the complement thereof, selected from the group consisting of SEQ ID NOs: 32, 59, 62, 70-76, 83, 84, 103, 130, 132, and 160-164.

26. The method of claim 11, wherein multiplex PCR is used.

27. The method of claim 1, comprising the use of at least one probe having a sequence, or the complement thereof, selected from the group consisting of SEQ ID NOs: 84, 163 and 164.

28. The method of claim 1, wherein said method comprises the use of at least one first amplification primer comprising a nucleic acid sequence or complement thereof selected from the group consisting of SEQ ID NOs: 112, 113, 114, 119, 120, 121, 122, 123, 150, 151, and 153, for the detection of MREJ type vii.

29. The method of claim 28, wherein said method further comprises the use of at least one second amplification primer and/or probe comprising a nucleic acid sequence or complement thereof selected from the group consisting of SEQ ID NOs: 64, 71, 72, 73, 74, 75, 76, 70, 103, 130, 132, 158, 159, 59, 62, 32, 83, 84, 160, 161, 162, 163, and 164.

* * * * *

SEQUENCE LISTING

<160> NUMBER OF SEQ ID NOS: 269

<210> SEQ ID NO 1
<211> LENGTH: 3050
<212> TYPE: DNA
<213> ORGANISM: Staphylococcus aureus

<400> SEQUENCE: 1

```
tcgtgccatt gatgcagagg gacatacatt agatatttgg ttgcgtaagc aacgagataa     60

tcattcagca tatgcgttta tcaaacgtct cattaaacaa tttggtaaac ctcaaaaggt    120

aattacagat caggcacctt caacgaaggt agcaatggct aaagtaatta aagcttttaa    180

acttaaacct gactgtcatt gtacatcgaa atatctgaat aacctcattg agcaagatca    240

ccgtcatatt aaagtaagaa agacaaggta tcaaagtatc aatacagcaa agaatacttt    300

aaaaggtatt gaatgtattt acgctctata taaaaagaac cgcaggtctc ttcagatcta    360

cggattttcg ccatgccacg aaattagcat catgctagca agttaagcga acactgacat    420

gataaattag tggttagcta tattttttta ctttgcaaca gaaccgaaaa taatctcttc    480

aatttatttt tatatgaatc ctgtgactca atgattgtaa tatctaaaga tttcagttca    540

tcatagacaa tgttcttttc aacatttttt atagcaaatt gattaaataa attctctaat    600

ttctcccgtt tgatttcact accatagatt atattatcat tgatatagtc aatgaataat    660

gacaaattat cactcataac agtcccaacc cctttatttt gatagactaa ttatcttcat    720
```

-continued

```
cattgtaaaa caaattacac cctttaaatt taactcaact taaatatcga caaattaaaa    780
aacaataaaa ttacttgaat attattcata atatattaac aactttatta tactgctctt    840
tatatataaa atcattaata attaaacaag ccttaaaata tttaactttt ttgtgattat    900
tacacattat cttatctgct ctttatcacc ataaaaatag aaaaaacaag attcctaaag    960
aatataggaa tcttgtttca gactgtggac aaactgattt tttatcagtt agcttattta   1020
gaaagtttta tttaaattac agtttctatt tttattagat cacaatttta ttttagctct   1080
tgttcaagta atcatttttc gccaaaaact ttatactgaa tagcttctac attaaatact   1140
ttgtcaatga gatcatctac atctttaaat tcagaataat ttgcatatgg atctataaaa   1200
taaaattgtg gttctttacc ggaaacatta aatattctta atattaaata tttctgctta   1260
tattctttca tagcaaacat ttcatttagc gacataaaaa atggttcctc aatactagaa   1320
gatgtagatg ttttaatttc aataaatttt tctacagctt tatctgtatt tgttggatca   1380
aaagctacta aatcatagcc atgaccgtgt tgagagcctg gattatcatt taaaatattc   1440
ctaaactgtt ctttcttatc ttcgtctatt ttattatcaa ttagctcatt aaagtaattt   1500
agcgctaatt tttctccaac tttaccggtt aatttattct ctttatttga tttttcaatt   1560
tctgaatcat ttttagtagt ctttgataca cctttttttat attttggaat tattccttta   1620
ggtgcttcca cttccttgag tgtcttatct ttttgtgctg ttctaatttc ttcaatttcg   1680
ctgtcttcct gtatttcgtc tatgctattg accaagctat cataggatgt ttttgtaact   1740
tttgaagcta attcattaaa tagttctaaa aatttcttta aatcctctag catatcttct   1800
tctgtgaatc cttcattcaa atcataatat ttgaatctta ttgatccatg agaatatcct   1860
gatggataat cattttttaa atcataagat gaatctttat tttctgcgta ataaaatctt   1920
ccagtattaa attcatttga tgtaatatat ttattgagtt cggaagataa agttaatgct   1980
ctttgttttg cagcattttt atcccgcgga aacatatcac ttatctttga ccatccttga   2040
ttcaaagata agtatatgcc ttctccttcc ggatgaaaaa gatataccaa ataatatcca   2100
tcctttgttt cttttgttat attctcatca tatattgaaa tccaaggaac tttactatag   2160
ttcccagtag caaccttccc tacaactgaa tatttatctt cttttatatg cacttttaac   2220
tgcttgggta acttatcatg gactaaagtt ttatatagat cacctttatc ccaatcagat   2280
tttttaacta cattattggt acgtttctct ttaattaatt taaggacctg cataaagttg   2340
tctatcattt gaaattccct cctattataa aatatattat gtctcatttt cttcaatatg   2400
tacttattta tattttaccg taatttacta tatttagttg cagaaagaat tttctcaaag   2460
ctagaacttt gcttcactat aagtattcag tataaagaat atttcgctat tatttacttg   2520
aaatgaaaga ctgcggaggc taactatgtc aaaaatcatg aacctcatta cttatgataa   2580
gcttctcctc gcataatctt aaatgctctg tacacttgtt caattaacac aacccgcatc   2640
atttgatgtg ggaatgtcat tttgctgaat gatagtgcgt agttactgcg ttgtaagacg   2700
tccttgtgca ggccgtttga tccgccaatg acgaaaacaa agtcgctttg cccttgggtc   2760
atgcgttggt tcaattcttg ggccaatcct tcggaagata gcatctttcc ttgtatttct   2820
aatgtaatga ctgtggattg tggtttgatt ttggctagta ttcgttggcc ttctttttct   2880
tttacttgct caatttcttt gtcactcata ttttctggtg ctttttcgtc tggaacttct   2940
atgatgtcta tcttggtgta tgggcctaaa cgtttttcat attctgctat ggcttgcttc   3000
caatatttct cttttagttt ccctacagct aaaatggtga ttttcatgtc              3050
```

<210> SEQ ID NO 2
<211> LENGTH: 3050
<212> TYPE: DNA
<213> ORGANISM: Staphylococcus aureus

<400> SEQUENCE: 2
acctcattga gcaagatcac cgtcatatta aagtaagaaa gacaaggtat caaagtatca 60
atacagcaaa gaatacttta aaaggtattg aatgtattta cgctctatat aaaaagaacc 120
gcaggtctct tcagatctac ggattttcgc catgccacga aattagcatc atgctagcaa 180
gttaagcgaa cactgacatg ataaattagt ggttagctat attttttac tttgcaacag 240 aaccgaaaat aatctcttca atttattttt atatgaatcc tgtgactcaa tgattgtaat 300
atctaaagat ttcagttcat catagacaat gttcttttca acatttttta tagcaaattg 360
attaaataaa ttctctaatt tctcccgttt gatttcacta ccatagatta tattatcatt 420
gatatagtca atgaataatg acaaattatc actcataaca gtcccaaccc ctttcttttg 480
atagactaat tatcttcatc attgtaaaac aaattacacc ctttaaattt aactcaactt 540
aaatatcgac aaattaaaaa acaataaaat tacttgaata ttattcataa tatattaaca 600
actttattat actgctcttt atatataaaa tcattaataa ttaaacaagc cttaaaatat 660
ttaacttttt tgtgattatt acacattatc ttatctgctc tttatcacca taaaaataga 720
aaaaacaaga ttcctaaaga atataggaat cttgtttcag actgtggaca aactgatttt 780
ttatcagtta gcttatttag aaagttttat ttaaattaca gtttctattt ttattagatc 840
acaattttat tttagctctt gttcaagtaa tcatttttcg ccaaaaactt tatactgaat 900
agcttctaca ttaaatactt tgtcaatgag atcatctaca tctttaaatt cagaataatt 960
tgcatatgga tctataaaat aaaattgtgg ttctttaccg gaaacattaa atattcttaa 1020
tattaaatat ttctgcttat attctttcat agcaaacatt tcatttagcg acataaaaaa 1080
tggttcctca atactagaag atgtagatgt tttaatttca ataaattttt ctacagcttt 1140
atctgtattt gttggatcaa aagctactaa atcatagcca tgaccgtgtt gagagcctgg 1200
attatcattt aaaatattcc taaactgttc tttcttatct tcgtctattt tattatcaat 1260
tagctcatta aagtaattta gcgctaattt ttctccaact ttaccggtta atttattctc 1320
tttatttgat ttttcaattt ctgaatcatt tttagtagtc tttgatacac ctttttttata 1380 ttttggaatt attcctttag gtgcttccac ttccttgagt gtcttatctt tttgtgctgt 1440
tctaatttct tcaatttcgc tgtcttcctg tatttcgtct atgctattga ccaagctatc 1500
ataggatgtt tttgtaactt ttgaagctaa ttcattaaat agttctaaaa atttctttaa 1560
atcctctagc atatcttctt ctgtgaatcc ttcattcaaa tcataatatt tgaatcttat 1620
tgatccatga gaatatcctg atggataatc attttttaaa tcataagatg aatctttatt 1680
ttctgcgtaa taaaatcttc cagtattaaa ttcatttgat gtaatatatt tattgagttc 1740
ggaagataaa gttaatgctc tttgttttgc agcattttta tcccgcggaa acatatcact 1800
tatctttgac catccttgat tcaaagataa gtatatgcct tctccttccg gatgaaaaag 1860
atataccaaa taatatccat cctttgtttc ttttgttata ttctcatcat atattgaaat 1920
ccaaggaact ttactatagt tcccagtagc aaccttccct acaactgaat atttatcttc 1980
ttttatatgc acttttaact gcttgggtaa cttatcatgg actaaagttt tatatagatc 2040
acctttatcc caatcagatt ttttaactac attattggta cgtttctctt taattaattt 2100
aaggacctgc ataaagttgt ctatcatttg aaattccctc ctattataaa atatattatg 2160

-continued

```
tctcattttc ttcaatatgt acttatttat attttaccgt aatttactat atttagttgc   2220

agaaagaatt ttctcaaagc tagaactttg cttcactata agtattcagt ataaagaata   2280

tttcgctatt atttacttga aatgaaagac tgcggaggct aactatgtca aaaatcatga   2340

acctcattac ttatgataag cttcttaaaa acataacagc aattcacata aacctcatat   2400

gttctgatac attcaaaatc cctttatgaa gcggctgaaa aaaccgcatc atttatgata   2460

tgcttctcca cgcataatct taaatgctct atacacttgc tcaattaaca caacccgcat   2520

catttgatgt gggaatgtca ttttgctgaa tgatagtgcg tagttactgc gttgtaagac   2580

gtccttgtgc aggccgtttg atccgccaat gacgaataca aagtcgcttt gcccttgggt   2640

catgcgttgg ttcaattctt gggccaatcc ttcggaagat agcatctttc cttgtatttc   2700

taatgtaatg actgtggatt gtggtttaat tttggctagt attcgttggc cttctttttc   2760

ttttacttgc tcaatttctt tgtcgctcat attttctggt gctttttcgt ctggaacttc   2820

tatgatgtct atcttggtgt atgggcctaa acgtttttca tattctgcta tggcttgctt   2880

ccaatatttc tcttttagtt tccctacagc taaaatggtg attttcatgt cgtttggtcc   2940

tccaaattgt tatcaacttt ccagttatcc acaagttatt aacttgttca cactgttccc   3000

tcttattata ccaatatttt ttgcagtttt tgatattttc ctgacattta              3050


<210> SEQ ID NO 3
<211> LENGTH: 3183
<212> TYPE: DNA
<213> ORGANISM: Staphylococcus aureus

<400> SEQUENCE: 3

ctgcagaggt aattattcca aacaatacca ttgatttcaa aggagaaaga gatgacgtta     60

gaacgcgtga aacaaattta ggaaacgcga ttgcagatgc tatggaagcg tatggcgtta    120

agaatttctc taaaaagact gactttgccg tgacaaatgg tggaggtatt cgtgcctcta    180

tcgcaaaagg taaggtgaca cgctatgatt taatctcagt attaccattt ggaaatacga    240

ttgcgcaaat tgatgtaaaa ggttcagacg tctggacggc tttcgaacat agtttaggcg    300

caccaacaac acaaaaggac ggtaagacag tgttaacagc gaatggcggt ttactacata    360

tctctgattc aatccgtgtt tactatgata taaataaacc gtctggcaaa cgaattaatg    420

ctattcaaat tttaaataaa gagacaggta agtttgaaaa tattgattta aaacgtgtat    480

atcacgtaac gatgaatgac ttcacagcat caggtggcga cggatatagt atgttcggtg    540

gtcctagaga agaaggtatt tcattagatc aagtactagc aagttattta aaaacagcta    600

acttagctaa gtatgatacg acagaaccac aacgtatgtt attaggtaaa ccagcagtaa    660

gtgaacaacc agctaaagga caacaaggta gcaaaggtag taagtctggt aaagatacac    720

aaccaattgg tgacgacaaa gtgatggatc cagcgaaaaa accagctcca ggtaaagttg    780

ttttgttgct agcgcataga ggaactgtta gtagcggtac agaaggttct ggtcgcacaa    840

tagaaggagc tactgtatca agcaagagtg ggaaacaatt ggctagaatg tcagtgccta    900

aaggtagcgc gcatgagaaa cagttaccaa aaactggaac taatcaaagt tcaagcccag    960

aagcgatgtt tgtattatta gcaggtatag gtttaatcgc gactgtacga cgtagaaaag   1020

ctagctaaaa tatattgaaa ataatactac tgtatttctt aaataagagg tacggtagtg   1080

tttttttatg aaaaaaagcg ataaccgttg ataaatatgg gatataaaaa cgaggataag   1140

taataagaca tcaaggtgtt tatccacaga aatggggata gttatccaga attgtgtaca   1200
```

-continued

```
atttaaagag aaatacccac aatgcccaca gagttatcca caaatacaca ggttatacac   1260

taaaaatcgg gcataaatgt caggaaaata tcaaaaactg caaaaaatat tggtataata   1320

agagggaaca gtgtgaacaa gttaataact tgtggataac tggaaagttg ataacaattt   1380

ggaggaccaa acgacatgaa aatcaccatt ttagctgtag ggaaactaaa agagaaatat   1440

tggaagcaag ccatagcaga atatgaaaaa cgtttaggcc catacaccaa gatagacatc   1500

atagaagttc cagacgaaaa agcaccagaa aatatgagtg acaaagaaat tgagcaagta   1560

aaagaaaaag aaggccaacg aatactagcc aaaatcaaac cacaatccac agtcattaca   1620

ttagaaatac aaggaaagat gctatcttcc gaaggattgg cccaagaatt gaaccaacgc   1680

atgacccaag ggcaaagcga ctttgttttc gtcattggcg gatcaaacgg cctgcacaag   1740

gacgtcttac aacgcagtaa ctacgcacta tcattcagca aaatgacatt cccacatcaa   1800

atgatgcggg ttgtgttaat tgaacaagtg tacagagcat ttaagattat gcgaggagag   1860

gcgtatcata agtaaaacta aaaaattctg tatgaggaga taataatttg gagggtgtta   1920

aatggtggac attaaatcca cgttcattca atatataaga tatatcacga taattgcgca   1980

tataacttaa gtagtagcta acagttgaaa ttaggcccta tcaaattggt ttatatctaa   2040

aatgattaat atagaatgct tctttttgtc cttattaaat tataaaagta actttgcaat   2100

agaaacagtt atttcataat caacagtcat tgacgtagct aagtaatgat aaataatcat   2160

aaataaaatt acagatattg acaaaaaata gtaaatattc caatgaagtt tcaaaagaac   2220

aattccaaga aattgagaat gtaaataata aggtcaaaga attttattaa gatttgaaag   2280

agtatcaatc aagaaagatg tagtttttta ataaactatt tggaaaataa ttatcataat   2340

ttaaaaactg acaatttgcg agactcataa aatgtaataa tggaaataga tgtaaaatat   2400

aattaagggg tgtaatatga agattaatat ttataaatct atttataatt ttcaggaaac   2460

aaatacaaat tttttagaga atctagaatc tttaaatgat gacaattatg aactgcttaa   2520

tgataaagaa cttgttagtg attcaaatga attaaaatta attagtaaag tttatatacg   2580

taaaaaagac aaaaaactat tagattggca attattaata aagaatgtat acctagatac   2640

tgaagaagat gacaatttat tttcagaatc cggtcatcat tttgatgcaa tattatttct   2700

caaagaagat actacattac aaaataatgt atatattata ccttttggac aagcatatca   2760

tgatataaat aatttgattg attatgactt cggaattgat tttgcagaaa gagcaatcaa   2820

aaatgaagac atagttaata aaaatgttaa ttttttttcaa caaaacaggc ttaaagagat   2880

tgttaattat agaaggaata gtgtagatta cgttagacct tcagaatctt atatatcagt   2940

ccaaggacat ccacagaatc ctcaaatttt tggaaaaaca atgacttgtg gtacaagtat   3000

ttcattgcgt gtaccgaata gaaagcagca attcatagat aaaattagtg tgataatcaa   3060

agaaataaac gctattatta atcttcctca aaaaattagt gaatttccta gaatagtaac   3120

tttaaaagac ttgaataaaa tagaagtatt agatacttta ttgctaaaaa aactatcgaa   3180

ttc                                                                 3183
```

<210> SEQ ID NO 4
<211> LENGTH: 479
<212> TYPE: DNA
<213> ORGANISM: Staphylococcus aureus

<400> SEQUENCE: 4

```
ttcgtcattg gcggatcaaa cggcctgcac aaggacgtct tacaacgcag taactacgca     60

ctatcattca gcaaaatgac attcccacat caaatgatgc gggttgtgtt aattgaacaa    120
```

```
gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agattttgtg ttagaaaca     479


<210> SEQ ID NO 5
<211> LENGTH: 480
<212> TYPE: DNA
<213> ORGANISM: Staphylococcus aureus

<400> SEQUENCE: 5

ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataac atgcctacga ttaataaaag gaagtttatt agattttgtg ttagaaacag    480


<210> SEQ ID NO 6
<211> LENGTH: 480
<212> TYPE: DNA
<213> ORGANISM: Staphylococcus aureus

<400> SEQUENCE: 6

ttcgtcattg gcggatcaaa cggcctgcac aaggacgtct tacaacgcag taactacgca     60

ctatcattca gcaaaatgac atccccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agatttgtgt tagaaacagt    480


<210> SEQ ID NO 7
<211> LENGTH: 480
<212> TYPE: DNA
<213> ORGANISM: Staphylococcus aureus

<400> SEQUENCE: 7

ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300
```

-continued

```
ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agattttgtg ttagaaacag    480
```

<210> SEQ ID NO 8
<211> LENGTH: 309
<212> TYPE: DNA
<213> ORGANISM: Staphylococcus aureus
<220> FEATURE:
<221> NAME/KEY: misc_feature
<222> LOCATION: 237
<223> OTHER INFORMATION: n = A,T,C or G

<400> SEQUENCE: 8

```
ggcggatcaa acggcctgca caaggacgtc ttacaacgca gtaactacgc actatcattc     60

agcaaaatga cattcccaca tcaaatgatg cgggttgtgt taattgaaca agtgtacaga    120

gcatttaaga ttatgcgtgg agaagcgtat cataaataaa actaaaaatt aggttgtgta    180

taatttaaaa atctaatgag atgtggagga attacatata tgaaatattg gattatncct    240

tgcaatatca tacgatgttt atagagtgtt taataaacca tttttcaact attgatgatc    300

tacaatata                                                            309
```

<210> SEQ ID NO 9
<211> LENGTH: 471
<212> TYPE: DNA
<213> ORGANISM: Staphylococcus aureus

<400> SEQUENCE: 9

```
ttggcggatc aaacggcctg cacaaggacg tcttacaacg cagtaactac gcactatcat     60

tcagcaaaat gacattccca catcaaatga tgcgggttgt gttaattgaa caagtgtaca    120

gagcatttaa gattatgcgt ggagaagcgt atcataaata aaactaaaaa ttaggttgtg    180

tataatttaa aaatttaatg agatgtggag gaattacata tatgaaatat tggattatac    240

cttgcaatat catacgatgt ttatagagtg tttaataaac catttttcaa ctattgatga    300

tctagaatat ataataactg tacaaattat attgattatg gaactacaat taaattaaga    360

aattgatgat gaaattttaa atttaaacta atggaatcaa gaaagaatga aaggaaatat    420

acaatgccta cgattaataa aaggaagttt attagatttt gtgttagaaa c             471
```

<210> SEQ ID NO 10
<211> LENGTH: 480
<212> TYPE: DNA
<213> ORGANISM: Staphylococcus aureus

<400> SEQUENCE: 10

```
ttcgtcattg gcggatcaaa cggcctgcac aaggacgtct tacaacgcag taactacgca     60

ctatcattca gcaaaatgac attcccacat caaatgatgc gggttgtgtt aattgaacaa    120

gtgtacagag catttaagat tatgcgtgga gaagcgtatc ataaataaaa ctaaaaatta    180

ggttgtgtat aatttaaaaa tttaatgaga tgtggaggaa ttacatatat gaaatattgg    240

attatacctt gcaatatcat acgatgttta tagagtgttt aataaaccat ttttcaacta    300

ttgatgatct agaatatata ataactgtac aaattatatt gattatggaa ctacaattaa    360

attaagaaat tgatgatgaa attttaaatt taaactaatg gaatcaagaa agaatgaaag    420

gaaatataca atgcctacga ttaataaaag gaagtttatt agattttgtg ttagaaacag    480
```

<210> SEQ ID NO 11
<211> LENGTH: 480
<212> TYPE: DNA
<213> ORGANISM: Staphylococcus aureus

<400> SEQUENCE: 11
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcgtatc ataaataaaa ctaaaaatta 180
ggttgtgtat aatttaaaaa tttaatgaga tgtggaggaa ttacatatat gaaatattgg 240
attatacctt gcaatatcat acgatgttta tagagtgttt aataaaccat ttttcaacta 300
ttgatgatct agaatatata ataactgtac aaattatatt gattatggaa ctacaattaa 360
attaagaaat tgatgatgaa attttaaatt taaactaatg gaatcaagaa agaatgaaag 420
gaaatataca atgcctacga ttaataaaag gaagtttatt agattttgtg ttagaaacag 480

<210> SEQ ID NO 12
<211> LENGTH: 480
<212> TYPE: DNA
<213> ORGANISM: Staphylococcus aureus

<400> SEQUENCE: 12
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcgtatc ataaataaaa ctaaaaatta 180
ggttgtgtat aatttaaaaa tttaatgaga tgtggaggaa ttacatatat gaaatattgg 240
attatacctt gcaatatcat acgatgttta tagagtgttt aataaaccat ttttcaacta 300
ttgatgatct agaatatata ataactgtac aaattatatt gattatggaa ctacaattaa 360
attaagaaat tgatgatgaa attttaaatt taaactaatg gaatcaagaa agaatgaaag 420
gaaatataca atgcctacga ttaataaaag gaagtttatt agattttgtg ttagaaacag 480

<210> SEQ ID NO 13
<211> LENGTH: 478
<212> TYPE: DNA
<213> ORGANISM: Staphylococcus aureus

<400> SEQUENCE: 13
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcgtatc ataaataaaa ctaaaaatta 180
ggttgtgtat aatttaaaaa tttaatgaga tgtggaggaa ttacatatat gaaatattgg 240
attatacctt gcaatatcat acgatgttta tagagtgttt aataaaccat ttttcaacta 300
ttgatgatct agaatatata ataactgtac aaattatatt gattatggaa ctacaattaa 360
attaagaaat tgatgatgaa attttaaatt taaactaatg gaatcaagaa agaatgaaag 420
gaaatataca atgcctacga ttaataaaag gaagtttatt agattttgtg ttagaaac 478

<210> SEQ ID NO 14
<211> LENGTH: 479
<212> TYPE: DNA
<213> ORGANISM: Staphylococcus aureus

<400> SEQUENCE: 14
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcgtatc ataaataaaa ctaaaaatta 180
ggttgtgtat aatttaaaaa tttaatgaga tgtggaggaa ttacatatat gaaatattgg 240
attatacctt gcaatatcat acgatgttta tagagtgttt aataaaccat ttttcaacta 300
ttgatgatct agaatatata ataactgtac aaattatatt gattatggaa ctacaattaa 360
attaagaaat tgatgatgaa attttaaatt taaactaatg gaatcaagaa agaatgaaag 420
gaaatataca atgcctacga ttaataaaag gaagtttatt agattttgtg ttagaaaca 479

<210> SEQ ID NO 15
<211> LENGTH: 480
<212> TYPE: DNA
<213> ORGANISM: Staphylococcus aureus
<220> FEATURE:
<221> NAME/KEY: misc_feature
<222> LOCATION: 406
<223> OTHER INFORMATION: n = A,T,C or G

<400> SEQUENCE: 15
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcgtatc ataaataaaa ctaaaaatta 180
ggttgtgtat aatttaaaaa tttaatgaga tgtggaggaa ttacatatat gaaatattgg 240
attatacctt gcaatatcat acgatgttta tagagtgttt aataaaccat ttttcaacta 300
ttgatgatct agaatatata ataactgtac aaattatatt gattatggaa ctacaattaa 360
attaagaaat tgatgatgaa attttaaatt taaactaatg gaatcncgaa agaatgaaag 420
gaaatataca atgcctacga ttaataaaag gaagtttatt agattttgtg ttagaaacag 480

<210> SEQ ID NO 16
<211> LENGTH: 480
<212> TYPE: DNA
<213> ORGANISM: Staphylococcus aureus

<400> SEQUENCE: 16
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcgtatc ataaataaaa ctaaaaatta 180
ggttgtgtat aatttaaaaa tttaatgaga tgtggaggaa ttacatatat gaaatattgg 240
attatacctt gcaatatcat acgatgttta tagagtgttt aataaaccat ttttcaacta 300
ttgatgatct agaatatata ataactgtac aaattatatt gattatggaa ctacaattaa 360
attaagaaat tgatgatgaa attttaaatt taaactaatg gaatcaagaa agaatgaaag 420
gaaatataca atgcctacga ttaataaaag gaagtttatt agattttgtg ttagaaacag 480

<210> SEQ ID NO 17
<211> LENGTH: 480
<212> TYPE: DNA
<213> ORGANISM: Staphylococcus aureus

<400> SEQUENCE: 17
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcatatc ataaatgatg cggtttttttc 180 agccgcttca taaagggatt ttgaatgtat cagaacatat gaggtttatg tgaattgctg 240
ttatgttttt aagaagctta tcataagtaa tgaggttcat gatttttgac atagttagcc 300
tccgcagtct ttcatttcaa gtaaataata gcgaaatatt ctttatactg aatacttata 360
gtgaagcaaa gttctagctt tgagaaaatt ctttctgcaa ctaaatatag taaattacgg 420
taaaatataa ataagtacat attgaagaaa atgagacata atatatttta taataggagg 480

<210> SEQ ID NO 18
<211> LENGTH: 480
<212> TYPE: DNA
<213> ORGANISM: Staphylococcus aureus

<400> SEQUENCE: 18
ttcgtcattg gcggatcaaa cggcctgcac aaggacgtct tacaacgcag taactacgca 60
ctatcattca gcaaaatgac attcccacat caaatgatgc gggttgtgtt aattgagcaa 120
gtgtatagag catttaagat tatgcgtgga gaagcatatc ataaatgatg cggtttttttc 180 agccgcttca taaagggatt ttgaatgtat cagaacatat gaggtttatg tgaattgctg 240
ttatgttttt aagaagctta tcataagtaa tgaggttcat gatttttgac atagttagcc 300
tccgcagtct ttcatttcaa gtaaataata gcgaaatatt ctttatactg aatacttata 360
gtgaagcaaa gttctagctt tgagaaaatt ctttctgcaa ctaaatatag taaattacgg 420
taaaatataa ataagtacat attgaagaaa atgagacata atatatttta taataggagg 480

<210> SEQ ID NO 19
<211> LENGTH: 458
<212> TYPE: DNA
<213> ORGANISM: Staphylococcus aureus

<400> SEQUENCE: 19
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaagcatatc ataaatgatg cggtttttttc 180 agccgcttca taaagggatt ttgaatgtat cagaacatat gaggtttatg tgaattgctg 240
ttatgttttt aagaagctta tcataagtaa tgaggttcat gatttttgac atagttagcc 300
tccgcagtct ttcatttcaa gtaaataata gcgaaatatt ctttatactg aatacttata 360
gtgaagcaaa gttctagctt tgagaaaatt ctttctgcaa ctaaatatag taaattacgg 420
taaaatataa ataagtacat attgaagaaa atgagaca 458

<210> SEQ ID NO 20
<211> LENGTH: 385
<212> TYPE: DNA
<213> ORGANISM: Staphylococcus aureus

<400> SEQUENCE: 20
ttcgtcattg gcggatcaaa cggcctgcac aaggacgtct tacaacgcag taactacgca 60
ctatcattca gcaaaatgac attcccacat caaatgatgc gggttgtgtt aattgagcaa 120
gtgtatagag catttaagat tatgcgtgga gaagcttatc ataagtaatg aggttcatga 180
tttttgacat agttagcctc cgcagtcttt catttcaagt aaataatagc gaaatattct 240
ttatactgaa tacttatagt gaagcaaagt tctagctttg agaaaattct ttctgcaact 300
aaatatagta aattacggta aaatataaat aagtacatat tgaagaaaat gagacataat 360
atattttata ataggaggga atttc 385

<210> SEQ ID NO 21
<211> LENGTH: 385
<212> TYPE: DNA
<213> ORGANISM: Staphylococcus aureus

<400> SEQUENCE: 21
ttcgtcattg gcggatcaaa cggcctgcac aaggacgtct tacaacgcag taactacgca 60
ctatcattca gcaaaatgac attcccacat caaatgatgc gggttgtgtt aattgagcaa 120
gtgtatagag catttaagat tatgcgtgga gaagcttatc ataagtaatg aggttcatga 180
tttttgacat agttagcctc cgcagtcttt catttcaagt aaataatagc gaaatattct 240
ttatactgaa tacttatagt gaagcaaagt tctagctttg agaaaattct ttctgcaact 300
aaatatagta aattacggta aaatataaat aagtacatat tgaagaaaat gagacataat 360
atattttata ataggaggga atttc 385

<210> SEQ ID NO 22
<211> LENGTH: 385
<212> TYPE: DNA
<213> ORGANISM: Staphylococcus aureus

<400> SEQUENCE: 22
ttcgtcattg gcggatcaaa cggcctgcac aaggacgtct tacaacgcag taactacgca 60
ctatcattca gcaaaatgac attcccacat caaatgatgc gggttgtgtt aattgagcaa 120
gtgtatagag catttaagat tatgcgtgga gaagcttatc ataagtaatg aggttcatga 180
tttttgacat agttagcctc cgcagtcttt catttcaagt aaataatagc gaaatattct 240
ttatactgaa tacttatagt gaagcaaagt tctagctttg agaaaattct ttctgcaact 300
aaatatagta aattacggta aaatataaat aagtacatat tgaagaaaat gagacataat 360
atattttata ataggaggga atttc 385

<210> SEQ ID NO 23
<211> LENGTH: 385
<212> TYPE: DNA
<213> ORGANISM: Staphylococcus aureus

<400> SEQUENCE: 23
ttcgtcattg gcggatcaaa cggcctgcac aaggacgtct tacaacgcag taactacgcg 60
ctatcattca gcaaaatgac attcccacat caaatgatgc gggttgtgtt aattgaacaa 120
gtgtacaaag catttaagat tatgcgagga gaagcttatc ataagtaatg aggttcatga 180
tttttgacat agttagcctc cgcagtcttt catttcaagt aaataatagc gaaatattct 240
ttatactgaa tacttatagt gaagcaaagt tctagctttg agaaaattct ttctgcaact 300
aaatatagta aattacggta aaatataaat aagtacatat tgaagaaaat gagacataat 360
atattttata ataggaggga atttc 385

<210> SEQ ID NO 24
<211> LENGTH: 340
<212> TYPE: DNA
<213> ORGANISM: Staphylococcus aureus

<400> SEQUENCE: 24
cgcagtaact acgcgctatc attcagcaaa atgacattcc cacatcaaat gatgcgggtt 60

```
gtgttagttg agcaagtgta catagcattt aagattatgc gaggagaagc ttatcataag    120

taatgaggtt catgattttt gacatagtta gcctccgcag tctttcattt caagtaaata    180

atagcgaaat attctttata ctgaatactt atagtgaagc aaagttctag ctttgagaaa    240

attctttctg caactaaata tagtaaatta cggtaaaata taaataagta catattgaag    300

aaaatgagac ataatatatt ttataatagg agggaatttc                          340


<210> SEQ ID NO 25
<211> LENGTH: 369
<212> TYPE: DNA
<213> ORGANISM: Staphylococcus aureus

<400> SEQUENCE: 25

caaacggcct gcacaaggac gtcttacaac gcagtaacta cgcactatca ttcagcaaaa     60

tgacattccc acatcaaatg atgcgggttg tgttaattga acaagtgtac agagcattta    120

agattatgcg aggagaagct tatcataagt aatgaggttc atgatttttg acatagttag    180

cctccgcagt ctttcatttc aagtaaataa tagcgaaata ttctttatac tgaatactta    240

tagtgaagca aagttctagc tttgagaaaa ttctttctgc aactaaatat agtaaattac    300

ggtaaaatat aaataagtac atattgaaga aaatgagaca taatatattt tataatagga    360

gggaatttc                                                            369


<210> SEQ ID NO 26
<211> LENGTH: 3050
<212> TYPE: DNA
<213> ORGANISM: Staphylococcus aureus

<400> SEQUENCE: 26

aatttggtaa acctcaaaag gtaattacag atcaggcacc ttcaacgaag gtagcaatgg     60

ctaaagtaat taaagctttt aaacttaaac ctgactgtca ttgtacatcg aaatatctga    120

ataacctcat tgagcaagat caccgtcata ttaaagtaag aaagacaagg tatcaaagta    180

tcaatacagc aaagaatact ttaaaaggta ttgaatgtat tcacgctcta tataaaaaga    240

accgcaggtc tcttcagatc tacggatttt cgccatgcca cgaaattagc atcatgctag    300

caagttaagc gaacactgac atgataaatt agtggttagc tatatttttt tactttgcaa    360

cagaaccgaa aataatctct tcaatttatt tttatatgaa tcctgtgact caatgattgt    420

aatatctaaa gatttcagtt catcatagac aatgttcttt tcaacatttt ttatagcaaa    480

ttgattaaat aaattctcta atttctcccg tttgatttca ctaccataga ttatattatc    540

attgatatag tcaatgaata atgacaaatt atcactcata acagtcccaa cccctttatt    600

ttgatagact aattatcttc atcattgtaa aacaaattac accctttaaa tttaactcaa    660

cttaaatatc gacaaattaa aaaacaataa aattacttga atattattca taatatatta    720

acaactttat tatactgctc tttatatata aaatcattaa taattaaaca agccttaaaa    780

tatttaactt ttttgtgatt attacacatt atcttatctg ctctttatca ccataaaaat    840

agaaaaaaca agattcctaa agaatatagg aatcttgttt cagactgtgg acaaactgat    900

tttttatcag ttagcttatt tagaaagttt tatttaaatt acagtttcta tttttattag    960

atcacaattt tattttagct cttgttcaag taatcatttt tcgccaaaaa ctttatactg   1020

aatagcttct acattaaata cttgtcaatg agatcatcta catctttaaa ttcagaataa   1080

ttcgcatatg gatctataaa ataaaattgt ggttctttac cggaaacatt aaatattctt   1140
```

-continued

```
aatattaaat atttctgctt atattctttc atagcaaaca tttcatttag cgacataaaa   1200

aatggttcct caatactaga agatgtagat gttttaattt caataaattt ttctacagct   1260

ttatctgtat ttgttggatc aaaagctact aaatcatagc catgaccgtg ttgagagcct   1320

ggattatcat ttaaaatatt cctaaactgt tctttcttat cttcgtctat tttattatca   1380

attagctcat taaagtaatt tagcgctaat ttttctccaa ctttaccggt taatttattc   1440

tctttatttg atttttcaat ttctgaatca tttttagtag tctttgatac acctttttta   1500

tattttggaa ttattccttt aggtgcttcc acttccttga gtgtcttatc tttttgtgct   1560

gttctaattt cttcaatttc gctgtcttcc tgtatttcgt ctatgctatt gaccaagcta   1620

tcataggatg tttttgtaac ttttgaagct aattcattaa atagttctaa aaatttcttt   1680

aaatcctcta gcatatcttc ttctgtgaat ccttcattca aatcataata tttgaatctt   1740

attgatccat gagaatatcc tgatggataa tcatttttta aatcataaga tgaatcttta   1800

ttttctgcgt aataaaatct tccagtatta aattcatttg atgtaatata tttattgagt   1860

tcggaagata aagttaatgc tctttgtttt gcagcatttt tatcccgcgg aaacatatca   1920

cttatctttg accatccttg attcaaagat aagtatatgc cttctccttc cggatgaaaa   1980

agatatacca aataatgtcc atcctttgtt tcttttgtta tattctcatc atatattgaa   2040

atccaaggaa ctttactata gttcccagta gcaaccttcc ctacaactga atatttatct   2100

tcttttatat gcacttttaa ctgcttgggt aacttatcat ggactaaagt tttatataga   2160

tcacctttat cccaatcaga ttttttaact acattattgg tacgtttctc tttaattaat   2220

ttaaggacct gcataaagtt gtctatcatt tgaaattccc tcctattata aaatatatta   2280

tgtctcattt tcttcaatat gtacttattt atattttacc gtaatttact atatttagtt   2340

gcagaaagaa ttttctcaaa gctagaactt tgcttcacta taagtattca gtataaagaa   2400

tatttcgcta ttatttactt gaaatgaaag actgcggagg ctaactatgt caaaaatcat   2460

gaacctcatt acttatgata agcttcttaa aaacataaca gcaattcaca taaacctcat   2520

atgttctgat acattcaaaa tccctttatg aagcggctga aaaaaccgca tcatttatga   2580

tatgcttctc ctcgcataat cttaaatgct ctgtacactt gttcaattaa cacaacccgc   2640

atcatttgat gtgggaatgt cattttgctg aatgatagtg cgtagttact gcgttgtaag   2700

acgtccttgt gcaggccgtt tgatccgcca atgacgaaaa caaagtcgct ttgcccttgg   2760

gtcatgcgtt ggttcaattc ttgggccaat ccttcggaag atagcatctt tccttgtatt   2820

tctaatgtaa tgactgtgga ttgtggtttg attttggcta gtattcgttg gccttctttt   2880

tcttttactt gctcaatttc tttgtcactc atattttctg gtgctttttc gtctggaact   2940

tctatgatgt ctatcttggt gtatgggcct aaacgttttt catattctgc tatggcttgc   3000

ttccaatatt tctcttttag tttccctaca gctaaaatgg tgattttcat              3050
```

<210> SEQ ID NO 27
<211> LENGTH: 657
<212> TYPE: DNA
<213> ORGANISM: Staphylococcus aureus

<400> SEQUENCE: 27

```
ccaccttcat atgacgtcta tccatttatg tatggcatga gtaacgaaga atataataaa     60

ttaaccgaag ataaaaaaga acctctgctc aacaagttcc agattacaac ttcaccaggt    120

tcaactcaaa aaatattaac agcaatgatt gggttaaata acaaaaacatt agacgataaa   180

acaagttata aaatcgatgg taaaggttgg caaaaagata aatcttgggg tggttacaac    240
```

```
gttacaagat atgaagtggt aaatggtaat atcgacttaa aacaagcaat agaatcatca    300

gataacattt tctttgctag agtagcactc gaattaggca gtaagaaatt tgaaaaaggc    360

atgaaaaaac taggtgttgg tgaagatata ccaagtgatt atccatttta taatgctcaa    420

atttcaaaca aaaatttaga taatgaaata ttattagctg attcaggtta cggacaaggt    480

gaaatactga ttaacccagt acagatcctt tcaatctata gcgcattaga aaataatggc    540

aatattaacg cacctcactt attaaaagac acgaaaaaca aagtttggaa gaaaaatatt    600

atttccaaag aaaatatcaa tctattaact gatggtatgc aacaagtcgt aaataaa       657
```

<210> SEQ ID NO 28
<211> LENGTH: 782
<212> TYPE: DNA
<213> ORGANISM: Staphylococcus aureus

<400> SEQUENCE: 28

```
caccttcata tgacgtctat ccatttatgt atggcatgag taacgaagaa tataataaat     60

taaccgaaga taaaaaagaa cctctgctca acaagttcca gattacaact tcaccaggtt    120

caactcaaaa aatattaaca gcaatgattg ggttaaataa caaaacatta gacgataaaa    180

caagttataa aatcgatggt aaaggttggc aaaaagataa atcttggggt ggttacaacg    240

ttacaagata tgaagtggta aatggtaata tcgacttaaa acaagcaata gaatcatcag    300

ataacatttt ctttgctaga gtagcactcg aattaggcag taagaaattt gaaaaaggca    360

tgaaaaaact aggtgttggt gaagatatac caagtgatta tccattttat aatgctcaaa    420

tttcaaacaa aaatttagat aatgaaatat tattagctga ttcaggttac ggacaaggtg    480

aaatactgat taacccagta cagatccttt caatctatag cgcattagaa aataatggca    540

atattaacgc acctcactta ttaaaagaca cgaaaaacaa agtttggaag aaaaatatta    600

tttccaaaga aaatatcaat ctattaactg atggtatgca acaagtcgta aataaaacac    660

ataaagaaga tatttataga tcttatgcaa acttaattgg caaatccggt actgcagaac    720

tcaaaatgaa acaaggagaa actggcagac aaattgggtg gtttatatca tatgataaag    780

at                                                                   782
```

<210> SEQ ID NO 29
<211> LENGTH: 744
<212> TYPE: DNA
<213> ORGANISM: Staphylococcus aureus

<400> SEQUENCE: 29

```
tatgacgtct atccatttat gtatggcatg agtaacgaag aatataataa attaaccgaa     60

gataaaaaag aacctctgct caacaagttc cagattacaa cttcaccagg ttcaactcaa    120

aaaatattaa cagcaatgat tgggttaaat aacaaaacat tagacgataa aacaagttat    180

aaaatcgatg gtaaaggttg gcaaaaagat aaatcttggg gtggttacaa cgttacaaga    240

tatgaagtgg taaatggtaa tatcgactta aaacaagcaa tagaatcatc agataacatt    300

ttctttgcta gagtagcact cgaattaggc agtaagaaat ttgaaaaagg catgaaaaaa    360

ctaggtgttg gtgaagatat accaagtgat tatccatttt ataatgctca aatttcaaac    420

aaaaatttag ataatgaaat attattagct gattcaggtt acggacaagg tgaaatactg    480

attaacccag tacagatcct ttcaatctat agcgcattag aaaataatgg caatattaac    540

gcacctcact tattaaaaga cacgaaaaac aaagtttgga agaaaaatat tatttccaaa    600
```

gaaaatatca atctattaac tgatggtatg caacaagtcg taaataaaac acataaagaa 660
gatatttata gatcttatgc aaacttaatt ggcaaatccg gtactgcaga actcaaaatg 720
aaacaaggag aaactggcag acaa 744

<210> SEQ ID NO 30
<211> LENGTH: 652
<212> TYPE: DNA
<213> ORGANISM: Staphylococcus aureus

<400> SEQUENCE: 30
ccaccttcat atgacgtcta tccatttatg tatggcatga gtaacgaaga atataataaa 60
ttaaccgaag ataaaaaaga acctctgctc aacaagttcc agattacaac ttcaccaggt 120
tcaactcaaa aaatattaac agcaatgatt gggttaaata acaaaacatt agacgataaa 180
acaagttata aaatcgatgg taaaggttgg caaaaagata aatcttgggg tggttacaac 240
gttacaagat atgaagtggt aaatggtaat atcgacttaa aacaagcaat agaatcatca 300
gataacattt tctttgctag agtagcactc gaattaggca gtaagaaatt tgaaaaaggc 360
atgaaaaaac taggtgttgg tgaagatata ccaagtgatt atccatttta taatgctcaa 420
atttcaaaca aaaatttaga taatgaaata ttattagctg attcaggtta cggacaaggt 480
gaaatactga ttaacccagt acagatcctt tcaatctata gcgcattaga aaataatggc 540
aatattaacg cacctcactt attaaaagac acgaaaaaca aagtttggaa gaaaaatatt 600
atttccaaag aaaatatcaa tctattaact gatggtatgc aacaagtcgt aa 652

<210> SEQ ID NO 31
<211> LENGTH: 2436
<212> TYPE: DNA
<213> ORGANISM: Staphylococcus aureus

<400> SEQUENCE: 31
ccaccttcat atgacgtcta tccatttatg tatggcatga gtaacgaaga atataataaa 60
ttaaccgaag ataaaaaaga acctctgctc aacaagttcc agattacaac ttcaccaggt 120
tcaactcaaa aaatattaac agcaatgatt gggttaaata acaaaacatt agacgataaa 180
acaagttata aaatcgatgg taaaggttgg caaaaagata aatcttgggg tggttacaac 240
gttacaagat atgaagtggt aaatggtaat atcgacttaa aacaagcaat agaatcatca 300
gataacattt tctttgctag agtagcactc gaattaggca gtaagaaatt tgaaaaaggc 360
atgaaaaaac taggtgttgg tgaagatata ccaagtgatt atccatttta taatgctcaa 420
atttcaaaca aaaatttaga taatgaaata ttattagctg attcaggtta cggacaaggt 480
gaaatactga ttaacccagt acagatcctt tcaatctata gcgcattaga aaataatggc 540
aatattaacg cacctcactt attaaaagac acgaaaaaca aagtttggaa gaaaaatatt 600
atttccaaag aaaatatcaa tctattaact gatggtatgc aacaagtcgt aaataaaaca 660
cataaagaag atatttatag atcttatgca aacttaattg gcaaatccgg tactgcagaa 720
ctcaaaatga aacaaggaga aactggcaga caaattgggt ggtttatatc atatgataaa 780
gataatccaa acatgatgat ggctattaat gttaaagatg tacaagataa aggaatggct 840
agctacaatg ccaaaatctc aggtaaagtg tatgatgagc tatatgagaa cggtaataaa 900
aaatacgata tagatgaata acaaaacagt gaagcaatcc gtaacgatgg ttgcttcact 960
gttttattat gaattattaa taagtgctgt tacttctccc ttaaatacaa tttcttcatt 1020
ttcattgtat gttgaaagtg acactgtaac gagtccattt tcttttttta tggatttctt 1080

```
atttgtaatt tcagcgataa cgtacaatgt attacctggg tatacaggtt taataaattt   1140

aacgttattc atttgtgttc ctgctacaac ttcttctccg tatttacctt cttctaccca   1200

taatttaaat gatattgaaa gtgtatgcat gccagatgca atgatacctt taaatctact   1260

ttgttctgct ttttctttat ctatatgcat atattgagga tcaaaagttg ttgcaaattg   1320

gataatttct tcttctgtaa tatgaaggct ttttgttttg aatgtttctc ctactataaa   1380

atcatcgtat ttcatatatg tctctctttc ttattcaaat taattttttta gtatgtaaca   1440

tgttaaaggt aagtctaccg tcactgaaac gtaagactca cctctaactt tctattgaga   1500

caaatgcacc attttatctg cattgtctgt aaagatacca tcaactcccc aattagcaag   1560

ttggtttgca cgtgctggtt tgtttacagt ccatacgttc aattcataac ccgcttcttt   1620

taccattttt actttttgctt tagtaagttt ggcatcttca gtgtttacta ttttagcatt   1680

acagtaatct aaaagtgttc tccagtcttc acgaaacgaa gttgtatgga atataactgc   1740

tctgttatat tgtggcatga tttcttctgc aagtttaaca agcacaacat taaagcttga   1800

aatgagcact tcttgattct gatttaagtt tgttaattgt tcttccactt gcttaaccat   1860

acttttagaa agtgctagtc cattcggtcc agtaatacct tttaattcta catttaaatt   1920

catattatat tcatttgcta tttttactac atcatcgaaa gttggcaaat gttcatcttt   1980

gaatttttca ccaaaccaag atcctgcaga agcatcttta atttcatcat aattcaattc   2040

agttatttcc ccggacatat ttgtagtccg ttctaaataa tcatcatgaa tgataatcag   2100

ttgttcatct tttgtaattg caacatctaa ctccaaccag tttatacctt ctacttctga   2160

agcagcttta aatgatgcaa ttgtattttc cggagcttta ctaggtaatc ctctatgtcc   2220

atatacagtt agcatattac ctctccttgc atttttattt ttttaattaa cgtaactgta   2280

ttatcacatt aatcgcactt ttatttccat taaaaagaga tgaatatcat aaataaagaa   2340

gtcgatagat tcgtattgat tatggagtta atctacgtct catctcattt ttaaaaaatc   2400

atttatgtcc caagctccat tttgtaatca agtcta                             2436
```

<210> SEQ ID NO 32
<211> LENGTH: 36
<212> TYPE: DNA
<213> ORGANISM: Artificial Sequence
<220> FEATURE:
<223> OTHER INFORMATION: Synthetic nucleic acid sequence

<400> SEQUENCE: 32

```
cgcttgccac atcaaatgat gcgggttgtg caagcg                               36
```

<210> SEQ ID NO 33
<211> LENGTH: 336
<212> TYPE: DNA
<213> ORGANISM: Staphylococcus epidermis

<400> SEQUENCE: 33

```
ctcattactt atgataagct tcttaaaaac ataacagcaa ttcacataaa cctcatatgt     60

tctgatacat tcaaaatccc tttatgaagc ggctgaaaaa accgcatcat ttatgatatg    120

cttcgcctct catgatctta aatgcgcgat aaatttgttc gatcaatatg acgcgcatat    180

ttggtgtggg aaggtcatat tgctaaaaga taaagcatag ttgctgcgtt gtaagacgtc    240

ttggtgtaaa ccattggagc cacctatgac aaatgtaaag tcgctttgac cttgtgtcat    300

gcgtgtttgt agttctttag cgagtccttc tgaaga                              336
```

<210> SEQ ID NO 34
<211> LENGTH: 260
<212> TYPE: DNA
<213> ORGANISM: Staphylococcus haemolyticus

<400> SEQUENCE: 34
ctcattactt atgataagct tcttaaaaac ataacagcaa tccacataaa cctcatatgt 60
tctgatacat tcaaaatccc tttatgaagc ggctgaaaaa accgcatcat ttatgatatg 120
cttccctcgc atgattttaa atgctctgta tacttgctcg attaagacaa cgcgcatcat 180
ttgatgtggg aatgtcattt tactgaatga aagtgcgtag ttgctgcgtt gtaagacgtc 240
ctcatgcaat ccatttgatc 260

<210> SEQ ID NO 35
<211> LENGTH: 225
<212> TYPE: DNA
<213> ORGANISM: Staphylococcus aureus

<400> SEQUENCE: 35
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaggcgtatc acaaataaaa ctaaaaatgg 180
agtaactatt aatatagtat aaattcaata tggtgataaa aacag 225

<210> SEQ ID NO 36
<211> LENGTH: 225
<212> TYPE: DNA
<213> ORGANISM: Staphylococcus aureus

<400> SEQUENCE: 36
ttcgtcattg gcggatcaaa cggcctgcac aaggacgtct tacaacgcag taactacgca 60
ctatcattca gcaaaatgac attcccacat caaatgatgc gggttgtgtt aattgaacaa 120
gtgtacagag catttaagat tatgcgtgga gaggcgtatc acaaataaaa ctaaaaatgg 180
agtaactatt aatatagtat aaattcaata tggtgataaa aacag 225

<210> SEQ ID NO 37
<211> LENGTH: 225
<212> TYPE: DNA
<213> ORGANISM: Staphylococcus aureus

<400> SEQUENCE: 37
ttcgtcattg gcggatcaaa cggcctgcac aaggacgtct tacaacgtag taactacgca 60
ctatcattca gcaaaatgac atttccacat caaatgatgc gggttgtgtt aattgaacaa 120
gtgtacagag catttaagat tatgcgtgga gaggcgtatc ataagtaatg aggttcatga 180
tttttgacat agttagcctc cgcagtcttt caagtaaata atatc 225

<210> SEQ ID NO 38
<211> LENGTH: 225
<212> TYPE: DNA
<213> ORGANISM: Staphylococcus aureus

<400> SEQUENCE: 38
ttcgtcattg gcggatcaaa cggcctgcac aaggacgtct tacaacgcag taactacgca 60
ctatcattta gcaaaatgac attcccacat caaatgatgc gggttgtgtt aattgaacaa 120
gtgtatagag catttaagat tatgcgtgga gaggcgtatc ataagtgatg cttgttagaa 180
tgatttttaa caatatgaaa tagctgtgga agctcaaaca tttgt 225

<210> SEQ ID NO 39
<211> LENGTH: 1500
<212> TYPE: DNA
<213> ORGANISM: Staphylococcus aureus

<400> SEQUENCE: 39
tgagtctggt aaagatacac aaccaattgg taaagagaaa gtgatgaatc cagcgaaaca 60
accagcgaca ggtaaagttg tgttgttacc agcgcataga ggaactgtta gtagcggtac 120
agaaggttct gatcgcgcat tagaaggaac tgctgtatca agtaagagtg ggaaacaatt 180
ggctaacatg tcagcgccta aaggtagcgc acatgagaaa cagttaccaa aaactggaac 240
tgatcaaagt tcaagcccag cagcgatgtt tgtattagta acaggtatag gtttaatcgc 300
gactgtacga cgtagaaaag ctagctaaaa tatattgaaa acaatactac tgtatttctt 360
aaataagagg tacggtagtg ttttttttatg gaaaaaagct ataaccgttg ataaatatgg 420
gatataaaaa cggggataag taataagaca tcaaggtatt tatccacaga aatggggata 480
gttatccaga attgtgtaca atttaaagag aaatacccac aatgcccaca gagttatcca 540
caaatacaca agttatacac tgaaaattgg gcatgaatgt cagaaaaata tcaaaaactg 600
caaaaaaact tggtataata agagggaaaa gtgtgaacaa gttaataact tgtggataac 660
tggaaagttg ataacaattt ggaggaccaa acgacatgaa aatcaccatt ttagctgtag 720
ggaaactaaa agagaaatat tggaagcaag ccatagcaga atatgaaaaa cgtttaggcc 780
catacaccaa gatagacatc atagaagtta cagacgaaaa agcaccagaa aatatgagcg 840
acaaagaaat cgagcaagta aaagaaaaag aaggccaacg aatactagcc aaaatcaaac 900
cacaatccac agtcattaca ttagaaatac aaggaaagat gctatcttcc gaaggattgg 960
cccaagaatt gaaccaacgc atgacccaag ggcaaagcga ctttgtattc gtcattggcg 1020
gatcaaacgg cctgcacaag gacgtcttac aacgtagtaa ctacgcacta tcattcagca 1080
aaatgacatt tccacatcaa atgatgcggg ttgtgttaat tgaacaagtg tacagagcat 1140
ttaagattat gcgtggagaa gcttatcata aatgatgcgg tttttttcttg aaaaatttaa 1200 ttagatatta gaatccttta atttatttga aaatcagaag tgagtaacaa tggtaagtga 1260
aatagttagt gcaataattg gaattatagg gatttattga gatgtatgga gatgcggggc 1320
atttatcgag tagattacaa ttagagcatg taggtgattt gctttttcat gcaagtaaag 1380
ataaactttt aaaaatccta taagaattta gaaactttag aataactaaa tattaaaaaa 1440
atatcgtatg aaagtgaaat taggatgaga gaccatagct aaattaaaaa ttttagcaaa 1500

<210> SEQ ID NO 40
<211> LENGTH: 1501
<212> TYPE: DNA
<213> ORGANISM: Staphylococcus aureus

<400> SEQUENCE: 40
ttgcacaacc aattggtaaa gacaaagtga tggatccagc gaaacaacca gcgccaagta 60
aagttgtatt gttgccagcg catagaggaa ctgttagtag tggtagagaa ggttctgatc 120
gcgcattgga aggaactgct gtatcaagta agagcgggaa acaattggct agcatgtcag 180
cgcctaaagg tagcacacat gagaagcagt taccaaaaac tggaactgat caaagttcaa 240
gcccagcagc gatgtttgta ttagtagcag gtataggttt aattgcgact gtacgacgta 300

```
gaaaagctag ctaaaatata ttgaaaacaa tactactgta tttcttaaac aagaggtacg    360
gtagtgtttt tttatgaaaa aaagctataa ccgttgataa atatgggata taaaaacggg    420
gataagtaat aagacatcaa ggtatttatc cacagaaatg gggatagtta tccagaattg    480
tgtacaattt aaagagaaat acccacaatg cccacagagt tatccacaaa tacacaggtt    540
atacactaaa aattgggcat gaatgtcaga aaaatatcaa aaactgcaaa gaatattggt    600
ataataagag ggaacagtgt gaacaagtta ataacttgtg gataactgga aagttgataa    660
caatttggag gaccaaacga catgaaaatc accattttag ctgtagggaa actaaaagag    720
aaatattgga agcaagccat agcagaatat gaaaaacgtt taggcccata caccaagata    780
gacatcatag aagttccaga cgaaaaagca ccagaaaata tgagcgacaa agaaattgag    840
caagtaaaag aaaaagaagg ccaacgaata ctagccaaaa tcaaaccaca atcaacagtc    900
attacattag aaatacaagg aaagatgcta tcttccgaag gattggccca agaattgaac    960
caacgcatga cccaagggca aagcgacttt gtattcgtca ttggcggatc aaacggcctg   1020
cacaaggacg tcttacaacg cagtaactac gcactatcat tcagcaaaat gacattccca   1080
catcaaatga tgcgggttgt gttaattgaa caagtgtaca gagcatttaa gattatgcgt   1140
ggagaagcat atcataaatg atgcggtttt ttcagccgct tcataaaggg attttgaatg   1200
tatcagaaca tatgaggttt atgtgaattg ctgttatgtt tttaagaagc ttatcataag   1260
taatgaggtt catgattttt gacatagtta gcctccgcag tctttcattt caagtaaata   1320
atagcgaaat attctttata ctgaatactt atagtgaagc aaagttctag ctttgagaaa   1380
attctttctg caactaaata tagtaaatta cggtaaaata taaataagta catattgaag   1440
aaaatgagac ataatatatt ttataatagg agggaatttc aaatgataga caactttatg   1500
c                                                                   1501
```

<210> SEQ ID NO 41
<211> LENGTH: 2480
<212> TYPE: DNA
<213> ORGANISM: Staphylococcus aureus

<400> SEQUENCE: 41

```
aaaccgtctg gcaaacgaat taatgctatt caaattttaa ataaagagac aggtaagttt     60
gaaaatattg atttaaaacg tgtatatcac gtaacgatga atgacttcac agcatcaggt    120
ggcgacggat atagtatgtt cggtggtcct agagaagaag gtatttcatt agatcaagta    180
ctagcaagtt atttaaaaac agctaactta gctaagtatg atacgacaga accacaacgt    240
atgttattag gtaaaccagc agtaagtgaa caaccagcta aaggacaaca aggtagcaaa    300
ggtagtaagt ctggtaaaga tacacaacca attggtgacg acaaagtgat ggatccagcg    360
aaaaaaccag ctccaggtaa agttgtattg ttgctagcgc atagaggaac tgttagtagc    420
ggtacagaag gttctggtcg cacaatagaa ggagctactg tatcaagcaa gagtgggaaa    480
caattggcta gaatgtcagt gcctaaaggt agcgcgcatg agaaacagtt accaaaaact    540
ggaactaatc aaagttcaag cccagaagcg atgtttgtat tattagcagg tataggttta    600
atcgcgactg tacgacgtag aaaagctagc taaaatatat tgaaaataat actactgtat    660
ttcttaaata agaggtacgg tagtgttttt ttatgaaaaa aagcgataac cgttgataaa    720
tatgggatat aaaaacgagg ataagtaata agacatcaag gtgtttatcc acagaaatgg    780
ggatagttat ccagaattgt gtacaattta aagagaaata cccacaatgc ccacagagtt    840
acccacaaat acacaggtta tacactaaaa atcgggcata aatgtcagga aaatatcaaa    900
```

```
aactgcaaaa aatattggta taataagagg gaacagtgtg aacaagttaa taacttgtgg    960

ataactggaa agttgataac aatttggagg accaaacgac atgaaaatca ccattttagc   1020

tgtagggaaa ctaaaagaga aatattggaa gcaagccata gcagaatatg aaaaacgttt   1080

aggcccatac accaagatag acatcataga agttccagac gaaaaagcac cagaaaatat   1140

gagtgacaaa gaaattgagc aagtaaaaga aaaagaaggc caacgaatac tagccaaaat   1200

caaaccacaa tccacagtca ttacattaga aatacaagga aagatgctat cttccgaagg   1260

attggcccaa gaattgaacc aacgcatgac ccaagggcaa agcgactttg ttttcgtcat   1320

tggcggatca aacggcctgc acaaggacgt cttacaacgc agtaactacg cactatcatt   1380

cagcaaaatg acattcccac atcaaatgat gcgggttgtg ttaattgaac aagtgtacag   1440

agcatttaag attatgcgag gagaagctta tcataagtaa tgaggttcat gatttttgac   1500

atagttagcc tccgcagtct ttcatttcaa gtaaataata gcgaaatatt ctttatactg   1560

aatacttata gtgaagcaaa gttctagctt tgagaaaatt ctttctgcaa ctaaatatag   1620

taaattacgg taaaatataa ataagtacat attgaagaaa atgagacata atatatttta   1680

taataggagg gaatttcaaa tgatagacaa ctttatgcag gtccttaaat taattaaaga   1740

gaaacgtacc aataatgtag ttaaaaaatc tgattgggat aaaggtgatc tatataaaac   1800

tttagtccat gataagttac ccaagcagtt aaaagtgcat ataaaagaag ataaatattc   1860

agttgtaggg aaggttgcta ctgggaacta tagtaaagtt ccttggattt caatatatga   1920

tgagaatata acaaaagaaa caaaggatgg atattatttg gtatatcttt ttcatccgga   1980

aggagaaggc atatacttat ctttgaatca aggatggtca aagataagtg atatgtttcc   2040

gcgggataaa aatgctgcaa aacaaagagc attaacttta tcttccgaac tcaataaata   2100

tattacatca aatgaattta atactggaag attttattac gcagaaaata aagattcatc   2160

ttatgattta aaaaatgatt atccatcagg atattctcat ggatcaataa gattcaaata   2220

ttatgatttg aatgaaggat tcacagaaga agatatgcta gaggatttaa agaaattttt   2280

agaactattt aatgaattag cttcaaaagt tacaaaaaca tcctatgata gcttggtcaa   2340

tagcatagac gaaatacagg aagacagcga aattgaagaa attagaacag cacaaaaaga   2400

taagacactc aaggaagtgg aagcacctaa aggaataatt ccaaaatata aaaaaggtgt   2460

atcaaagact actaaaaatg                                               2480
```

<210> SEQ ID NO 42
<211> LENGTH: 1045
<212> TYPE: DNA
<213> ORGANISM: Staphylococcus aureus

<400> SEQUENCE: 42

```
ccagtttttt gtttaatgaa caaggtaaat tacgagataa tatttgaaga aaacaataaa     60

gtagagatgg atttccatat cctctttagt agcggttttt atctgtaagg tttattaata    120

attaaataaa taggcgggat agttatatat agcttattaa tgaaagaata tgattattaa    180

tttagtatta tattttaata ttaaaaagaa gatatgaaat aattattcat accttccacc    240

ttacaataat tagttttcaa tcgaatatta agattattag tagtcttaaa agttaagact    300

tccttatatt aatgacctaa tttattattt gcctcatgaa ttatcttttt atttctttga    360

tatgtcccaa accacatcgt gatatacact acaataaata ttatgatgaa actaataata    420

ttctcaaagt tcagatggaa ccaacctgct agaatagcga gtgggaagaa taggattatc    480
```

-continued

```
atcaatataa agtgaactac agtctgtttt gttatactcc aatcggtatc tgtaaatatc    540

aaattaccat aagtaaacaa aattccaatc aatgcccata gtgctacaca tattagcata    600

ataaccgctt cattaaagtt ttcataataa attttaccca taaaagaatc tggatatagt    660

ggtacatatt tatcccttga aaaaaataag tgaagtaatg acagaaatca taagaccagt    720

gaacgcacct tttgaacag cgtggaataa tttttcata gtgagatgga ccattccatt    780

tgtttctaac ttcaagtgat caatgtaatt tagattgata atttctgatt ttgaaatacg    840

cacgaatatt gaaccgacaa gctcttcaat ttggtaaagt cgctgataaa gttttaaagc    900

tttattattc attgttatcg catacctgtt tatcttctac tatgaactgt gcaatttgtt    960

ctagatcaat tgggtaaaca tgatggttct gttgcaaagt aaaaaaatat agctaaccac   1020

taatttatca tgtcagtgtt cgctt                                          1045
```

<210> SEQ ID NO 43
<211> LENGTH: 1118
<212> TYPE: DNA
<213> ORGANISM: Staphylococcus aureus

<400> SEQUENCE: 43

```
cagagcattt aagattatgc gtggagaagc gtaccacaaa tgatgcggtt ttttatccag     60

ttttttgttt aatgaacaag gtaaattacg agataatatt tgaagaaaac aataaagtag    120

agatggattt ccatatcctc tttagtagcg gtttttatct gtaaggttta ttaataatta    180

aataaatagg cgggatagtt atatatagct tattaatgaa agaatatgat tattaattta    240

gtattatatt ttaatattaa aaagaagata tgaaataatt attcatacct tccaccttac    300

aataattagt tttcaatcga atattaagat tattagtagt cttaaaagtt aagacttcct    360

tatattaatg acctaattta ttatttgcct catgaattat ctttttattt ctttgatatg    420

tcccaaacca catcgtgata tacactacaa taaatattat gatgaaacta ataatattct    480

caaagttcag atggaaccaa cctgctagaa tagcgagtgg gaagaatagg attatcatca    540

atataaagtg aactacagtc tgttttgtta tactccaatc ggtatctgta aatatcaaat    600

taccataagt aaacaaaatt ccaatcaatg cccatagtgc tacacatatt agcataataa    660

ccgcttcatt aaagttttca taataaattt tacccataaa agaatctgga tatagtagta    720

catatttatc ccttgaaaaa aataagtgaa gtaatgacag aaatcataag accagtgaac    780

gcaccttttt gaacagcgtg gaataatttt ttcatagtga gatggaccat tccatttgtt    840

tctaacttca agtgatcaat gtaatttaga ttgataattt ctgattttga aatacgcacg    900

aatattgaac cgacaagctc ttcaatttgg taaagtcgct gataaagttt taaagcttta    960

ttattcattg ttatcgcata cctgtttatc ttctactatg aactgtgcaa tttgttctag   1020

atcaattggg taaacatgat ggttctgttg caaagtaaaa aaatatagct aaccactaat   1080

ttatcatgtc agtgttcgct taacttgcta gcatgatg                           1118
```

<210> SEQ ID NO 44
<211> LENGTH: 1118
<212> TYPE: DNA
<213> ORGANISM: Staphylococcus aureus

<400> SEQUENCE: 44

```
cagagcattt aagattatgc gtggagaagc gtaccacaaa tgatgcggtt ttttatccag     60

ttttttgttt aatgaacaag gtaaattacg agataatatt tgaagaaaac aataaagtag    120

agatggattt ccatatcctc tttagtagcg gtttttatct gtaaggttta ttaataatta    180
```

```
aataaatagg cgggatagtt atatatagct tattaatgaa agaatatgat tattaattta    240

gtattatatt ttaatattaa aaagaagata tgaaataatt attcatacct tccaccttac    300

aataattagt tttcaatcga atattaagat tattagtagt cttaaaagtt aagacttcct    360

tatattaatg acctaattta ttatttgcct catgaattat ctttttattt ctttgatatg    420

tcccaaacca catcgtgata tacactacaa taaatattat gatgaaacta ataatattct    480

caaagttcag atggaaccaa cctgctagaa tagcgagtgg gaagaatagg attatcatca    540

atataaagtg aactacagtc tgttttgtta tactccaatc ggtatctgta aatatcaaat    600

taccataagt aaacaaaatt ccaatcaatg cccatagtgc tacacatatt agcataataa    660

ccgcttcatt aaagttttca taataaattt tacccataaa agaatctgga tatagtagta    720

catatttatc ccttgaaaaa aataagtgaa gtaatgacag aaatcataag accagtgaac    780

gcaccttttt gaacagcgtg gaataatttt ttcatagtga gatggaccat tccatttgtt    840

tctaacttca agtgatcaat gtaatttaga ttgataattt ctgattttga aatacgcacg    900

aatattgaac cgacaagctc ttcaatttgg taaagtcgct gataaagttt taaagcttta    960

ttattcattg ttatcgcata cctgtttatc ttctactatg aactgtgcaa tttgttctag   1020

atcaattggg taaacatgat ggttctgttg caaagtaaaa aaatatagct aaccactaat   1080

ttatcatgtc agtgttcgct taacttgcta gcatgatg                           1118
```

<210> SEQ ID NO 45
<211> LENGTH: 1113
<212> TYPE: DNA
<213> ORGANISM: Staphylococcus aureus

<400> SEQUENCE: 45

```
agcatttaag attatgcgtg gagaagcgta ccacaaatga tgcggttttt tatccagttt     60

tttgtttaat gaacaaggta aattacgaga taatatttga agaaaacaat aaagtagaga    120

tggatttcca tatcctcttt agtagcggtt tttatctgta aggtttatta ataattaaat    180

aaataggcgg gatagttata tatagcttat taatgaaaga atatgattat taatttagta    240

ttatatttta atattaaaaa gaagatatga aataattatt cataccttcc accttacaat    300

aattagtttt caatcgaata ttaagattat tagtagtctt aaaagttaag acttccttat    360

attaatgacc taatttatta tttgcctcat gaattatctt tttatttctt tgatatgtcc    420

caaaccacat cgtgatatac actacaataa atattatgat gaaactaata atattctcaa    480

agttcagatg gaaccaacct gctagaatag cgagtgggaa gaataggatt atcatcaata    540

taaagtgaac tacagtctgt tttgttatac tccaatcggt atctgtaaat atcaaattac    600

cataagtaaa caaaattcca atcaatgccc atagtgctac acatattagc ataataaccg    660

cttcattaaa gttttcataa taaattttac ccataaaaga atctggatat agtggtacat    720

atttatccct tgaaaaaaat aagtgaagta atgacagaaa tcataagacc agtgaacgca    780

cctttttgaa cagcgtggaa taatttttc atagtgagat ggaccattcc atttgtttct    840

aacttcaagt gatcaatgta atttagattg ataatttctg attttgaaat acgcacgaat    900

attgaaccga caagctcttc aatttggtaa agtcgctgat aaagttttaa agctttatta    960

ttcattgtta tcgcatacct gtttatcttc tactatgaac tgtgcaattt gttctagatc   1020

aattgggtaa acatgatggt tctgttgcaa agtaaaaaaa tatagctaac cactaattta   1080

tcatgtcagt gttcgcttaa cttgctagca tga                                1113
```

<210> SEQ ID NO 46
<211> LENGTH: 2153
<212> TYPE: DNA
<213> ORGANISM: Staphylococcus aureus

<400> SEQUENCE: 46

```
ctgtagggaa actaaaagag aaatactgga agcaagccat agcagaatat gaaaaacgtt     60
taggcccata caccaagata gacatcatag aagttccaga cgaaaaagca ccagaaaata    120
tgagcgacaa agaaatcgag caagtaaaag aaaaagaagg ccaacgaata ctagccaaaa    180
tcaaaccaca atccacagtc attacattag aaatacaagg aaagatgcta tcttccgaag    240
gattggccca agaattgaac caacgcatga cccaagggca aagcgacttt gtattcgtca    300
ttggcggatc aaacggcctg cacaaggacg tcttacaacg cagtaactac gcactatcat    360
tcagcaaaat gacattccca catcaaatga tgcgggttgt gttaattgaa caagtgtaca    420
gagcatttaa gattatgcgt ggagaagcgt accacaaatg atgcggtttt ttatccagtt    480
ttttgtttaa tgaacaaggt aaattacgag ataatatttg aagaaaacaa taaagtagag    540
atggatttcc atatcctctt tagtagcggt ttttatctgt aaggtttatt aataattaaa    600
taaataggcg ggatagttat atatagctta ttaatgaaag aatatgatta ttaatttagt    660
attatatttt aatattaaaa agaagatatg aaataattat tcataccttc caccttacaa    720
taattagttt tcaatcgaat attaagatta ttagtagtct taaaagttaa gacttcctta    780
tattaatgac ctaatttatt atttgcctca tgaattatct ttttatttct ttgatatgtc    840
ccaaaccaca tcgtgatata cactacaata aatattatga tgaaactaat aatattctca    900
aagttcagat ggaaccaacc tgctagaata gcgagtggga agaataggat tatcatcaat    960
ataaagtgaa ctacagtctg ttttgttata ctccaatcgg tatctgtaaa tatcaaatta   1020
ccataagtaa acaaaattcc aatcaatgcc catagtgcta cacatattag cataataacc   1080
gcttcattaa agttttcata ataaatttta cccataaaag aatctggata tagtggtaca   1140
tatttatccc ttgaaaaaaa taagtgaagt aatgacagaa atcataagac cagtgaacgc   1200
accttttttga acagcgtgga ataatttttt catagtgaga tggaccattc catttgtttc   1260
taacttcaag tgatcaatgt aatttagatt gataatttct gattttgaaa tacgcacgaa   1320
tattgaaccg acaagctctt caatttggta aagtcgctga taaagtttta aagctttatt   1380
attcattgtt atcgcatacc tgtttatctt ctactatgaa ctgtgcaatt tgttctagat   1440
caattgggta aacatgatgg ttctgttgca aagtaaaaaa atatagctaa ccactaattt   1500
atcatgtcag tgttcgctta acttgctagc atgatgctaa tttcgtggca tggcgaaaat   1560
ccgtagatct gatgagacct gcggttcttt ttatatagag cgtaaataca ttcaatacct   1620
tttaaagtat tctttgctgt attgatactt tgataccttg tctttcttac tttaatatga   1680
cggtgatctt gctcaatgag gttattcaaa tatttcgatg tacaatgaca gtcaggttta   1740
agtttaaaag ctttaattac tttagccatt gctaccttcg ttgaaggtgc ctgatctgta   1800
attacctttt gaggtttacc aaattgttta atgagacgtt taataaacgc atatgctgaa   1860
tgattatctc gttgcttacg caaccaaata tctaatgtat gtccctctgc atcaatggca   1920
cgatataaat agctccattt tccttttatt ttgatgtacg tctcatcaat acgccatttg   1980
taataagctt ttttatgctt tttcttccaa atttgatata aaattggggc atattcttga   2040
acccaacggt agaccgttga atgatgaacg tttacaccac gtccccttaa tatttcagat   2100
atatcacgat aactcaatgc atatcttaga tagtagccaa cggctacagt gat          2153
```

<210> SEQ ID NO 47
<211> LENGTH: 737
<212> TYPE: DNA
<213> ORGANISM: Staphylococcus aureus

<400> SEQUENCE: 47
tttaagatta tgcgtggaga agcatatcat aaatgatgcg gttatttcag ccgtaatttt 60
ataatataaa gcagagttta ttaaatttta atgattactt tttattaaga attaattcta 120
gttgatatat tataatgtga aacacaaaat aataatttgt aattgttagt ttataggcat 180
ctgtatttgg aatttttttgt agactattta aaaaatagtg tatataagta ttgagttcat 240
gtattaactg tctttttca tcgttcatca agtataagga tgtagagatt tgttggataa 300
tttcttcgga tgtttttaaa attatcatta aattagatgg tatctgatct tgagttttgt 360
ttttagtgta tgtatatttt aaaaaatttt tgattgttgt tatttgactc tcttttaatt 420
tgacaccctc atcaataaat gtgttaaata tatcttcatt tgtacttaaa tcatcaaaat 480
ttgccaacaa atatttgaac gtctctaaat cattatgttt gagttccgtt ttgctattcc 540
ataattccaa accatttggt agaaagccca agctgtgatt ttgatctccc catatagctg 600
aatttaaatc agtgagttga ttaatttttt caacacagaa atgtaatttt ggaatgagga 660
atcgaagttg ttcttctact tgctgtactt ttcttttgtt ttcaataaaa tttctacacc 720
atactgttat caaaccg 737

<210> SEQ ID NO 48
<211> LENGTH: 1592
<212> TYPE: DNA
<213> ORGANISM: Staphylococcus aureus

<400> SEQUENCE: 48
aactaaaaga gaaatattgg aagcaagcca tagcagaata tgaaaaacgt ttaggcccat 60
acaccaagat agacatcata gaagttccag acgaaaaagc accagaaaat atgagtgaca 120
aagaaattga gcaagtaaaa gaaaaagaag gccaacgaat actagccaaa atcaaaccac 180
aatccacagt cattacatta gaaatacaag gaaagatgct atcttccgaa ggattggccc 240
aagaattgaa ccaacgcatg acccaagggc aaagcgactt tgttttcgtc attggcggat 300
caaacggcct gcacaaggac gtcttacaac gcagtaacta cgcactatca ttcagcaaaa 360
tgacattccc acatcaaatg atgcgggttg tgttaattga acaagtgtac agagcattta 420
agattatgcg aggagaagca tatcataaat gatgcggtta tttcagccgt aattttataa 480
tataaagcag agtttattaa attttaatga ttactttta ttaagaatta attctagttg 540
atatattata atgtgaaaca caaaataata atttgtaatt gttagtttat aggcatctgt 600
atttggaatt ttttgtagac tatttaaaaa atagtgtata taagtattga gttcatgtat 660
taactgtctt ttttcatcgt tcatcaagta taaggatgta gagatttgtt ggataatttc 720
ttcggatgtt tttaaaatta tcattaaatt agatggtatc tgatcttgag ttttgttttt 780
agtgtatgta tattttaaaa aatttttgat tgttgttatt tgactctctt ttaatttgac 840
accctcatca ataaatgtgt taaatatatc ttcatttgta cttaaatcat caaaatttgc 900
caacaaatat ttgaacgtct ctaaatcatt atgtttgagt tccgttttgc tattccataa 960
ttccaaacca tttggtagaa agcccaagct gtgattttga tctccccata tagctgaatt 1020
taaatcagtg agttgattaa tttttcaac acagaaatgt aattttggaa tgaggaatcg 1080

-continued

```
aagttgttct tctacttgct gtacttttct tttgttttca ataaaatttc tacaccatac   1140

tgttatcaaa ccgccaatta ttgtgcacaa tcctccaatg attgtagata aaattgacaa   1200

tatattacac acctttctta gaggtttatt aacatctatt tttgaattta aaattattac   1260

tttggtagcg ttataaccta tttaacagat tagagaaaaa ttgaatgatc gattgaagaa   1320

tttccaaaat accgtcccat atgcgttgaa ggagatttct attttcttct gtattcaaat   1380

ctttggcttt atcctttgct ttattcaata aatcatctga gttttttca atatttttta   1440

atacatcttt ggcattttgt ttaaatactt taggatcgga agttagggca ttagagtttg   1500

ccacattaat catattatta ttaatcattt gaatttgatt atctgataat atctctgata   1560

acctacgctc atcgaggact ttattaacag tg                                 1592
```

<210> SEQ ID NO 49
<211> LENGTH: 730
<212> TYPE: DNA
<213> ORGANISM: Staphylococcus aureus

<400> SEQUENCE: 49

```
agcatttaag attatgcgtg gagaagcata tcataaatga tgcggttatt tcagccgtaa     60

ttttataata taaagcagag tttattaaat tttaatgatt acttttttatt aagaattaat    120

tctagttgat atattataat gtgaaacaca aaataataat ttgtaattgt tagtttatag    180

gcatctgtat ttggaatttt ttgtagacta tttaaaaaat agtgtatata agtattgagt    240

tcatgtatta actgtctttt ttcatcgttc atcaagtata aggatgtaga gatttgttgg    300

ataatttctt cggatgtttt taaaattatc attaaattag atggtatctg atcttgagtt    360

ttgtttttag tgtatgtata ttttaaaaaa tttttgattg ttgttatttg actctctttt    420

aatttgacac cctcatcaat aaatgtgtta aatatatctt catttgtact taaatcatca    480

aaatttgcca acaaatattt gaacgtctct aaatcattat gtttgagttc cgttttgcta    540

ttccataatt ccaaaccatt tggtagaaag cccaagctgt gattttgatc tccccatata    600

gctgaattta aatcagtgag ttgattaatt ttttcaacac agaaatgtaa ttttggaatg    660

aggaatcgaa gttgttcttc tacttgctgt acttttcttt tgttttcaat aaaatttcta    720

caccatactg                                                          730
```

<210> SEQ ID NO 50
<211> LENGTH: 1696
<212> TYPE: DNA
<213> ORGANISM: Staphylococcus aureus

<400> SEQUENCE: 50

```
aaagagaaat attggaagca agccatagca gaatatgaaa aacgtttagg cccatacacc     60

aagatagaca tcatagaagt tccagacgaa aaagcaccag aaaatatgag tgacaaagaa    120

attgagcaag taaaagaaaa agaaggccaa cgaatactag ccaaaatcaa accacaatcc    180

acagtcatta cattagaaat acaaggaaag atgctatctt ccgaaggatt ggcccaagaa    240

ttgaaccaac gcatgaccca agggcaaagc gactttgttt tcgtcattgg cggatcaaac    300

ggcctgcaca aggacgtctt acaacgcagt aactacgcac tatcattcag caaaatgaca    360

ttcccacatc aaatgatgcg ggttgtgtta attgaacaag tgtacagagc atttaagatt    420

atgcgaggag aagcatatca taaatgatgc ggttatttca gccgtaattt tataatataa    480

agcagagttt attaaatttt aatgattact tttattaag aattaattct agttgatata    540

ttataatgtg aaacacaaaa taataatttg taattgttag tttataggca tctgtatttg    600
```

```
gaatttttttg tagactattt aaaaaatagt gtatataagt attgagttca tgtattaact    660

gtcttttttc atcgttcatc aagtataagg atgtagagat ttgttggata atttcttcgg    720

atgtttttaa aattatcatt aaattagatg gtatctgatc ttgagttttg tttttagtgt    780

atgtatattt taaaaaattt ttgattgttg ttatttgact ctcttttaat ttgacaccct    840

catcaataaa tgtgttaaat atatcttcat ttgtacttaa atcatcaaaa tttgccaaca    900

aatatttgaa cgtctctaaa tcattatgtt tgagttccgt tttgctattc cataattcca    960

aaccatttgg tagaaagccc aagctgtgat tttgatctcc ccatatagct gaatttaaat   1020

cagtgagttg attaattttt tcaacacaga aatgtaattt tggaatgagg aatcgaagtt   1080

gttcttctac ttgctgtact tttcttttgt tttcaataaa atttctacac catactgtta   1140

tcaaaccgcc aattattgtg cacaatcctc caatgattgt agataaaatt gacaatatat   1200

tacacacctt tcttagaggt ttattaacat ctatttttga atttaaaatt attactttgg   1260

tagcgttata acctatttaa cagattagag aaaaattgaa tgatcgattg aagaatttcc   1320

aaaataccgt cccatatgcg ttgaaggaga tttctatttt cttctgtatt caaatctttg   1380

gctttatcct ttgctttatt caataaatca tctgagtttt tttcaatatt ttttaataca   1440

tctttggcat tttgtttaaa tactttagga tcggaagtta gggcattaga gtttgccaca   1500

ttaatcatat tattattaat catttgaatt tgattatctg ataatatctc tgataaccta   1560

cgctcatcga ggactttatt aacagtgtct tcaacttgtt gttgtgtgat ttgtttatct   1620

tgattttgtt taatatctgc aagttgttct ttaatatctg ctatagaagc atttaaagct   1680

tcatctgaat acccat                                                   1696
```

<210> SEQ ID NO 51
<211> LENGTH: 2122
<212> TYPE: DNA
<213> ORGANISM: Staphylococcus aureus

<400> SEQUENCE: 51

```
ggaaactaaa agagaaatat tggaagcaag ccatagcaga atatgaaaaa cgtttaggcc     60

catacaccaa gatagacatc atagaagttc cagacgaaaa agcaccagaa aatatgagcg    120

acaaagaaat tgagcaagta aaagaaaaag aaggccaacg aatactagcc aaaatcaaac    180

cacaatcaac agtcattaca ttagaaatac aaggaaagat gctatcttcc gaaggattgg    240

cccaagaatt gaaccaacgc atgacccaag ggcaaagcga ctttgtattc gtcattggcg    300

gatcaaacgg cctgcacaag gacgtcttac aacgcagtaa ctacgcacta tcattcagca    360

aaatgacatt cccacatcaa atgatgcggg ttgtgttaat tgaacaagtg tacagagcat    420

ttaagattat gcgtggagaa gcgtaccaca aatgatgcgg tttttatcc agttttttgt    480

ttaatgaaca aggtaaatta cgagataata tttgaagaaa acaataaagt agagatggat    540

ttccatatcc tctttagtag cggtttttat ctgtaaggtt tattaataat taaataaata    600

ggcgggatag ttatatatag cttattaatg aaagaatatg attattaatt tagtattata    660

ttttaatatt aaaaagaaga tatgaaataa ttattcatac cttccacctt acaataatta    720

gttttcaatc gaatattaag attattagta gtcttaaaag ttaagacttc cttatattaa    780

tgacctaatt tattatttgc ctcatgaatt atctttttat ttctttgata tgtcccaaac    840

cacatcgtga tatacactac aataaatatt atgatgaaac taataatatt ctcaaagttc    900

agatggaacc aacctgctag aatagcgagt gggaagaata ggattatcat caatataaag    960
```

tgaactacag tctgttttgt tatactccaa tcggtatctg taaatatcaa attaccataa 1020
gtaaacaaaa ttccaatcaa tgcccatagt gctacacata ttagcataat aaccgcttca 1080
ttaaagtttt cataataaat tttacccata aaagaatctg gatatagtgg tacatattta 1140
tcccttgaaa aaaataagtg aagtaatgac agaaatcata agaccagtga acgcaccttt 1200
ttgaacagcg tggaataatt ttttcatagt gagatggacc attccatttg tttctaactt 1260
caagtgatca atgtaattta gattgataat ttctgatttt gaaatacgca cgaatattga 1320
accgacaagc tcttcaattt ggtaaagtcg ctgataaagt tttaaagctt tattattcat 1380
tgttatcgca tacctgttta tcttctacta tgaactgtgc aatttgttct agatcaattg 1440
ggtaaacatg atggttctgt tgcaaagtaa aaaaatatag ctaaccacta atttatcatg 1500
tcagtgttcg cttaacttgc tagcatgatg ctaatttcgt ggcatggcga aaatccgtag 1560
atctgatgag acctgcggtt ctttttatat agagcgtaaa tacattcaat accttttaaa 1620
gtattctttg ctgtattgat actttgatac cttgtctttc ttactttaat atgacggtga 1680
tcttgctcaa tgaggttatt cagatatttc gatgtacaat gacagtcagg tttaagttta 1740
aaagctttaa ttactttagc cattgctacc ttcgttgaag gtgcctgatc tgtaattacc 1800
ttttgaggtt taccaaattg tttaatgaga cgtttgataa acgcatatgc tgaatgatta 1860
tctcgttgct tacgcaacca aatatctaat gtatgtccct ctgcatcaat ggcacgatat 1920
aaatagctcc attttccttt tattttgatg tacgtctcat caatacgcca tttgtaataa 1980 gctttttat gctttttctt ccaaatttga tacaaaattg gggcatattc ttgaacccaa 2040
cggtagaccg ttgaatgatg aacgtttaca ccacgttccc ttaatatttc agatatatca 2100
cgataactca atgtatatct ta 2122

<210> SEQ ID NO 52
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 52
gatagactaa ttatcttcat c 21

<210> SEQ ID NO 53
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 53
cagactgtgg acaaactgat t 21

<210> SEQ ID NO 54
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 54
tgagatcatc tacatcttta 20

<210> SEQ ID NO 55
<211> LENGTH: 20

<212> TYPE: DNA
<213> ORGANISM: Artificial Sequence
<220> FEATURE:
<223> OTHER INFORMATION: Synthetic nucleic acid sequence

<400> SEQUENCE: 55
ggatcaaaag ctactaaatc 20

<210> SEQ ID NO 56
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 56
atgctctttg ttttgcagca 20

<210> SEQ ID NO 57
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 57
atgaaagact gcggaggcta act 23

<210> SEQ ID NO 58
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 58
atattctaga tcatcaatag ttg 23

<210> SEQ ID NO 59
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 59
aagaattgaa ccaacgcatg a 21

<210> SEQ ID NO 60
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 60
gttcaagccc agaagcgatg t 21

<210> SEQ ID NO 61
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 61
tcgggcataa atgtcaggaa aat 23

<210> SEQ ID NO 62
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 62
aaacgacatg aaaatcacca t 21

<210> SEQ ID NO 63
<211> LENGTH: 33
<212> TYPE: DNA
<213> ORGANISM: Artificial Sequence
<220> FEATURE:
<223> OTHER INFORMATION: Synthetic nucleic acid sequence

<400> SEQUENCE: 63
ttattaggta aaccagcagt aagtgaacaa cca 33

<210> SEQ ID NO 64
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 64
ggatcaaacg gcctgcaca 19

<210> SEQ ID NO 65
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 65
cacagaaatg taattttgga atgagg 26

<210> SEQ ID NO 66
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 66
gtcaaaaatc atgaacctca ttacttatg 29

<210> SEQ ID NO 67
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 67
atttcatata tgtaattcct ccacatctc 29

<210> SEQ ID NO 68
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 68
tctacggatt ttcgccatgc 20

<210> SEQ ID NO 69
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 69
aacaggtgaa ttattagcac ttgtaag 27

<210> SEQ ID NO 70
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 70
atcaaatgat gcgggttgtg t 21

<210> SEQ ID NO 71
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 71
tcattggcgg atcaaacgg 19

<210> SEQ ID NO 72
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 72
acaacgcagt aactacgcac ta 22

<210> SEQ ID NO 73
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 73
taactacgca ctatcattca gc 22

<210> SEQ ID NO 74
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 74
acatcaaatg atgcgggttg tg 22

<210> SEQ ID NO 75
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 75
tcaaatgatg cgggttgtgt ta 22

<210> SEQ ID NO 76
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 76
caaatgatgc gggttgtgtt aatt 24

<210> SEQ ID NO 77
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 77
ctactatgaa ctgtgcaatt tgttct 26

<210> SEQ ID NO 78
<211> LENGTH: 2007
<212> TYPE: DNA
<213> ORGANISM: Staphylococcus aureus

<400> SEQUENCE: 78
atgaaaaaga taaaaattgt tccacttatt ttaatagttg tagttgtcgg gtttggtata 60
tatttttatg cttcaaaaga taaagaaatt aataatacta ttgatgcaat tgaagataaa 120
aatttcaaac aagtttataa agatagcagt tatatttcta aaagcgataa tggtgaagta 180
gaaatgactg aacgtccgat aaaaatatat aatagtttag gcgttaaaga tataaacatt 240
caggatcgta aaataaaaaa agtatctaaa aataaaaaac gagtagatgc tcaatataaa 300
attaaaacaa actacggtaa cattgatcgc aacgttcaat ttaattttgt taaagaagat 360
ggtatgtgga agttagattg ggatcatagc gtcattattc caggaatgca gaaagaccaa 420
agcatacata ttgaaaattt aaaatcagaa cgtggtaaaa ttttagaccg aaacaatgtg 480
gaattggcca atacaggaac acatatgaga ttaggcatcg ttccaaagaa tgtatctaaa 540
aaagattata aagcaatcgc taaagaacta agtatttctg aagactatat caacaacaaa 600
tggatcaaaa ttgggtacaa gatgatacct tcgttccact ttaaaaccgt taaaaaaatg 660
gatgaatatt taagtgattt cgcaaaaaaa tttcatctta caactaatga aacagaaagt 720
cgtaactatc ctctagaaaa agcgacttca catctattag gttatgttgg tcccattaac 780
tctgaagaat taaaacaaaa agaatataaa ggctataaag atgatgcagt tattggtaaa 840
aagggactcg aaaaacttta cgataaaaag ctccaacatg aagatggcta tcgtgtcaca 900
atcgttgacg ataatagcaa tacaatcgca catacattaa tagagaaaaa gaaaaaagat 960
ggcaaagata ttcaactaac tattgatgct aaagttcaaa agagtattta taacaacatg 1020
aaaaatgatt atggctcagg tactgctatc caccctcaaa caggtgaatt attagcactt 1080
gtaagcacac cttcatatga cgtctatcca tttatgtatg gcatgagtaa cgaagaatat 1140
aataaattaa ccgaagataa aaaagaacct ctgctcaaca agttccagat tacaacttca 1200
ccaggttcaa ctcaaaaaat attaacagca atgattgggt taaataacaa aacattagac 1260
gataaaacaa gttataaaat cgatggtaaa ggttggcaaa aagataaatc ttggggtggt 1320
tacaacgtta caagatatga agtggtaaat ggtaatatcg acttaaaaca agcaatagaa 1380
tcatcagata acattttctt tgctagagta gcactcgaat taggcagtaa gaaatttgaa 1440
aaaggcatga aaaaactagg tgttggtgaa gatataccaa gtgattatcc attttataat 1500
gctcaaattt caaacaaaaa tttagataat gaaatattat tagctgattc aggttacgga 1560
caaggtgaaa tactgattaa cccagtacag atcctttcaa tctatagcgc attagaaaat 1620
aatggcaata ttaacgcacc tcacttatta aaagacacga aaaacaaagt ttggaagaaa 1680
aatattattt ccaaagaaaa tatcaatcta ttaaatgatg gtatgcaaca agtcgtaaat 1740
aaaacacata aagaagatat ttatagatct tatgcaaact taattggcaa atccggtact 1800
gcagaactca aaatgaaaca aggagaaagt ggcagacaaa ttgggtggtt tatatcatat 1860
gataaagata atccaaacat gatgatggct attaatgtta aagatgtaca agataaagga 1920
atggctagct acaatgccaa aatctcaggt aaagtgtatg atgagctata tgagaacggt 1980
aataaaaaat acgatataga tgaataa 2007

<210> SEQ ID NO 79
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 79
caaatattat ctcgtaattt accttgttc 29

<210> SEQ ID NO 80
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 80
ctctgcttta tattataaaa ttacggctg 29

<210> SEQ ID NO 81
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 81
attgctgtta atattttttg agttgaa 27

<210> SEQ ID NO 82
<211> LENGTH: 2007
<212> TYPE: DNA
<213> ORGANISM: Staphylococcus aureus

<400> SEQUENCE: 82
atgaaaaaga taaaaattgt tccacttatt ttaatagttg tagttgtcgg gtttggtata 60

-continued

```
tatttttatg cttcaaaaga taaagaaatt aataatacta ttgatgcaat tgaagataaa    120

aatttcaaac aagtttataa agatagcagt tatatttcta aaagcgataa tggtgaagta    180

gaaatgactg aacgtccgat aaaaatatat aatagtttag gcgttaaaga tataaacatt    240

caggatcgta aaataaaaaa agtatctaaa aataaaaaac gagtagatgc tcaatataaa    300

attaaaacaa actacggtaa cattgatcgc aacgttcaat ttaattttgt taaagaagat    360

ggtatgtgga agttagattg ggatcatagc gtcattattc caggaatgca gaaagaccaa    420

agcatacata ttgaaaattt aaaatcagaa cgtggtaaaa ttttagaccg aaacaatgtg    480

gaattggcca atacaggaac agcatatgag ataggcatcg ttccaaagaa tgtatctaaa    540

aaagattata aagcaatcgc taaagaacta agtatttctg aagactatat caaacaacaa    600

atggatcaaa attgggtaca agatgatacc ttcgttccac ttaaaaccgt taaaaaaatg    660

gatgaatatt taagtgattt cgcaaaaaaa tttcatctta caactaatga aacagaaagt    720

cgtaactatc ctctagaaaa agcgacttca catctattag gttatgttgg tcccattaac    780

tctgaagaat taaaacaaaa agaatataaa ggctataaag atgatgcagt tattggtaaa    840

aagggactcg aaaaacttta cgataaaaag ctccaacatg aagatggcta tcgtgtcaca    900

atcgttgacg ataatagcaa tacaatcgca catacattaa tagagaaaaa gaaaaaagat    960

ggcaaagata ttcaactaac tattgatgct aaagttcaaa agagtattta taacaacatg   1020

aaaaatgatt atggctcagg tactgctatc caccctcaaa caggtgaatt attagcactt   1080

gtaagcacac cttcatatga cgtctatcca tttatgtatg gcatgagtaa cgaagaatat   1140

aataaattaa ccgaagataa aaaagaacct ctgctcaaca agttccagat tacaacttca   1200

ccaggttcaa ctcaaaaaat attaacagca atgattgggt taaataacaa aacattagac   1260

gataaaacaa gttataaaat cgatggtaaa ggttggcaaa aagataaatc ttggggtggt   1320

tacaacgtta caagatatga agtggtaaat ggtaatatcg acttaaaaca agcaatagaa   1380

tcatcagata acattttctt tgctagagta gcactcgaat taggcagtaa gaaatttgaa   1440

aaaggcatga aaaaactagg tgttggtgaa gatataccaa gtgattatcc attttataat   1500

gctcaaattt caaacaaaaa tttagataat gaaatattat tagctgattc aggttacgga   1560

caaggtgaaa tactgattaa cccagtacag atcctttcaa tctatagcgc attagaaaat   1620

aatggcaata ttaacgcacc tcacttatta aaagacacga aaacaaagt ttggaagaaa    1680

aatattattt ccaaagaaaa tatcaatcta ttaactgatg gtatgcaaca agtcgtaaat   1740

aaaacacata aagaagatat ttatagatct tatgcaaact taattggcaa atccggtact   1800

gcagaactca aaatgaaaca aggagaaact ggcagacaaa ttgggtggtt tatatcatat   1860

gataaagata atccaaacat gatgatggct attaatgtta aagatgtaca agataaagga   1920

atggctagct acaatgccaa aatctcaggt aaagtgtatg atgagctata tgagaacggt   1980

aataaaaaat acgatataga tgaataa                                       2007
```

<210> SEQ ID NO 83
<211> LENGTH: 36
<212> TYPE: DNA
<213> ORGANISM: Artificial Sequence
<220> FEATURE:
<223> OTHER INFORMATION: Synthetic nucleic acid sequence

<400> SEQUENCE: 83

```
cccaccccac atcaaatgat gcgggttgtg ggtggg                               36
```

<210> SEQ ID NO 84
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 84
cccgcgcgta gttactgcgt tgtaagacgt ccgcggg 37

<210> SEQ ID NO 85
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 85
gtttttatca ccatattgaa tttatac 27

<210> SEQ ID NO 86
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 86
atttacttga aagactgcgg aggag 25

<210> SEQ ID NO 87
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 87
tgtttgagct tccacagcta tttc 24

<210> SEQ ID NO 88
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 88
ccctataatt ccaattattg cactaac 27

<210> SEQ ID NO 89
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 89
atgaggagat aataatttgg agggt 25

<210> SEQ ID NO 90
<211> LENGTH: 2007
<212> TYPE: DNA
<213> ORGANISM: Staphylococcus aureus

<400> SEQUENCE: 90
atgaaaaaga taaaaattgt tccacttatt ttaatagttg tagttgtcgg gtttggtata 60
tatttttatg cttccaaaga taaagaaatt aataatacta ttgatgcaat tgaagataaa 120
aatttcaaac aagtttataa agatagcagt tatatttcta aaagcgataa tggtgaagta 180
gaaatgactg aacgtccgat aaaaatatat aatagtttag gcgttaaaga tataaacatt 240
caggatcgta aaataaaaaa agtatctaaa aataaaaaac gagtagatgc tcaatataaa 300
attaaaacaa actacggtaa cattgatcgc aacgttcaat ttaattttgt taaagaagat 360
ggtatgtgga agttagattg ggatcatagc gtcattattc caggaatgca gaaagaccaa 420
agcatacata ttgaaaattt aaaatcagaa cgtggtaaaa ttttagaccg aaacaatgtg 480
gaattggcca atacaggaac agcatatgag ataggcatcg ttccaaagaa tgtatctaaa 540
aaagattata aagcaatcgc taaagaacta agtatttctg aagactatat caaacaacaa 600
atggatcaaa attgggtaca agatgatacc ttcgttccac ttaaaaccgt taaaaaaatg 660
gatgaatatt taagtgattt cgcaaaaaaa tttcatctta caactaatga aacagaaagt 720
cgtaactatc ctctaggaaa agcgacttca catctattag gttatgttgg tcccattaac 780
tctgaagaat taaaacaaaa agaatataaa ggctataaag atgatgcagt tattggtaaa 840
aagggactcg aaaaacttta cgataaaaag ctccaacatg aagatggcta tcgtgtcaca 900
atcgttgacg ataatagcaa tacaatcgca catacattaa tagagaaaaa gaaaaaagat 960
ggcaaagata ttcaactaac tattgatgct aaagttcaaa agagtattta taacaacatg 1020
aaaaatgatt atggctcagg tactgctatc caccctcaaa caggtgaatt attagcactt 1080
gtaagcacac cttcatatga cgtctatcca tttatgtatg gcatgagtaa cgaagaatat 1140
aataaattaa ccgaagataa aaaagaacct ctgctcaaca agttccagat tacaacttca 1200
ccaggttcaa ctcaaaaaat attaacagca atgattgggt taaataacaa aacattagac 1260
gataaaacaa gttataaaat cgatggtaaa ggttggcaaa aagataaatc ttggggtggt 1320
tacaacgtta caagatatga agtggtaaat ggtaatatcg acttaaaaca agcaatagaa 1380
tcatcagata acattttctt tgctagagta gcactcgaat taggcagtaa gaaatttgaa 1440
aaaggcatga aaaaactagg tgttggtgaa gatataccaa gtgattatcc attttataat 1500
gctcaaattt caaacaaaaa tttagataat gaaatattat tagctgattc aggttacgga 1560
caaggtgaaa tactgattaa cccagtacag atcctttcaa tctatagcgc attagaaaat 1620
aatggcaata ttaacgcacc tcacttatta aaagacacga aaacaaagt ttggaagaaa 1680 aatattattt ccaaagaaaa tatcaatcta ttaactgatg gtatgcaaca agtcgtaaat 1740
aaaacacata aagaagatat ttatagatct tatgcaaact taattggcaa atccggtact 1800
gcagaactca aaatgaaaca aggagaaact ggcagacaaa ttgggtggtt tatatcatat 1860
gataaagata atccaaacat gatgatggct attaatgtta aagatgtaca agataaagga 1920
atggctagct acaatgccaa aatctcaggt aaagtgtatg atgagctata tgagaacggt 1980
aataaaaaat acgatataga tgaataa 2007

<210> SEQ ID NO 91
<211> LENGTH: 2007
<212> TYPE: DNA
<213> ORGANISM: Staphylococcus aureus

<400> SEQUENCE: 91
atgaaaaaga taaaaattgt tccacttatt ttaatagttg tagttgtcgg gtttggtata 60
tatttttatg cttcaaaaga taaagaaatt aataatacta ttgatgcaat tgaagataaa 120

```
aatttcaaac aagtttataa agatagcagt tatatttcta aaagcgataa tggtgaagta    180
gaaatgactg aacgtccgat aaaaatatat aatagtttag gcgttaaaga tataaacatt    240
caggatcgta aaataaaaaa agtatctaaa aataaaaaac gagtagatgc tcaatataaa    300
attaaaacaa actacggtaa cattgatcgc aacgttcaat ttaattttgt taaagaagat    360
ggtatgtgga agttagattg ggatcatagc gtcattattc caggaatgca gaaagaccaa    420
agcatacata ttgaaaattt aaaatcagaa cgtggtaaaa ttttagaccg aaacaatgtg    480
gaattggcca atacaggaac agcatatgag ataggcatcg ttccaaagaa tgtatctaaa    540
aaagattata aagcaatcgc taaagaacta agtatttctg aagactatat caaacaacaa    600
atggatcaaa agtgggtaca agatgatacc ttcgttccac ttaaaaccgt taaaaaaatg    660
gatgaatatt taagtgattt cgcaaaaaaa tttcatctta caactaatga aacagaaagt    720
cgtaactatc ctctagaaaa agcgacttca catctattag gttatgttgg tcccattaac    780
tctgaagaat taaaacaaaa agaatataaa ggctataaag atgatgcagt tattggtaaa    840
aagggactcg aaaaacttta cgataaaaag ctccaacatg aagatggcta tcgtgtcaca    900
atcgttgacg ataatagcaa tacaatcgca catacattaa tagagaaaaa gaaaaaagat    960
ggcaaagata ttcaactaac tattgatgct aaagttcaaa agagtattta taacaacatg   1020
aaaaatgatt atggctcagg tactgctatc caccctcaaa caggtgaatt attagcactt   1080
gtaagcacac cttcatatga cgtctatcca tttatgtatg gcatgagtaa cgaagaatat   1140
aataaattaa ccgaagataa aaaagaacct ctgctcaaca agttccagat tacaacttca   1200
ccaggttcaa ctcaaaaaat attaacagca atgattgggt taaataacaa aacattagac   1260
gataaaacaa gttataaaat cgatggtaaa ggttggcaaa aagataaatc ttggggtggt   1320
tacaacgtta caagatatga agtggtaaat ggtaatatcg acttaaaaca agcaatagaa   1380
tcatcagata acattttctt tgctagagta gcactcgaat taggcagtaa gaaatttgaa   1440
aaaggcatga aaaaactagg tgttggtgaa gatataccaa gtgattatcc attttataat   1500
gctcaaattt caaacaaaaa tttagataat gaaatattat tagctgattc aggttacgga   1560
caaggtgaaa tactgattaa cccagtacag atcctttcaa tctatagcgc attagaaaat   1620
aatggcaata ttaacgcacc tcacttatta aaagacacga aaacaaagt ttggaagaaa   1680
aatattattt ccaaagaaaa tatcaatcta ttaactgatg gtatgcaaca agtcgtaaat   1740
aaaacacata aagaagatat ttatagatct tatgcaaact taattggcaa atccggtact   1800
gcagaactca aaatgaaaca aggagaaact ggcagacaaa ttgggtggtt tatatcatat   1860
gataaagata atccaaacat gatgatggct attaatgtta aagatgtaca agataaagga   1920
atggctagct acaatgccaa aatctcaggt aaagtgtatg atgagctata tgagaacggt   1980
aataaaaaat acgatataga tgaataa                                      2007
```

<210> SEQ ID NO 92
<211> LENGTH: 675
<212> TYPE: DNA
<213> ORGANISM: Staphylococcus aureus

<400> SEQUENCE: 92

```
atgaactatt tcagatataa acaatttaac aaggatgtta tcactgtagc cgttggctac     60
tatctaagat atacattgag ttatcgtgat atatctgaaa tattaaggga acgtggtgta    120
aacgttcatc attcaacggt ctaccgttgg gttcaagaat atgccccaat tttgtatcaa    180
```

```
atttggaaga aaaagcataa aaaagcttat tacaaatggc gtattgatga gacgtacatc    240

aaaataaaag gaaaatggag ctatttatat cgtgccattg atgcagaggg acatacatta    300

gatatttggt tgcgtaagca acgagataat cattcagcat atgcgtttat caaacgtctc    360

attaaacaat ttggtaaacc tcaaaaggta attacagatc aggcaccttc aacgaaggta    420

gcaatggcta aagtaattaa agcttttaaa cttaaacctg actgtcattg tacatcgaaa    480

tatctgaata acctcattga gcaagatcac cgtcatatta aagtaagaaa gacaaggtat    540

caaagtatca atacagcaaa gaatacttta aaaggtattg aatgtattta cgctctatat    600

aaaaagaacc gcaggtctct tcagatctac ggattttcgc catgccacga aattagcatc    660

atgctagcaa gttaa                                                      675
```

```
<210> SEQ ID NO 93
<211> LENGTH: 675
<212> TYPE: DNA
<213> ORGANISM: Staphylococcus aureus

<400> SEQUENCE: 93

atgaactatt tcagatataa acaatttaac aaggatgtta tcactgtagc cgttggctac     60

tatctaagat atacattgag ttatcgtgat atatctgaaa tattaaggga acgtggtgta    120

aacgttcatc attcaacggt ctaccgttgg gttcaagaat atgccccaat tttgtatcaa    180

atttggaaga aaaagcataa aaaagcttat tacaaatggc gtattgatga gacgtacatc    240

aaaataaaag gaaaatggag ctatttatat cgtgccattg atgcagaggg acatacatta    300

gatatttggt tgcgtaagca acgagataat cattcagcat atgcgtttat caaacgtctc    360

attaaacaat ttggtaaacc tcaaaaggta attacagatc aggcaccttc aacgaaggta    420

gcaatggcta aagtaattaa agcttttaaa cttaaacctg actgtcattg tacatcgaaa    480

tatctgaata acctcattga gcaagatcac cgtcatatta aagtaagaaa gacaaggtat    540

caaagtatca atacagcaaa gaatacttta aaaggtattg aatgtattta cgctctatat    600

aaaaagaacc gcaggtctct tcagatctac ggattttcgc catgccacga aattagcatc    660

atgctagcaa gttaa                                                      675
```

```
<210> SEQ ID NO 94
<211> LENGTH: 675
<212> TYPE: DNA
<213> ORGANISM: Staphylococcus aureus

<400> SEQUENCE: 94

atgaactatt tcagatataa acaatttaac aaggatgtta tcactgtagc cgttggctac     60

tatctaagat atacattgag ttatcgtgat atatctgaaa tattaaggga acgtggtgta    120

aacgttcatc attcaacggt ctaccgttgg gttcaagaat atgccccaat tttgtatcaa    180

atttggaaga aaaagcataa aaaagcttat tacaaatggc gtattgatga gacgtacatc    240

aaaataaaag gaaaatggag ctatttatat cgtgccattg atgcagaggg acatacatta    300

gatatttggt tgcgtaagca acgagttaat cattcagcat atgcgtttat caaacgtctc    360

attaaacaat ttggtaaacc tcaaaaggta attacagatc aggcaccttc aacgaaggta    420

gcaatggcta aagtaattaa agcttttaaa cttaaacctg actgtcattg tacatcgaaa    480

tatctgaata acctcattga gcaagatcac cgtcatatta aagtaagaaa gacaaggtat    540

caaagtatca atacagcaaa gaatacttta aaaggtattg aatgtattca cgctctatat    600

aaaaagaacc gcaggtctct tcagatctac ggattttcgc catgccacga aattagcatc    660
```

atgctagcaa gttaa 675

<210> SEQ ID NO 95
<211> LENGTH: 675
<212> TYPE: DNA
<213> ORGANISM: Staphylococcus aureus

<400> SEQUENCE: 95
atgaactatt tcagatataa acaatttaac aaggatgtta tcactgtagc cgttggctac 60
tatctaagat atacattgag ttatcgtgat atatctgaaa tattaaggga acgtggtgta 120
aacgttcatc attcaacggt ctaccgttgg gttcaagaat atgccccaat tttgtatcaa 180
atttggaaga aaaagcataa aaaagcttat tacaaatggc gtattgatga gacgtacatc 240
aaaataaaag gaaaatggag ctatttatat cgtgccattg atgcagaggg acatacatta 300
gatatttggt tgcgtaagca acgagataat cattcagcat atgcgtttat caaacgtctc 360
attaaacaat ttggtaaacc tcaaaaggta attacagatc aggcaccttc aacgaaggta 420
gcaatggcta aagtaattaa agcttttaaa cttaaacctg actgtcattg tacatcgaaa 480
tatctgaata acctcattga gcaagatcac cgtcatatta aagtaagaaa gacaaggtat 540
caaagtatca atacagcaaa gaatacttta aaaggtattg aatgtattta cgctctatat 600
aaaaagaacc gcaggtctct tcagatctac ggattttcgc catgccacga aattagcatc 660
atgctagcaa gttaa 675

<210> SEQ ID NO 96
<211> LENGTH: 28
<212> TYPE: DNA
<213> ORGANISM: Artificial Sequence
<220> FEATURE:
<223> OTHER INFORMATION: Synthetic nucleic acid sequence

<400> SEQUENCE: 96
gtaaagtgta tgatgagcta tatgagaa 28

<210> SEQ ID NO 97
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 97
gctgaaaaaa ccgcatcatt trtgrta 27

<210> SEQ ID NO 98
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 98
tttagtttta tttatgatac gcttctcca 29

<210> SEQ ID NO 99
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 99
gctgaaaaaa ccgcatcatt tatgata 27

<210> SEQ ID NO 100
<211> LENGTH: 28
<212> TYPE: DNA
<213> ORGANISM: Artificial Sequence
<220> FEATURE:
<223> OTHER INFORMATION: Synthetic nucleic acid sequence

<400> SEQUENCE: 100
ctatgtcaaa aatcatgaac ctcattac 28

<210> SEQ ID NO 101
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 101
ggaggctaac tatgtcaaaa atc 23

<210> SEQ ID NO 102
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 102
ctctataaac atcgtatgat attgc 25

<210> SEQ ID NO 103
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 103
accaaacgac atgaaaatca 20

<210> SEQ ID NO 104
<211> LENGTH: 1256
<212> TYPE: DNA
<213> ORGANISM: Staphylococcus aureus

<400> SEQUENCE: 104
ttcagaaaaa tgattaatgt gtttcaataa aatctctcct tctttgtgaa catattcatt 60
tttatactaa ttaatataat ttccaaaaaa gtttctgttt aaaagtgaaa aatattattt 120
accgtttgac ttaaatcttc aatatatagg tgtttatatg tatcattttg cgccaatttg 180
aataaacggg aatcaagtct gtttctgagt ttatttcaac tttcttatag taaacattgt 240
cttaatatga tgaacttcaa taaaactttc cctatgcccc ataaaatttt ctcaaaatca 300
aaaataacat accttacaac ttttaccgtc gatatcaatt gctcttttct taatttagga 360
ttgctttcaa attttgtact ataacgtgaa actacttttc cttctttata attaaaattt 420
actaattcac aatcattttt acttccattt acaaaaaacat ccactgtttc taacacaaaa 480
tctaataaac ttccttttat taatcgtagg cattgtatat ttcctttcat tctttcttga 540
ttccattagt ttaaatttaa aatttcatcc atcaatttct taatttaatt gtagttccat 600
aatcaatata atttgtacag ttattatata ttctagatca tcaatagttg aaaaatggtt 660
tattaaacac tctataaaca tcgtatgata ttgcaaggta taatccaata tttcatatat 720
gtaattcctc cacatctcat taaattttta aattatacac aacctaattt ttagttttat 780
ttatgatacg cttctccacg cataatctta aatgctctgt acacttgttc aattaacaca 840
acccgcatca tttgatgtgg gaatgtcatt ttgctgaatg atagtgcgta gttactgcgt 900
tgtaagacgt ccttgtgcag gccgtttgat ccgccaatga cgaatacaaa gtcgctttgc 960
ccttgggtca tgcgttggtt caattcttgg gccaatcctt cggaagatag catctttcct 1020
tgtatttcta atgtaatgac tgttgattgt ggtttgattt tggctagtat tcgttggcct 1080
tctttttctt ttacttgctc aatttctttg tcgctcatat tttctggtgc tttttcgtct 1140
ggaacttcta tgatgtctat cttggtgtat gggcctaaac gtttttcata ttctgctatg 1200
gcttgcttcc aatatttctc ttttagtttc cctacagcta aaatggtgat tttcat 1256

<210> SEQ ID NO 105
<211> LENGTH: 28
<212> TYPE: DNA
<213> ORGANISM: Artificial Sequence
<220> FEATURE:
<221> NAME/KEY: misc_feature
<222> LOCATION: 27
<223> OTHER INFORMATION: n = inosine
<220> FEATURE:
<223> OTHER INFORMATION: Synthetic nucleic acid sequence

<400> SEQUENCE: 105
tcatgaacct cattacttat gataagnt 28

<210> SEQ ID NO 106
<211> LENGTH: 28
<212> TYPE: DNA
<213> ORGANISM: Artificial Sequence
<220> FEATURE:
<221> NAME/KEY: misc_feature
<222> LOCATION: 27
<223> OTHER INFORMATION: n = inosine
<220> FEATURE:
<223> OTHER INFORMATION: Synthetic nucleic acid sequence

<400> SEQUENCE: 106
gaaaaaaccg catcatttat gatatgnt 28

<210> SEQ ID NO 107
<211> LENGTH: 30
<212> TYPE: DNA
<213> ORGANISM: Artificial Sequence
<220> FEATURE:
<221> NAME/KEY: misc_feature
<222> LOCATION: 29
<223> OTHER INFORMATION: n = inosine
<220> FEATURE:
<223> OTHER INFORMATION: Synthetic nucleic acid sequence

<400> SEQUENCE: 107
cctaattttt agttttattt atgatacgnt 30

<210> SEQ ID NO 108
<211> LENGTH: 35
<212> TYPE: DNA
<213> ORGANISM: Artificial Sequence
<220> FEATURE:
<221> NAME/KEY: misc_feature
<222> LOCATION: 34

<223> OTHER INFORMATION: n = inosine
<220> FEATURE:
<223> OTHER INFORMATION: Synthetic nucleic acid sequence

<400> SEQUENCE: 108
cacaacctaa tttttagttt tatttatgat acgnt 35

<210> SEQ ID NO 109
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 109
tgataagcca ttcattcacc ctaa 24

<210> SEQ ID NO 110
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 110
aaggactcct aatttatgtc taattcc 27

<210> SEQ ID NO 111
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 111
atgggagtcc ttcgctattc tgtg 24

<210> SEQ ID NO 112
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 112
cactttttat tcttcaaaga tttgagc 27

<210> SEQ ID NO 113
<211> LENGTH: 28
<212> TYPE: DNA
<213> ORGANISM: Artificial Sequence
<220> FEATURE:
<223> OTHER INFORMATION: Synthetic nucleic acid sequence

<400> SEQUENCE: 113
atggaaattc ttaatcttta cttgtacc 28

<210> SEQ ID NO 114
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 114
agcatcttct ttacatcgct tact 24

<210> SEQ ID NO 115
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 115
cagcaattcw cataaacctc ata 23

<210> SEQ ID NO 116
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 116
acaaactttg aggggatttt tagtaaa 27

<210> SEQ ID NO 117
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 117
tatattgtgg catgatttct tc 22

<210> SEQ ID NO 118
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 118
cgaatggact agcactttct aaa 23

<210> SEQ ID NO 119
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 119
ttgaggatca aaagttgttg c 21

<210> SEQ ID NO 120
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 120
cgatgatttt atagtaggag a 21

<210> SEQ ID NO 121
<211> LENGTH: 28
<212> TYPE: DNA
<213> ORGANISM: Artificial Sequence
<220> FEATURE:

<223> OTHER INFORMATION: Synthetic nucleic acid sequence

<400> SEQUENCE: 121
ttcaatctct aaatctaaat cagttttg 28

<210> SEQ ID NO 122
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 122
aggcgagaaa atggaacata tcaa 24

<210> SEQ ID NO 123
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 123
ggtacaagta aagattaaga atttcc 26

<210> SEQ ID NO 124
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 124
agacaacttt atgcaggtcc tt 22

<210> SEQ ID NO 125
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 125
taactgcttg ggtaacctta tc 22

<210> SEQ ID NO 126
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 126
tattgcaggt ttcgatgttg a 21

<210> SEQ ID NO 127
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 127
tgacccatat cgcctaaaat ac 22

<210> SEQ ID NO 128
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 128
aaaggacaac aaggtagcaa ag 22

<210> SEQ ID NO 129
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 129
tctgtggata aacaccttga tg 22

<210> SEQ ID NO 130
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 130
gtttgatccg ccaatgac 18

<210> SEQ ID NO 131
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 131
ggcataaatg tcaggaaaat atc 23

<210> SEQ ID NO 132
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 132
gaggaccaaa cgacatgaaa atc 23

<210> SEQ ID NO 133
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 133
ttcgaggttg atgggaagca 20

<210> SEQ ID NO 134
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 134
cgctcgactc agggtgtt 18

<210> SEQ ID NO 135
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 135
cgttgaagat gcctttga 18

<210> SEQ ID NO 136
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 136
ttttgcaaca gccattcg 18

<210> SEQ ID NO 137
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 137
gcacacatgt tgtaagtttg c 21

<210> SEQ ID NO 138
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 138
acgcaaactt acaacatgtg tg 22

<210> SEQ ID NO 139
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 139
cgtttgtctg atttggagga ag 22

<210> SEQ ID NO 140
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 140
tttcttcatc atcggtcata aaat 24

<210> SEQ ID NO 141
<211> LENGTH: 23

<212> TYPE: DNA
<213> ORGANISM: Artificial Sequence
<220> FEATURE:
<223> OTHER INFORMATION: Synthetic nucleic acid sequence

<400> SEQUENCE: 141
ctacgtgaat caaaaacaat gga 23

<210> SEQ ID NO 142
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 142
tactgcaaag tctcgttcat cc 22

<210> SEQ ID NO 143
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 143
cataccattt tgaacgatga cctc 24

<210> SEQ ID NO 144
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 144
atgtctggtc aactttccga ctc 23

<210> SEQ ID NO 145
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 145
caatcggtat ctgtaaatat caaat 25

<210> SEQ ID NO 146
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 146
tcgcatacct gtttatcttc tact 24

<210> SEQ ID NO 147
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 147
ttggttccat ctgaactttg ag 22

<210> SEQ ID NO 148
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 148
aatggcttat caaagtgaat atgc 24

<210> SEQ ID NO 149
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 149
taatttcctt tttttccatt cctc 24

<210> SEQ ID NO 150
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 150
actagaatct ccaaatgaat ccagt 25

<210> SEQ ID NO 151
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 151
tggagttaat ctacgtctca tctc 24

<210> SEQ ID NO 152
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 152
gttcatacag aagactcctt tttg 24

<210> SEQ ID NO 153
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 153
agttttgatt atccgaataa atgct 25

<210> SEQ ID NO 154
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 154
tttaaattca gctatatggg gaga 24

<210> SEQ ID NO 155
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 155
ttccgttttg ctattccata at 22

<210> SEQ ID NO 156
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 156
cctctgataa aaaacttgtg aaat 24

<210> SEQ ID NO 157
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 157
actactcctg gaattacaaa ctgg 24

<210> SEQ ID NO 158
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 158
gccaaaatta aaccacaatc cac 23

<210> SEQ ID NO 159
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 159
cattttgctg aatgatagtg cgta 24

<210> SEQ ID NO 160
<211> LENGTH: 48
<212> TYPE: DNA
<213> ORGANISM: Artificial Sequence
<220> FEATURE:
<223> OTHER INFORMATION: Synthetic nucleic acid sequence

<400> SEQUENCE: 160
cgaccggatt cccacatcaa atgatgcggg ttgtgttaat tccggtcg 48

-continued

<210> SEQ ID NO 161
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 161
cccgcgcrta gttactrcgt tgtaagacgt ccgcggg 37

<210> SEQ ID NO 162
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 162
ccccgtagtt actgcgttgt aagacgggg 29

<210> SEQ ID NO 163
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 163
cccgcgcata gttactgcgt tgtaagacgt ccgcggg 37

<210> SEQ ID NO 164
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 164
cccgcgcgta gttactacgt tgtaagacgt ccgcggg 37

<210> SEQ ID NO 165
<211> LENGTH: 1282
<212> TYPE: DNA
<213> ORGANISM: Staphylococcus aureus

<400> SEQUENCE: 165
accattttag ctgtagggaa actaaaagag aaatattgga agcaagccat agcagaatat 60
gaaaaacgtt taggcccata caccaagata gacatcatag aagttccaga cgaaaaagca 120
ccagaaaata tgagcgacaa agaaattgag caagtaaaag aaaaagaagg ccaacgaata 180
ctagccaaaa tcaaaccaca atccacagtc attacattag aaatacaagg aaagatgcta 240
tcttccgaag gattggccca agaattgaac caacgcatga cccaagggca aagcgacttt 300
gtattcgtca ttggcggatc aaacggcctg cacaaggacg tcttacaacg cagtaactat 360
gcactatcat ttagcaaaat gacattccca catcaaatga tgcgggttgt gttaattgaa 420
caagtgtata gagcatttaa gattatgcgt ggagaagcgt accacaaata aaactaaaaa 480
atatgagaaa attattaaat tagctcaaat ctttgaagaa taaaaagtga atattaagtt 540
tgataattta ggtacaagta aagattaaga atttccatta tttaatacat ggtgtgtaaa 600
tcgacttctt tttgtattag atgtttgcag taagcgatgt aaagaagatg ctaataaata 660
tgtgaggaat gattacgata ctagataagc ggctaatgaa attttttaaa gtacatatat 720
agacatattt ttcatttagt aaaattttga atttcacttt gctaagacta gtgtctagaa 780
atttataatg atttattaac acctatttga aacttaagta taataaatga ttcggatttt 840
atttttaata aagacaaact tgaacgtagc aaagtagttt ttatgataaa taataagttt 900
taataatgtg acgcttttat ataagcacat tattatgaac aatgtgaatt gagcatctac 960
aattacatta ataaatatat aaatgatgat ttaaattcac atatatttat aatacacata 1020
ctatatgaaa gttttgatta tccgaataaa tgctaaaatt aataaaataa ttaaaggaat 1080
catacttatt atacgtatac gtttagctac tgaactactg gattcatttg gagattctag 1140
tagttctttt tcaatctcta aatctaaatc agttttgtaa taaccattaa ttcctaatct 1200
ttcatctagc tctgtacttt tttcatcatt tttatctttg ttgatatgtt ccattttctc 1260
gcctcttttt aatcaagtag aa 1282

<210> SEQ ID NO 166
<211> LENGTH: 1108
<212> TYPE: DNA
<213> ORGANISM: Staphylococcus aureus

<400> SEQUENCE: 166
accattttag ctgtagggaa actaaaagag aaatattgga agcaagccat agcagaatat 60
gaaaaacgtt taggcccata caccaagata gacatcatag aagttccaga cgaaaaagca 120
ccagaaaata tgagcgacaa agaaattgag caagtaaaag aaaaagaagg ccaacgaata 180
ctagccaaaa tcaaaccaca atccacagtc attacattag aaatacaagg aaagatgcta 240
tcttccgaag gattggccca agaattgaac caacgcatga cccaagggca aagcgacttt 300
gtattcgtca ttggcggatc aaacggcctg cacaaggacg tcttacaacg cagtaactat 360
gcactatcat ttagcaaaat gacattccca catcaaatga tgcgggttgt gttaattgaa 420
caagtgtata gagcatttaa gattatgcgt ggagaagcgt accacaaata aaactaaaaa 480
atatgagaaa attattaaat tagctcaaat ctttgaagaa taaaaagtga atattaagtt 540
tgataattta ggtacaagta aagattaaga atttccatta tttaatacat ggtgtgtaaa 600
tcgacttctt tttgtattag atgtttgcag taagcgatgt aaagaagatg ctaataaata 660
tgtgaggaat gattacgata ctagataagc ggctaatgaa attttttaaa gtacatatat 720
agacatattt ttcatttagt aaaattttga atttcacttt gctaagacta gtgtctagaa 780
atttataatg atttattaac acctatttga aacttaagta taataaatga ttcggatttt 840
atttttaata aagacaaact tgaacgtagc aaagtagttt ttatgataaa taataagttt 900
taataatgtg acgcttttat ataagcacat tattatgaac aatgtgaatt gagcatctac 960
aattacatta ataaatatat aaatgatgat ttaaattcac atatatttat aatacacata 1020
ctatatgaaa gttttgatta tccgaataaa tgctaaaatt aataaaataa ttaaaggaat 1080
catacttatt atacgtatac gtttagct 1108

<210> SEQ ID NO 167
<211> LENGTH: 1530
<212> TYPE: DNA
<213> ORGANISM: Staphylococcus aureus

<400> SEQUENCE: 167
ttagctgtag ggaaactaaa agagaaatat tggaagcaag ccatagcaga atatgaaaaa 60
cgtttaggcc catacaccaa gatagacatc atagaagttc cagacgaaaa agcaccagaa 120

```
aatatgagcg acaaagaaat tgagcaagta aaagaaaaag aaggccaacg aatactagcc    180
aaaatcaaac cacaatccac agtcattaca ttagaaatac aaggaaagat gctatcttcc    240
gaaggattgg cccaagaatt gaaccaacgc atgacccaag ggcaaagcga ctttgtattc    300
gtcattggcg gatcaaacgg cctgcacaag gacgtcttac aacgcagtaa ctatgcacta    360
tcatttagca aaatgacatt cccacatcaa atgatgcggg ttgtgttaat tgaacaagtg    420
tatagagcat ttaagattat gcgtggagaa gcatatcata aatgatgcgg tttttcagc     480
cgcttcataa agggggtga  tcatatcgga acgtatgagg tttatgagaa ttgctgctat    540
gtttttatga agcgtatcat aaatgatgca gtttttgata atttttctt tatcagagat    600
tttactaaaa atcccctcaa agtttgtttt tttcaacttc aactttgaag ggaataaata    660
aggaacttat ttatatttat cctttatctc attaatatct atttttttat taataatatt    720
ataaatatta aattctttag aaaagtcact atcactctta ttcttcatac taaacgttat    780
taatctaata atatcagcta ctatttcttt aaattctatt gcatcttctt ttttataagt    840
agcgcctgta tgaacaattt tatttctcat accatagtaa tctttcatat atttttttac    900
acaattttta atttcattag aattatccaa atctagatta tcaattgtct ttaataaatg    960
atcattaaca acattagcat acccacatcc aagcttcttt tttatctctt catcacttaa   1020
attttcatct aatttataat atctttctaa aaaatttgtg ataaaaactt ctaatgcagt   1080
ctgaatttgt acaattgcta aattatagtc agatttataa aaagaacgtt caccttttct   1140
catagccaaa acataaatat tgctaggatg attattgaaa atattataat tttttttaat   1200
atttaataaa tcactttttt tgatagatga atactgatct tcttctatct ttccaggcat   1260
gtcaatcatg aaaatactca tctcttttat atttccatct atagtatata ttatataata   1320
tggaatactt aatatatccc ctaatgatag ctggtatata ttatgatact gatatttaac   1380
gctaataatt ttaataagat tatttagaca attaaattgc ttattaaaaa ttttcgttag   1440
actattactt ttctttgatt ccctagaagt agaatttgat ttcaattttt taaactgatt   1500
gtgcttgatt attgaagtta tttcaacata                                    1530
```

<210> SEQ ID NO 168
<211> LENGTH: 1256
<212> TYPE: DNA
<213> ORGANISM: Staphylococcus aureus

<400> SEQUENCE: 168

```
gctgtaggga aactaaaaga gaaatattgg aagcaagcca tagcagaata tgaaaaacgt     60
ttaggcccat acaccaagat agacatcata gaagttccag acgaaaaagc accagaaaat    120
atgagcgaca aagaaattga gcaagtaaaa gaaaaagaag gccaacgaat actagccaaa    180
attaaaccac aatccacagt cattacatta gaaatacaag gaaagatgct atcttccgaa    240
ggattggccc aagaattgaa ccaacgcatg acccaagggc aaagcgactt tgtattcgtc    300
attggcggat caaacggcct gcacaaggac gtcttacaac gcagtaacta cgcactatca    360
ttcagcaaaa tgacattccc acatcaaatg atgcgggttg tgttaattga gcaagtgtat    420
agagcattta agattatgcg tggagaagca tatcataaat gatgcggttt tttcagccgc    480
ttcataaagg gatttgaat  gtatcagaac atatgaggtt tatgtgaatt gctgttatgt    540
ttttaagaag catatcataa gtgatgcggt ttttattaat tagttgctaa aaaatgaagt    600
atgcaatatt aattattatt aaattttgat atatttaaag aaagattaag tttagggtga    660
atgaatggct tatcaaagtg aatatgcatt agaaaatgaa gtacttcaac aacttgagga    720
```

attgaactat gaaagagtaa atatacataa tattaaatta gaaattaatg aatatctcaa 780
agaactagga gtgttgaaaa atgaataagc agacaaatac tccagaacta agatttccag 840
agtttgatga ggaatggaaa aaaaggaaat taggtgaagt agtaaattat aaaaatggtg 900
gttcatttga aagtttagtg aaaaaccatg gtgtatataa actcataact cttaaatctg 960
ttaatacaga aggaaagttg tgtaattctg gaaaatatat cgatgataaa tgtgttgaaa 1020
cattgtgtaa tgatacttta gtaatgatac tgagcgagca agcaccagga ctagttggaa 1080
tgactgcaat tatacctaat aataatgagt atgtactaaa tcaacgagta gcagcactag 1140
tgcctaaaca atttatagat agtcaatttc tatctaagtt aattaataga aaccagaaat 1200
atttcagtgt gagatctgct ggaacaaaag tgaaaaatat ttctaaagga catgta 1256

<210> SEQ ID NO 169
<211> LENGTH: 846
<212> TYPE: DNA
<213> ORGANISM: Staphylococcus aureus

<400> SEQUENCE: 169
ttacattaga aatacaagga aagatgctat cttccgaagg attggcccaa gaattgaacc 60
aacgcatgac ccaagggcaa agcgactttg ttttcgtcat tggcggatca aacggcctgc 120
acaaggacgt cttacaacgc agtaactacg cactatcatt cagcaaaatg acattcccac 180
atcaaatgat gcgggttgtg ttaattgaac aagtgtacag agcatttaag attatgcgag 240
gagaagctta tcataagtaa tgaggttcat gatttttgac atagttagcc tccgcagtct 300
ttcatttcaa gtaaataata gcgaaatatt ctttatactg aatacttata gtgaagcaaa 360
gttctagctt tgagaaaatt ctttctgcaa ctaaatatag taaattacgg taaaatataa 420
ataagtacat attgaagaaa atgagacata atatatttta taataggagg gaatttcaaa 480
tgatagacaa ctttatgcag gtccttaaat taattaaaga gaaacgtacc aataatgtag 540
ttaaaaaatc tgattgggat aaaggtgatc tatataaaac tttagtccat gataagttac 600
ccaagcagtt aaaagtgcat ataaaagaag ataaatattc agttgtaggg aaggttgcta 660
ctgggaacta tagtaaagtt ccttggattt caatatatga tgagaatata acaaaagaaa 720
caaaggatgg atattatttg gtatatcttt ttcatccgga aggagaaggc atatacttat 780
ctttgaatca aggatggtca aagataagtg atatgtttcc gcgggataaa aatgctgcaa 840
aacaaa 846

<210> SEQ ID NO 170
<211> LENGTH: 1270
<212> TYPE: DNA
<213> ORGANISM: Staphylococcus aureus

<400> SEQUENCE: 170
cattagaaat acaaggaaag atgctatctt ccgaaggatt ggcccaagaa ttgaaccaac 60
gcatgaccca agggcaaagc gactttgtat tcgtcattgg cggatcaaac ggcctgcaca 120
aggacgtctt acaacgcagt aactatgcac tatcatttag caaaatgaca ttcccacatc 180
aaatgatgcg ggttgtgtta attgaacaag tgtatagagc atttaagatt atgcgtggag 240
aagcatatca taaatgatgc ggtttttttca gccgcttcat aaagggattt tgaatgtatc 300
agaacatatg aggtttatgt gaattgctgt tatgttttta agaagcttat cataagtaat 360
gaggttcatg atttttgaca tagttagcct ccgcagtctt tcatttcaag taaataatag 420

```
cgaaatattc tttatactga atacttatag tgaagcaaag ttctagcttt gagaaaattc    480

tttctgcaac taaatatagt aaattacggt aaaatataaa taagtacata ttgaagaaaa    540

tgagacataa tatattttat aataggaggg aatttcaaat gatagacaac tttatgcagg    600

tccttaaatt aattaaagag aaacgtacca ataatgtagt taaaaaatct gattgggata    660

aaggtgatct atataaaact ttagtccatg ataagttacc caagcagtta aaagtgcata    720

taaaagaaga taaatattca gttgtaggga aggttgctac tgggaactat agtaaagttc    780

cttggatttc aatatatgat gagaatataa caaaagaaac aaaggatgga tattatttgg    840

tatatctttt tcatccggaa ggagaaggca tatacttatc tttgaatcaa ggatggtcaa    900

agataagtga tatgtttccg cgggataaaa atgctgcaaa acaaagagca ttaactttat    960

cttccgaact caataaatat attacatcaa atgaatttaa tactggaaga ttttattacg   1020

cagaaaataa agattcatct tatgatttaa aaaatgatta tccatcagga tattctcatg   1080

gatcaataag attcaaatat tatgatttga atgaaggatt cacagaagaa gatatgctag   1140

aggatttaaa gaaattttta gaactattta atgaattagc ttcaaaagtt acaaaaaacat   1200

cctatgatag cttggtcaat agcatagacg aaatacagga agacagcgaa attgaagaaa   1260

ttagaacagc                                                          1270
```

<210> SEQ ID NO 171
<211> LENGTH: 991
<212> TYPE: DNA
<213> ORGANISM: Staphylococcus aureus

<400> SEQUENCE: 171

```
accattttag ctgtagggaa actaaaagag aaatactgga agcaagccat agcagaatat     60

gaaaaacgtt taggcccata caccaagata gacatcatag aagttccaga cgaaaaagca    120

ccagaaaata tgaactacaa agaaattgag caagtaaaag aaaaagaagg ccaacgaata    180

ctagccaaaa tcaaaccaca atcaacagtc attacattag aaatacaagg aaagatgcta    240

tcttccgaag gattggccca agaattgaac caacgcatga cccaagggca aagcgacttt    300

gtattcgtca ttggcggatc aaacggcctg cacaaggacg tcttacaacg cagtaactac    360

gcactatcat tcagcaaaat gacattccca catcaaatga tgcgggttgt gttaattgaa    420

caagtgtaca gagcatttaa gattatgcga ggagaagcgt atcataagtg atggtaaaaa    480

atatgagtaa gtagatgaag agtgaaaatc agattaatta ataataatgt atcaaattta    540

aataaagggg tttttaagta tgaatttaag aggtcatgaa aatagactta aatttcatgc    600

gaaatatgat gtgacaccta tatcacattt aaaattatta gaaggtcaaa agaaagacgg    660

tgaaggcggc atactgacag atagctatta ctgtttttca tacagcttaa aaggtaattc    720

taaaaaagtt ttaggtacgt ttaattgtgg ttatcatatt gctgaagatt tactaaaatt    780

atcaaatcaa gataaattac ctttatttaa cccgtttaaa gtaattaatg aaggtaatca    840

attgcagggc gtaacgaata aaggtaattt aaatattaat aggcaaagaa aacagtataa    900

tgaagtggct ttacagcttt caaatgctat taatttaatc ataatttgtt atgaggataa    960

tattaaagaa ccactttcaa cgataaaata c                                   991
```

<210> SEQ ID NO 172
<211> LENGTH: 748
<212> TYPE: DNA
<213> ORGANISM: Staphylococcus aureus

<400> SEQUENCE: 172
atcgtttaac gtgtcacatg atgcgataga tccgcaattt tatattttcc ataataacta 60
taagaagttt acgattttaa cagatacggg ttacgtgtct gatcgtatga aaggtatgat 120
acgtggcagc gatgcattta tttttgagag taatcatgac gtcgatatgt tgagaatgtg 180
tcgttatcca tggaagacga aacaacgcat tttaggcgat atgggtcatg tatctaatga 240
ggatgcgggt catgcgatga cagacgtgat tacaggtaac acgaaacgta tttacttatc 300
gcatttatca caagataata atatgaaaga tttggcgcgt atgagtgttg gccaagtatt 360
gaacgaacac gatattgata cggaaaaaga agtattgcta tgtgatacgg ataaagctat 420
tccaacacca atatatacaa tataaatgag agtcatccga taaagttccg cactgctgtg 480
aaacgacttt atcgggtgct tttttatgtt gttggtggga aatggctgtt gttgagttga 540
atcggattga ttgaaatgtg taaaataatt cgatattaaa tgtaatttat aaataattta 600
cataaaatca aacattttaa tataaggatt atgataatat attggtgtat gacagttaat 660
ggagggaacg aaatgaaagc tttattactt aaaacaagtg tatggctcgt tttgcttttt 720
agtgtgatgg gattatggca tgtctcga 748

<210> SEQ ID NO 173
<211> LENGTH: 917
<212> TYPE: DNA
<213> ORGANISM: Staphylococcus aureus

<400> SEQUENCE: 173
aaatacaagg aaagatgcta tcttccgaag gattggccca agaattgaac caacgcatga 60
cccaagggca aagcgacttt gtattcgtca ttggcggatc aaacggcctg cacaaggacg 120
tcttacaacg tagtaactac gcactatcat tcagcaaaat gacattccca catcaaatga 180
tgcgggttgt gttaattgag caagtgtata gagcatttaa gattatgcgt ggagaagcat 240
atcataaatg atgcggtttt ttcagccgct tcataaaggg attttgaatg tatcagaaca 300
tatgaggttt atgtgaattg ctgttatgtt tttaagaagc ttatcataag taatgaggtt 360
catgattttt gacatagtta gcctccgcag tctttcattt caagtaaata atagcgaaat 420
attctttata ctgaatactt atagtgaagc aaagttctag ctttgagaaa attctttctg 480
caactaaata tagtaaatta cggtaaaata taaataagta catattgaag aaaatgagac 540
ataatatatt ttataatagg agggaatttc aaatgataga caactttatg caggtcctta 600
aattaattaa agagaaacgt accaataatg tagttaaaaa atctgattgg gataaaggtg 660
atctatataa aactttagtc catgataagt tacccaagca gttaaaagtg catataaaag 720
aagataaata ttcagttgta gggaaggttg ctactgggaa ctatagtaaa gttccttgga 780
tttcaatata tgatgagaat ataacaaaag aaacaaagga tggatattat ttggtatatc 840
tttttcatcc ggaaggagaa ggcatatact tatctttgaa tcaaggatgg tcaaagataa 900
gtgatatgtt tccgcgg 917

<210> SEQ ID NO 174
<211> LENGTH: 1132
<212> TYPE: DNA
<213> ORGANISM: Staphylococcus aureus

<400> SEQUENCE: 174
gctgtaggga aactaaaaga gaaatattgg aagcaagcca tagcagaata tgaaaaacgt 60
ttaggcccat acaccaagat agacatcata gaagttccag acgaaaaagc accagaaaat 120

```
atgagcgaca aagaaattga gcaagtaaaa gaaaaagaag gccaacgaat actagccaaa    180
atcaaaccac aatcaacagt cattacatta gaaatacaag gaaagatgct atcttccgaa    240
ggattggccc aagaattgaa ccaacgcatg acccaagggc aaagcgactt tgtattcgtc    300
attggcggat caaacggcct gcacaaggac gtcttacaac gtagtaacta cgcactatca    360
ttcagcaaaa tgacattccc acatcaaatg atgcgggttg tgttaattga gcaagtgtat    420
agagcattta agattatgcg tggagaagca tatcataaat gatgcggttt tttcagccgc    480
ttcataaagg gattttgaat gtatcagaac atatgaggtt tatgtgaatt gctgttatgt    540
ttttaagaag cttatcataa gtaatgaggt tcatgatttt tgacatagtt agcctccgca    600
gtctttcatt tcaagtaaat aatagcgaaa tattctttat actgaatact tatagtgaag    660
caaagttcta gctttgagaa aattctttct gcaactaaat atagtaaatt acggtaaaat    720
ataaataagt acatattgaa gaaaatgaga cataatatat tttataatag gagggaattt    780
caaatgatag acaactttat gcaggtcctt aaattaatta aagagaaacg taccaataat    840
gtagttaaaa aatctgattg ggataaaggt gatctatata aaactttagt ccatgataag    900
ttacccaagc agttaaaagt gcatataaaa gaagataaat attcagttgt agggaaggtt    960
gctactggga actatagtaa agttccttgg atttcaatat atgatgagaa tataacaaaa   1020
gaaacaaagg atggatatta tttggtatat ctttttcatc cggaaggaga aggcatatac   1080
ttatctttga atcaaggatg gtcaaagata agtgatatgt ttccgcggga ta           1132
```

<210> SEQ ID NO 175
<211> LENGTH: 1133
<212> TYPE: DNA
<213> ORGANISM: Staphylococcus aureus

<400> SEQUENCE: 175

```
agctgtaggg aaactaaaag agaaatattg gaagcaagcc atagcagaat atgaaaaacg     60
tttaggccca tacaccaaga tagacatcat agaagttcca gacgaaaaag caccagaaaa    120
tatgagcgac aaagaaattg agcaagtaaa agaaaaagaa ggccaacgaa tactagccaa    180
aatcaaacca caatcaacag tcattacatt agaaatacaa ggaaagatgc tatcttccga    240
aggattggcc caagaattga accaacgcat gacccaaggg caaagcgact ttgtattcgt    300
cattggcgga tcaaacggcc tgcacaagga cgtcttacaa cgtagtaact acgcactatc    360
attcagcaaa atgacattcc cacatcaaat gatgcgggtt gtgttaattg agcaagtgta    420
tagagcattt aagattatgc gtggagaagc atatcataaa tgatgcggtt ttttcagccg    480
cttcataaag ggattttgaa tgtatcagaa catatgaggt ttatgtgaat tgctgttatg    540
tttttaagaa gcttatcata agtaatgagg ttcatgattt ttgacatagt tagcctccgc    600
agtctttcat ttcaagtaaa taatagcgaa atattcttta tactgaatac ttatagtgaa    660
gcaaagttct agctttgaga aaattctttc tgcaactaaa tatagtaaat tacggtaaaa    720
tataaataag tacatattga agaaaatgag acataatata ttttataata ggagggaatt    780
tcaaatgata gacaacttta tgcaggtcct taaattaatt aaagagaaac gtaccaataa    840
tgtagttaaa aaatctgatt gggataaagg tgatctatat aaaactttag tccatgataa    900
gttacccaag cagttaaaag tgcatataaa agaagataaa tattcagttg tagggaaggt    960
tgctactggg aactatagta aagttccttg gatttcaata tatgatgaga atataacaaa   1020
agaaacaaag gatggatatt atttggtata tctttttcat ccggaaggag aaggcatata   1080
cttatctttg aatcaaggat ggtcaaagat aagtgatatg tttccgcggg ata          1133
```

<210> SEQ ID NO 176
<211> LENGTH: 1087
<212> TYPE: DNA
<213> ORGANISM: Staphylococcus aureus

<400> SEQUENCE: 176
actaaaagag aaatattgga agcaagccat agcagaatat gaaaaacgtt taggcccata 60
caccaagata gacatcatag aagttccaga cgaaaaagca ccagaaaata tgagcgacaa 120
agaaattgag caagtaaaag aaaaagaagg ccaacgaata ctagccaaaa tcaaaccaca 180
atcaacagtc attacattag aaatacaagg aaagatgcta tcttccgaag gattggcaca 240
agaattgaac caacgcatga cccaagggca aagcgacttt gtattcgtca ttggcggatc 300
aaacggcctg cacaaggacg tcttacaacg tagtaactac gcactatcat tcagcaaaat 360
gacattccca catcaaatga tgcgggttgt gttaattgag caagtgtata gagcgtttaa 420
gattatgcgt ggagaagcat atcataaatg atgcggtttt ttcagccgct tcataaaggg 480
attttgaatg tatcagaaca tatgaggttt atgtgaattg ctgttatgtt tttaagaagc 540
ttatcataag taatgaggtt catgattttt gacatagtta gcctccgcag tctttcattt 600
caagtaaata atagcgaaat attctttata ctgaatactt atagtgaagc aaagttctag 660
ctttgagaaa attctttctg caactaaata tagtaaatta cggtaaaata taaataagta 720
catattgaag aaaatgagac ataatatatt ttataatagg agggaatttc aaatgataga 780
caactttatg caggtcctta aattaattaa agagaaacgt accaataatg tagttaaaaa 840
atctgattgg gataaaggtg atctatataa aactttagtc catgataagt tacccaagca 900
gttaaaagtg catataaaag aagataaata ttcagttgta gggaaggttg ctactgggaa 960
ctatagtaaa gttccttgga tttcaatata tgatgagaat ataacaaaag aaacaaagga 1020
tggatattat ttggtatatc tttttcatcc ggaaggagaa ggcatatact tatctttgaa 1080
tcaagga 1087

<210> SEQ ID NO 177
<211> LENGTH: 903
<212> TYPE: DNA
<213> ORGANISM: Staphylococcus aureus

<400> SEQUENCE: 177
caaggaaaga tgctatcttc cgaaggattg gcccaagaat tgaaccaacg catgacccaa 60
gggcaaagcg actttgtatt cgtcattggc ggatcaaacg gcctgcacaa ggacgtctta 120
caacgtagta actacgcact atcattcagc aaaatgacat tcccacatca aatgatgcgg 180
gttgtgttaa ttgagcaagt gtatagagca tttaagatta tgcgtggaga agcatatcat 240
aaatgatgcg gtttttcag ccgcttcata aagggatttt gaatgtatca gaacatatga 300
ggtttatgtg aattgctgtt atgtttttaa gaagcttatc ataagtaatg aggttcatga 360
tttttgacat agttagcctc cgcagtcttt catttcaagt aaataatagc gaaatattct 420
ttatactgaa tacttatagt gaagcaaagt tctagctttg agaaaattct ttctgcaact 480
aaatatagta aattacggta aaatataaat aagtacatat tgaagaaaat gagacataat 540
atattttata ataggaggga atttcaaatg atagacaact ttatgcaggt ccttaaatta 600
attaaagaga aacgtaccaa taatgtagtt aaaaaatctg attgggataa aggtgatcta 660
tataaaactt tagtccatga taagttaccc aagcagttaa aagtgcatat aaaagaagat 720

-continued aaatattcag ttgtagggaa ggttgctact gggaactata gtaaagttcc ttggatttca 780
atatatgatg agaatataac aaaagaaaca aaggatggat attatttggt atatcttttt 840
catccggaag gagaaggcat atacttatct ttgaatcaag gatggtcaaa gataagtgat 900
atg 903

<210> SEQ ID NO 178
<211> LENGTH: 1114
<212> TYPE: DNA
<213> ORGANISM: Staphylococcus aureus

<400> SEQUENCE: 178
ggaaactaaa agagaaatat tggaagcaag ccatagcaga atatgaaaaa cgtttaggcc 60
catacaccaa gatagacatc atagaagttc cagacgaaaa agcaccagaa aatatgagcg 120
acaaagaaat tgagcaagta aaagaaaaag aaggccaacg aatactagcc aaaatcaaac 180
cacaatcaac agtcattaca ttagaaatac aaggaaagat gctatcttcc gaaggattgg 240
cccaagaatt gaaccaacgc atgacccaag ggcaaagcga ctttgtattc gtcattggcg 300
gatcaaacgg cctgcacaag gacgtcttac aacgtagtaa ctacgcacta tcattcagca 360
aaatgacatt cccacatcaa atgatgcggg ttgtgttaat tgagcaagtg tatagagcat 420
ttaagattat gcgtggagaa gcatatcata aatgatgcgg ttttttcagc cgcttcataa 480
agggattttg aatgtatcag aacatatgag gtttatgtga attgctgtta tgtttttaag 540
aagcttatca taagtaatga ggttcatgat ttttgacata gttagcctcc gcagtctttc 600
atttcaagta aataatagcg aaatattctt tatactgaat acttatagtg aagcaaagtt 660
ctagctttga gaaaattctt tctgcaacta aatatagtaa attacggtaa aatataaata 720
agtacatatt gaagaaaatg agacataata tattttataa taggagggaa tttcaaatga 780
tagacaactt tatgcaggtc cttaaattaa ttaaagagaa acgtaccaat aatgtagtta 840
aaaaatctga ttgggataaa ggtgatctat ataaaacttt agtccatgat aagttaccca 900
agcagttaaa agtgcatata aaagaagata aatattcagt tgtagggaag gttgctactg 960
ggaactatag taaagttcct tggatttcaa tatatgatga gaatataaca aaagaaacaa 1020
aggatggata ttatttggta tatctttttc atccggaagg agaaggcata tacttatctt 1080
tgaatcaagg atggtcaaag ataagtgata tgtt 1114

<210> SEQ ID NO 179
<211> LENGTH: 1121
<212> TYPE: DNA
<213> ORGANISM: Staphylococcus aureus

<400> SEQUENCE: 179
ggaaactaaa agagaaatat tggaagcaag ccatagcaga atatgaaaaa cgtttaggcc 60
catacaccaa gatagacatc atagaagttc cagacgaaaa agcaccagaa aatatgagcg 120
acaaagaaat tgagcaagta aaagaaaaag aaggccaacg aatactagcc aaaatcaaac 180
cacaatccac agtcattaca ttagaaatac aaggaaagat gctatcttcc gaaggattgg 240
cccaagaatt gaaccaacgc atgacccaag ggcaaagcga ctttgtattc gtcattggcg 300
gatcaaacgg cctgcacaag gacgtcttac aacgcagtaa ctatgcacta tcatttagca 360
aaatgacatt cccacatcaa atgatgcggg ttgtgttaat tgaacaagtg tatagagcat 420
ttaagattat gcgtggagaa gcatatcata aatgatgcgg ttttttcagc cgcttcataa 480
agggattttg aatgtatcag aacatatgag gtttatgtga attgctgtta tgtttttaag 540
aagcttatca taagtaatga ggttcatgat ttttgacata gttagcctcc gcagtctttc 600
atttcaagta aataatagcg aaatattctt tatactgaat acttatagtg aagcaaagtt 660
ctagctttga gaaaattctt tctgcaacta aatatagtaa attacggtaa aatataaata 720
agtacatatt gaagaaaatg agacataata tattttataa taggagggaa tttcaaatga 780
tagacaactt tatgcaggtc cttaaattaa ttaaagagaa acgtaccaat aatgtagtta 840
aaaaatctga ttgggataaa ggtgatctat ataaaacttt agtccatgat aagttaccca 900
agcagttaaa agtgcatata aaagaagata aatattcagt tgtagggaag gttgctactg 960
ggaactatag taaagttcct tggatttcaa tatatgatga gaatataaca aaagaaacaa 1020
aggatggata ttatttggta tatctttttc atccggaagg agaaggcata tacttatctt 1080
tgaatcaagg atggtcaaag ataagtgata tgtttccgcg g 1121

<210> SEQ ID NO 180
<211> LENGTH: 1121
<212> TYPE: DNA
<213> ORGANISM: Staphylococcus aureus

<400> SEQUENCE: 180
tagctgtagg gaaactaaaa gagaaatatt ggaagcaagc catagcagaa tatgaaaaac 60
gtttaggccc atacaccaag atagacatca tagaagttcc agacgaaaaa gcaccagaaa 120
atatgagcga caaagaaatt gagcaagtaa aagaaaaaga aggccaacga atactagcca 180
aaatcaaacc acaatccaca gtcattacat tagaaataca aggaaagatg ctatcttccg 240
aaggattggc ccaagaattg aaccaacgca tgacccaagg gcaaagcgac tttgtattcg 300
tcattggcgg atcaaacggc ctgcacaagg acgtcttaca acgcagtaac tatgcactat 360
catttagcaa aatgacattc ccacatcaaa tgatgcgggt tgtgttaatt gaacaagtgt 420
atagagcatt taagattatg cgtggagaag catatcataa atgatgcggt tttttcagcc 480
gcttcataaa gggattttga atgtatcaga acatatgagg tttatgtgaa ttgctgttat 540
gtttttaaga agcttatcat aagtaatgag gttcatgatt tttgacatag ttagcctccg 600
cagtctttca tttcaagtaa ataatagcga aatattcttt atactgaata cttatagtga 660
agcaaagttc tagctttgag aaaattcttt ctgcaactaa atatagtaaa ttacggtaaa 720
atataaataa gtacatattg aagaaaatga gacataatat attttataat aggagggaat 780
ttcaaatgat agacaacttt atgcaggtcc ttaaattaat taaagagaaa cgtaccaata 840
atgtagttaa aaaatctgat tgggataaag gtgatctata taaaacttta gtccatgata 900
agttacccaa gcagttaaaa gtgcatataa aagaagataa atattcagtt gtagggaagg 960
ttgctactgg gaactatagt aaagttcctt ggatttcaat atatgatgag aatataacaa 1020
aagaaacaaa ggatggatat tatttggtat atctttttca tccggaagga gaaggcatat 1080
acttatcttt gaatcaagga tggtcaaaga taagtgatat g 1121

<210> SEQ ID NO 181
<211> LENGTH: 1131
<212> TYPE: DNA
<213> ORGANISM: Staphylococcus aureus

<400> SEQUENCE: 181
ctgtagggaa actaaaagag aaatattgga agcaagccat agcagaatat gaaaaacgtt 60
taggcccata caccaagata gacatcatag aagttccaga cgaaaaagca ccagaaaata 120

-continued

```
tgagcgacaa agaaattgag caagtaaaag aaaaagaagg ccaacgaata ctagccaaaa    180

tcaaaccaca atccacagtc attacattag aaatacaagg aaagatgcta tcttccgaag    240

gattggccca agaattgaac caacgcatga cccaagggca aagcgacttt gtattcgtca    300

ttggcggatc aaacggcctg cacaaggacg tcttacaacg cagtaactat gcactatcat    360

ttagcaaaat gacattccca catcaaatga tgcgggttgt gttaattgaa caagtgtata    420

gagcatttaa gattatgcgt ggagaagcat atcataaatg atgcggtttt ttcagccgct    480

tcataaaggg attttgaatg tatcagaaca tatgaggttt atgtgaattg ctgttatgtt    540

tttaagaagc ttatcataag taatgaggtt catgattttt gacatagtta gcctccgcag    600

tctttcattt caagtaaata atagcgaaat attctttata ctgaatactt atagtgaagc    660

aaagttctag ctttgagaaa attctttctg caactaaata tagtaaatta cggtaaaata    720

taaataagta catattgaag aaaatgagac ataatatatt ttataatagg agggaatttc    780

aaatgataga caactttatg caggtcctta aattaattaa agagaaacgt accaataatg    840

tagttaaaaa atctgattgg gataaaggtg atctatataa aactttagtc catgataagt    900

tacccaagca gttaaaagtg catataaaag aagataaata ttcagttgta gggaaggttg    960

ctactgggaa ctatagtaaa gttccttgga tttcaatata tgatgagaat ataacaaaag   1020

aaacaaagga tggatattat ttggtatatc tttttcatcc ggaaggagaa ggcatatact   1080

tatctttgaa tcaaggatgg tcaaagataa gtgatatgtt tccgcgggat a            1131
```

```
<210> SEQ ID NO 182
<211> LENGTH: 896
<212> TYPE: DNA
<213> ORGANISM: Staphylococcus aureus

<400> SEQUENCE: 182

cattagaaat acaaggaaag atgctatctt ccgaaggatt ggcccaagaa ttgaaccaac     60

gcatgaccca agggcaaagc gactttgtat tcgtcattgg cggatcaaac ggcctgcaca    120

aggacgtctt acaacgcagt aactatgcac tatcatttag caaaatgaca ttcccacatc    180

aaatgatgcg ggttgtgtta attgaacaag tgtatagagc atttaagatt atgcgtggag    240

aagcatatca taaatgatgc ggttttttca gccgcttcat aaagggattt tgaatgtatc    300

agaacatatg aggtttatgt gaattgctgt tatgttttta agaagcttat cataagtaat    360

gaggttcatg atttttgaca tagttagcct ccgcagtctt tcatttcaag taaataatag    420

cgaaatattc tttatactga atacttatag tgaagcaaag ttctagcttt gagaaaattc    480

tttctgcaac taaatatagt aaattacggt aaaatataaa taagtacata ttgaagaaaa    540

tgagacataa tatattttat aataggaggg aatttcaaat gatagacaac tttatgcagg    600

tccttaaatt aattaaagag aaacgtacca ataatgtagt taaaaaatct gattgggata    660

aaggtgatct atataaaact ttagtccatg ataagttacc caagcagtta aaagtgcata    720

taaaagaaga taaatattca gttgtaggga aggttgctac tgggaactat agtaaagttc    780

cttggatttc aatatatgat gagaatataa caaaagaaac aaaggatgga tattatttgg    840

tatatctttt tcatccggaa ggagaaggca tatacttatc tttgaatcaa ggatgg        896
```

```
<210> SEQ ID NO 183
<211> LENGTH: 1125
<212> TYPE: DNA
<213> ORGANISM: Staphylococcus aureus

<400> SEQUENCE: 183
```

ggaaactaaa agagaaatat tggaagcaag ccatatcaga atatgaaaaa cgtttaggcc 60
catacaccaa gatagacatc atagaagttc cagacgaaaa agcaccagaa aatatgagcg 120
acaaagaaat cgagcaagta aaagaaaaag aaggccaacg aatactagcc aaaatcaaac 180
cacaatcaac agtcattaca ttagaaatac aaggaaagat gctatcttcc gaaggattgg 240
ctcaagaatt gaaccaacgc atgacccaag ggcaaagcga ctttgtattc gttattggcg 300
gatcaaacgg cctgcacaag gacgtcttac aacgcagtaa ctatgcacta tcattcagca 360
aaatgacatt tccacatcag atgatgcggg ttgtgttaat tgagcaagtg tatagagcat 420
ttaagattat gcgtggggaa gcatatcata aatgatgcgg ttttttcagc cgcttcataa 480
agggattttg aatgtatcag aacatatgag gtttatgtga attgctgtta tgtttttaag 540
aagcttatca taagtaatga ggttcatgat ttttgacata gttagcctcc gcagtctttc 600
atttcaagta aataatagcg aaatattctt tatactgaat acttatagtg aagcaaagtt 660
ctagctttga gaaaattctt tctgcaacta aatatagtaa attacggtaa aatataaata 720
agtacatatt gaagaaaatg agacataata tattttataa taggagggaa tttcaaatga 780
tagacaactt tatgcaggtc cttaaattaa ttaaagagaa acgtaccaat aatgtagtta 840
aaaaatctga ttgggataaa ggtgatctat ataaaacttt agtccatgat aagttaccca 900
agcagttaaa agtgcatata aaagaagata aatattcagt tgtagggaag gttgctactg 960
ggaactatag taaagttcct tggatttcaa tatatgatga gaatataaca aaagaaacaa 1020
aggatggata ttatttggta tatctttttc atccggaagg agaaggcata tacttatctt 1080
tgaatcaagg atggtcaaag ataagtgata tgtttccgcg ggata 1125

<210> SEQ ID NO 184
<211> LENGTH: 679
<212> TYPE: DNA
<213> ORGANISM: Staphylococcus aureus

<400> SEQUENCE: 184
ataagaggga acagtgtgaa caagttaata acttgtggat aactggaaag ttgataacaa 60
tttggaggac caaacgacat gaaaatcacc attttagctg tagggaaact aaaagagaaa 120
tattggaagc aagccatagc agaatatgaa aaacgtttag gcccatacac caagatagac 180
atcatagaag ttccagacga aaaagcacca gaaaatatga gcgacaaaga aattgagcaa 240
gtaaaagaaa aagaaggcca acgaatacta gccaaaatca aaccacaatc cacagtcatt 300
acattagaaa tacaaggaaa gatgctatct tccgaaggat tggcccaaga attgaaccaa 360
cgcatgaccc aagggcaaag cgactttgta ttcgtcattg gcggatcaaa cggcctgcac 420
aaggacgtct tacaacgcag taactatgca ctatcattta gcaaaatgac attcccacat 480
caaatgatgc gggttgtgtt aattgaacaa gtgtatagag catttaagat tatgcgtgga 540
gaggcttatc ataaataaaa ctaaaaatta gattgtgtat aatttaaaaa tttaatgaga 600
tgtggaggaa ttacatatat gaaatattgg agtatacctt gcaatatcat acgatgttta 660
tagagtgttt aataaacca 679

<210> SEQ ID NO 185
<211> LENGTH: 1125
<212> TYPE: DNA
<213> ORGANISM: Staphylococcus aureus

<400> SEQUENCE: 185

-continued

```
ggaaactaaa agagaaatat tggaagcaag ccatagcaga atatgaaaaa cgtttaggcc     60
catacaccaa gatagacatc atagaagttc cagacgaaaa agcaccagaa aatatgagcg    120
acaaagaaat tgagcaagta aaagaaaaag aaggccaacg aatactagcc aaaatcaaac    180
cacaatcaac agtcattaca ttagaaatac aaggaaagat gctatcttcc gaaggattgg    240
cacaagaatt gaaccaacgc atgacccaag ggcaaagcga ctttgtattc gtcattggcg    300
gatcaaacgg cctgcacaag gacgtcttac aacgtagtaa ctacgcacta tcattcagca    360
aaatgacatt cccacatcaa atgatgcggg ttgtgttaat tgagcaagtg tatagagcgt    420
ttaagattat gcgtggagaa gcatatcata aatgatgcgg ttttttcagc cgcttcataa    480
agggattttg aatgtatcag aacatatgag gtttatgtga attgctgtta tgtttttaag    540
aagcttatca taagtaatga ggttcatgat ttttgacata gttagcctcc gcagtctttc    600
atttcaagta aataatagcg aaatattctt tatactgaat acttatagtg aagcaaagtt    660
ctagctttga gaaaattctt tctgcaacta aatatagtaa attacggtaa aatataaata    720
agtacatatt gaagaaaatg agacataata tattttataa taggagggaa tttcaaatga    780
tagacaactt tatgcaggtc cttaaattaa ttaaagagaa acgtaccaat aatgtagtta    840
aaaaatctga ttgggataaa ggtgatctat ataaaacttt agtccatgat aagttaccca    900
agcagttaaa agtgcatata aaagaagata aatattcagt tgtagggaag gttgctactg    960
ggaactatag taaagttcct tggatttcaa tatatgatga gaatataaca aaagaaacaa   1020
aggatggata ttatttggta tatctttttc atccggaagg agaaggcata tacttatctt   1080
tgaatcaagg atggtcaaag ataagtgata tgtttccgcg ggata                   1125
```

<210> SEQ ID NO 186
<211> LENGTH: 926
<212> TYPE: DNA
<213> ORGANISM: Staphylococcus aureus

<400> SEQUENCE: 186

```
tacattagaa atacaaggaa agatgctatc ttccgaagga ttggcccaag aattgaacca     60
acgcatgacc caagggcaaa gcgactttgt attcgtcatt ggcggatcaa acggcctgca    120
caaggacgtc ttacaacgca gtaactatgc actatcattt agcaaaatga cattcccaca    180
tcaaatgatg cgggttgtgt taattgaaca agtgtataga gcatttaaga ttatgcgtgg    240
agaagcatat cataaatgat gcggtttttt cagccgcttc ataaagggat tttgaatgta    300
tcagaacata tgaggtttat gtgaattgct gttatgtttt taagaagctt atcataagta    360
atgaggttca tgatttttga catagttagc ctccgcagtc tttcatttca agtaaataat    420
agcgaaatat tctttatact gaatacttat agtgaagcaa agttctagct ttgagaaaat    480
tctttctgca actaaatata gtaaattacg gtaaaatata aataagtaca tattgaagaa    540
aatgagacat aatatatttt ataataggag ggaatttcaa atgatagaca actttatgca    600
ggtccttaaa ttaattaaag agaaacgtac caataatgta gttaaaaaat ctgattggga    660
taaaggtgat ctatataaaa ctttagtcca tgataagtta cccaagcagt taaaagtgca    720
tataaaagaa gataaatatt cagttgtagg gaaggttgct actgggaact atagtaaagt    780
tccttggatt tcaatatatg atgagaatat aacaaaagaa acaaaggatg gatattattt    840
ggtatatctt tttcatccgg aaggagaagg catatactta tctttgaatc aaggatggtc    900
aaagataagt gatatgtttc cgcggg                                         926
```

<210> SEQ ID NO 187
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 187
ggatgtgggt atgctaatgt tgtt 24

<210> SEQ ID NO 188
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 188
tgaacaattt tatttctcat accatag 27

<210> SEQ ID NO 189
<211> LENGTH: 2154
<212> TYPE: DNA
<213> ORGANISM: Staphylococcus aureus

<400> SEQUENCE: 189
cggtaataaa aaatacgata tagatgaata acaaaacagt gaagcaatcc gtaacgatgg 60
ttgcttcact gttttattat gaattattaa taagtgctgt tacttctccc ttaaatacaa 120
tttcttcatt ttcattgtat gttgaaagtg acactgtaac gagtccattt tcttttttta 180
tggatttctt atttgtaatt tcagcgataa cgtacaatgt attacctggg tatacaggtt 240
taataaattt aacgttattc atttgtgttc ctgctacaac ttcttctccg tatttacctt 300
cttctaccca taatttaaat gatattgaaa gtgtatgcat gccagatgca atgatacctt 360
taaatctact ttgttctgct ttttctttat ctatatgcat atattgagga tcaaaagttg 420
ttgcaaattg gataatttct tcttctgtaa tatgaaggct ttttgttttg aatgtttctc 480
ctactataaa atcatcgtat ttcatatatg tctctctttc ttattcaaat taattttta 540 gtatgtaaca tgttaaaggt aagtctaccg tcactgaaac gtaagactca cctctaactt 600
tctattgaga caaatgcacc attttatctg cattgtctgt aaagatacca tcaactcccc 660
aattagcaag ttggtttgca cgtgctggtt tgtttacagt ccatacgttc aattcataac 720
ccgcttcttt taccattttt acttttgctt tagtaagttt ggcatcttca gtgtttacta 780
ttttagcatt acagtaatct aaaagtgttc tccagtcttc acgaaacgaa gttgtatgga 840
atataactgc tctgttatat tgtggcatga tttcttctgc aagtttaaca agcacaacat 900
taaagcttga aatgagcact tcttgattct gatttaagtt tgttaattgt tcttccactt 960
gcttaaccat acttttagaa agtgctagtc cattcggtcc agtaatacct tttaattcta 1020
catttaaatt catattatat tcatttgcta tttttactac atcatcgaaa gttggcaaat 1080
gttcatcttt gaatttttca ccaaaccaag atcctgcaga agcatcttta atttcatcat 1140
aattcaattc agttatttcc ccggacatat ttgtagtccg ttctaaataa tcatcatgaa 1200
tgataatcag ttgttcatct tttgtaattg caacatctaa ctccaaccag tttatacctt 1260
ctacttctga agcagcttta aatgatgcaa ttgtattttc cggagcttta ctaggtaatc 1320
ctctatgtcc atatacagtt agcatattac ctctccttgc atttttattt ttttaattaa 1380
cgtaactgta ttatcacatt aatcgcactt ttatttccat taaaaagaga tgaatatcat 1440

```
aaataaagaa gtcgatagat tcgtattgat tatggagtta atctacgtct catctcattt   1500
ttaaaaaatc atttatgtcc caagctccat tttgtaatca agtctagttt ttcggttctg   1560
ttgcaaagtt gaatttatag tataatttta acaaaaagga gtcttctgta tgaactattt   1620
cagatataaa caatttaaca aggatgttat cactgtagcc gttggctact atctaagata   1680
tacattgagt tatcgtgata tatctgaaat attaagggaa cgtggtgtaa acgttcatca   1740
ttcaacggtc taccgttggg ttcaagaata tgccccaatt ttgtatcaaa tttggaagaa   1800
aaagcataaa aaagcttatt acaaatggcg tattgatgag acgtacatca aaataaaagg   1860
aaaatggagc tatttatatc gtgccattga tgcagaggga catacattag atatttggtt   1920
gcgtaagcaa cgagataatc attcagcata tgcgtttatc aaacgtctca ttaaacaatt   1980
tggtaaacct caaaaggtaa ttacagatca ggcaccttca acgaaggtag caatggctaa   2040
agtaattaaa gcttttaaac ttaaacctga ctgtcattgt acatcgaaat atctgaataa   2100
cctcattgag caagatcacc gtcatattaa agtaagaaag acaaggtatc aaag         2154
```

```
<210> SEQ ID NO 190
<211> LENGTH: 2410
<212> TYPE: DNA
<213> ORGANISM: Staphylococcus aureus

<400> SEQUENCE: 190

ccaccttcat atgacgtcta tccatttatg tatggcatga gtaacgaaga atataataaa     60
ttaaccgaag ataaaaaaga acctctgctc aacaagttcc agattacaac ttcaccaggt    120
tcaactcaaa aaatattaac agcaatgatt gggttaaata acaaaacatt agacgataaa    180
acaagttata aaatcgatgg taaaggttgg caaaaagata aatcttgggg tggttacaac    240
gttacaagat atgaagtggt aaatggtaat atcgacttaa aacaagcaat agaatcatca    300
gataacattt tctttgctag agtagcactc gaattaggca gtaagaaatt tgaaaaaggc    360
atgaaaaaac taggtgttgg tgaagatata ccaagtgatt atccatttta taatgctcaa    420
atttcaaaca aaaatttaga taatgaaata ttattagctg attcaggtta cggacaaggt    480
gaaatactga ttaacccagt acagatcctt tcaatctata gcgcattaga aaataatggc    540
aatattaacg cacctcactt attaaaagac acgaaaaaca aagtttggaa gaaaaatatt    600
atttccaaag aaaatatcaa tctattaact gatggtatgc aacaagtcgt aaataaaaca    660
cataaagaag atatttatag atcttatgca aacttaattg gcaaatccgg tactgcagaa    720
ctcaaaatga aacaaggaga aactggcaga caaattgggt ggtttatatc atatgataaa    780
gataatccaa acatgatgat ggctattaat gttaaagatg tacaagataa aggaatggct    840
agctacaatg ccaaaatctc aggtaaagtg tatgatgagc tatatgagaa cggtaataaa    900
aaatacgata tagatgaata acaaaacagt gaagcaatcc gtaacgatgg ttgcttcact    960
gttttattat gaattattaa taagtgctgt tacttctccc ttaaatacaa tttcttcatt   1020
ttcattgtat gttgaaagtg acactgtaac gagtccattt tctttttta tggatttctt   1080
atttgtaatt tcagcgataa cgtacaatgt attacctggg tatacaggtt taataaattt   1140
aacgttattc atttgtgttc ctgctacaac ttcttctccg tatttacctt cttctaccca   1200
taatttaaat gatattgaaa gtgtatgcat gccagatgca atgatacctt taaatctact   1260
ttgttctgct ttttctttat ctatatgcat atattgagga tcaaaagttg ttgcaaattg   1320
gataatttct tcttctgtaa tatgaaggct ttttgttttg aatgtttctc ctactataaa   1380
atcatcgtat ttcatatatg tctctctttc ttattcaaat taattttta gtatgtaaca    1440
```

```
tgttaaaggt aagtctaccg tcactgaaac gtaagactca cctctaactt tctattgaga   1500
caaatgcacc attttatctg cattgtctgt aaagatacca tcaactcccc aattagcaag   1560
ttggtttgca cgtgctggtt tgtttacagt ccatacgttc aattcataac ccgcttcttt   1620
taccattttt acttttgctt tagtaagttt ggcatcttca gtgtttacta ttttagcatt   1680
acagtaatct aaaagtgttc tccagtcttc acgaaacgaa gttgtatgga atataactgc   1740
tctgttatat tgtggcatga tttcttctgc aagtttaaca agcacaacat taaagcttga   1800
aatgagcact tcttgattct gatttaagtt tgttaattgt tcttccactt gcttaaccat   1860
acttttagaa agtgctagtc cattcggtcc agtaatacct tttaattcta catttaaatt   1920
catattatat tcatttgcta tttttactac atcatcgaaa gttggcaaat gttcatcttt   1980
gaatttttca ccaaaccaag atcctgcaga agcatcttta atttcatcat aattcaattc   2040
agttatttcc ccggacatat ttgtagtccg ttctaaataa tcatcatgaa tgataatcag   2100
ttgttcatct tttgtaattg caacatctaa ctccaaccag tttatacctt ctacttctga   2160
agcagcttta aatgatgcaa ttgtattttc cggagcttta ctaggtaatc ctctatgtcc   2220
atatacagtt agcatattac ctctccttgc atttttattt ttttaattaa cgtaactgta   2280
ttatcacatt aatcgcactt ttatttccat taaaaagaga tgaatatcat aaataaagaa   2340
gtcgatagat tcgtattgat tatggagtta atctacgtct catctcattt ttaaaaaatc   2400
atttatgtcc                                                          2410
```

<210> SEQ ID NO 191
<211> LENGTH: 1858
<212> TYPE: DNA
<213> ORGANISM: Staphylococcus aureus

<400> SEQUENCE: 191

```
caccttcata tgacgtctat ccatttatgt atggcatgag taacgaagaa tataataaat     60
taaccgaaga taaaaaagaa cctctgctca acaagttcca gattacaact tcaccaggtt    120
caactcaaaa aatattaaca gcaatgattg ggttaaataa caaaacatta gacgataaaa    180
caagttataa aatcgatggt aaaggttggc aaaaagataa atcttggggt ggttacaacg    240
ttacaagata tgaagtggta aatggtaata tcgacttaaa acaagcaata gaatcatcag    300
ataacatttt ctttgctaga gtagcactcg aattaggcag taagaaattt gaaaaaggca    360
tgaaaaaact aggtgttggt gaagatatac caagtgatta tccattttat aatgctcaaa    420
tttcaaacaa aaatttagat aatgaaatat tattagctga ttcaggttac ggacaaggtg    480
aaatactgat taacccagta cagatccttt caatctatag cgcattagaa aataatggca    540
atattaacgc acctcactta ttaaaagaca cgaaaaacaa agtttggaag aaaaatatta    600
tttccaaaga aaatatcaat ctattaactg atggtatgca acaagtcgta aataaaacac    660
ataaagaaga tatttataga tcttatgcaa acttaattgg caaatccggt actgcagaac    720
tcaaaatgaa acaaggagaa actggcagac aaattgggtg gtttatatca tatgataaag    780
ataatccaaa catgatgatg gctattaatg ttaaagatgt acaagataaa ggaatggcta    840
gctacaatgc caaaatctca ggtaaagtgt atgatgagct atatgagaac ggtaataaaa    900
aatacgatat agatgaataa caaaacagtg aagcaatccg taacgatggt tgcttcactg    960
ttttattatg aattattaat aagtgctgtt acttctccct taaatacaat ttcttcattt   1020
tcattgtatg ttgaaagtga cactgtaacg agtccatttt cttttttat ggatttctta   1080
```

-continued

```
tttgtaattt cagcgataac gtacaatgta ttacctgggt atacaggttt aataaattta   1140
acgttattca tttgtgttcc tgctacaact tcttctccgt atttaccttc ttctacccat   1200
aatttaaatg atattgaaag tgtatgcatg ccagatgcaa tgataccttt aaatctactt   1260
tgttctgctt tttctttatc tatatgcata tattgaggat caaaagttgt tgcaaattgg   1320
ataatttctt cttctgtaat atgaaggctt tttgttttga atgtttctcc tactataaaa   1380
tcatcgtatt tcatatatgt ctctctttct tattcaaatt aatttttag tatgtaacat   1440
gttaaaggta agtctaccgt cactgaaacg taagactcac ctctaacttt ctattgagac   1500
aaatgcacca ttttatctgc attgtctgta aagataccat caactcccca attagcaagt   1560
tggtttgcac gtgctggttt gtttacagtc catacgttca attcataacc cgcttctttt   1620
accattttta cttttgcttt agtaagtttg gcatcttcag tgtttactat tttagcatta   1680
cagtaatcta aaagtgttct ccagtcttca cgaaacgaag ttgtatggaa tataactgct   1740
ctgttatatt gtggcatgat ttcttctgca agtttaacaa gcacaacatt aaagcttgaa   1800
atgagcactt cttgattctg atttaagttt gttaattgtt cttccacttg cttaacca     1858
```

<210> SEQ ID NO 192
<211> LENGTH: 1861
<212> TYPE: DNA
<213> ORGANISM: Staphylococcus aureus

<400> SEQUENCE: 192

```
ccaccttcat atgacgtcta tccatttatg tatggcatga gtaacgaaga atataataaa     60
ttaaccgaag ataaaaaaga acctctgctc aacaagttcc agattacaac ttcaccaggt    120
tcaactcaaa aaatattaac agcaatgatt gggttaaata acaaaaacatt agacgataaa   180
acaagttata aaatcgatgg taaaggttgg caaaaaagata aatcttgggg tggttacaac   240
gttacaagat atgaagtggt aaatggtaat atcgacttaa aacaagcaat agaatcatca    300
gataacattt tctttgctag agtagcactc gaattaggca gtaagaaatt tgaaaaaggc    360
atgaaaaaac taggtgttgg tgaagatata ccaagtgatt atccatttta taatgctcaa    420
atttcaaaca aaaatttaga taatgaaata ttattagctg attcaggtta cggacaaggt    480
gaaatactga ttaacccagt acagatcctt tcaatctata gcgcattaga aaataatggc    540
aatattaacg cacctcactt attaaaagac acgaaaaaca aagtttggaa gaaaaatatt    600
atttccaaag aaaatatcaa tctattaact gatggtatgc aacaagtcgt aaataaaaca    660
cataaagaag atatttatag atcttatgca aacttaattg gcaaatccgg tactgcagaa    720
ctcaaaatga aacaaggaga aactggcaga caaattgggt ggtttatatc atatgataaa    780
gataatccaa acatgatgat ggctattaat gttaaagatg tacaagataa aggaatggct    840
agctacaatg ccaaaatctc aggtaaagtg tatgatgagc tatatgagaa cggtaataaa    900
aaatacgata tagatgaata acaaaaacagt gaagcaatcc gtaacgatgg ttgcttcact   960
gttttattat gaattattaa taagtgctgt tacttctccc ttaaatacaa tttcttcatt   1020
ttcattgtat gttgaaagtg acactgtaac gagtccattt tcttttttta tggatttctt   1080
atttgtaatt tcagcgataa cgtacaatgt attacctggg tatacaggtt taataaattt   1140
aacgttattc atttgtgttc ctgctacaac ttcttctccg tatttacctt cttctaccca   1200
taatttaaat gatattgaaa gtgtatgcat gccagatgca atgatacctt taaatctact   1260
ttgttctgct tttctttat ctatatgcat atattgagga tcaaaagttg ttgcaaattg   1320
gataatttct tcttctgtaa tatgaaggct ttttgttttg aatgtttctc ctactataaa   1380
```

```
atcatcgtat ttcatatatg tctctctttc ttattcaaat taattttta gtatgtaaca   1440
tgttaaaggt aagtctaccg tcactgaaac gtaagactca cctctaactt tctattgaga   1500
caaatgcacc attttatctg cattgtctgt aaagatacca tcaactcccc aattagcaag   1560
ttggtttgca cgtgctggtt tgtttacagt ccatacgttc aattcataac ccgcttcttt   1620
taccattttt acttttgctt tagtaagttt ggcatcttca gtgtttacta ttttagcatt   1680
acagtaatct aaaagtgttc tccagtcttc acgaaacgaa gttgtatgga atataactgc   1740
tctgttatat tgtggcatga tttcttctgc aagtttaaca agcacaacat taaagcttga   1800
aatgagcact tcttgattct gatttaagtt tgttaattgt tcttccactt gcttaaccat   1860
a                                                                   1861
```

<210> SEQ ID NO 193
<211> LENGTH: 1861
<212> TYPE: DNA
<213> ORGANISM: Staphylococcus aureus

<400> SEQUENCE: 193

```
ccaccttcat atgacgtcta tccatttatg tatggcatga gtaacgaaga atataataaa     60
ttaaccgaag ataaaaaaga acctctgctc aacaagttcc agattacaac ttcaccaggt    120
tcaactcaaa aaatattaac agcaatgatt gggttaaata acaaaacatt agacgataaa    180
acaagttata aaatcgatgg taaaggttgg caaaaagata aatcttgggg tggttacaac    240
gttacaagat atgaagtggt aaatggtaat atcgacttaa aacaagcaat agaatcatca    300
gataacattt tctttgctag agtagcactc gaattaggca gtaagaaatt tgaaaaaggc    360
atgaaaaaac taggtgttgg tgaagatata ccaagtgatt atccatttta taatgctcaa    420
atttcaaaca aaaatttaga taatgaaata ttattagctg attcaggtta cggacaaggt    480
gaaatactga ttaacccagt acagatcctt tcaatctata gcgcattaga aaataatggc    540
aatattaacg cacctcactt attaaaagac acgaaaaaca aagtttggaa gaaaaatatt    600
atttccaaag aaaatatcaa tctattaact gatggtatgc aacaagtcgt aaataaaaca    660
cataaagaag atatttatag atcttatgca aacttaattg gcaaatccgg tactgcagaa    720
ctcaaaatga aacaaggaga aactggcaga caaattgggt ggtttatatc atatgataaa    780
gataatccaa acatgatgat ggctattaat gttaaagatg tacaagataa aggaatggct    840
agctacaatg ccaaaatctc aggtaaagtg tatgatgagc tatatgagaa cggtaataaa    900
aaatacgata tagatgaata acaaaacagt gaagcaatcc gtaacgatgg ttgcttcact    960
gttttattat gaattattaa taagtgctgt tacttctccc ttaaatacaa tttcttcatt   1020
ttcattgtat gttgaaagtg acactgtaac gagtccattt tcttttttta tggatttctt   1080
atttgtaatt tcagcgataa cgtacaatgt attacctggg tatacaggtt taataaattt   1140
aacgttattc atttgtgttc ctgctacaac ttcttctccg tatttacctt cttctaccca   1200
taatttaaat gatattgaaa gtgtatgcat gccagatgca atgatacctt taaatctact   1260
ttgttctgct ttttctttat ctatatgcat atattgagga tcaaaagttg ttgcaaattg   1320
gataatttct tcttctgtaa tatgaaggct ttttgttttg aatgtttctc ctactataaa   1380
atcatcgtat ttcatatatg tctctctttc ttattcaaat taattttta gtatgtaaca   1440
tgttaaaggt aagtctaccg tcactgaaac gtaagactca cctctaactt tctattgaga   1500
caaatgcacc attttatctg cattgtctgt aaagatacca tcaactcccc aattagcaag   1560
```

ttggtttgca cgtgctggtt tgtttacagt ccatacgttc aattcataac ccgcttcttt 1620
taccattttt acttttgctt tagtaagttt ggcatcttca gtgtttacta ttttagcatt 1680
acagtaatct aaaagtgttc tccagtcttc acgaaacgaa gttgtatgga atataactgc 1740
tctgttatat tgtggcatga tttcttctgc aagtttaaca agcacaacat taaagcttga 1800
aatgagcact tcttgattct gatttaagtt tgttaattgt tcttccactt gcttaaccat 1860
a 1861

<210> SEQ ID NO 194
<211> LENGTH: 1052
<212> TYPE: DNA
<213> ORGANISM: Staphylococcus aureus

<400> SEQUENCE: 194
cggtaataaa aaatacgata tagatgaata acaaaacagt gaagcaatcc gtaacgatgg 60
ttgcttcact gttttattat gaattattaa taagtgctgt tacttctccc ttaaatacaa 120
tttcttcatt ttcattgtat gttgaaagtg acactgtaac gagtccattt tcttttttta 180
tggatttctt atttgtaatt tcagcgataa cgtacaatgt attacctggg tatacaggtt 240
taataaattt aacgttattc atttgtgttc ctgctacaac ttcttctccg tatttacctt 300
cttctaccca taatttaaat gatattgaaa gtgtatgcat gccagatgca atgatacctt 360
taaatctact ttgttctgct ttttctttat ctatatgcat atattgagga tcaaaagttg 420
ttgcaaattg gataatttct tcttctgtaa tatgaaggct ttttgttttg aatgtttctc 480
ctactataaa atcatcgtat ttcatatatg tctctctttc ttattcaaat taattttta 540 gtatgtaaca tgttaaaggt aagtctaccg tcactgaaac gtaagactca cctctaactt 600
tctattgaga caaatgcacc attttatctg cattgtctgt aaagatacca tcaactcccc 660
aattagcaag ttggtttgca cgtgctggtt tgtttacagt ccatacgttc aattcataac 720
ccgcttcttt taccattttt acttttgctt tagtaagttt ggcatcttca gtgtttacta 780
ttttagcatt acagtaatct aaaagtgttc tccagtcttc acgaaacgaa gttgtatgga 840
atataactgc tctgttatat tgtggcatga tttcttctgc aagtttaaca agcacaacat 900
taaagcttga aatgagcact tcttgattct gatttaagtt tgttaattgt tcttccactt 960
gcttaaccat acttttagaa agtgctagtc cattcggtcc agtaatacct tttaattcta 1020
catttaaatt catattatat tcatttgcta tt 1052

<210> SEQ ID NO 195
<211> LENGTH: 3101
<212> TYPE: DNA
<213> ORGANISM: Staphylococcus aureus

<400> SEQUENCE: 195
cttcatatga cgtctatcca tttatgtatg gcatgagtaa cgaagaatat aataaattaa 60
ccgaagataa aaaagaacct ctgctcaaca agttccagat tacaacttca ccaggttcaa 120
ctcaaaaaat attaacagca atgattgggt taaataacaa aacattagac gataaaacaa 180
gttataaaat cgatggtaaa ggttggcaaa aagataaatc ttggggtggt tacaacgtta 240
caagatatga agtggtaaat ggtaatatcg acttaaaaca agcaatagaa tcatcagata 300
acattttctt tgctagagta gcactcgaat taggcagtaa gaaatttgaa aaaggcatga 360
aaaaactagg tgttggtgaa gatataccaa gtgattatcc attttataat gctcaaattt 420
caaacaaaaa tttagataat gaaatattat tagctgattc aggttacgga caaggtgaaa 480

```
tactgattaa cccagtacag atcctttcaa tctatagcgc attagaaaat aatggcaata    540
ttaacgcacc tcacttatta aaagacacga aaaacaaagt ttggaagaaa aatattattt    600
ccaaagaaaa tatcaatcta ttaactgatg gtatgcaaca agtcgtaaat aaaacacata    660
aagaagatat ttatagatct tatgcaaact taattggcaa atccggtact gcagaactca    720
aaatgaaaca aggagaaact ggcagacaaa ttgggtggtt tatatcatat gataaagata    780
atccaaacat gatgatggct attaatgtta aagatgtaca agataaagga atggctagct    840
acaatgccaa aatctcaggt aaagtgtatg atgagctata tgagaacggt aataaaaaat    900
acgatataga tgaataacaa aacagtgaag caatccgtaa cgatggttgc ttcactgttt    960
tattatgaat tattaataag tgctgttact tctcccttaa atacaatttc ttcattttca   1020
ttgtatgttg aaagtgacac tgtaacgagt ccattttctt tttttatgga tttcttattt   1080
gtaatttcag cgataacgta caatgtatta cctgggtata caggtttaat aaatttaacg   1140
ttattcattt gtgttcctgc tacaacttct tctccgtatt taccttcttc tacccataat   1200
ttaaatgata ttgaaagtgt atgcatgcca gatgcaatga tacctttaaa tctactttgt   1260
tctgcttttt ctttatctat atgcatatat tgaggatcaa aagttgttgc aaattggata   1320
atttcttctt ctgtaatatg aaggcttttt gttttgaatg tttctcctac tataaaatca   1380
tcgtatttca tatatgtctc tctttcttat tcaaattaat tttttagtat gtaacatgtt   1440
aaaggtaagt ctaccgtcac tgaaacgtaa gactcacctc taactttcta ttgagacaaa   1500
tgcaccattt tatctgcatt gtctgtaaag ataccatcaa ctccccaatt agcaagttgg   1560
tttgcacgtg ctggtttgtt tacagtccat acgttcaatt cataacccgc ttcttttacc   1620
atttttactt ttgctttagt aagtttggca tcttcagtgt ttactatttt agcattacag   1680
taatctaaaa gtgttctcca gtcttcacga aacgaagttg tatggaatat aactgctctg   1740
ttatattgtg gcatgatttc ttctgcaagt ttaacaagca caacattaaa gcttgaaatg   1800
agcacttctt gattctgatt taagtttgtt aattgttctt ccacttgctt aaccatactt   1860
ttagaaagtg ctagtccatt cggtccagta ataccttta attctacatt taaattcata    1920
ttatattcat ttgctatttt tactacatca tcgaaagttg gcaaatgttc atctttgaat   1980
ttttcaccaa accaagatcc tgcagaagca tctttaattt catcataatt caattcagtt   2040
atttccccgg acatatttgt agtccgttct aaataatcat catgaatgat aatcagttgt   2100
tcatcttttg taattgcaac atctaactcc aaccagttta taccttctac ttctgaagca   2160
gctttaaatg atgcaattgt attttccgga gctttactag gtaatcctct atgtccatat   2220
acagttagca tattacctct ccttgcattt ttattttttt aattaacgta actgtattat   2280
cacattaatc gcacttttat ttccattaaa aagagatgaa tatcataaat aaagaagtcg   2340
atagattcgt attgattatg gagttaatct acgtctcatc tcatttttaa aaaatcattt   2400
atgtcccaag ctccatttg taatcaagtc tagtttttcg gttctgttgc aaagttgaat    2460
ttatagtata attttaacaa aaaggagtct tctgtatgaa ctatttcaga tataaacaat   2520
ttaacaagga tgttatcact gtagccgttg gctactatct aagatataca ttgagttatc   2580
gtgatatatc tgaaatatta agggaacgtg gtgtaaacgt tcatcattca acggtctacc   2640
gttgggttca agaatatgcc ccaattttgt atcaaatttg gaagaaaaag cataaaaaag   2700
cttattacaa atggcgtatt gatgagacgt acatcaaaat aaaaggaaaa tggagctatt   2760
tatatcgtgc cattgatgca gagggacata cattagatat ttggttgcgt aagcaacgag   2820
```

```
ataatcattc agcatatgcg tttatcaaac gtctcattaa acaatttggt aaacctcaaa   2880

aggtaattac agatcaggca ccttcaacga aggtagcaat ggctaaagta attaaagctt   2940

ttaaacttaa acctgactgt cattgtacat cgaaatatct gaataacctc attgagcaag   3000

atcaccgtca tattaaagta agaaagacaa ggtatcaaag tatcaataca gcaaagaata   3060

ctttaaaagg tattgaatgt atttacgctc tatataaaaa g                       3101
```

<210> SEQ ID NO 196
<211> LENGTH: 3506
<212> TYPE: DNA
<213> ORGANISM: Staphylococcus aureus

<400> SEQUENCE: 196

```
ccaccttcat atgacgtcta tccatttatg tatggcatga gtaacgaaga atataataaa     60

ttaaccgaag ataaaaaaga acctctgctc aacaagttcc agattacaac ttcaccaggt    120

tcaactcaaa aaatattaac agcaatgatt gggttaaata acaaaacatt agacgataaa    180

acaagttata aaatcgatgg taaaggttgg caaaaagata aatcttgggg tggttacaac    240

gttacaagat atgaagtggt aaatggtaat atcgacttaa aacaagcaat agaatcatca    300

gataacattt tctttgctag agtagcactc gaattaggca gtaagaaatt tgaaaaaggc    360

atgaaaaaac taggtgttgg tgaagatata ccaagtgatt atccatttta taatgctcaa    420

atttcaaaca aaaatttaga taatgaaata ttattagctg attcaggtta cggacaaggt    480

gaaatactga ttaacccagt acagatcctt tcaatctata gcgcattaga aaataatggc    540

aatattaacg cacctcactt attaaaagac acgaaaaaca aagtttggaa gaaaaatatt    600

atttccaaag aaaatatcaa tctattaact gatggtatgc aacaagtcgt aaataaaaca    660

cataaagaag atatttatag atcttatgca aacttaattg gcaaatccgg tactgcagaa    720

ctcaaaatga aacaaggaga aactggcaga caaattgggt ggtttatatc atatgataaa    780

gataatccaa acatgatgat ggctattaat gttaaagatg tacaagataa aggaatggct    840

agctacaatg ccaaaatctc aggtaaagtg tatgatgagc tatatgagaa cggtaataaa    900

aaatacgata tagatgaata acaaaacagt gaagcaatcc gtaacgatgg ttgcttcact    960

gttttattat gaattattaa taagtgctgt tacttctccc ttaaatacaa tttcttcatt   1020

ttcattgtat gttgaaagtg acactgtaac gagtccattt tctttttta tggatttctt   1080

atttgtaatt tcagcgataa cgtacaatgt attacctggg tatacaggtt taataaattt   1140

aacgttattc atttgtgttc ctgctacaac ttcttctccg tatttacctt cttctaccca   1200

taatttaaat gatattgaaa gtgtatgcat gccagatgca atgatacctt taaatctact   1260

ttgttctgct ttttctttat ctatatgcat atattgagga tcaaaagttg ttgcaaattg   1320

gataatttct tcttctgtaa tatgaaggct ttttgttttg aatgtttctc ctactataaa   1380

atcatcgtat ttcatatatg tctctctttc ttattcaaat taattttta gtatgtaaca   1440

tgttaaaggt aagtctaccg tcactgaaac gtaagactca cctctaactt tctattgaga   1500

caaatgcacc attttatctg cattgtctgt aaagatacca tcaactcccc aattagcaag   1560

ttggtttgca cgtgctggtt tgtttacagt ccatacgttc aattcataac ccgcttcttt   1620

taccattttt actttgctt tagtaagttt ggcatcttca gtgtttacta ttttagcatt   1680

acagtaatct aaaagtgttc tccagtcttc acgaaacgaa gttgtatgga atataactgc   1740

tctgttatat tgtggcatga tttcttctgc aagtttaaca agcacaacat taaagcttga   1800

aatgagcact tcttgattct gatttaagtt tgttaattgt tcttccactt gcttaaccat   1860
```

acttttagaa agtgctagtc cattcggtcc agtaatacct tttaattcta catttaaatt 1920
catattatat tcatttgcta tttttactac atcatcgaaa gttggcaaat gttcatcttt 1980
gaatttttca ccaaaccaag atcctgcaga agcatcttta atttcatcat aattcaattc 2040
agttatttcc ccggacatat ttgtagtccg ttctaaataa tcatcatgaa tgataatcag 2100
ttgttcatct tttgtaattg caacatctaa ctccaaccag tttatacctt ctacttctga 2160
agcagcttta aatgatgcaa ttgtattttc cggagcttta ctaggtaatc ctctatgtcc 2220
atatacagtt agcatattac ctctccttgc atttttattt ttttaattaa cgtaactgta 2280
ttatcacatt aatcgcactt ttatttccat taaaaagaga tgaatatcat aaataaagaa 2340
gtcgatagat tcgtattgat tatggagtta atctacgtct catctcattt ttaaaaaatc 2400
atttatgtcc caagctccat tttgtaatca agtctagttt ttctgtaccc cttatctgca 2460
attttactta ggattgcttt taacttaccc cttatcagca attttactga gaactgcttt 2520
taacgcacct cttatctgca attttgccta gaactgcttt taacgtacct cttatctgca 2580
attttactga gaactgcttt taacttaccc cttatcagca attttgcatg gaattgcttt 2640
taacgtacct cttatctgca attttactta gaactgcttt taacaaacct cttatctgca 2700
attttactta gaactgcttt taacgtacct cttatctgta attttactga gaactgcttt 2760
taacaaacct cttatctgca attttactta gaactgcttt taacaaacct cttatctgca 2820
attttactta gaattgcttt tactattcct cttattagta taatctcagt aagaatgcgt 2880
ataaaaatga aaattacaac cgattttgta agtgctgacg cctgagggaa tagtatgtgc 2940
gagagactaa tggctcgagc catacccta ggcaagcatg cacgtacaaa atcgtaagat 3000
aaaaaaataa gcatatcact gtaaacttta aaaaatcagt ttagtgatat gcttatttat 3060
ttcgagttag gatttatgtc ccaagctcat caagcacaat cggccactag tttatttctc 3120
tatcttatat gttctgatat ggtcttctat actgtataag tatacttttg aatatggatc 3180
ttgtgtcaat tcacgttcga aatcaaattc ttgattatca aatctgttaa agaatgtttc 3240
gtattcttcg actgataatt gctctctaga ttctagcata tttaagtgtt tctctttatc 3300
taatgctttg tcatatcctt taacgattga accactaaag atttctccta ctgctcctga 3360
accataacta aatagacata ctttctcttc tggttggaat gtgtggttct gtaataacga 3420
aattaaactt aagtataatg atcctgtata aatgttacca acatctctat tccataatac 3480
ggttctgttg caaagttgaa tttata 3506

<210> SEQ ID NO 197
<211> LENGTH: 928
<212> TYPE: DNA
<213> ORGANISM: Staphylococcus aureus

<400> SEQUENCE: 197
tacattagaa atacaaggaa agatgctatc ttccgaagga ttggcccaag aattgaacca 60
acgcatgacc caagggcaaa gcgactttgt attcgtcatt ggcggatcaa acggcctgca 120
caaggacgtc ttacaacgca gtaactacgc actatcattc agcaaaatga cattcccaca 180
tcaaatgatg cgggttgtgt taattgaaca agtgtacaga gcatttaaga ttatgcgtgg 240
agaagcatat cataaatgat gcggtttttt cagccgcttc ataaagggat tttgaatgta 300
tcagaacata tgaggtttat gtgaattgct gttatgtttt taagaagctt atcataagta 360
atgaggttca tgatttttga catagttagc ctccgcagtc tttcatttca agtaaataat 420
agcgaaatat tctttatact gaatacttat agtgaagcaa agttctagct ttgagaaaat 480
tctttctgca actaaatata gtaaattacg gtaaaatata aataagtaca tattgaagaa 540
aatgagacat aatatatttt ataataggag ggaatttcaa atgatagaca actttatgca 600
ggtccttaaa ttaattaaag agaaacgtac caataatgta gttaaaaaat ctgattggga 660
taaaggtgat ctatataaaa ctttagtcca tgataagtta cccaagcagt taaaagtgca 720
tataaaagaa gataaatatt cagttgtagg gaaggttgct actgggaact atagtaaagt 780
tccttggatt tcaatatatg atgagaatat aacaaaagaa acaaaggatg gatattattt 840
ggtatatctt tttcatccgg aaggagaagg catatactta tctttgaatc aaggatggtc 900
aaagataagt gatatgtttc cgcgggat 928

<210> SEQ ID NO 198
<211> LENGTH: 782
<212> TYPE: DNA
<213> ORGANISM: Staphylococcus aureus

<400> SEQUENCE: 198
caatgcccac agagttatcc acaaatacac aggttataca ctaaaaattg ggcatgaatg 60
tcagaaaaat atcaaaaact gcaaagaata ttggtataat aagagggaac agtgtgaaca 120
agttaataac ttgtggataa ctggaaagtt gataacaatt tggaggacca aacgacatga 180
aaatcaccat tttagctgta gggaaactaa aagagaaata ttggaagcaa gccatagcag 240
aatatgaaaa acgtttaggc ccatacacca agatagacat catagaagtt ccagacgaaa 300
aagcaccaga aaatatgagc gacaaagaaa ttgagcaagt aaaagaaaaa gaaggccaac 360
gaatactagc caaaatcaaa ccacaatcaa cagtcattac attagaaata caaggaaaga 420
tgctatcttc cgaaggattg gcccaagaat tgaaccaacg catgacccaa gggcaaagcg 480
actttgtatt cgtcattggc ggatcaaacg gcctgcacaa ggacgtctta caacgcagta 540
actacgcact atcattcagc aaaatgacat tcccacatca aatgatgcgg gttgtgttaa 600
ttgaacaagt gtacagagca tttaagatta tgcgtggaga agcgtatcat aaataaaact 660
aaaaattagg ttgtgtataa tttaaaaatt taatgagatg tggaggaatt acatatatga 720
aatattggat tataccttgc aatatcatac gatgtttata gagtgtttaa taaaccattt 780
tt 782

<210> SEQ ID NO 199
<211> LENGTH: 709
<212> TYPE: DNA
<213> ORGANISM: Staphylococcus aureus

<400> SEQUENCE: 199
tacattagaa atacaaggaa agatgctatc ttccgaagga ttggcccaag aattgaacca 60
acgcatgacc caagggcaaa gcgactttgt tttcgtcatt ggcggatcaa acggcctgca 120
caaggacgtc ttacaacgca gtaactacgc actatcattc agcaaaatga cattcccaca 180
tcaaatgatg cgggttgtgt taattgaaca agtgtacaga gcatttaaga ttatgcgagg 240
agaagcttat cataagtaat gaggttcatg atttttgaca tagttagcct ccgcagtctt 300
tcatttcaag taaataatag cgaaatattc tttatactga atacttatag tgaagcaaag 360
ttctagcttt gagaaaattc tttctgcaac taaatatagt aaattacggt aaaatataaa 420
taagtacata ttgaagaaaa tgagacataa tatattttat aataggaggg aatttcaaat 480
gatagacaac tttatgcagg tccttaaatt aattaaagag aaacgtacca ataatgtagt 540
taaaaaatct gattgggata aaggtgatct atataaaact ttagtccatg ataagttacc 600
caagcagtta aaagtgcata taaaagaaga taaatattca gttgtaggga aggttgctac 660
tgggaactat agtaaagttc cttggatttc aatatatgat gagaatata 709

<210> SEQ ID NO 200
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 200
gtgggaaatg gctgttgttg ag 22

<210> SEQ ID NO 201
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 201
ttcgttccct ccattaactg tc 22

<210> SEQ ID NO 202
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 202
aaaagaaaga cggtgaaggc 20

<210> SEQ ID NO 203
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 203
cacttcatta tactgttttc tttgc 25

<210> SEQ ID NO 204
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 204
tcaccgtctt tcttttgacc tt 22

<210> SEQ ID NO 205
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 205
tgagatctgc tggaacaaaa gtgaa 25

<210> SEQ ID NO 206
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 206
cggtcgagtt tgctgaagaa 20

<210> SEQ ID NO 207
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 207
tcccctaatg atagctggta tatatt 26

<210> SEQ ID NO 208
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 208
tctagggaat caaagaaaag taatagt 27

<210> SEQ ID NO 209
<211> LENGTH: 32
<212> TYPE: DNA
<213> ORGANISM: Artificial Sequence
<220> FEATURE:
<223> OTHER INFORMATION: Synthetic nucleic acid sequence

<400> SEQUENCE: 209
caacaargrc aatgtgayrt attatgytgt ta 32

<210> SEQ ID NO 210
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 210
gataayatwg gmgaacaagt caraaatgg 29

<210> SEQ ID NO 211
<211> LENGTH: 35
<212> TYPE: DNA
<213> ORGANISM: Artificial Sequence
<220> FEATURE:
<223> OTHER INFORMATION: Synthetic nucleic acid sequence

<400> SEQUENCE: 211
ccrtattgat tgwtracacg rccacartaa ttwgg 35

<210> SEQ ID NO 212
<211> LENGTH: 32
<212> TYPE: DNA
<213> ORGANISM: Artificial Sequence
<220> FEATURE:
<221> NAME/KEY: misc_feature
<222> LOCATION: 30
<223> OTHER INFORMATION: n = inosine
<220> FEATURE:
<223> OTHER INFORMATION: Synthetic nucleic acid sequence

<400> SEQUENCE: 212
atrttsartg gttcattttt gaaatagatn cc 32

<210> SEQ ID NO 213
<211> LENGTH: 32
<212> TYPE: DNA
<213> ORGANISM: Artificial Sequence
<220> FEATURE:
<223> OTHER INFORMATION: Synthetic nucleic acid sequence

<400> SEQUENCE: 213
acgtgtcggt atctatgtwc gtgtatcaac rg 32

<210> SEQ ID NO 214
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 214
tgttatgrtc tacaaaacaa accgaytagc 30

<210> SEQ ID NO 215
<211> LENGTH: 34
<212> TYPE: DNA
<213> ORGANISM: Artificial Sequence
<220> FEATURE:
<223> OTHER INFORMATION: Synthetic nucleic acid sequence

<400> SEQUENCE: 215
gawtaataat rggggaatgc ttaccttcag ctat 34

<210> SEQ ID NO 216
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 216
ggtttttgac tgacttgttt tttacg 26

<210> SEQ ID NO 217
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 217
tagaaytgtt ttttatgatt accrtcttt 29

<210> SEQ ID NO 218
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 218

```
ggcaaaaaya aagacgaagt gctgag                                          26


<210> SEQ ID NO 219
<211> LENGTH: 721
<212> TYPE: DNA
<213> ORGANISM: Staphylococcus aureus

<400> SEQUENCE: 219

tgtagcttta ggtgaagggt taggtccttc aataggggga ataatagcac attatattca     60

ttggtcttac ctacttatac ttcctatgat tacaatagta actatacctt ttcttattaa    120

agtaatggta cctggtaaat caacaaaaaa tacattagat atcgtaggta ttgttttaat    180

gtctataagt attatatgtt ttatgttatt tacgacaaat tataattgga ctttttttaat   240

actcttcaca atcttttttg tgatttttat taaacatatt tcaagagttt ctaacccttt    300

tattaatcct aaactaggga aaaacattcc gtttatgctt ggtttgtttt ctggtgggct    360

aatattttct atagtagctg gttttatatc aatggtgcct tatatgatga aaactattta    420

tcatgtaaat gtagcgacaa taggtaatag tgttattttt cctggaacca tgagtgttat    480

tgtttttggt tattttggtg gtttttttagt ggatagaaaa ggatcattat ttgtttttat   540

tttaggatca ttgtctatct ctataagttt tttaactatt gcattttttg ttgagtttag    600

tatgtggttg actactttta tgtttatatt tgttatgggc ggattatctt ttactaaaac    660

agttatatca aaaatagtat caagtagtct ttctgaagaa gaagttgctt ctggaagagt    720

t                                                                    721


<210> SEQ ID NO 220
<211> LENGTH: 1791
<212> TYPE: DNA
<213> ORGANISM: Staphylococcus aureus

<400> SEQUENCE: 220

atccggtact gcagaactca aaatgaaaca aggagaaact ggcagacaaa ttgggtggtt     60

tatatcatat gataaagata atccaaacat gatgatggct attaatgtta aagatgtaca    120

agataaagga atggctagct acaatgccaa aatctcaggt aaagtgtatg atgagctata    180

tgagaacggt aataaaaaat acgatataga tgaataacaa aacagtgaag caatccgtaa    240

cgatggttgc ttcactgttt tattatgaat tattaataag tgctgttact tctcccttaa    300

atacaatttc ttcattttca ttgtatgttg aaagtgacac tgtaacgagt ccattttctt    360

tttttatgga tttcttattt gtaatttcag cgataacgta caatgtatta cctgggtata    420

caggtttaat aaatttaacg ttattcattt gtgttcctgc tacaacttct tctccgtatt    480

taccttcttc tacccataat ttaaatgata ttgaaagtgt atgcatgcca gatgcaatga    540

tacctttaaa tctactttgt tctgcttttt ctttatctat atgcatatat tgaggatcaa    600

aagttgttgc aaattggata atttcttctt ctgtaatatg aaggcttttt gttttgaatg    660

tttctcctac tataaaatca tcgtatttca tatatgtctc tctttcttat tcaaattaat    720

tttttagtat gtaacatgtt aaaggtaagt ctaccgtcac tgaaacgtaa gactcacctc    780

taactttcta ttgagacaaa tgcaccattt tatctgcatt gtctgtaaag ataccatcaa    840

ctccccaatt agcaagttgg tttgcacgtg ctggtttgtt tacagtccat acgttcaatt    900

cataacccgc ttcttttacc atttttactt ttgctttagt aagtttggca tcttcagtgt    960

ttactatttt agcattacag taatctaaaa gtgttctcca gtcttcacga aacgaagttg   1020

tatggaatat aactgctctg ttatattgtg gcatgatttc ttctgcaagt ttaacaagca   1080
```

-continued caacattaaa gcttgaaatg agcacttctt gattctgatt taagtttgtt aattgttctt 1140
ccacttgctt aaccatactt ttagaaagtg ctagtccatt cggtccagta ataccttttta 1200 attctacatt taaattcata ttatattcat ttgctatttt tactacatca tcgaaagttg 1260
gcaaatgttc atctttgaat ttttcaccaa accaagatcc tgcagaagca tctttaattt 1320
catcataatt caattcagtt atttccccgg acatatttgt agtccgttct aaataatcat 1380
catgaatgat aatcagttgt tcatcttttg taattgcaac atctaactcc aaccagttta 1440
taccttctac ttctgaagca gctttaaatg atgcaattgt attttccgga gctttactag 1500
gtaatcctct atgtccatat acagttagca tattacctct ccttgcattt ttattttttt 1560
aattaacgta actgtattat cacattaatc gcacttttat ttccattaaa aagagatgaa 1620
tatcataaat aaagaagtcg atagattcgt attgattatg gagttaatct acgtctcatc 1680
tcatttttaa aaaatcattt atgtcccaag ctccattttg taatcaagtc tagtttttct 1740
gtacccctta tctgcaattt tacttaggat tgcttttaac ttacccctta t 1791

<210> SEQ ID NO 221
<211> LENGTH: 600
<212> TYPE: DNA
<213> ORGANISM: Staphylococcus aureus

<400> SEQUENCE: 221
aagtgctgac gcctgaggga atagtatgtg cgagagacta atggctcgag ccatacccct 60
aggcaagcat gcacgtacaa aatcgtaaga taaaaaaata agcatatcac tgtaaacttt 120
aaaaaatcag tttagtgata tgcttattta tttcgagtta ggatttatgt cccaagctca 180
tcaagcacaa tcggccacta gtttatttct ctatcttata tgttctgata tggtcttcta 240
tactgtataa gtatactttt gaatatggat cttgtgtcaa ttcacgttcg aaatcaaatt 300
cttgattatc aaatctgtta aagaatgttt cgtattcttc gactgataat tgctctctag 360
attctagcat atttaagtgt ttctctttat ctaatgcttt gtcatatcct ttaacgattg 420
aaccactaaa gatttctcct actgctcctg aaccataact aaatagacat actttctctt 480
ctggttggaa tgtgtggttc tgtaataacg aaattaaact taagtataat gatcctgtat 540
aaatgttacc aacatctcta ttccataata cggttctgtt gcaaagttga atttatagta 600

<210> SEQ ID NO 222
<211> LENGTH: 1640
<212> TYPE: DNA
<213> ORGANISM: Staphylococcus aureus

<400> SEQUENCE: 222
gggtggttta tatcatatga taaagataat ccaaacatga tgatggctat taatgttaaa 60
gatgtacaag ataaaggaat ggctagctac aatgccaaaa tctcaggtaa agtgtatgat 120
gagctatatg agaacggtaa taaaaaatac gatatagatg aataacaaaa cagtgaagca 180
atccgtaacg atggttgctt cactgtttta ttatgaatta ttaataagtg ctgttacttc 240
tcccttaaat acaatttctt cattttcatt gtatgttgaa agtgacactg taacgagtcc 300
attttctttt tttatggatt tcttatttgt aatttcagcg ataacgtaca atgtattacc 360
tgggtataca ggtttaataa atttaacgtt attcatttgt gttcctgcta caacttcttc 420
tccgtattta ccttcttcta cccataattt aaatgatatt gaaagtgtat gcatgccaga 480
tgcaatgata cctttaaatc tactttgttc tgctttttct ttatctatat gcatatattg 540
aggatcaaaa gttgttgcaa attggataat ttcttcttct gtaatatgaa ggctttttgt 600
tttgaatgtt tctcctacta taaaatcatc gtatttcata tatgtctctc tttcttattc 660
aaattaattt tttagtatgt aacatgttaa aggtaagtct accgtcactg aaacgtaaga 720
ctcacctcta actttctatt gagacaaatg caccatttta tctgcattgt ctgtaaagat 780
accatcaact ccccaattag caagttggtt tgcacgtgct ggtttgttta cagtccatac 840
gttcaattca taacccgctt cttttaccat ttttactttt gctttagtaa gtttggcatc 900
ttcagtgttt actattttag cattacagta atctaaaagt gttctccagt cttcacgaaa 960
cgaagttgta tggaatataa ctgctctgtt atattgtggc atgatttctt ctgcaagttt 1020
aacaagcaca acattaaagc ttgaaatgag cacttcttga ttctgattta agtttgttaa 1080
ttgttcttcc acttgcttaa ccatactttt agaaagtgct agtccattcg gtccagtaat 1140
accttttaat tctacattta aattcatatt atattcattt gctattttta ctacatcatc 1200
gaaagttggc aaatgttcat ctttgaattt ttcaccaaac caagatcctg cagaagcatc 1260
tttaatttca tcataattca attcagttat ttccccggac atatttgtag tccgttctaa 1320
ataatcatca tgaatgataa tcagttgttc atcttttgta attgcaacat ctaactccaa 1380
ccagtttata ccttctactt ctgaagcagc tttaaatgat gcaattgtat tttccggagc 1440
tttactaggt aatcctctat gtccatatac agttagcata ttacctctcc ttgcattttt 1500 attttttttaa ttaacgtaac tgtattatca cattaatcgc acttttattt ccattaaaaa 1560
gagatgaata tcataaataa agaagtcgat agattcgtat tgattatgga gttaatctac 1620
gtctcatctc atttttaaaa 1640

<210> SEQ ID NO 223
<211> LENGTH: 592
<212> TYPE: DNA
<213> ORGANISM: Staphylococcus aureus

<400> SEQUENCE: 223
aattcaactt tgcaacagaa ccgtattatg gaatagagat gttggtaaca tttatacagg 60
atcattatac ttaagtttaa tttcgttatt acagaaccac acattccaac cagaagagaa 120
agtatgtcta tttagttatg gttcaggagc agtaggagaa atctttagtg gttcaatcgt 180
taaaggatat gacaaagcat tagataaaga gaaacactta aatatgctag aatctagaga 240
gcaattatca gtcgaagaat acgaaacatt ctttaacaga tttgataatc aagaatttga 300
tttcgaacgt gaattgacac aagatccata ttcaaaagta tacttataca gtatagaaga 360
ccatatcaga acatataaga tagagaaata aactagtggc cgattgtgct tgatgagctt 420
gggacataaa tcctaactcg aaataaataa gcatatcact aaactgattt tttaaagttt 480
acagtgatat gcttattttt ttatcttacg attttgtacg tgcatgcttg cctaggggta 540
tggctcgagc cattagtctc tcgcacatac tattccctca ggcgtcagca ct 592

<210> SEQ ID NO 224
<211> LENGTH: 2386
<212> TYPE: DNA
<213> ORGANISM: Staphylococcus aureus

<400> SEQUENCE: 224
caccttcata tgacgtctat ccatttatgt atggcatgag taacgaagaa tataataaat 60
taaccgaaga taaaaaagaa cctctgctca acaagttcca gattacaact tcaccaggtt 120
caactcaaaa aatattaaca gcaatgattg ggttaaataa caaaacatta gacgataaaa 180

```
caagttataa aatcgatggt aaaggttggc aaaaagataa atcttggggt ggttacaacg    240
ttacaagata tgaagtggta aatggtaata tcgacttaaa acaagcaata gaatcatcag    300
ataacatttt ctttgctaga gtagcactcg aattaggcag taagaaattt gaaaaaggca    360
tgaaaaaact aggtgttggt gaagatatac caagtgatta tccattttat aatgctcaaa    420
tttcaaacaa aaatttagat aatgaaatat tattagctga ttcaggttac ggacaaggtg    480
aaatactgat taacccagta cagatccttt caatctatag cgcattagaa aataatggca    540
atattaacgc acctcactta ttaaaagaca cgaaaaacaa agtttggaag aaaaatatta    600
tttccaaaga aaatatcaat ctattaactg atggtatgca acaagtcgta aataaaacac    660
ataaagaaga tatttataga tcttatgcaa acttaattgg caaatccggt actgcagaac    720
tcaaaatgaa acaaggagaa actggcagac aaattgggtg gtttatatca tatgataaag    780
ataatccaaa catgatgatg gctattaatg ttaaagatgt acaagataaa ggaatggcta    840
gctacaatgc caaaatctca ggtaaagtgt atgatgagct atatgagaac ggtaataaaa    900
aatacgatat agatgaataa caaaacagtg aagcaatccg taacgatggt tgcttcactg    960
ttttattatg aattattaat aagtgctgtt acttctccct taaatacaat ttcttcattt   1020
tcattgtatg ttgaaagtga cactgtaacg agtccatttt ctttttttat ggatttctta   1080
tttgtaattt cagcgataac gtacaatgta ttacctgggt atacaggttt aataaattta   1140
acgttattca tttgtgttcc tgctacaact tcttctccgt atttaccttc ttctacccat   1200
aatttaaatg atattgaaag tgtatgcatg ccagatgcaa tgataccttt aaatctactt   1260
tgttctgctt tttctttatc tatatgcata tattgaggat caaaagttgt tgcaaattgg   1320
ataatttctt cttctgtaat atgaaggctt tttgttttga atgtttctcc tactataaaa   1380
tcatcgtatt tcatatatgt ctctctttct tattcaaatt aattttttag tatgtaacat   1440
gttaaaggta agtctaccgt cactgaaacg taagactcac ctctaacttt ctattgagac   1500
aaatgcacca ttttatctgc attgtctgta aagataccat caactcccca attagcaagt   1560
tggtttgcac gtgctggttt gtttacagtc catacgttca attcataacc cgcttctttt   1620
accattttta cttttgcttt agtaagtttg gcatcttcag tgtttactat tttagcatta   1680
cagtaatcta aaagtgttct ccagtcttca cgaaacgaag ttgtatggaa tataactgct   1740
ctgttatatt gtggcatgat ttcttctgca agtttaacaa gcacaacatt aaagcttgaa   1800
atgagcactt cttgattctg atttaagttt gttaattgtt cttccacttg cttaaccata   1860
cttttagaaa gtgctagtcc attcggtcca gtaatacctt ttaattctac atttaaattc   1920
atattatatt catttgctat ttttactaca tcatcgaaag ttggcaaatg ttcatctttg   1980
aatttttcac caaaccaaga tcctgcagaa gcatctttaa tttcatcata attcaattca   2040
gttatttccc cggacatatt tgtagtccgt tctaaataat catcatgaat gataatcagt   2100
tgttcatctt ttgtaattgc aacatctaac tccaaccagt ttataccttc tacttctgaa   2160
gcagctttaa atgatgcaat tgtattttcc ggagctttac taggtaatcc tctatgtcca   2220
tatacagtta gcatattacc tctccttgca tttttatttt tttaattaac gtaactgtat   2280
tatcacatta atcgcacttt tatttccatt aaaaagagat gaatatcata aataaagaag   2340
tcgatagatt cgtattgatt atggagttaa tctacgtctc atctca                  2386
```

<210> SEQ ID NO 225
<211> LENGTH: 623
<212> TYPE: DNA

<213> ORGANISM: Staphylococcus aureus

<400> SEQUENCE: 225
tgaaaattac aaccgatttt gtaagtgctg acgcctgagg gaatagtatg tgcgagagac 60
taatggctcg agccataccc ctaggcaagc atgcacgtac aaaatcgtaa gataaaaaaa 120
taagcatatc actgtaaact ttaaaaaatc agtttagtga tatgcttatt tatttcgagt 180
taggatttat gtcccaagct catcaagcac aatcggccac tagtttattt ctctatctta 240
tatgttctga tatggtcttc tatactgtat aagtatactt ttgaatatgg atcttgtgtc 300
aattcacgtt cgaaatcaaa ttcttgatta tcaaatctgt taaagaatgt ttcgtattct 360
tcgactgata attgctctct agattctagc atatttaagt gtttctcttt atctaatgct 420
ttgtcatatc ctttaacgat tgaaccacta aagatttctc ctactgctcc tgaaccataa 480
ctaaatagac atactttctc ttctggttgg aatgtgtggt tctgtaataa cgaaattaaa 540
cttaagtata atgatcctgt ataaatgtta ccaacatctc tattccataa tacggttctg 600
ttgcaaagtt gaatttatag tat 623

<210> SEQ ID NO 226
<211> LENGTH: 651
<212> TYPE: DNA
<213> ORGANISM: Staphylococcus aureus

<400> SEQUENCE: 226
atgaaaaata tttcagaatt ctcagcccaa cttgatcaaa cttttgatca aggggaagcc 60
gtctctatgg agtggttatt ccgtccgttg ctaaaaatgc tggcggaggg cgatccagtc 120
cccgttgagg acatcgcggc ggagaccggg aagcccgtcg aggaagttaa gcaagtccta 180
cagactctac ctagtgtgga acttgatgag cagggccgtg tcgtcggtta tggcctcaca 240
ctgttcccta ccccccatcg cttcgaggtt gatgggaagc aactatatgc atggtgcgcc 300
cttgacacac ttatgttccc agcactcatc ggccggacgg tccacatcgc ttcgccttgt 360
cacggcaccg gtaagtccgt ccggttgacg gtggaaccgg accgcgttgt aagcgtcgag 420
ccttcaacag ccgttgtctc gattgttaca ccagatgaaa tggcctcggt tcggtcggcc 480
ttctgtaacg acgttcactt tttcagttca ccgagtgcag cccaagactg gcttaaccaa 540
caccctgagt cgagcgtttt gcccgttgaa gatgcctttg aactgggtcg ccatttggga 600
gcgcgttatg aggagtcagg acctactaat gggtcctgtt gtaacattta a 651

<210> SEQ ID NO 227
<211> LENGTH: 563
<212> TYPE: DNA
<213> ORGANISM: Staphylococcus aureus

<400> SEQUENCE: 227
atgaatcttg aaaaagggaa tatagaaagg aaaaaacatg gtgtccatgt taatgagtat 60
ttgcaaagtg taagtaaccc gaatgtctat gcagctggag atgctgcagc aacggatggc 120
ttgcccctca cacctgtagc cagtgcagat tctcatgtcg tagcatctaa tttattgaaa 180
gggaacagca aaaaaattga atatcccgtg attccatctg ctgtatttac cgtacctaaa 240
atggcatcgg taggtatgag cgaggaggaa gccaaaaact ctggccggaa tattaaagta 300
aagcagaaaa acatctccga ctggtttacg tataaacgga caaatgagga ctttgctgcg 360
tttaaagtgc tgattgacga agatcatgat caaattgttg gtgctcattt gattagtaat 420
gaagccgatg aactgattaa tcattttgca acagccattc gttttgggat ttcaaccaaa 480
gaattgaaac aaatgatatt tgcctatcca acggcagctt cggacattgc acacatgttg 540
taagtttgcg ttttgtgaga tgt 563

<210> SEQ ID NO 228
<211> LENGTH: 1380
<212> TYPE: DNA
<213> ORGANISM: Staphylococcus aureus

<400> SEQUENCE: 228
ttgtttagtt tatataaaaa atttaaaggt ttgttttata gcgttttatt ttggctttgt 60
attctttcat tttttagtgt attaaatgaa atggttttaa atgtttcttt acctgatatt 120
gcaaatcatt ttaatactac tcctggaatt acaaactggg taaacactgc atatatgtta 180
actttttcga taggaacagc agtatatgga aaattatctg attatataaa tataaaaaaa 240
ttgttaatta ttggtattag tttgagctgt cttggttcat tgattgcttt tattggtcac 300
aatcactttt ttattttgat ttttggtagg ttagtacaag gagtaggatc tgctgcattc 360
ccttcactga ttatggtggt tgtagctaga aatattacaa gaaaaaaaca aggcaaagcc 420
tttggtttta taggatcaat tgtagcttta ggtgaagggt taggtccttc aataggggga 480 ataaatagcac attatattca ttggtcttac ctacttatac ttcctatgat tacaatagta 540
actatacctt ttcttattaa agtaatggta cctggtaaat caacaaaaaa tacattagat 600
atcgtaggta ttgttttaat gtctataagt attatatgtt ttatgttatt tacgacaaat 660
tataattgga ctttttttaat actcttcaca atctttttttg tgatttttat taaacatatt 720
tcaagagttt ctaacccttt tattaatcct aaactaggga aaaacattcc gtttatgctt 780
ggtttgtttt ctggtgggct aatattttct atagtagctg gttttatatc aatggtgcct 840
tatatgatga aaactattta tcatgtaaat gtagcgacaa taggtaatag tgttattttt 900
cctggaacca tgagtgttat tgtttttggt tattttggtg gtttttttagt ggatagaaaa 960 ggatcattat ttgtttttat tttaggatca ttgtctatct ctataagttt tttaactatt 1020 gcatttttttg ttgagtttag tatgtggttg actactttta tgtttatatt tgttatgggc 1080
ggattatctt ttactaaaac agttatatca aaaatagtat caagtagtct ttctgaagaa 1140
gaagttgctt ctggaatgag tttgctaaat ttcacaagtt ttttatcaga gggaacaggt 1200
atagcaattg taggaggttt attgtcacta caattgatta atcgtaaact agttctggaa 1260
tttataaatt attcttctgg agtgtatagt aatattcttg tagccatggc tatccttatt 1320
attttatgtt gtcttttgac gattattgta tttaaacgtt ctgaaaagca gtttgaatag 1380

<210> SEQ ID NO 229
<211> LENGTH: 1365
<212> TYPE: DNA
<213> ORGANISM: Staphylococcus aureus

<400> SEQUENCE: 229
atgagaatag tgaatggacc aataataatg actagagaag aaagaatgaa gattgttcat 60
gaaattaagg aacgaatatt ggataaatat ggggatgatg ttaaggctat tggtgtttat 120
ggctctcttg gtcgtcagac tgatgggccc tattcggata ttgagatgat gtgtgtcatg 180
tcaacagaag aagcagagtt cagccatgaa tggacaaccg gtgagtggaa ggtggaagtg 240
aattttgata gcgaagagat tctactagat tatgcatctc aggtggaatc agattggcct 300
cttacacatg gtcaattttt ctctattttg ccgatttatg attcaggtgg atacttagag 360

```
aaagtgtatc aaactgctaa atcggtagaa gcccaaacgt tccacgatgc gatttgtgcc    420
cttatcgtag aagagctgtt tgaatatgca ggcaaatggc gtaatattcg tgtgcaagga    480
ccgacaacat ttctaccatc cttgactgta caggtagcaa tggcaggtgc catgttgatt    540
ggtctgcatc atcgcatctg ttatacgacg agcgcttcgg tcttaactga agcagttaag    600
caatcagatc ttccttcagg ttatgaccat ctgtgccagt tcgtaatgtc tggtcaactt    660
tccgactctg agaaacttct ggaatcgcta gagaatttct ggaatgggat tcaggagtgg    720
acagaacgac acggatatat agtggatgtg tcaaaacgca taccattttg aacgatgacc    780
tctaataatt gttaatcatg ttggttacgt atttattaac ttctcctagt attagtaatt    840
atcatggctg tcatggcgca ttaacggaat aaagggtgtg cttaaatcgg gccattttgc    900
gtaataagaa aaaggattaa ttatgagcga attgaattaa taataaggta atagatttac    960
attagaaaat gaaaggggat tttatgcgtg agaatgttac agtctatccc ggcattgcca   1020
gtcggggata ttaaaaagag tataggtttt tattgcgata aactaggttt cactttggtt   1080
caccatgaag atggattcgc agttctaatg tgtaatgagg ttcggattca tctatgggag   1140
gcaagtgatg aaggctggcg ctctcgtagt aatgattcac cggtttgtac aggtgcggag   1200
tcgtttattg ctggtactgc tagttgccgc attgaagtag agggaattga tgaattatat   1260
caacatatta agcctttggg cattttgcac cccaatacat cattaaaaga tcagtggtgg   1320
gatgaacgag actttgcagt aattgatccc gacaacaatt tgatt                   1365
```

<210> SEQ ID NO 230
<211> LENGTH: 831
<212> TYPE: DNA
<213> ORGANISM: Staphylococcus aureus

<400> SEQUENCE: 230

```
atgggggttt cttttaatat tatgtgtcct aatagtagca tttattcaga tgaaaaatca     60
agggttttag tggacaagac aaagagtgga aaagtgagac catggagaga aaagaaaatc    120
gctaatgttg attactttga acttctgcat attcttgaat ttaaaaaggc tgaaagagta    180
aaagattgtg ctgaaatatt agagtataaa caaaatcgtg aaacaggcga aagaaagttg    240
tatcgagtgt ggttttgtaa atccaggctt tgtccaatgt gcaactggag gagagcaatg    300
aaacatggca ttcagtcaca aaaggttgtt gctgaagtta ttaaacaaaa gccaacagtt    360
cgttggttgt ttctcacatt aacagttaaa aatgtttatg atggcgaaga attaaataag    420
agtttgtcag atatggctca aggatttcgc cgaatgacgc aatataaaaa aattaataaa    480
aatcttgttg gttttatgcg tgcaacggaa gtgacaataa ataataaaga taattcttat    540
aatcagcaca tgcatgtatt ggtatgtgtg gaaccaactt attttaagaa tacagaaaac    600
tacgtgaatc aaaaacaatg gattcaattt tggaaaaagg caatgaaatt agactatgat    660
ccaaatgtaa aagttcaaat gattcgaccg aaaaataaat ataaatcgga tatacaatcg    720
gcaattgacg aaactgcaaa atatcctgta aaggatacgg attttatgac cgatgatgaa    780
gaaaagaatt tgtaacgttt gtctgatttg gaggaaggtt tacaccgtaa a             831
```

<210> SEQ ID NO 231
<211> LENGTH: 4193
<212> TYPE: DNA
<213> ORGANISM: Staphylococcus aureus

<400> SEQUENCE: 231

```
atgagccgct tgatacgcat gagtgtatta gcaagtggta gtacaggtaa cgccactttt     60
```

```
gtagaaaatg aaaaaggtag tctattagtt gatgttggtt tgactggcaa gaaaatggaa    120
gaattgttta gtcaaattga ccgtaatatt caagatttaa atggtatttt agtaacccat    180
gaacatattg atcatattaa aggattaggt gttttggcgc gtaaatatca attgccaatt    240
tatgcgaatg aaaagacttg gcaggcaatt gaaaagaaag atagtcgcat ccctatggat    300
cagaaattca tttttaatcc ttatgaaaca aaatctattg caggtttcga tgttgaatcg    360
tttaacgtgt cacatgatgc aatagatccg caattttata ttttccataa taactataag    420
aagtttacga ttttaacgga tacgggttac gtgtctgatc gtatgaaagg tatgatacgt    480
ggcagcgatg cgtttatttt tgagagtaat catgacgtcg atatgttgag aatgtgtcgt    540
tatccatgga agacgaaaca acgtatttta ggcgatatgg gtcatgtatc taatgaggat    600
gcgggtcatg cgatgacaga tgtgattaca ggtaacacga aacgtattta cctatcgcat    660
ttatcacaag acaataacat gaaagatttg gcgcgtatga gtgttggcca agtattgaac    720
gaacacgata ttgatacgga aaaagaagta ttgctatgtg atacggataa agctattcca    780
acgccaatat atacaatata aatgagagtc accctataaa gttcggcact gctgtgagac    840
gactttatcg ggtgcttttt tatgttattg gtgggaaatg gctgttgttg gaattaaggt    900
tctatttgaa atgtaaaaaa taattcgata ttaaatgtaa tttataaata atttacataa    960
aatcaatcat tttaatataa ggattatgat aatatattgg tgtatgacag ttaatggagg   1020
gaacgaaatg aaagctttat tacttaaaac aagtgtatgg ctcgttttgc tttttagtgt   1080
gatgggatta tggcaagtct cgaacgcggc tgagcagtat acaccaatca aagcacatgt   1140
agtaacaacg atagacaaag caacaacaga taagcaacaa gtaacgccaa caaaggaagc   1200
ggctcatcaa tttggtgaag aagcggcaac caacgtatca gcatcagcac agggaacagc   1260
tgatgaaata aacaataaag taacatccaa cgcatttttct aacaaaccat ctacagcagt  1320
ttcaacaaaa gtaaacgaaa cgcacgatgt agatacacaa caagcctcaa cacaaaaacc   1380
aactcaatca gcaacattca cattatcaaa tgctaaaaca gcatcacttt caccacgaat   1440
gtttgctgcc aatgtaccac aaacaacaac acataaaata ttacatacaa atgatatcca   1500
tggccgacta gccgaagaaa aagggcgtgt catcggtatg gctaaattaa aaacaataaa   1560
agaacaagaa aagcctgatt taatgttaga cgcaggagac gccttccaag gtttaccact   1620
ttcaaaccag tctaaaggtg aagaaatggc taaagcaatg aatgcagtag gttatgatgc   1680
tatggcagtg ggtaaccatg aatttgactt tggatacgat cagttgaaaa agttagaggg   1740
tatgttagac ttcccgatgc taagtactaa cgtttacaaa gatgggaaac gcgcgtttaa   1800
gccttcaaca attgtaacga aaaatggtat tcgttatgga attattggcg taacgacacc   1860
agaaacaaag acgaaaacaa gacctgaggg cattaaaggt gttgaattta gagatccatt   1920
acaaagtgtg acagcagaaa tgatgcgtat ttataaagac gtagatacat ttgttgttat   1980
atcacattta gggattgatc cttcaacaca agaaacatgg cgtggtgatt acttagtgaa   2040
acaattaagt caaaatccac aattgaagaa acgtattaca gtcattgatg gtcattcaca   2100
taccgtactt caaaatggtc aaatttataa caatgatgca ttagcacaaa caggtacagc   2160
acttgcgaat atcggtaagg ttacatttaa ttaccgcaat ggagaggtat caaatattaa   2220
accgtcattg attaatgtta aagacgttga aaatgtaaca ccgaacaaag cattagctga   2280
acaaattaat caagctgatc aaacatttag agcacaaaca gcagaggtta ttattccaaa   2340
taataccatt gatttcaaag gagaaagaga tgacgttaga acgcgtgaaa caaatttagg   2400
```

-continued

```
aaacgcgatt gcagatgcta tggaagcgta tggcgttaag aatttctcta aaaagactga   2460
ctttgccgtg acaaatggtg gaggtattcg tgcctctatc gcaaaaggta aggtgacacg   2520
ctatgattta atctcagtat taccatttgg aaatacgatt gcgcaaattg atgtaaaagg   2580
ttcagacgtc tggacagctt tcgaacatag tttaggtgca ccaacaacac aaaaagacgg   2640
taagacagta ttaacagcga atggcggttt actacatatc tctgattcaa ttcgtgttta   2700
ctatgatatg aataaaccgt ctggcaaacg aattaacgct attcaaattt taaataaaga   2760
gacaggtaag tttgaaaata ttgatttaaa acgtgtatat catgtaacga tgaatgactt   2820
cacagcatca ggtggcgacg gatatagtat gttcggtggc cctagagaag aaggtatttc   2880
attagatcaa gtactagcaa gttatttaaa aacagctaac atagctaagt atgatacgac   2940
agaaccacaa cgtatgttat taggtaaacc agcagtaagt gaacaaccag ctaaaggaca   3000
acaaggtagc aaaggtagtg agtctggtaa agatgtacaa ccaattggtg acgacaaagc   3060
gatgaatcca gcgaaacaac cagcgacagg taaagttgta ttgttaccaa cgcatagagg   3120
aactgttagt agcggtacag aaggttctgg tcgcacatta gaaggagcta ctgtatcaag   3180
caagagtggg aaccaattgg ttagaatgtc agtgcctaaa ggtagcgcgc atgagaaaca   3240
gttaccaaaa actggaacta atcaaagctc aagcccagca gcgatgtttg tattagtagc   3300
aggtataggt ttaatcgcga ctgtacgacg tagaaaagct agttaaaata tattgaaaac   3360
aatactactg tatttcttaa ataagaggta cggtagtgtt tttttatgga aaaaagctat   3420
aaacgttgat aaacatggga tataaaaacg gggataagta ataagacatc aaggtgttta   3480
tccacagaaa tggggatagt tatccagaat tgtgtacaat ttaaagagaa atacccacaa   3540
tgcccacaga gttatccaca aatacacaag ttatacacta aaaattgggc ataaatgtca   3600
ggaaaatatc aaaaactgca aaaaatattg gtataataag agggaacagt gtgaacaagt   3660
taataacttg tggataactg gaaagttgat aacaatttgg aggaccaaac gacatgaaaa   3720
tcaccatttt agctgtaggg aaactaaaag agaaatattg gaagcaagcc atagcagaat   3780
atgaaaaacg tttaggccca tacaccaaga tagacatcat agaagttcca gacgaaaaag   3840
caccagaaaa tatgagcgac aaagaaattg agcaagtaaa agaaaaagaa ggccaacgaa   3900
tactagccaa aattaaacca caatccacag tcattacatt agaaatacaa ggaaagatgc   3960
tatcttccga aggattggcc caagaattga accaacgcat gacccaaggg caaagcgact   4020
ttgtattcgt cattggcgga tcaaacggcc tgcacaagga cgtcttacaa cgcagtaact   4080
acgcactatc attcagcaaa atgacattcc cacatcaaat gatgcgggtt gtgttaattg   4140
agcaagtgta tagagcattt aagattatgc gtggagaagc atatcataaa tga          4193
```

<210> SEQ ID NO 232
<211> LENGTH: 2996
<212> TYPE: DNA
<213> ORGANISM: Staphylococcus aureus

<400> SEQUENCE: 232

```
atgaaacgag ccattggtta tttgcgccaa agtacaacga aacaacaatc actcccagct     60
caaaagcaag caatagaatt attagctcca aagcacaata ttcaaaatat ccaatacatt    120
agtgataagc aatcaggcag aacagataat cgaacaggct atcaacaagt caccgaacgc    180
atccaacaaa gacaatgtga cgtattatgt tgttatcgct tgaatcgact tcatcgcaac    240
ttgaaaaatg cattaaaact catgaaactc tgtcaaaaat atcatgttca tattctaagt    300
gttcatgatg gctattttga tatggataaa gcgtttgatc gcctaaaact caatatattc    360
```

-continued

```
atgagtctgg ctgaacttga atccgataat attggagaac aagtcaaaaa tggacttaga    420
gaaaaggcaa aacaaggtaa actcataacg acccatgcgc ctttcggtta tcactatcaa    480
aatggtactt tcatcattaa taatgatgaa tcacctaccg tcaaagctgt attcaattat    540
tatcttcaag gatatggcta caagaagatt gcacaatatt tagaagacga taataaactt    600
attacccgca agccttatca ggtacgaaat ataattatga acccaaatta ttgtggtcgt    660
gtcatcaatc aatatggtca atataacaat atggtaccac ctattgtttc ggcaacgaaa    720
tatgaacatg ctcaagcaat ccgtaataag aagcaacttc actgtatacc ttcagagaat    780
cagctgaaac aaaagatcaa atgtccttgt tgtgactcaa cactgacaaa tatgacaata    840
agaaaaaaac atacattgcg atattatatt tgtcctaaaa atatgaatga atctcgcttt    900
gtctgttcat tcaaaggaat aaatgcacaa aaattagaag ttcaagtctt agctacatgt    960
cagaacttct ttcaaaacca acagctctat tcaaaaatta ataatgcaat tcatcaacgc   1020
ctcaaaaaac aaagagtgat agaagctaaa agtacgctaa ctcaagaaca actgatagat   1080
aaacttgcca aaggtatgat tgatgctgaa tcattcagaa aacagactca tttgatgaat   1140
caaaagcaca aaaccatatc ctccataagt gataatcagt tacaaacatc actacaaaag   1200
gttatacaga aaagtttcac gttaaacatg ctgcatccct atattgatga aattcgcatt   1260
acaaaaaata aagcccttgt tgggatctat ttcaaaaatg aaccattgaa cattgtgaac   1320
caaacctcgc aatcatcgat tgcttaatca gaaaggatga aaaaatcatg caacaactca   1380
aacaaaaacg tgtcggtatc tatgttcgtg tatcaacgga aatccaaagt actgaaggct   1440
atagtatcga tggacaaatc aatcaaattc gagaatattg tgatttcaat aactttgttg   1500
ttgtagatgt atacgcggat agaggtatct ctggaaaatc tatgaaccga ccagaactac   1560
aacgtttgtt aaaagatgcg aacgaaggtc agattgattc tgttatggtc tacaaaaacaa  1620
accgactagc acgtaacact tctgacttac tcaaaattgt tgaagacctt catcgtcaaa   1680
atgtcgaatt cttcagctta tctgagcgta tggaagtcaa tacaagcagt ggtaaattga   1740
tgctacaaat tctagcgagt ttttcagaat ttgaaagaaa taatattgtc gaaaatgtat   1800
tcatgggtca aacccgacgc gctcaagaag gctattatca aggcaatttg ccgctgggct   1860
atgacaaaat accggatagc aagcatgaac tcatgataaa ccaacatgaa gcgaatattg   1920
tcaaatatat atttgagtca tatgctaaag gccacggata tcgtaaaatt gcgaatgcac   1980
tcaatcacaa aggatacgtg actaaaaaag gaaagccttt cagtattggt tcagtgacct   2040
atatcttatc taatccattc tatgttggta aaattcaatt cgcaaagtac aaagattgga   2100
atgaaaagcg tcgtaaaggg ctgaatgata aaccaataat agctgaaggt aagcattccc   2160
ctattattat tcaagactta tgggataaag tccaattacg taaaaaacaa gtcagtcaaa   2220
aacctcaagt ccacggtaaa ggaactaatc tattaacagg tatcgttcat tgtccacaat   2280
gtggtgcacc aatggcagct agtaacacaa cgaacacatt gaaagatggt accaagaagc   2340
gaatacgtta ttattcttgc agtaacttcc gaaacaaagg ctcaaaagta tgttctgcga   2400
atagcgttag agctgatgtg attgagaaat acgtcatgga tcaaatactc gaaattgtca   2460
aaagtgataa agtcattaac caagtcttag aacgtgtcaa tcaagaaaat aaagtcgata   2520
ttggtgcatt gaaccacgat atcgcttata aacaacaaca atacgatgaa gtcagcggga   2580
aactccataa tttagttaaa accattgaag ataatccgga cctaacatct gcattgaaag   2640
caactattca tcaatatgaa acacaactca atgacattac aaatcaaatg aatcaactca   2700
```

-continued

```
aacagcaaca aaatcaagag aaactatctt atgatacgaa acaaatcgct gccctattac   2760

aacgaatatt tcaaaatata gaatcaatgg ataaagcaca actcaaagca ttatatctta   2820

cagtcattga ccgtattgat attcgtaaag acggtaatca taaaaaacag ttctacgtta   2880

cactaaaact caataatgaa attattaaac aacttttcaa taatacccct ctcgacgaag   2940

tgctcctcag cacttcgtct ttatttttgc ctcaaacgct ctttcttcaa atctaa       2996
```

<210> SEQ ID NO 233
<211> LENGTH: 1410
<212> TYPE: DNA
<213> ORGANISM: Staphylococcus aureus

<400> SEQUENCE: 233

```
gctgtaggga aactaaaaga gaaatattgg aagcaagcca tagcagaata tgaaaaacgt     60

ttaggcccat acaccaagat agacatcata gaagttccag acgaaaaagc accagaaaat    120

atgagcgaca aagaaattga gcaagtaaaa gaaaaagaag gccaacgaat actagccaaa    180

attaaaccac aatccacagt cattacatta gaaatacaag gaaagatgct atcttccgaa    240

ggattggccc aagaattgaa ccaacgcatg acccaagggc aaagcgactt tgtattcgtc    300

attggcggat caaacggcct gcacaaggac gtcttacaac gcagtaacta cgcactatca    360

ttcagcaaaa tgacattccc acatcaaatg atgcgggttg tgttaattga gcaagtgtat    420

agagcattta agattatgcg tggagaagca tatcataaat gatgcggttt tttcagccgc    480

ttcataaagg gattttgaat gtatcagaac atatgaggtt tatgtgaatt gctgttatgt    540

ttttaagaag catatcataa gtgatgcggt ttttattaat tagttgctaa aaaatgaagt    600

atgcaatatt aattattatt aaattttgat atatttaaag aaagattaag tttagggtga    660

atgaatggct tatcaaagtg aatatgcatt agaaaatgaa gtacttcaac aacttgagga    720

attgaactat gaaagagtaa atatacataa tattaaatta gaaattaatg aatatctcaa    780

agaactagga gtgttgaaaa atgaataagc agacaaatac tccagaacta agatttccag    840

agtttgatga ggaatggaaa aaaaggaaat taggtgaagt agtaaattat aaaaatggtg    900

gttcatttga aagtttagtg aaaaaccatg gtgtatataa actcataact cttaaatctg    960

ttaatacaga aggaaagttg tgtaattctg gaaaatatat cgatgataaa tgtgttgaaa   1020

cattgtgtaa tgatacttta gtaatgatac tgagcgagca agcaccagga ctagttggaa   1080

tgactgcaat tatacctaat aataatgagt atgtactaaa tcaacgagta gcagcactag   1140

tgcctaaaca atttatagat agtcaatttc tatctaagtt aattaataga aaccagaaat   1200

atttcagtgt gagatctgct ggaacaaaag tgaaaaatat ttctaaagga catgtagaaa   1260

actttaattt tttatctcct aattacactg aacaacaaaa aataggtaat ttcttcagca   1320

aactcgaccg ccagattgag ttagaagaag agaaacttga actcttatag caacaaaagc   1380

gtggatatat ttcagaagat ttttctcaag                                    1410
```

<210> SEQ ID NO 234
<211> LENGTH: 60
<212> TYPE: DNA
<213> ORGANISM: Staphylococcus aureus

<400> SEQUENCE: 234

```
tatgtcaaaa atcatgaacc tcattactta tgataccttg tgcaggccgt ttgatccgcc     60
```

<210> SEQ ID NO 235
<211> LENGTH: 60

<212> TYPE: DNA
<213> ORGANISM: Staphylococcus aureus

<400> SEQUENCE: 235
tatgtcaaaa atcatgaacc tcattactta tgataccttg tgcaggccgt ttgatccgcc 60

<210> SEQ ID NO 236
<211> LENGTH: 60
<212> TYPE: DNA
<213> ORGANISM: Staphylococcus aureus

<400> SEQUENCE: 236
tatgtcaaaa atcatgaacc tcattactta tgataccttg tgcaggccgt ttgatccgcc 60

<210> SEQ ID NO 237
<211> LENGTH: 60
<212> TYPE: DNA
<213> ORGANISM: Staphylococcus aureus

<400> SEQUENCE: 237
tatgtcaaaa atcatgaacc tcattactta tgataccttg tgcaggccgt ttgatccgcc 60

<210> SEQ ID NO 238
<211> LENGTH: 60
<212> TYPE: DNA
<213> ORGANISM: Staphylococcus aureus

<400> SEQUENCE: 238
tatgtcaaaa atcatgaacc tcattactta tgataccttg tgcaggccgt ttgatccgcc 60

<210> SEQ ID NO 239
<211> LENGTH: 60
<212> TYPE: DNA
<213> ORGANISM: Staphylococcus aureus

<400> SEQUENCE: 239
tatgtcaaaa atcatgaacc tcattactta tgataccttg tgcaggccgt ttgatccgcc 60

<210> SEQ ID NO 240
<211> LENGTH: 60
<212> TYPE: DNA
<213> ORGANISM: Staphylococcus aureus

<400> SEQUENCE: 240
tatgtcaaaa atcatgaacc tcattactta tgataccttg tgcaggccgt ttgatccgcc 60

<210> SEQ ID NO 241
<211> LENGTH: 60
<212> TYPE: DNA
<213> ORGANISM: Staphylococcus aureus

<400> SEQUENCE: 241
tatgtcaaaa atcatgaacc tcattactta tgataccttg tgcaggccgt ttgatccgcc 60

<210> SEQ ID NO 242
<211> LENGTH: 60
<212> TYPE: DNA
<213> ORGANISM: Staphylococcus aureus

<400> SEQUENCE: 242
tatgtcaaaa atcatgaacc tcattactta tgataccttg tgcaggccgt ttgatccgcc 60

<210> SEQ ID NO 243

<211> LENGTH: 60
<212> TYPE: DNA
<213> ORGANISM: Staphylococcus aureus

<400> SEQUENCE: 243
tatgtcaaaa atcatgaacc tcattactta tgataccttg tgcaggccgt ttgatccgcc 60

<210> SEQ ID NO 244
<211> LENGTH: 60
<212> TYPE: DNA
<213> ORGANISM: Staphylococcus aureus

<400> SEQUENCE: 244
tatgtcaaaa atcatgaacc tcattactta tgataccttg tgcaggccgt ttgatccgcc 60

<210> SEQ ID NO 245
<211> LENGTH: 60
<212> TYPE: DNA
<213> ORGANISM: Staphylococcus aureus

<400> SEQUENCE: 245
tatgtcaaaa atcatgaacc tcattactta tgataccttg tgcaggccgt ttgatccgcc 60

<210> SEQ ID NO 246
<211> LENGTH: 25
<212> TYPE: DNA
<213> ORGANISM: Staphylococcus aureus

<400> SEQUENCE: 246
cttggtgtaa accattggag ccacc 25

<210> SEQ ID NO 247
<211> LENGTH: 21
<212> TYPE: DNA
<213> ORGANISM: Staphylococcus aureus

<400> SEQUENCE: 247
cctcatgcaa tccatttgat c 21

<210> SEQ ID NO 248
<211> LENGTH: 29
<212> TYPE: DNA
<213> ORGANISM: Synthetic

<400> SEQUENCE: 248
gtcaaaaatc atgaacctca ttacttatg 29

<210> SEQ ID NO 249
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 249
tgtgcaggcc gtttgatcc 19

<210> SEQ ID NO 250
<211> LENGTH: 35
<212> TYPE: DNA
<213> ORGANISM: Staphylococcus aureus

<400> SEQUENCE: 250
acaaggacgt cttacaacgc agtaactatg cacta 35

<210> SEQ ID NO 251
<211> LENGTH: 35
<212> TYPE: DNA
<213> ORGANISM: Staphylococcus aureus

<400> SEQUENCE: 251
acaaggacgt cttacaacgc agtaactatg cacta 35

<210> SEQ ID NO 252
<211> LENGTH: 35
<212> TYPE: DNA
<213> ORGANISM: Staphylococcus aureus

<400> SEQUENCE: 252
acaaggacgt cttacaacgc agtaactatg cacta 35

<210> SEQ ID NO 253
<211> LENGTH: 35
<212> TYPE: DNA
<213> ORGANISM: Staphylococcus aureus

<400> SEQUENCE: 253
acaaggacgt cttacaacgc agtaactatg cacta 35

<210> SEQ ID NO 254
<211> LENGTH: 35
<212> TYPE: DNA
<213> ORGANISM: Staphylococcus aureus

<400> SEQUENCE: 254
acaaggacgt cttacaacgc agtaactatg cacta 35

<210> SEQ ID NO 255
<211> LENGTH: 35
<212> TYPE: DNA
<213> ORGANISM: Staphylococcus aureus

<400> SEQUENCE: 255
acaaggacgt cttacaacgc agtaactatg cacta 35

<210> SEQ ID NO 256
<211> LENGTH: 35
<212> TYPE: DNA
<213> ORGANISM: Staphylococcus aureus

<400> SEQUENCE: 256
acaaggacgt cttacaacgc agtaactatg cacta 35

<210> SEQ ID NO 257
<211> LENGTH: 35
<212> TYPE: DNA
<213> ORGANISM: Staphylococcus aureus

<400> SEQUENCE: 257
acaaggacgt cttacaacgt agtaactacg cacta 35

<210> SEQ ID NO 258
<211> LENGTH: 35
<212> TYPE: DNA
<213> ORGANISM: Staphylococcus aureus

<400> SEQUENCE: 258
acaaggacgt cttacaacgt agtaactacg cacta 35

<210> SEQ ID NO 259
<211> LENGTH: 35
<212> TYPE: DNA
<213> ORGANISM: Staphylococcus aureus

<400> SEQUENCE: 259
acaaggacgt cttacaacgt agtaactacg cacta 35

<210> SEQ ID NO 260
<211> LENGTH: 35
<212> TYPE: DNA
<213> ORGANISM: Staphylococcus aureus

<400> SEQUENCE: 260
acaaggacgt cttacaacgt agtaactacg cacta 35

<210> SEQ ID NO 261
<211> LENGTH: 35
<212> TYPE: DNA
<213> ORGANISM: Staphylococcus aureus

<400> SEQUENCE: 261
acaaggacgt cttacaacgt agtaactacg cacta 35

<210> SEQ ID NO 262
<211> LENGTH: 35
<212> TYPE: DNA
<213> ORGANISM: Staphylococcus aureus

<400> SEQUENCE: 262
acaaggacgt cttacaacgt agtaactacg cacta 35

<210> SEQ ID NO 263
<211> LENGTH: 35
<212> TYPE: DNA
<213> ORGANISM: Staphylococcus aureus

<400> SEQUENCE: 263
acaaggacgt cttacaacgc agtaactacg cacta 35

<210> SEQ ID NO 264
<211> LENGTH: 35
<212> TYPE: DNA
<213> ORGANISM: Staphylococcus aureus

<400> SEQUENCE: 264
acaaggacgt cttacaacgc agtaactacg cacta 35

<210> SEQ ID NO 265
<211> LENGTH: 35
<212> TYPE: DNA
<213> ORGANISM: Staphylococcus aureus

<400> SEQUENCE: 265
accaagacgt cttacaacgc agcaactatg cttta 35

<210> SEQ ID NO 266
<211> LENGTH: 35
<212> TYPE: DNA
<213> ORGANISM: Staphylococcus aureus

<400> SEQUENCE: 266

-continued

```
atgaggacgt cttacaacgc agcaactacg cactt                               35


<210> SEQ ID NO 267
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 267

gacgtcttac aacgcagtaa ctatg                                          25


<210> SEQ ID NO 268
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 268

gacgtcttac aacgtagtaa ctacg                                          25


<210> SEQ ID NO 269
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 269

gacgtcttac aacgcagtaa ctacg                                          25
```